United States Patent
Presnell et al.

(10) Patent No.: US 6,875,845 B2
(45) Date of Patent: Apr. 5, 2005

(54) MOUSE CYTOKINE RECEPTOR

(75) Inventors: Scott R. Presnell, Tacoma, WA (US);
Wenfeng Xu, Mukilteo, WA (US);
Wayne Kindsvogel, Seattle, WA (US);
Zhi Chen, Bellevue, WA (US)

(73) Assignee: ZymoGenetics, Inc., Seattle, WA (US)

( * ) Notice: Subject to any disclaimer, the term of this patent is extended or adjusted under 35 U.S.C. 154(b) by 139 days.

(21) Appl. No.: 10/090,365

(22) Filed: Mar. 4, 2002

(65) Prior Publication Data

US 2003/0077706 A1 Apr. 24, 2003

Related U.S. Application Data

(60) Provisional application No. 60/273,035, filed on Mar. 2, 2001, and provisional application No. 60/279,232, filed on Mar. 27, 2001.

(51) Int. Cl.[7] .................... C07K 14/705; C07K 14/475
(52) U.S. Cl. .................... 530/351; 530/810; 530/387.3; 514/12
(58) Field of Search .................... 530/351, 387.3, 530/810; 514/12

(56) References Cited

FOREIGN PATENT DOCUMENTS

| WO | WO98/37193 | 8/1998 |
|---|---|---|
| WO | WO01/36467 | 5/2001 |
| WO | WO01/40467 | 6/2001 |
| WO | WO02/024912 | 3/2002 |
| WO | WO02/066647 | 8/2002 |

OTHER PUBLICATIONS

Dumoutier, L et al., *J. Immunol.* 167:3545–3549, 2001.
Dumoutier, L et al., *J. Immunol.* 166:7090–7095, 2001.
Kotenko, SV et al., *J. Immunol.* 166:7096–7013, 2001.
Xu, W et al., Proc. *Nat. Acad. Sci.* 98:9511–9516, 2001.
Gruenberg, BH et al., *Genes and Immunity* 2:329–334, 2001.
Xie, M H et al., *J. Biol. Chem.* 275:31335–31339, 2000.
L. Dumoutier, et al. *Journal of Immunology* 164: 1814–1819, 2000.
L. Dumoutier, et al. *Proc. Nat. Acad. Sci.* 97:10144–10149, 2000.
L. Dumoutier, et al. *Genes and Immunity.* 1:488–494, 2000.
Xu, X. et al., EMBL Database, Chinese National Human Genome Center at Shanghai, Oct. 5, 2000: AV714177.
Incyte Pharmaceuticals, Inc. clone. 1999: SHLW01158999.

*Primary Examiner*—Janet Andres
*Assistant Examiner*—Fozia Hamud
(74) *Attorney, Agent, or Firm*—Jennifer K. Johnson

(57) ABSTRACT

Cytokines and their receptors have proven usefulness in both basic research, animal models, and as therapeutics. The present invention provides a new cytokine receptor designated as "mouse Zcytor16," which can bind and antagonize the IL-TIF cytokine.

19 Claims, 1 Drawing Sheet

```
           10         20         30         40         50         60
hzcytor16  MMPKHCFLGFLISFFLTGVAGTQSTHESLKPQRVQFQSRNFHNILQWQPGRALTGNSSVY
           :::::::..:.::  ..:..:..:...  .::. :::::::::::..::.:.:..:.::
mzcytor16  MMPKHCLLGLLI-ILLSSATEIQPARVSLTLQKVRFQSRNFHNILHWQAGSSLPSNNSIY
           10         20         30         40         50

70         80         90        100        110        120
hzcytor16  FVQYKIYGQRQWKNKEDCWGTQELSCDLTSETSDIQEPYYGRVRAASAGSYSEWSMTPRF
           :::::::..::.::: :::::..:::::::::..:::.::.::::::::::.:..::::
mzcytor16  FVQYKMYGQSQWEDKVDCWGTTALFCDLTNETLDPYELYYGRVMTACAGRHSAWTRTPRF
           60         70         80         90        100        110

130        140        150        160        170        180
hzcytor16  TPWWETKIDPPVMNITQVNGSLLVILHAPNLPYRYQKEKNVSIEDYYELLYRVFIINNSL
           ::::::::.::::..::..::.:::.:::..::.:..:.:.::::..::::::::::::
mzcytor16  TPWWETKLDPPVVTITRVNASLRVLLRPPELPNRNQSGKNASMETYYGLVYRVFTINNSL
           120        130        140        150        160        170

190        200        210        220        230
hzcytor16  EKEQKVYEGAHRAVEIEALTPHSSYCVVAEIYQPMLDRRSQRSEERCVEIP
           ::::::.:::.:::::::::.::::::::::.:::.::::.:::::::.:
mzcytor16  EKEQKAYEGTQRAVEIEGLIPHSSYCVVAEMYQPMFDRRSPRSKERCVQIP
           180        190        200        210        220        230
```

FIG. 1

MOUSE CYTOKINE RECEPTOR

REFERENCE TO RELATED APPLICATIONS

This application is related to Provisional Application 60/273,035, filed on Mar. 2, 2001. This application is also related to Provisional Application 60/279,232, filed on Mar. 27, 2001. Under 35 U.S.C. §119(e)(1), this application claims benefit of said Provisional Applications.

TECHNICAL FIELD

The present invention relates generally to a new protein expressed by mouse cells that is a murine ortholog to human Zcytor16 (U.S. patent application Ser. No. 09/728,911). In particular, the present invention relates to a novel gene that encodes a receptor, designated as "mouse Zcytor16," and to nucleic acid molecules encoding mouse Zcytor16 polypeptides, and antibodies to the polypeptide.

BACKGROUND OF THE INVENTION

Cytokines are soluble, small proteins that mediate a variety of biological effects, including the regulation of the growth and differentiation of many cell types (see, for example, Arai et al., *Annu. Rev. Biochem.* 59:783(1990); Mosmann, *Curr. Opin. Immunol.* 3:311 (1991); Paul and Seder, *Cell* 76:241(1994)). Proteins that constitute the cytokine group include interleukins, interferons, colony stimulating factors, tumor necrosis factors, and other regulatory molecules. For example, human interleukin-17 is a cytokine which stimulates the expression of interleukin-6, intracellular adhesion molecule 1, interleukin-8, granulocyte macrophage colony-stimulating factor, and prostaglandin E2 expression, and plays a role in the preferential maturation of CD34+ hematopoietic precursors into neutrophils (Yao et al., *J. Immunol.* 155:5483 (1995); Fossiez et al., *J. Exp. Med.* 183:2593 (1996)).

Receptors that bind cytokines are typically composed of one or more integral membrane proteins that bind the cytokine with high affinity and transduce this binding event to the cell through the cytoplasmic portions of the certain receptor subunits. Cytokine receptors have been grouped into several classes on the basis of similarities in their extracellular ligand binding domains. For example, the receptor chains responsible for binding and/or transducing the effect of interferons are members of the class II cytokine receptor family, based upon a characteristic about 200 residue extracellular domain.

The demonstrated in vivo activities of cytokines and their receptors illustrate the clinical potential of, and need for, other cytokines, cytokine receptors, cytokine agonists, and cytokine antagonists.

BRIEF DESCRIPTION OF THE DRAWINGS

FIG. 1 is an alignment of human Zcytor16 (hZcytor16) (SEQ ID NO:2), and mouse Zcytor16 (mZcytor16) (SEQ ID NO:38). The ":" in the figure indicates amino acids that are identical between the mouse and human sequences, and the "." in the figure indicates amino acids that are conserved substitutions. There is a 66.2% identity between the human and mouse sequences over the entire sequence (231 amino acid overlap).

BRIEF SUMMARY OF THE INVENTION

The present invention provides a novel receptor, designated "mouse Zcytor16." The present invention also provides mouse Zcytor16 polypeptides and mouse Zcytor16 fusion proteins, as well as nucleic acid molecules encoding such polypeptides and proteins, and methods for using these nucleic acid molecules and amino acid sequences.

DETAILED DESCRIPTION OF THE INVENTION

1. Overview

An illustrative nucleotide sequence that encodes mouse Zcytor16 is provided by SEQ ID NO:37. The encoded polypeptide has the following amino acid sequence: MMPKHCLLGL LIILLSSATE IQPARVSLTL QKVRFQSRNF HNILHWQAGS SLPSNNSIYF VQYKMYGQSQ WEDKVDCWGT TALFCDLTNE TLDPYELYYG RVMTACAGRH SAWTRTPRFT PWWETKLDPP VVTITRVNAS LRVLLRPPEL PNRNQSGKNA SMETYYGLVY RVFTINNSLE KEQKAYEGTQ RAVEIEGLIP HSSYCVVAEM YQPMFDRRSP RSKERCVQIP (SEQ ID NO:38). The 230 amino acid polypeptide represents the extracellular domain, also called a cytokine-binding domain, of a new class II cytokine receptor. Features of the Zcytor16 polypeptide include putative signal sequences at amino acid residues 1 to 23 of SEQ ID NO:38, and a mature soluble receptor polypeptide from residues 24 to 230 of SEQ ID NO:38. The receptor has two fibronectin III domains, also called immunoglobulin superfamily (Ig) domains, characteristic of the class II cytokine receptor family that comprise amino acid residues 31 to 122 (fibronectin III domain I), and 131 to 229 (fibronectin III domain II) of SEQ ID NO:38, and a linker that resides between the Ig domains (i.e., at amino acid residues 127–130 of SEQ ID NO:38). Thus molecules of the present invention include polypepetides that include a cytokine binding domain comprising amino acids 31 to 229 of SEQ ID NO:38. Moreover, additional variants of the zcytor16 polypeptide include polyepeptides that comprise amino acid residues 27 to 122, 24 to 122, 31 to 126, 27 to 126, or 24 to 126, (fibronectin III domain I), and 131 to 229 or 230 (fibronectin III domain II) of SEQ ID NO:38, and a linker that resides between the Ig domains (i.e., at amino acid residues 123–130, or 127–130 of SEQ ID NO:38). Thus molecules of the present invention include polypepetides that include a cytokine binding domain comprising amino acids 24, or 27, to 229 or 230 of SEQ ID NO:38. In addition, zcytor16 contains conserved motifs and residues characteristic of class II cytokines: an SXWS (SEQ ID NO:46)—like motif from residue 219–222 of SEQ ID NO:38; conserved Tryptophan residues at residues 46, 71, and 113 of SEQ ID NO:38; and conserved Cysteine residues at residues 77, 85, 205, and 226 of SEQ ID NO:38. The mouse Zcytor16 gene is specifically expressed in Lung, Pancreas, Placenta, Salivary Gland, Skeletal Muscle, Skin, Small Intestine, Smooth Muscle, Spleen, Stomach, and Testis cDNAs and is expected to be expressed in specific mononuclear cells, such as activated T-cell and B-cell subsets. Alignment of the polypeptide sequences shows that mouse Zcytor16 (SEQ ID NO:38) is an ortholog of the human Zcytor16 sequence (SEQ ID NO:2) (U.S. patent application Ser. No. 09/728, 911) as shown in FIG. 1.

Another illustrative nucleotide sequence that encodes a preferred mouse Zcytor16 is provided by SEQ ID NO:47. The encoded polypeptide has the following amino acid sequence: MMPKHCLLGL LIILLSSATE IQPARVSLTPQ KVRFQSRNFH NILHWQAGSSLPSNNSIYFVQYK-MYGQSQWEDKVDCWGTTALFCDLTNETLD PYELYYGRVMTACAGRHSAWTRTPRFTPW-WETKLDPPVVTITRVNASLRVLL RPPELPNRNQSGKNASMETYYGLVYRVF-TINNSLEKEQKAYEGTQRAVEIEGLI PHSSYCVVAE- MYQPMFDRRSPRSKERCVHIP (SEQ ID NO:48). The 230 amino acid polypeptide represents the extracellular domain, also called a cytokine-binding domain, of a new class II cytokine receptor. The SEQ ID NO:48 sequence differs from SEQ ID NO:38 by two amino acids: amino acid 30 (Leu) and 228 (Gln) shown in SEQ ID NO:38 are amino acids 30 (Pro) and 228 (His) shown in SEQ ID NO:48. Features of the Zcytor16 polypeptide include putative signal sequences at amino acid residues 1 to 23 of SEQ ID NO:48, and a mature soluble receptor polypeptide from residues 24 to 230 of SEQ ID NO:48. The receptor has two fibronectin III domains, also called immunoglobulin superfamily (Ig) domains, characteristic of the class II cytokine receptor family that comprise amino acid residues 31 to 122 (fibronectin III domain I), and 131 to 229 (fibronectin III domain II) of SEQ ID NO:48, and a linker that resides between the Ig domains (i.e., at amino acid residues 127–130 of SEQ ID NO:48). Thus molecules of the present invention include polypepetides that include a cytokine binding domain comprising amino acids 31 to 229 of SEQ ID NO:48. Moreover, additional variants of the zcytor16 polypeptide include polyepeptides that comprise amino acid residues 27 to 122, 24 to 122, 31 to 126, 27 to 126, or 24 to 126, (fibronectin III domain I), and 131 to 229 or 230 (fibronectin III domain II) of SEQ ID NO:48, and a linker that resides between the Ig domains (i.e., at amino acid residues 123–130, or 127–130 of SEQ ID NO:48). Thus molecules of the present invention include polypepetides that include a cytokine binding domain comprising amino acids 24, or 27, to 229 or 230 of SEQ ID NO:48. In addition, zcytor16 contains conserved motifs and residues characteristic of class II cytokines: an SXWS (SEQ ID NO:46)—like motif from residue 219–222 of SEQ ID NO:48; conserved Tryptophan residues at residues 46, 71, and 113 of SEQ ID NO:48; and conserved Cysteine residues at residues 77, 85, 205, and 226 of SEQ ID NO:48.

An illustrative nucleotide sequence that encodes human Zcytor16 is provided by SEQ ID NO:1. The encoded polypeptide has the following amino acid sequence: MMP-KHCFLGF LISFFLTGVA GTQSTHESLK PQRVQFQSRN FHNILQWQPG RALTGNSSVY FVQYKIYGQR QWKNKEDCWG TQELSCDLTS ETSDIQEPYY GRVRAASAGS YSEWSMTPRF TPWWETKIDP PVM-NITQVNG SLLVILHAPN LPYRYQKEKN VSIEDYYELL YRVFIINNSL EKEQKVYEGA HRAVEIEALT PHSSYCVVAE IYQPMLDRRS QRSEER-CVEI P (SEQ ID NO:2). The 231 amino acid polypeptide represents the extracellular domain, also called a cytokine-binding domain, of a new class II cytokine receptor. Features of the Zcytor16 polypeptide include putative signal sequences at amino acid residues 1 to 21, or 1 to 22 of SEQ ID NO:2, and a mature soluble receptor polypeptide from residues 22 to 231 or 23 to 231 of SEQ ID NO:2. The receptor has two fibronectin m domains, also called immunoglobulin superfamily (Ig) domains, characteristic of the class II cytokine receptor family that comprise amino acid residues 32 to 123 (fibronectin III domain I), and 132 to 230 (fibronectin III domain II) of SEQ ID NO:2, and a linker that resides between the Ig domains (i.e., at amino acid residues 128–131 of SEQ ID NO:2). Thus molecules of the present invention include polypepetides that include a cytokine binding domain comprising amino acids 32 to 230 of SEQ ID NO:2. Moreover, additional variants of the zcytor16 polypeptide include polyepeptides that comprise amino acid residues 28 to 123, 23 to 123, 22 to 123, or 32 to 127, 28 to 127, 23 to 127, 22 to 127, (fibronectin III domain I), and 132 to 230 or 231 (fibronectin III domain II) of SEQ ID NO:2, and a linker that resides between the Ig domains (i.e., at amino acid residues 124–131, or 128–131 of SEQ ID NO:2). Thus molecules of the present invention include polypepetides that include a cytokine binding domain comprising amino acids 22, 23, or 28 to 132 to 230 or 231 of SEQ ID NO:2. In addition, zcytor16 contains conserved motifs and residues characteristic of class II cytokines: an SXWS (SEQ ID NO:46) motif from residue 220–223 of SEQ ID NO:2; conserved Tryptophan residues at residues 47, 72, and 114 of SEQ ID NO:2; and conserved Cysteine residues at residues 78, 86, 206, and 227 of SEQ ID NO:2. The Zcytor16 gene is expressed in monocytes, lymphoid, placenta, spleen, tonsil and other tissues, and resides in human chromosome 6q23-q24.

The corresponding polynucleotides encoding the zcytor16 polypeptide regions, domains, motifs, residues and sequences described above are as shown in SEQ ID NO:1 (human zcytor16) and SEQ ID NO:37, and SEQ ID NO:47 (mouse zcytor16).

As described below, the present invention provides isolated polypeptides comprising an amino acid sequence that is at least 70%, at least 80%, or at least 90% identical to a reference amino acid sequence of SEQ ID NO:38 or SEQ ID NO:48 selected from the group consisting of: (a) amino acid residues amino acid residues 24 to 230, or 27 to 230, (b) amino acid residues 27 to 126, (c) amino acid residues 131 to 230 and (d) amino acid residues amino acid residues 1 to 230. The present invention also provides isolated polypeptides as disclosed above that specifically bind with an antibody that specifically binds with a polypeptide consisting of the amino acid sequence of SEQ ID NO:38 or SEQ ID NO:48. Illustrative polypeptides include polypeptides comprising either amino acid residues 24 to 230, or 27 to 230 of SEQ ID NO:38 or SEQ ID NO:48 or a fragment thereof described herein. Moreover, the present invention also provides isolated polypeptides as disclosed above that bind IL-TIF (e.g., human IL-TIF polypeptide sequence as shown in SEQ ID NO:15 or mouse IL-TIF polypeptide sequence as shown in SEQ ID NO:41). The human IL-TIF polynucleotide sequence is shown in SEQ ID NO:14. The mouse IL-TIF polynucleotide sequence is shown in SEQ ID NO:40.

The present invention also provides isolated polypeptides comprising at least 15 contiguous amino acid residues of an amino acid sequence of SEQ ID NO:38 or SEQ ID NO:48 selected from the group consisting of: (a) amino acid residues amino acid residues 24 to 230, or 27 to 230, (b) amino acid residues 27 to 126, (c) amino acid residues 131 to 230 and (d) amino acid residues amino acid residues 1 to 230. Illustrative polypeptides include polypeptides that either comprise, or consist of, amino acid residues (a) to (d). Moreover, the present invention also provides isolated polypeptides as disclosed above that bind IL-TIF.

The present invention also includes variant mouse Zcytor16 polypeptides, wherein the amino acid sequence of the variant polypeptide shares an identity with amino acid residues 24 to 230, or 27 to 230 of SEQ ID NO:38 or SEQ ID NO:48 selected from the group consisting of at least 70% identity, at least 80% identity, at least 90% identity, at least 95% identity, or greater than 95% identity, and wherein any difference between the amino acid sequence of the variant polypeptide and the corresponding amino acid sequence of SEQ ID NO:38 or SEQ ID NO:48 is due to one or more conservative amino acid substitutions. Moreover, the present invention also provides isolated polypeptides as disclosed above that bind IL-TIF.

The present invention further provides antibodies and antibody fragments that specifically bind with such polypeptides. Exemplary antibodies include polyclonal antibodies, murine monoclonal antibodies, humanized antibodies derived from murine monoclonal antibodies, and human monoclonal antibodies. Illustrative antibody fragments include F(ab')₂, F(ab)₂, Fab', Fab, Fv, scFv, and minimal recognition units. The present invention further includes compositions comprising a carrier and a peptide, polypeptide, or antibody described herein.

The present invention also provides isolated nucleic acid molecules that encode a mouse Zcytor16 polypeptide, wherein the nucleic acid molecule is selected from the group consisting of: (a) a nucleic acid molecule comprising the nucleotide sequence of SEQ ID NO:39 or SEQ ID NO:49, (b) a nucleic acid molecule encoding an amino acid sequence that comprises either amino acid residues 24 to 230, or 27 to 230 of SEQ ID NO:38 or SEQ ID NO:48 and (c) a nucleic acid molecule that remains hybridized following stringent wash conditions to a nucleic acid molecule comprising the nucleotide sequence of nucleotides 77 or 86 to 697 of SEQ ID NO:37 or SEQ ID NO:47, or the complement of the nucleotide sequence of nucleotides 77 or 86 to 697 of SEQ ID NO:37 or SEQ ID NO:47. Illustrative nucleic acid molecules include those in which any difference between the amino acid sequence encoded by nucleic acid molecule (c) and the corresponding amino acid sequence of SEQ ID NO:38 or SEQ ID NO:48 is due to a conservative amino acid substitution. The present invention further contemplates isolated nucleic acid molecules that comprise nucleotides 8 to 697 of SEQ ID NO:37 or SEQ ID NO:47. Moreover, the present invention also provides isolated polynucleotides that encode polypeptides as disclosed above that bind IL-TIF.

The present invention also includes vectors and expression vectors comprising such nucleic acid molecules. Such expression vectors may comprise a transcription promoter, and a transcription terminator, wherein the promoter is operably linked with the nucleic acid molecule, and wherein the nucleic acid molecule is operably linked with the transcription terminator. The present invention further includes recombinant host cells and recombinant viruses comprising these vectors and expression vectors. Illustrative host cells include bacterial, yeast, fungal, insect, mammalian, and plant cells. Recombinant host cells comprising such expression vectors can be used to produce mouse Zcytor16 polypeptides by culturing such recombinant host cells that comprise the expression vector and that produce the mouse Zcytor16 protein, and, optionally, isolating the mouse Zcytor16 protein from the cultured recombinant host cells.

In addition, the present invention provides pharmaceutical compositions comprising a pharmaceutically acceptable carrier and at least one of such an expression vector or recombinant virus comprising such expression vectors. The present invention further includes pharmaceutical compositions, comprising a pharmaceutically acceptable carrier and a polypeptide described herein.

The present invention also contemplates methods for detecting the presence of mouse Zcytor16 RNA in a biological sample, comprising the steps of (a) contacting a mouse Zcytor16 nucleic acid probe under hybridizing conditions with either (i) test RNA molecules isolated from the biological sample, or (ii) nucleic acid molecules synthesized from the isolated RNA molecules, wherein the probe has a nucleotide sequence comprising a portion of the nucleotide sequence of SEQ ID NO:37 or SEQ ID NO:47, or its complement, and (b) detecting the formation of hybrids of the nucleic acid probe and either the test RNA molecules or the synthesized nucleic acid molecules, wherein the presence of the hybrids indicates the presence of mouse Zcytor16 RNA in the biological sample. For example, suitable probes consist of the following nucleotide sequences of SEQ ID NO:37 or SEQ ID NO:47: nucleotides 77, 86, or 100 to 373;, nucleotides 77, 86, or 100 to 694 or 697; nucleotides 401 to 694 or 697; and nucleotides 8 to 694 or 697. Other suitable probes consist of the complement of these nucleotide sequences, or a portion of the nucleotide sequences or their complements.

The present invention further provides methods for detecting the presence of mouse Zcytor16 polypeptide in a biological sample, comprising the steps of: (a) contacting the biological sample with an antibody or an antibody fragment that specifically binds with a polypeptide consisting of the amino acid sequence of SEQ ID NO:38 or SEQ ID NO:48, wherein the contacting is performed under conditions that allow the binding of the antibody or antibody fragment to the biological sample, and (b) detecting any of the bound antibody or bound antibody fragment. Such an antibody or antibody fragment may further comprise a detectable label selected from the group consisting of radioisotope, fluorescent label, chemiluminescent label, enzyme label, bioluminescent label, and colloidal gold.

The present invention also provides kits for performing these detection methods. For example, a kit for detection of Zcytor16 gene expression may comprise a container that comprises a nucleic acid molecule, wherein the nucleic acid molecule is selected from the group consisting of (a) a nucleic acid molecule comprising the nucleotide sequence of nucleotides 77, 86, or 100 to 694 or 697, or 8 to 694 or 697 of SEQ ID NO:37 or SEQ ID NO:47, (b) a nucleic acid molecule that is a fragment of (a) consisting of at least eight nucleotides. Such a kit may also comprise a second container that comprises one or more reagents capable of indicating the presence of the nucleic acid molecule. On the other hand, a kit for detection of mouse Zcytor16 protein may comprise a container that comprises an antibody, or an antibody fragment, that specifically binds with a polypeptide consisting of the amino acid sequence of SEQ ID NO:38 or SEQ ID NO:48.

The present invention also contemplates anti-idiotype antibodies, or anti-idiotype antibody fragments, that specifically bind an antibody or antibody fragment that specifically binds a polypeptide consisting of the amino acid sequence of SEQ ID NO:38 or SEQ ID NO:48. An exemplary anti-idiotype antibody binds with an antibody that specifically binds a polypeptide consisting of amino acid residues 24 to 230, or 27 to 230 of SEQ ID NO:38 or SEQ ID NO:48.

The present invention also provides isolated nucleic acid molecules comprising a nucleotide sequence that encodes a mouse Zcytor16 secretion signal sequence and a nucleotide sequence that encodes a biologically active polypeptide, wherein the mouse Zcytor16 secretion signal sequence comprises an amino acid sequence of residues 1 to 23 of SEQ ID NO:38 or SEQ ID NO:48. Illustrative biologically active polypeptides include Factor VIIa, proinsulin, insulin, follicle stimulating hormone, tissue type plasminogen activator, tumor necrosis factor, interleukin, colony stimulating factor, interferon, erythropoietin, and thrombopoietin. Moreover, the present invention provides fusion proteins comprising a mouse Zcytor16 secretion signal sequence and a polypeptide, wherein the mouse Zcytor16 secretion signal sequence comprises an amino acid sequence of residues 1 to 23, of SEQ ID NO:38 or SEQ ID NO:48.

The present invention also provides fusion proteins, comprising a mouse Zcytor16 polypeptide and an immunoglobulin moiety. In such fusion proteins, the immunoglobulin moiety may be an immunoglobulin heavy chain constant region, such as a human $F_C$ fragment. The present invention further includes isolated nucleic acid molecules that encode such fusion proteins.

The present invention also provides monomeric, homodimeric, heterodimeric and multimeric receptors comprising a mouse Zcytor16 extracellular domain. Such receptors are soluble or membrane bound, and act as antagonists of the Zcytor16 ligand, IL-TIF (e.g., the human IL-TIF as shown in SEQ ID NO:15, and mouse IL-TIF shown in SEQ ID NO:41). In a preferred embodiment, such receptors are soluble receptors comprising at least one mouse Zcytor16 extracellular domain polypeptide comprising amino acids 24 to 230, or 27 to 230 of SEQ ID NO:38 or SEQ ID NO:48. The present invention further includes isolated nucleic acid molecules that encode such receptor polypeptides.

The present invention also provides polyclonal and monoclonal antibodies to monomeric, homodimeric, heterodimeric and multimeric receptors comprising a mouse Zcytor16 extracellular domain such as those described above. Moreover, such antibodies can be used antagonize the binding to the Zcytor16 ligand, IL-TIF (SEQ ID NO:15, and SEQ ID NO:41), to the Zcytor16 receptor.

The present invention also provides a method for detecting a cancer in a patient, comprising: obtaining a tissue or biological sample from a patient; incubating the tissue or biological sample with an antibody as described above under conditions wherein the antibody binds to its complementary polypeptide in the tissue or biological sample; visualizing the antibody bound in the tissue or biological sample; and comparing levels of antibody bound in the tissue or biological sample from the patient to a normal control tissue or biological sample, wherein an increase in the level of antibody bound to the patient tissue or biological sample relative to the normal control tissue or biological sample is indicative of a cancer in the patient.

The present invention also provides a method for detecting a cancer in a patient, comprising: obtaining a tissue or biological sample from a patient; labeling a polynucleotide comprising at least 14 contiguous nucleotides of SEQ ID NO:37 or SEQ ID NO:47 or the complement of SEQ ID NO:37 or SEQ ID NO:47; incubating the tissue or biological sample with under conditions wherein the polynucleotide will hybridize to complementary polynucleotide sequence; visualizing the labeled polynucleotide in the tissue or biological sample; and comparing the level of labeled polynucleotide hybridization in the tissue or biological sample from the patient to a normal control tissue or biological sample, wherein an increase in the labeled polynucleotide hybridization to the patient tissue or biological sample relative to the normal control tissue or biological sample is indicative of a cancer in the patient.

These and other aspects of the invention will become evident upon reference to the following detailed description. In addition, various references are identified below and are incorporated by reference in their entirety.

2. Definitions

In the description that follows, a number of terms are used extensively. The following definitions are provided to facilitate understanding of the invention.

As used herein, "nucleic acid" or "nucleic acid molecule" refers to polynucleotides, such as deoxyribonucleic acid (DNA) or ribonucleic acid (RNA), oligonucleotides, fragments generated by the polymerase chain reaction (PCR), and fragments generated by any of ligation, scission, endonuclease action, and exonuclease action. Nucleic acid molecules can be composed of monomers that are naturally-occurring nucleotides (such as DNA and RNA), or analogs of naturally-occurring nucleotides (e.g., α-enantiomeric forms of naturally-occurring nucleotides), or a combination of both. Modified nucleotides can have alterations in sugar moieties and/or in pyrimidine or purine base moieties. Sugar modifications include, for example, replacement of one or more hydroxyl groups with halogens, alkyl groups, amines, and azido groups, or sugars can be functionalized as ethers or esters. Moreover, the entire sugar moiety can be replaced with sterically and electronically similar structures, such as aza-sugars and carbocyclic sugar analogs. Examples of modifications in a base moiety include alkylated purines and pyrimidines, acylated purines or pyrimidines, or other well-known heterocyclic substitutes. Nucleic acid monomers can be linked by phosphodiester bonds or analogs of such linkages. Analogs of phosphodiester linkages include phosphorothioate, phosphorodithioate, phosphoroselenoate, phosphorodiselenoate, phosphoroanilothioate, phosphoranilidate, phosphoramidate, and the like. The term "nucleic acid molecule" also includes so-called "peptide nucleic acids," which comprise naturally-occurring or modified nucleic acid bases attached to a polyamide backbone. Nucleic acids can be either single stranded or double stranded.

The term "complement of a nucleic acid molecule" refers to a nucleic acid molecule having a complementary nucleotide sequence and reverse orientation as compared to a reference nucleotide sequence. For example, the sequence 5' ATGCACGGG 3' is complementary to 5' CCCGTGCAT 3'.

The term "contig" denotes a nucleic acid molecule that has a contiguous stretch of identical or complementary sequence to another nucleic acid molecule. Contiguous sequences are said to "overlap" a given stretch of a nucleic acid molecule either in their entirety or along a partial stretch of the nucleic acid molecule.

The term "degenerate nucleotide sequence" denotes a sequence of nucleotides that includes one or more degenerate codons as compared to a reference nucleic acid molecule that encodes a polypeptide. Degenerate codons contain different triplets of nucleotides, but encode the same amino acid residue (i.e., GAU and GAC triplets each encode Asp).

The term "structural gene" refers to a nucleic acid molecule that is transcribed into messenger RNA (mRNA), which is then translated into a sequence of amino acids characteristic of a specific polypeptide.

An "isolated nucleic acid molecule" is a nucleic acid molecule that is not integrated in the genomic DNA of an organism. For example, a DNA molecule that encodes a growth factor that has been separated from the genomic DNA of a cell is an isolated DNA molecule. Another example of an isolated nucleic acid molecule is a chemically-synthesized nucleic acid molecule that is not integrated in the genome of an organism. A nucleic acid molecule that has been isolated from a particular species is smaller than the complete DNA molecule of a chromosome from that species.

A "nucleic acid molecule construct" is a nucleic acid molecule, either single- or double-stranded, that has been modified through human intervention to contain segments of nucleic acid combined and juxtaposed in an arrangement not existing in nature.

"Linear DNA" denotes non-circular DNA molecules having free 5' and 3' ends. Linear DNA can be prepared from closed circular DNA molecules, such as plasmids, by enzymatic digestion or physical disruption.

"Complementary DNA (cDNA)" is a single-stranded DNA molecule that is formed from an mRNA template by the enzyme reverse transcriptase. Typically, a primer complementary to portions of mRNA is employed for the initiation of reverse transcription. Those skilled in the art also use the term "cDNA" to refer to a double-stranded DNA molecule consisting of such a single-stranded DNA molecule and its complementary DNA strand. The term "cDNA" also refers to a clone of a cDNA molecule synthesized from an RNA template.

"Probes and/or primers" as used herein can be RNA or DNA. DNA can be either cDNA or genomic DNA. Polynucleotide probes and primers are single or double-stranded DNA or RNA, generally synthetic oligonucleotides, but may be generated from cloned cDNA or genomic sequences or its complements. Analytical probes will generally be at least 20 nucleotides in length, although somewhat shorter probes (14–17 nucleotides) can be used. PCR primers are at least 5 nucleotides in length, preferably 15 or more nt, more preferably 20–30 nt. Short polynucleotides can be used when a small region of the gene is targeted for analysis. For gross analysis of genes, a polynucleotide probe may comprise an entire exon or more. Probes can be labeled to provide a detectable signal, such as with an enzyme, biotin, a radionuclide, fluorophore, chemiluminescer, paramagnetic particle and the like, which are commercially available from many sources, such as Molecular Probes, Inc., Eugene, Oreg., and Amersham Corp., Arlington Heights, Ill., using techniques that are well known in the art.

A "promoter" is a nucleotide sequence that directs the transcription of a structural gene. Typically, a promoter is located in the 5' non-coding region of a gene, proximal to the transcriptional start site of a structural gene. Sequence elements within promoters that function in the initiation of transcription are often characterized by consensus nucleotide sequences. These promoter elements include RNA polymerase binding sites, TATA sequences, CAAT sequences, differentiation-specific elements (DSEs; McGehee et al., *Mol. Endocrinol.* 7:551 (1993)), cyclic AMP response elements (CREs), serum response elements (SREs; Treisman, *Seminars in Cancer Biol.* 1:47 (1990)), glucocorticoid response elements (GREs), and binding sites for other transcription factors, such as CRE/ATF (O'Reilly et al., *J. Biol. Chem.* 267:19938 (1992)), AP2 (Ye et al., *J. Biol. Chem.* 269:25728 (1994)), SPI, cAMP response element binding protein (CREB; Loeken, *Gene Expr.* 3:253 (1993)) and octamer factors (see, in general, Watson et al., eds., *Molecular Biology of the Gene*, 4th ed. (The Benjamin/Cummings Publishing Company, Inc. 1987), and Lemaigre and Rousseau, *Biochem. J.* 303:1 (1994)). If a promoter is an inducible promoter, then the rate of transcription increases in response to an inducing agent. In contrast, the rate of transcription is not regulated by an inducing agent if the promoter is a constitutive promoter. Repressible promoters are also known.

A "core promoter" contains essential nucleotide sequences for promoter function, including the TATA box and start of transcription. By this definition, a core promoter may or may not have detectable activity in the absence of specific sequences that may enhance the activity or confer tissue specific activity.

A "regulatory element" is a nucleotide sequence that modulates the activity of a core promoter. For example, a regulatory element may contain a nucleotide sequence that binds with cellular factors enabling transcription exclusively or preferentially in particular cells, tissues, or organelles. These types of regulatory elements are normally associated with genes that are expressed in a "cell-specific," "tissue-specific," or "organelle-specific" manner.

An "enhancer" is a type of regulatory element that can increase the efficiency of transcription, regardless of the distance or orientation of the enhancer relative to the start site of transcription.

"Heterologous DNA" refers to a DNA molecule, or a population of DNA molecules, that does not exist naturally within a given host cell. DNA molecules heterologous to a particular host cell may contain DNA derived from the host cell species (i.e., endogenous DNA) so long as that host DNA is combined with non-host DNA (i.e., exogenous DNA). For example, a DNA molecule containing a non-host DNA segment encoding a polypeptide operably linked to a host DNA segment comprising a transcription promoter is considered to be a heterologous DNA molecule. Conversely, a heterologous DNA molecule can comprise an endogenous gene operably linked with an exogenous promoter. As another illustration, a DNA molecule comprising a gene derived from a wild-type cell is considered to be heterologous DNA if that DNA molecule is introduced into a mutant cell that lacks the wild-type gene.

A "polypeptide" is a polymer of amino acid residues joined by peptide bonds, whether produced naturally or synthetically. Polypeptides of less than about 10 amino acid residues are commonly referred to as "peptides."

A "protein" is a macromolecule comprising one or more polypeptide chains. A protein may also comprise non-peptidic components, such as carbohydrate groups. Carbohydrates and other non-peptidic substituents may be added to a protein by the cell in which the protein is produced, and will vary with the type of cell. Proteins are defined herein in terms of their amino acid backbone structures; substituents such as carbohydrate groups are generally not specified, but may be present nonetheless.

A peptide or polypeptide encoded by a non-host DNA molecule is a "heterologous" peptide or polypeptide.

An "integrated genetic element" is a segment of DNA that has been incorporated into a chromosome of a host cell after that element is introduced into the cell through human manipulation. Within the present invention, integrated genetic elements are most commonly derived from linearized plasmids that are introduced into the cells by electroporation or other techniques. Integrated genetic elements are passed from the original host cell to its progeny.

A "cloning vector" is a nucleic acid molecule, such as a plasmid, cosmid, or bacteriophage, that has the capability of replicating autonomously in a host cell. Cloning vectors typically contain one or a small number of restriction endonuclease recognition sites that allow insertion of a nucleic acid molecule in a determinable fashion without loss of an essential biological function of the vector, as well as nucleotide sequences encoding a marker gene that is suitable for use in the identification and selection of cells transformed with the cloning vector. Marker genes typically include genes that provide antibiotic resistance, e.g., tetracycline resistance or ampicillin resistance.

An "expression vector" is a nucleic acid molecule encoding a gene that is expressed in a host cell. Typically, an expression vector comprises a transcription promoter, a gene, and a transcription terminator. Gene expression is usually placed under the control of a promoter, and such a gene is said to be "operably linked to" the promoter. Similarly, a regulatory element and a core promoter are operably linked if the regulatory element modulates the activity of the core promoter.

A "recombinant host" is a cell that contains a heterologous nucleic acid molecule, such as a cloning vector or expression vector. In the present context, an example of a recombinant host is a cell that produces mouse Zcytor16 from an expression vector. In contrast, mouse Zcytor16 can be produced by a cell that is a "natural source" of mouse Zcytor16, and that lacks an expression vector.

"Integrative transformants" are recombinant host cells, in which heterologous DNA has become integrated into the genomic DNA of the cells.

A "fusion protein" is a hybrid protein expressed by a nucleic acid molecule comprising nucleotide sequences of at least two polynucleotides, genes, or cDNAs. For example, a fusion protein can comprise at least part of a mouse Zcytor16 polypeptide fused with a polypeptide that binds an affinity matrix. Such a fusion protein provides a means to isolate large quantities of mouse Zcytor16 using affinity chromatography.

The term "receptor" denotes a cell-associated protein that binds to a bioactive molecule termed a "ligand." This interaction mediates the effect of the ligand on the cell. Receptors can be membrane bound, cytosolic or nuclear; monomeric (e.g., thyroid stimulating hormone receptor, beta-adrenergic receptor) or multimeric (e.g., PDGP receptor, growth hormone receptor, IL-3 receptor, GM-CSF receptor, G-CSF receptor, erythropoietin receptor and IL-6 receptor). Membrane-bound receptors are characterized by a multi-domain structure comprising an extracellular ligand-binding domain and an intracellular effector domain that is typically involved in signal transduction. In certain membrane-bound receptors, the extracellular ligand-binding domain and the intracellular effector domain are located in separate polypeptides that comprise the complete functional receptor.

In general, the binding of ligand to receptor results in a conformational change in the receptor that causes an interaction between the effector domain and other molecule(s) in the cell, which in turn leads to an alteration in the metabolism of the cell. Metabolic events that are often linked to receptor-ligand interactions include gene transcription, phosphorylation, dephosphorylation, increases in cyclic AMP production, mobilization of cellular calcium, mobilization of membrane lipids, cell adhesion, hydrolysis of inositol lipids and hydrolysis of phospholipids.

A "soluble receptor" is a receptor polypeptide that is not bound to a cell membrane. Soluble receptors are most commonly ligand-binding receptor polypeptides that lack transmembrane and cytoplasmic domains, and other linkage to the cell membrane such as via glycophosphoinositol (gpi). Soluble receptors can comprise additional amino acid residues, such as affinity tags that provide for purification of the polypeptide or provide sites for attachment of the polypeptide to a substrate, or immunoglobulin constant region sequences. Many cell-surface receptors have naturally occurring, soluble counterparts that are produced by proteolysis or translated from alternatively spliced mRNAs. Soluble receptors can be monomeric, homodimeric, heterodimeric, or multimeric, with multimeric receptors generally not comprising more than 9 subunits, preferably not comprising more than 6 subunits, and most preferably not comprising more than 3 subunits. Receptor polypeptides are said to be substantially free of transmembrane and intracellular polypeptide segments when they lack sufficient portions of these segments to provide membrane anchoring or signal transduction, respectively. Soluble receptors of class I and class II cytokine receptors generally comprise the extracellular cytokine binding domain free of a transmembrane domain and intracellular domain. For example, representative soluble receptors include a soluble receptor for CRF2-4 (Genbank Accession No. Z17227) as shown in SEQ ID NO:35; a soluble receptor for IL-10R (Genbank Accession No.s U00672 and NM_001558) as shown in SEQ ID NO:36; and a soluble receptor for zcytor11 (U.S. Pat. No. 5,965,704) as shown in SEQ ID NO:34. It is well within the level of one of skill in the art to delineate what sequences of a known class I or class II cytokine sequence comprise the extracellular cytokine binding domain free of a transmembrane domain and intracellular domain. Moreover, one of skill in the art using the genetic code can readily determine polynucleotides that encode such soluble receptor polypeptides.

The term "secretory signal sequence" denotes a DNA sequence that encodes a peptide (a "secretory peptide") that, as a component of a larger polypeptide, directs the larger polypeptide through a secretory pathway of a cell in which it is synthesized. The larger polypeptide is commonly cleaved to remove the secretory peptide during transit through the secretory pathway.

An "isolated polypeptide" is a polypeptide that is essentially free from contaminating cellular components, such as carbohydrate, lipid, or other proteinaceous impurities associated with the polypeptide in nature. Typically, a preparation of isolated polypeptide contains the polypeptide in a highly purified form, i.e., at least about 80% pure, at least about 90% pure, at least about 95% pure, greater than 95% pure, or greater than 99% pure. One way to show that a particular protein preparation contains an isolated polypeptide is by the appearance of a single band following sodium dodecyl sulfate (SDS)-polyacrylamide gel electrophoresis of the protein preparation and Coomassie Brilliant Blue staining of the gel. However, the term "isolated" does not exclude the presence of the same polypeptide in alternative physical forms, such as dimers or alternatively glycosylated or derivatized forms.

The terms "amino-terminal" and "carboxyl-terminal" are used herein to denote positions within polypeptides. Where the context allows, these terms are used with reference to a particular sequence or portion of a polypeptide to denote proximity or relative position. For example, a certain sequence positioned carboxyl-terminal to a reference sequence within a polypeptide is located proximal to the carboxyl terminus of the reference sequence, but is not necessarily at the carboxyl terminus of the complete polypeptide.

The term "expression" refers to the biosynthesis of a gene product. For example, in the case of a structural gene, expression involves transcription of the structural gene into mRNA and the translation of mRNA into one or more polypeptides.

The term "splice variant" is used herein to denote alternative forms of RNA transcribed from a gene. Splice variation arises naturally through use of alternative splicing sites within a transcribed RNA molecule, or less commonly between separately transcribed RNA molecules, and may result in several mRNAs transcribed from the same gene. Splice variants may encode polypeptides having altered amino acid sequence. The term splice variant is also used herein to denote a polypeptide encoded by a splice variant of an mRNA transcribed from a gene.

As used herein, the term "immunomodulator" includes cytokines, stem cell growth factors, lymphotoxins, co-stimulatory molecules, hematopoietic factors, and synthetic analogs of these molecules.

The term "complement/anti-complement pair" denotes non-identical moieties that form a non-covalently associated, stable pair under appropriate conditions. For instance, biotin and avidin (or streptavidin) are prototypical members of a complement/anti-complement pair. Other exemplary complement/anti-complement pairs include receptor/ligand pairs, antibody/antigen (or hapten or epitope) pairs, sense/antisense polynucleotide pairs, and the like. Where subsequent dissociation of the complement/anti-complement pair is desirable, the complement/anti-complement pair preferably has a binding affinity of less than $10^9 M^{-1}$.

An "anti-idiotype antibody" is an antibody that binds with the variable region domain of an immunoglobulin. In the present context, an anti-idiotype antibody binds with the variable region of an anti-mouse Zcytor16 antibody, and thus, an anti-idiotype antibody mimics an epitope of mouse Zcytor16.

An "antibody fragment" is a portion of an antibody such as $F(ab')_2$, $F(ab)_2$, Fab', Fab, and the like. Regardless of structure, an antibody fragment binds with the same antigen that is recognized by the intact antibody. For example, an anti-mouse Zcytor16 monoclonal antibody fragment binds with an epitope of mouse Zcytor16.

The term "antibody fragment" also includes a synthetic or a genetically engineered polypeptide that binds to a specific antigen, such as polypeptides consisting of the light chain variable region, "Fv" fragments consisting of the variable regions of the heavy and light chains, recombinant single chain polypeptide molecules in which light and heavy variable regions are connected by a peptide linker ("scFv proteins"), and minimal recognition units consisting of the amino acid residues that mimic the hypervariable region.

A "chimeric antibody" is a recombinant protein that contains the variable domains and complementary determining regions derived from a rodent antibody, while the remainder of the antibody molecule is derived from a human antibody.

"Humanized antibodies" are recombinant proteins in which murine complementarity determining regions of a monoclonal antibody have been transferred from heavy and light variable chains of the murine immunoglobulin into a human variable domain.

As used herein, a "therapeutic agent" is a molecule or atom which is conjugated to an antibody moiety to produce a conjugate which is useful for therapy. Examples of therapeutic agents include drugs, toxins, immunomodulators, chelators, boron compounds, photoactive agents or dyes, and radioisotopes.

A "detectable label" is a molecule or atom which can be conjugated to an antibody moiety to produce a molecule useful for diagnosis. Examples of detectable labels include chelators, photoactive agents, radioisotopes, fluorescent agents, paramagnetic ions, or other marker moieties.

The term "affinity tag" is used herein to denote a polypeptide segment that can be attached to a second polypeptide to provide for purification or detection of the second polypeptide or provide sites for attachment of the second polypeptide to a substrate. In principal, any peptide or protein for which an antibody or other specific binding agent is available can be used as an affinity tag. Affinity tags include a poly-histidine tract, protein A (Nilsson et al., *EMBO J.* 4:1075 (1985); Nilsson et al., *Methods Enzymol.* 198:3 (1991)), glutathione S transferase (Smith and Johnson, *Gene* 67:31 (1988)), Glu-Glu affinity tag (Grussenmeyer et al., *Proc. Natl. Acad. Sci. USA* 82:7952 (1985)), substance P, FLAG peptide (Hopp et al., *Biotechnology* 6:1204 (1988)), streptavidin binding peptide, or other antigenic epitope or binding domain. See, in general, Ford et al., *Protein Expression and Purification* 2:95 (1991). DNA molecules encoding affinity tags are available from commercial suppliers (e.g., Pharmacia Biotech, Piscataway, N.J.).

A "naked antibody" is an entire antibody, as opposed to an antibody fragment, which is not conjugated with a therapeutic agent. Naked antibodies include both polyclonal and monoclonal antibodies, as well as certain recombinant antibodies, such as chimeric and humanized antibodies.

As used herein, the term "antibody component" includes both an entire antibody and an antibody fragment.

An "immunoconjugate" is a conjugate of an antibody component with a therapeutic agent or a detectable label.

As used herein, the term "antibody fusion protein" refers to a recombinant molecule that comprises an antibody component and a mouse Zcytor16 polypeptide component. Examples of an antibody fusion protein include a protein that comprises a mouse Zcytor16 extracellular domain, and either an Fc domain or an antigen-biding region.

A "target polypeptide" or a "target peptide" is an amino acid sequence that comprises at least one epitope, and that is expressed on a target cell, such as a tumor cell, or a cell that carries an infectious agent antigen. T cells recognize peptide epitopes presented by a major histocompatibility complex molecule to a target polypeptide or target peptide and typically lyse the target cell or recruit other immune cells to the site of the target cell, thereby killing the target cell.

An "antigenic peptide" is a peptide which will bind a major histocompatibility complex molecule to form an MHC-peptide complex which is recognized by a T cell, thereby inducing a cytotoxic lymphocyte response upon presentation to the T cell. Thus, antigenic peptides are capable of binding to an appropriate major histocompatibility complex molecule and inducing a cytotoxic T cells response, such as cell lysis or specific cytokine release against the target cell which binds or expresses the antigen. The antigenic peptide can be bound in the context of a class I or class II major histocompatibility complex molecule, on an antigen presenting cell or on a target cell.

In eukaryotes, RNA polymerase II catalyzes the transcription of a structural gene to produce mRNA. A nucleic acid molecule can be designed to contain an RNA polymerase II template in which the RNA transcript has a sequence that is complementary to that of a specific mRNA. The RNA transcript is termed an "anti-sense RNA" and a nucleic acid molecule that encodes the anti-sense RNA is termed an "anti-sense gene." Anti-sense RNA molecules are capable of binding to mRNA molecules, resulting in an inhibition of mRNA translation.

An "anti-sense oligonucleotide specific for mouse Zcytor16" or a "mouse Zcytor16 anti-sense oligonucleotide" is an oligonucleotide having a sequence (a) capable of forming a stable triplex with a portion of the mouse Zcytor16 gene, or (b) capable of forming a stable duplex with a portion of an mRNA transcript of the mouse Zcytor16 gene.

A "ribozyme" is a nucleic acid molecule that contains a catalytic center. The term includes RNA enzymes, self-splicing RNAs, self-cleaving RNAs, and nucleic acid molecules that perform these catalytic functions. A nucleic acid molecule that encodes a ribozyme is termed a "ribozyme gene."

An "external guide sequence" is a nucleic acid molecule that directs the endogenous ribozyme, RNase P, to a particular species of intracellular mRNA, resulting in the cleavage of the mRNA by RNase P. A nucleic acid molecule that encodes an external guide sequence is termed an "external guide sequence gene."

The term "variant mouse Zcytor16 gene" refers to nucleic acid molecules that encode a polypeptide having an amino acid sequence that is a modification of SEQ ID NO:38 or SEQ ID NO:48. Such variants include naturally-occurring polymorphisms of mouse Zcytor16 genes, as well as synthetic genes that contain conservative amino acid substitutions of the amino acid sequence of SEQ ID NO:38 or SEQ ID NO:48. Additional variant forms of mouse Zcytor16 genes are nucleic acid molecules that contain insertions or deletions of the nucleotide sequences described herein. A variant mouse Zcytor16 gene can be identified, for example, by determining whether the gene hybridizes with a nucleic acid molecule having the nucleotide sequence of SEQ ID NO:37 or SEQ ID NO:47, or its complement, under stringent conditions.

Alternatively, variant mouse Zcytor16 genes can be identified by sequence comparison. Two amino acid sequences have "100% amino acid sequence identity" if the amino acid residues of the two amino acid sequences are the same when aligned for maximal correspondence. Similarly, two nucleotide sequences have "100% nucleotide sequence identity" if the nucleotide residues of the two nucleotide sequences are the same when aligned for maximal correspondence. Sequence comparisons can be performed using standard software programs such as those included in the LASER-GENE bioinformatics computing suite, which is produced by DNASTAR (Madison, Wis.). Other methods for comparing two nucleotide or amino acid sequences by determining optimal alignment are well-known to those of skill in the art (see, for example, Peruski and Peruski, *The Internet and the New Biology: Tools for Genomic and Molecular Research* (ASM Press, Inc. 1997), Wu et al. (eds.), "Information Superhighway and Computer Databases of Nucleic Acids and Proteins," in *Methods in Gene Biotechnology*, pages 123–151 (CRC Press, Inc. 1997), and Bishop (ed.), *Guide to Human Genome Computing*, 2nd Edition (Academic Press, Inc. 1998)). Particular methods for determining sequence identity are described below.

Regardless of the particular method used to identify a variant mouse Zcytor16 gene or variant mouse Zcytor16 polypeptide, a variant gene or polypeptide encoded by a variant gene may be functionally characterized the ability to bind specifically to an anti-mouse Zcytor16 antibody. A variant mouse Zcytor16 gene or variant mouse Zcytor16 polypeptide may also be functionally characterized the ability to bind to its ligand, IL-TIF, using a biological or biochemical assay described herein.

The term "allelic variant" is used herein to denote any of two or more alternative forms of a gene occupying the same chromosomal locus. Allelic variation arises naturally through mutation, and may result in phenotypic polymorphism within populations. Gene mutations can be silent (no change in the encoded polypeptide) or may encode polypeptides having altered amino acid sequence. The term allelic variant is also used herein to denote a protein encoded by an allelic variant of a gene.

The term "ortholog" denotes a polypeptide or protein obtained from one species that is the functional counterpart of a polypeptide or protein from a different species. Sequence differences among orthologs are the result of speciation.

"Paralogs" are distinct but structurally related proteins made by an organism. Paralogs are believed to arise through gene duplication. For example, α-globin, β-globin, and myoglobin are paralogs of each other.

The present invention includes functional fragments of mouse Zcytor16 genes. Within the context of this invention, a "functional fragment" of a mouse Zcytor16 gene refers to a nucleic acid molecule that encodes a portion of a mouse Zcytor16 polypeptide which is a domain described herein or at least specifically binds with an anti-mouse Zcytor16 antibody.

Due to the imprecision of standard analytical methods, molecular weights and lengths of polymers are understood to be approximate values. When such a value is expressed as "about" X or "approximately" X, the stated value of X will be understood to be accurate to ±10%.

3. Production of Mouse Zcytor16 Polynucleotides or Genes

Nucleic acid molecules encoding a mouse Zcytor16 gene can be obtained by screening a mouse cDNA or genomic library using polynucleotide probes based upon SEQ ID NO:37 or SEQ ID NO:47. These techniques are standard and well-established.

As an illustration, a nucleic acid molecule that encodes a mouse Zcytor16 gene can be isolated from a cDNA library. In this case, the first step would be to prepare the cDNA library by isolating RNA from a tissue, such as a tissue wherein mouse Zcytor16 is specifically expressed, using methods well-known to those of skill in the art. In general, RNA isolation techniques must provide a method for breaking cells, a means of inhibiting RNase-directed degradation of RNA, and a method of separating RNA from DNA, protein, and polysaccharide contaminants. For example, total RNA can be isolated by freezing tissue in liquid nitrogen, grinding the frozen tissue with a mortar and pestle to lyse the cells, extracting the ground tissue with a solution of phenol/chloroform to remove proteins, and separating RNA from the remaining impurities by selective precipitation with lithium chloride (see, for example, Ausubel et al. (eds.), *Short Protocols in Molecular Biology*, 3$^{rd}$ Edition, pages 4-1 to 4-6 (John Wiley & Sons 1995) ["Ausubel (1995)"]; Wu et al., *Methods in Gene Biotechnology*, pages 33–41 (CRC Press, Inc. 1997) ["Wu (1997)"]).

Alternatively, total RNA can be isolated by extracting ground tissue with guanidinium isothiocyanate, extracting with organic solvents, and separating RNA from contaminants using differential centrifugation (see, for example, Chirgwin et al., *Biochemistry* 18:52 (1979); Ausubel (1995) at pages 4-1 to 4-6; Wu (1997) at pages 33–41).

In order to construct a cDNA library, poly(A)$^+$ RNA must be isolated from a total RNA preparation. Poly(A)$^+$ RNA can be isolated from total RNA using the standard technique of oligo(dT)-cellulose chromatography (see, for example, Aviv and Leder, *Proc. Nat'l Acad. Sci. USA* 69:1408 (1972); Ausubel (1995) at pages 4-11 to 4-12).

Double-stranded cDNA molecules are synthesized from poly(A)$^+$ RNA using techniques well-known to those in the art. (see, for example, Wu (1997) at pages 41–46). Moreover, commercially available kits can be used to synthesize double-stranded cDNA molecules. For example, such kits are available from Life Technologies, Inc. (Gaithersburg, Md.), CLONTECH Laboratories, Inc. (Palo Alto, Calif.), Promega Corporation (Madison, Wis.) and STRATAGENE (La Jolla, Calif.).

Various cloning vectors are appropriate for the construction of a cDNA library. For example, a cDNA library can be prepared in a vector derived from bacteriophage, such as a λgt10 vector. See, for example, Huynh et al., "Constructing and Screening cDNA Libraries in λgt10 and λgt11," in *DNA Cloning: A Practical Approach Vol. I*, Glover (ed.), page 49 (IRL Press, 1985); Wu (1997) at pages 47–52.

Alternatively, double-stranded cDNA molecules can be inserted into a plasmid vector, such as a pBLUESCRIPT vector (STRATAGENE; La Jolla, Calif.), a LAMDAGEM-4 (Promega Corp.) or other commercially available vectors. Suitable cloning vectors also can be obtained from the American Type Culture Collection (Manassas, Va.).

To amplify the cloned cDNA molecules, the cDNA library is inserted into a prokaryotic host, using standard techniques. For example, a cDNA library can be introduced into competent *E. coli* DH5 or DH10B cells, which can be obtained, for example, from Life Technologies, Inc. or GIBCO BRL (Gaithersburg, Md.).

A human genomic library can be prepared by means well known in the art (see, for example, Ausubel (1995) at pages 5-1 to 5-6; Wu (1997) at pages 307–327). Genomic DNA can be isolated by lysing tissue with the detergent Sarkosyl, digesting the lysate with proteinase K, clearing insoluble debris from the lysate by centrifugation, precipitating nucleic acid from the lysate using isopropanol, and purifying resuspended DNA on a cesium chloride density gradient.

DNA fragments that are suitable for the production of a genomic library can be obtained by the random shearing of genomic DNA or by the partial digestion of genomic DNA with restriction endonucleases. Genomic DNA fragments can be inserted into a vector, such as a bacteriophage or cosmid vector, in accordance with conventional techniques, such as the use of restriction enzyme digestion to provide appropriate termini, the use of alkaline phosphatase treatment to avoid undesirable joining of DNA molecules, and ligation with appropriate ligases. Techniques for such manipulation are well known in the art (see, for example, Ausubel (1995) at pages 5-1 to 5-6; Wu (1997) at pages 307–327).

Alternatively, human genomic libraries can be obtained from commercial sources such as Research Genetics (Huntsville, Ala.) and the American Type Culture Collection (Manassas, Va).

A library containing cDNA or genomic clones can be screened with one or more polynucleotide probes based upon SEQ ID NO:37 or SEQ ID NO:47, using standard methods (see, for example, Ausubel (1995) at pages 6-1 to 6-11).

Nucleic acid molecules that encode a mouse Zcytor16 gene can also be obtained using the polymerase chain reaction (PCR) with oligonucleotide primers having nucleotide sequences that are based upon the nucleotide sequences of the mouse to Zcytor16 gene, as described herein. General methods for screening libraries with PCR are provided by, for example, Yu et al., "Use of the Polymerase Chain Reaction to Screen Phage Libraries," in *Methods in Molecular Biology, Vol. 15: PCR Protocols: Current Methods and Applications*, White (ed.), pages 211–215 (Humana Press, Inc. 1993). Moreover, techniques for using PCR to isolate related genes are described by, for example, Preston, "Use of Degenerate Oligonucleotide Primers and the Polymerase Chain Reaction to Clone Gene Family Members," in *Methods in Molecular Biology, Vol. 15: PCR Protocols: Current Methods and Applications*, White (ed.), pages 317–337 (Humana Press, Inc. 1993).

Anti-mouse Zcytor16 antibodies, produced as described below, can also be used to isolate DNA sequences that encode mouse Zcytor16 genes from cDNA libraries. For example, the antibodies can be used to screen λgt11 expression libraries, or the antibodies can be used for immunoscreening following hybrid selection and translation (see, for example, Ausubel (1995) at pages 6-12 to 6-16; Margolis et al., "Screening λ expression libraries with antibody and protein probes," in *DNA Cloning 2: Expression Systems, 2nd Edition*, Glover et al. (eds.), pages 1–14 (Oxford University Press 1995)).

As an alternative, a mouse Zcytor16 gene can be obtained by synthesizing nucleic acid molecules using mutually priming long oligonucleotides and the nucleotide sequences described herein (see, for example, Ausubel (1995) at pages 8-8 to 8-9). Established techniques using the polymerase chain reaction provide the ability to synthesize DNA molecules at least two kilobases in length (Adang et al., *Plant Molec. Biol.* 21:1131 (1993), Bambot et al., *PCR Methods and Applications* 2:266 (1993), Dillon et al., "Use of the Polymerase Chain Reaction for the Rapid Construction of Synthetic Genes," in *Methods in Molecular Biology, Vol. 15: PCR Protocols: Current Methods and Applications*, White (ed.), pages 263–268, (Humana Press, Inc. 1993), and Holowachuk et al., *PCR Methods Appl.* 4:299 (1995)).

The nucleic acid molecules of the present invention can also be synthesized with "gene machines" using protocols such as the phosphoramidite method. If chemically-synthesized double stranded DNA is required for an application such as the synthesis of a gene or a gene fragment, then each complementary strand is made separately. The production of short genes (60 to 80 base pairs) is technically straightforward and can be accomplished by synthesizing the complementary strands and then annealing them. For the production of longer genes (>300 base pairs), however, special strategies may be required, because the coupling efficiency of each cycle during chemical DNA synthesis is seldom 100%. To overcome this problem, synthetic genes (double-stranded) are assembled in modular form from single-stranded fragments that are from 20 to 100 nucleotides in length. For reviews on polynucleotide synthesis, see, for example, Glick and Pasternak, *Molecular Biotechnology, Principles and Applications of Recombinant DNA* (ASM Press 1994), Itakura et al., *Annu. Rev. Biochem.* 53:323 (1984), and Climie et al., *Proc. Nat'l Acad. Sci. USA* 87:633 (1990).

The sequence of a mouse Zcytor16 cDNA or mouse Zcytor16 genomic fragment can be determined using standard methods. Mouse Zcytor16 polynucleotide sequences disclosed herein can also be used as probes or primers to clone 5' non-coding regions of a mouse Zcytor16 gene. Because mouse Zcytor16 is expressed in a limited number of specific tissues, promoter elements from a mouse Zcytor16 gene can be used to direct the expression of heterologous genes in, for example, specific tissues of transgenic animals or patients treated with gene therapy. The identification of genomic fragments containing a mouse Zcytor16 promoter or regulatory element can be achieved using well-established techniques, such as deletion analysis (see, generally, Ausubel (1995)).

Cloning of 5' flanking sequences also facilitates production of mouse Zcytor16 proteins by "gene activation," as disclosed in U.S. Pat. No. 5,641,670. Briefly, expression of an endogenous mouse Zcytor16 gene in a cell is altered by introducing into the mouse Zcytor16 locus a DNA construct comprising at least a targeting sequence, a regulatory sequence, an exon, and an unpaired splice donor site. The targeting sequence is a mouse Zcytor16 5' non-coding sequence that permits homologous recombination of the construct with the endogenous mouse Zcytor16 locus, whereby the sequences within the construct become operably linked with the endogenous mouse Zcytor16 coding sequence. In this way, an endogenous mouse Zcytor16 promoter can be replaced or supplemented with other regulatory sequences to provide enhanced, tissue-specific, or otherwise regulated expression.

4. Production of Mouse Zcytor16 Gene Variants

The present invention provides a variety of nucleic acid molecules, including DNA and RNA molecules, that encode the mouse Zcytor16 polypeptides disclosed herein. Those skilled in the art will readily recognize that, in view of the degeneracy of the genetic code, considerable sequence variation is possible among these polynucleotide molecules. SEQ ID NO:3 is a degenerate nucleotide sequence that encompasses all nucleic acid molecules that encode the human Zcytor16 polypeptide of SEQ ID NO:2. Similarly, SEQ ID NO:39 is a degenerate nucleotide sequence that encompasses all nucleic acid molecules that encode the mouse Zcytor16 polypeptide of SEQ ID NO:38; and SEQ ID NO:49 is a degenerate nucleotide sequence that encompasses all nucleic acid molecules that encode the mouse Zcytor16 polypeptide of SEQ ID NO:48. Those skilled in the art will recognize that the degenerate sequence of SEQ ID NO:39 and SEQ ID NO:49 also provides all RNA sequences encoding SEQ ID NO:38 and SEQ ID NO:48 respectively, by substituting U for T. Moreover, the present invention also provides isolated soluble monomeric, homodimeric, heterodimeric and multimeric receptor polypeptides that comprise at least one mouse Zcytor16 receptor subunit that is substantially homologous to the receptor polypeptide of SEQ ID NO:38 or SEQ ID NO:48. Thus, the present invention contemplates mouse Zcytor16 polypeptide-encoding nucleic acid molecules comprising nucleotide 1 to nucleotide 693 of SEQ ID NO:39, and nucleic acid molecules comprising nucleotide 1 to nucleotide 693 of SEQ ID NO:49, and their RNA equivalents. Moreover, mouse zcytor16 fragments described herein in SEQ ID NO:37, SEQ ID NO:38, SEQ ID NO:47 and SEQ ID NO:48 with reference to SEQ ID NO:39 and SEQ ID NO:49, are also contemplated.

Table 1 sets forth the one-letter codes used within SEQ ID NO:39 or SEQ ID NO:49 to denote degenerate nucleotide positions. "Resolutions" are the nucleotides denoted by a code letter. "Complement" indicates the code for the complementary nucleotide(s). For example, the code Y denotes either C or T, and its complement R denotes A or G, A being complementary to T, and G being complementary to C.

TABLE 1

| Nucleotide | Resolution | Complement | Resolution |
|---|---|---|---|
| A | A | T | T |
| C | C | G | G |
| G | G | C | C |
| T | T | A | A |
| R | A\|G | Y | C\|T |
| Y | C\|T | R | A\|G |
| M | A\|C | K | G\|T |
| K | G\|T | M | A\|C |
| S | C\|G | S | C\|G |
| W | A\|T | W | A\|T |
| H | A\|C\|T | D | A\|G\|T |
| B | C\|G\|T | V | A\|C\|G |
| V | A\|C\|G | B | C\|G\|T |
| D | A\|G\|T | H | A\|C\|T |
| N | A\|C\|G\|T | N | A\|C\|G\|T |

The degenerate codons used in SEQ ID NO:39 or SEQ ID NO:49, encompassing all possible codons for a given amino acid, are set forth in Table 2.

TABLE 2

| Amino Acid | One Letter Code | Codons | Degenerate Codon |
|---|---|---|---|
| Cys | C | TGC TGT | TGY |
| Ser | S | AGC AGT TCA TCC TCG TCT | WSN |
| Thr | T | ACA ACC ACG ACT | ACN |
| Pro | P | CCA CCC CCG CCT | CCN |
| Ala | A | GCA GCC GCG GCT | GCN |
| Gly | G | GGA GGC GGG GGT | GGN |
| Asn | N | AAC AAT | AAY |
| Asp | D | GAC GAT | GAY |
| Glu | E | GAA GAG | GAR |
| Gln | Q | CAA CAG | CAR |
| His | H | CAC CAT | CAY |
| Arg | R | AGA AGG CGA CGC CGG CGT | MGN |
| Lys | K | AAA AAG | AAR |
| Met | M | ATG | ATG |
| Ile | I | ATA ATC ATT | ATH |
| Leu | L | CTA CTC CTG CTT TTA TTG | YTN |
| Val | V | GTA GTC GTG GTT | GTN |
| Phe | F | TTC TTT | TTY |
| Tyr | Y | TAC TAT | TAY |
| Trp | W | TGG | TGG |
| Ter | . | TAA TAG TGA | TRR |
| Asn\|Asp | B | | RAY |
| Glu\|Gln | Z | | SAR |
| Any | X | | NNN |

One of ordinary skill in the art will appreciate that some ambiguity is introduced in determining a degenerate codon, representative of all possible codons encoding an amino acid. For example, the degenerate codon for serine (WSN) can, in some circumstances, encode arginine (AGR), and the degenerate codon for arginine (MGN) can, in some circumstances, encode serine (AGY). A similar relationship exists between codons encoding phenylalanine and leucine. Thus, some polynucleotides encompassed by the degenerate sequence may encode variant amino acid sequences, but one of ordinary skill in the art can easily identify such variant sequences by reference to the amino acid sequences of SEQ ID NO:38 or SEQ ID NO:48. Variant sequences can be readily tested for functionality as described herein.

Different species can exhibit "preferential codon usage." In general, see, Grantham et al., *Nucl. Acids Res.* 8:1893 (1980), Haas et al. *Curr. Biol.* 6:315 (1996), Wain-Hobson et al, *Gene* 13:355 (1981), Grosjean and Fiers, *Gene* 18:199 (1982), Holm, *Nuc. Acids Res.* 14:3075 (1986), Ikemura, *J. Mol. Biol.* 158:573 (1982), Sharp and Matassi, *Curr. Opin. Mol. Biol.* 4:851 (1994), Kane, *Curr. Opin. Biotechnol.*

6:494 (1995), and Makrides, *Microbiol. Rev.* 60:512 (1996). As used herein, the term "preferential codon usage" or "preferential codons" is a term of art referring to protein translation codons that are most frequently used in cells of a certain species, thus favoring one or a few representatives of the possible codons encoding each amino acid (See Table 2). For example, the amino acid threonine (Thr) may be encoded by ACA, ACC, ACG, or ACT, but in mammalian cells ACC is the most commonly used codon; in other species, for example, insect cells, yeast, viruses or bacteria, different Thr codons may be preferential. Preferential codons for a particular species can be introduced into the polynucleotides of the present invention by a variety of methods known in the art. Introduction of preferential codon sequences into recombinant DNA can, for example, enhance production of the protein by making protein translation more efficient within a particular cell type or species. Therefore, the degenerate codon sequences disclosed herein serve as a template for optimizing expression of polynucleotides in various cell types and species commonly used in the art and disclosed herein. Sequences containing preferential codons can be tested and optimized for expression in various species, and tested for functionality as disclosed herein.

The present invention further provides variant polypeptides and nucleic acid molecules that represent counterparts from other species (orthologs). These species include, but are not limited to mammalian, avian, amphibian, reptile, fish, insect and other vertebrate and invertebrate species. Of particular interest are Zcytor16 polypeptides from other mammalian species, including human, rat, porcine, ovine, bovine, canine, feline, equine, and other primate polypeptides. Orthologs of mouse Zcytor16 can be cloned using information and compositions provided by the present invention in combination with conventional cloning techniques. For example, a mouse Zcytor16 cDNA can be cloned using mRNA obtained from a tissue or cell type that expresses mouse Zcytor16 as disclosed herein. Suitable sources of mRNA can be identified by probing northern blots with probes designed from the sequences disclosed herein. A library is then prepared from mRNA of a positive tissue or cell line.

A Zcytor16-encoding cDNA can be isolated by a variety of methods, such as by probing with a complete or partial cDNA or with one or more sets of degenerate probes based on the disclosed sequences. A CDNA can also be cloned using the polymerase chain reaction with primers designed from the representative mouse Zcytor16 sequences disclosed herein. In addition, a cDNA library can be used to transform or transfect host cells, and expression of the eDNA of interest can be detected with an antibody to mouse Zcytor16 polypeptide.

Those skilled in the art will recognize that the sequence disclosed in SEQ ID NO:37 or SEQ ID NO:47 represents a single allele of mouse Zcytor16, and that allelic variation and alternative splicing are expected to occur. Allelic variants of this sequence can be cloned by probing cDNA or genomic libraries from different individuals according to standard procedures. Allelic variants of the nucleotide sequences disclosed herein, including those containing silent mutations and those in which mutations result in amino acid sequence changes, are within the scope of the present invention, as are proteins which are allelic variants of the amino acid sequences disclosed herein. cDNA molecules generated from alternatively spliced mRNAs, which retain the properties of the mouse Zcytor16 polypeptide are included within the scope of the present invention, as are polypeptides encoded by such cDNAs and mRNAs. Allelic variants and splice variants of these sequences can be cloned by probing cDNA or genomic libraries from different individuals or tissues according to standard procedures known in the art.

Using the methods discussed above, one of ordinary skill in the art can prepare a variety of polypeptides that comprise a soluble receptor subunit that is substantially homologous to SEQ ID NO:37 or SEQ ID NO:47, or SEQ ID NO:38 or SEQ ID NO:48, amino acids 24 to 230, or 27 to 230 of SEQ ID NO:38 or SEQ ID NO:48, or allelic variants thereof and retain the ligand-binding properties of the wild-type mouse Zcytor16 receptor. Such polypeptides may also include additional polypeptide segments as generally disclosed herein.

Within certain embodiments of the invention, the isolated nucleic acid molecules can hybridize under stringent conditions to nucleic acid molecules comprising nucleotide sequences disclosed herein. For example, such nucleic acid molecules can hybridize under stringent conditions to nucleic acid molecules comprising the nucleotide sequence of SEQ ID NO:37 or SEQ ID NO:47, to nucleic acid molecules consisting of the nucleotide sequence of nucleotides 8 to 694 or 697; or 77, 86, or 100 to 694 or 697 of SEQ ID NO:37 or SEQ ID NO:47, or to nucleic acid molecules comprising a nucleotide sequence complementary to SEQ ID NO:37 or SEQ ID NO:47 or to nucleotides 8 to 694 or 697; or 77, 86, or 100 to 694 or 697 of SEQ ID NO:37 or SEQ ID NO:47, or fragments thereof. In general, stringent conditions are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe.

A pair of nucleic acid molecules, such as DNA-DNA, RNA-RNA and DNA-RNA, can hybridize if the nucleotide sequences have some degree of complementarity. Hybrids can tolerate mismatched base pairs in the double helix, but the stability of the hybrid is influenced by the degree of mismatch. The $T_m$ of the mismatched hybrid decreases by 1° C. for every 1–1.5% base pair mismatch. Varying the stringency of the hybridization conditions allows control over the degree of mismatch that will be present in the hybrid. The degree of stringency increases as the hybridization temperature increases and the ionic strength of the hybridization buffer decreases. Stringent hybridization conditions encompass temperatures of about 5–25° C. below the $T_m$ of the hybrid and a hybridization buffer having up to 1 M Na$^+$. Higher degrees of stringency at lower temperatures can be achieved with the addition of formamide which reduces the $T_m$ of the hybrid about 1° C. for each 1% formamide in the buffer solution. Generally, such stringent conditions include temperatures of 20–70° C. and a hybridization buffer containing up to 6×SSC and 0–50% formamide. A higher degree of stringency can be achieved at temperatures of from 40–70° C. with a hybridization buffer having up to 4×SSC and from 0–50% formamide. Highly stringent conditions typically encompass temperatures of 42–70° C. with a hybridization buffer having up to 1×SSC and 0–50% formamide. Different degrees of stringency can be used during hybridization and washing to achieve maximum specific binding to the target sequence. Typically, the washes following hybridization are performed at increasing degrees of stringency to remove non-hybridized polynucleotide probes from hybridized complexes.

The above conditions are meant to serve as a guide and it is well within the abilities of one skilled in the art to adapt these conditions for use with a particular polynucleotide hybrid. The $T_m$ for a specific target sequence is the temperature (under defined conditions) at which 50% of the target sequence will hybridize to a perfectly matched probe sequence. Those conditions which influence the $T_m$ include, the size and base pair content of the polynucleotide probe, the ionic strength of the hybridization solution, and the presence of destabilizing agents in the hybridization solution. Numerous equations for calculating $T_m$ are known in the art, and are specific for DNA, RNA and DNA-RNA hybrids and polynucleotide probe sequences of varying length (see, for example, Sambrook et al., *Molecular Cloning: A Laboratory Manual*, Second Edition (Cold Spring Harbor Press 1989); Ausubel et al., (eds.), *Current Protocols in Molecular Biology* (John Wiley and Sons, Inc. 1987); Berger and Kimmel (eds.), *Guide to Molecular Cloning Techniques*, (Academic Press, Inc. 1987); and Wetmur, *Crit. Rev. Biochem. Mol. Biol.* 26:227 (1990)). Sequence analysis software such as OLIGO 6.0 (LSR; Long Lake, Minn.) and *Primer Premier* 4.0 (Premier Biosoft International; Palo Alto, Calif.), as well as sites on the Internet, are available tools for analyzing a given sequence and calculating $T_m$ based on user defined criteria. Such programs can also analyze a given sequence under defined conditions and identify suitable probe sequences. Typically, hybridization of longer polynucleotide sequences, >50 base pairs, is performed at temperatures of about 20–25° C. below the calculated $T_m$. For smaller probes, <50 base pairs, hybridization is typically carried out at the $T_{m\ 1\ or}$ 5–10° C. below. This allows for the maximum rate of hybridization for DNA-DNA and DNA-RNA hybrids.

The length of the polynucleotide sequence influences the rate and stability of hybrid formation. Smaller probe sequences, <50 base pairs, reach equilibrium with complementary sequences rapidly, but may form less stable hybrids. Incubation times of anywhere from minutes to hours can be used to achieve hybrid formation. Longer probe sequences come to equilibrium more slowly, but form more stable complexes even at lower temperatures. Incubations are allowed to proceed overnight or longer. Generally, incubations are carried out for a period equal to three times the calculated Cot time. Cot time, the time it takes for the polynucleotide sequences to reassociate, can be calculated for a particular sequence by methods known in the art.

The base pair composition of polynucleotide sequence will effect the thermal stability of the hybrid complex, thereby influencing the choice of hybridization temperature and the ionic strength of the hybridization buffer. A-T pairs are less stable than G-C pairs in aqueous solutions containing sodium chloride. Therefore, the higher the G-C content, the more stable the hybrid. Even distribution of G and C residues within the sequence also contribute positively to hybrid stability. In addition, the base pair composition can be manipulated to alter the $T_m$ of a given sequence. For example, 5-methyldeoxycytidine can be substituted for deoxycytidine and 5-bromodeoxyuridine can be substituted for thymidine to increase the $T_m$, whereas 7-deazz-2'-deoxyguanosine can be substituted for guanosine to reduce dependence on $T_m$.

The ionic concentration of the hybridization buffer also affects the stability of the hybrid. Hybridization buffers generally contain blocking agents such as Denhardt's solution (Sigma Chemical Co., St. Louis, Mo.), denatured salmon sperm DNA, tRNA, milk powders (BLOTTO), heparin or SDS, and a $Na^+$ source, such as SSC (1×SSC: 0.15 M sodium chloride, 15 mM sodium citrate) or SSPE (1×SSPE: 1.8 M NaCl, 10 mM $NaH_2PO_4$, 1 mM EDTA, pH 7.7). Typically, hybridization buffers contain from between 10 mM–1 M $Na^+$. The addition of destabilizing or denaturing agents such as formamide, tetralkylammonium salts, guanidinium cations or thiocyanate cations to the hybridization solution will alter the $T_m$ of a hybrid. Typically, formamide is used at a concentration of up to 50% to allow incubations to be carried out at more convenient and lower temperatures. Formamide also acts to reduce non-specific background when using RNA probes.

As an illustration, a nucleic acid molecule encoding a variant mouse Zcytor16 polypeptide can be hybridized with a nucleic acid molecule having the nucleotide sequence of SEQ ID NO:37 or SEQ ID NO:47 (or its complement) at 42° C. overnight in a solution comprising 50% formamide, 5×SSC, 50 mM sodium phosphate (pH 7.6), 5×Denhardt's solution (100×Denhardt's solution: 2% (w/v) Ficoll 400, 2% (w/v) polyvinylpyrrolidone, and 2% (w/v) bovine serum albumin), 10% dextran sulfate, and 20 μg/ml denatured, sheared salmon sperm DNA. One of skill in the art can devise variations of these hybridization conditions. For example, the hybridization mixture can be incubated at a higher temperature, such as about 65° C., in a solution that does not contain formamide. Moreover, premixed hybridization solutions are available (e.g., EXPRESSHYB Hybridization Solution from CLONTECH Laboratories, Inc.), and hybridization can be performed according to the manufacturer's instructions.

Following hybridization, the nucleic acid molecules can be washed to remove non-hybridized nucleic acid molecules under stringent conditions, or under highly stringent conditions. Typical stringent washing conditions include washing in a solution of 0.5×–2×SSC with 0.1% sodium dodecyl sulfate (SDS) at 55–65° C. As an illustration, nucleic acid molecules encoding a variant mouse Zcytor16 polypeptide remain hybridized with a nucleic acid molecule having the nucleotide sequence of SEQ ID NO:37 or SEQ ID NO:47 (or its complement) under stringent washing conditions, in which the wash stringency is equivalent to 0.5×–2×SSC with 0.1% SDS at 55–65° C., including 0.5×SSC with 0.1% SDS at 55° C., or 2×SSC with 0.1% SDS at 65° C. One of skill in the art can readily devise equivalent conditions, for example, by substituting SSPE for SSC in the wash solution.

Typical highly stringent washing conditions include washing in a solution of 0.1×–0.2×SSC with 0.1% sodium dodecyl sulfate (SDS) at 50–65° C. For example, nucleic acid molecules encoding a variant mouse Zcytor16 polypeptide remain hybridized with a nucleic acid molecule having the nucleotide sequence of SEQ ID NO:37 or SEQ ID NO:47 (or its complement) under highly stringent washing conditions, in which the wash stringency is equivalent to 0.1×–0.2×SSC with 0.1% SDS at 50–65° C., including 0.1×SSC with 0.1% SDS at 50° C., or 0.2×SSC with 0.1% SDS at 65° C.

The present invention also provides isolated mouse Zcytor16 polypeptides that have a substantially similar sequence identity to the polypeptides of SEQ ID NO:38 or SEQ ID NO:48, or their orthologs. The term "substantially similar sequence identity" is used herein to denote polypeptides having at least 70%, at least 80%, at least 90%, at least 95% or greater than 95% sequence identity to the sequences shown in SEQ ID NO:38 or SEQ ID NO:48, or their orthologs.

The present invention also contemplates mouse Zcytor16 variant nucleic acid molecules that can be identified using two criteria: a determination of the similarity between the encoded polypeptide with the amino acid sequence of SEQ ID NO:38 or SEQ ID NO:48, and a hybridization assay, as described above. Such mouse Zcytor16 variants include nucleic acid molecules (1) that remain hybridized with a nucleic acid molecule having the nucleotide sequence of SEQ ID NO:37 or SEQ ID NO:47 (or its complement) under stringent washing conditions, in which the wash stringency is equivalent to 0.5×–2×SSC with 0.1% SDS at 55–65° C., and (2) that encode a polypeptide having at least 70%, at least 80%, at least 90%, at least 95% or greater than 95% sequence identity to the amino acid sequence of SEQ ID NO:38 or SEQ ID NO:48. Alternatively, mouse Zcytor16 variants can be characterized as nucleic acid molecules (1) that remain hybridized with a nucleic acid molecule having the nucleotide sequence of SEQ ID NO:37 or SEQ ID NO:47 (or its complement) under highly stringent washing conditions, in which the wash stringency is equivalent to 0.1×–0.2×SSC with 0.1% SDS at 50–65° C., and (2) that encode a polypeptide having at least 70%, at least 80%, at least 90%, at least 95% or greater than 95% sequence identity to the amino acid sequence of SEQ ID NO:38 or SEQ ID NO:48.

Percent sequence identity is determined by conventional methods. See, for example, Altschul et al., *Bull. Math. Bio.* 48:603 (1986), and Henikoff and Henikoff, *Proc. Natl. Acad. Sci. USA* 89:10915 (1992). Briefly, two amino acid sequences are aligned to optimize the alignment scores using a gap opening penalty of 10, a gap extension penalty of 1, and the "BLOSUM62" scoring matrix of Henikoff and Henikoff (ibid.) as shown in Table 3 (amino acids are indicated by the standard one-letter codes). The percent identity is then calculated as: ([Total number of identical matches]/[length of the longer sequence plus the number of gaps introduced into the longer sequence in order to align the two sequences])(100).

sequence that have either the highest density of identities (if the ktup variable is 1) or pairs of identities (if ktup=2), without considering conservative amino acid substitutions, insertions, or deletions. The ten regions with the highest density of identities are then rescored by comparing the similarity of all paired amino acids using an amino acid substitution matrix, and the ends of the regions are "trimmed" to include only those residues that contribute to the highest score. If there are several regions with scores greater than the "cutoff" value (calculated by a predetermined formula based upon the length of the sequence and the ktup value), then the trimmed initial regions are examined to determine whether the regions can be joined to form an approximate alignment with gaps. Finally, the highest scoring regions of the two amino acid sequences are aligned using a modification of the Needleman-Wunsch-Sellers algorithm (Needleman and Wunsch, *J. Mol. Biol.* 48:444 (1970); Sellers, *SIAM J. Appl. Math.* 26:787 (1974)), which allows for amino acid insertions and deletions. Illustrative parameters for FASTA analysis are: ktup=1, gap opening penalty=10, gap extension penalty=1, and substitution matrix=BLOSUM62. These parameters can be introduced into a FASTA program by modifying the scoring matrix file ("SMATRIX"), as explained in Appendix 2 of Pearson, *Meth. Enzymol.* 183:63 (1990).

FASTA can also be used to determine the sequence identity of nucleic acid molecules using a ratio as disclosed above. For nucleotide sequence comparisons, the ktup value can range between one to six, preferably from three to six, most preferably three, with other parameters set as described above.

The present invention includes nucleic acid molecules that encode a polypeptide having a conservative amino acid

TABLE 3

|   | A | R | N | D | C | Q | E | G | H | I | L | K | M | F | P | S | T | W | Y | V |
|---|---|---|---|---|---|---|---|---|---|---|---|---|---|---|---|---|---|---|---|---|
| A | 4 | | | | | | | | | | | | | | | | | | | |
| R | -1 | 5 | | | | | | | | | | | | | | | | | | |
| N | -2 | 0 | 6 | | | | | | | | | | | | | | | | | |
| D | -2 | -2 | 1 | 6 | | | | | | | | | | | | | | | | |
| C | 0 | -3 | -3 | -3 | 9 | | | | | | | | | | | | | | | |
| Q | -1 | 1 | 0 | 0 | -3 | 5 | | | | | | | | | | | | | | |
| E | -1 | 0 | 0 | 2 | -4 | 2 | 5 | | | | | | | | | | | | | |
| G | 0 | -2 | 0 | -1 | -3 | -2 | -2 | 6 | | | | | | | | | | | | |
| H | -2 | 0 | 1 | -1 | -3 | 0 | 0 | -2 | 8 | | | | | | | | | | | |
| I | -1 | -3 | -3 | -3 | -1 | -3 | -3 | -4 | -3 | 4 | | | | | | | | | | |
| L | -1 | -2 | -3 | -4 | -1 | -2 | -3 | -4 | -3 | 2 | 4 | | | | | | | | | |
| K | -1 | 2 | 0 | -1 | -3 | 1 | 1 | -2 | -1 | -3 | -2 | 5 | | | | | | | | |
| M | -1 | -1 | -2 | -3 | -1 | 0 | -2 | -3 | -2 | 1 | 2 | -1 | 5 | | | | | | | |
| F | -2 | -3 | -3 | -3 | -2 | -3 | -3 | -3 | -1 | 0 | 0 | -3 | 0 | 6 | | | | | | |
| P | -1 | -2 | -2 | -1 | -3 | -1 | -1 | -2 | -2 | -3 | -3 | -1 | -2 | -4 | 7 | | | | | |
| S | 1 | -1 | 1 | 0 | -1 | 0 | 0 | 0 | -1 | -2 | -2 | 0 | -1 | -2 | -1 | 4 | | | | |
| T | 0 | -1 | 0 | -1 | -1 | -1 | -1 | -2 | -2 | -1 | -1 | -1 | -1 | -2 | -1 | 1 | 5 | | | |
| W | -3 | -3 | -4 | -4 | -2 | -2 | -3 | -2 | -2 | -3 | -2 | -3 | -1 | 1 | -4 | -3 | -2 | 11 | | |
| Y | -2 | -2 | -2 | -3 | -2 | -1 | -2 | -3 | 2 | -1 | -1 | -2 | -1 | 3 | -3 | -2 | -2 | 2 | 7 | |
| V | 0 | -3 | -3 | -3 | -1 | -2 | -2 | -3 | -3 | 3 | 1 | -2 | 1 | -1 | -2 | -2 | 0 | -3 | -1 | 4 |

Those skilled in the art appreciate that there are many established algorithms available to align two amino acid sequences. The "FASTA" similarity search algorithm of Pearson and Lipman is a suitable protein alignment method for examining the level of identity shared by an amino acid sequence disclosed herein and the amino acid sequence of a putative mouse Zcytor16 variant. The FASTA algorithm is described by Pearson and Lipman, *Proc. Nat'l Acad. Sci. USA* 85:2444 (1988), and by Pearson, *Meth. Enzymol.* 183:63 (1990). Briefly, FASTA first characterizes sequence similarity by identifying regions shared by the query sequence (e.g., SEQ ID NO:38 or SEQ ID NO:48) and a test change, compared with an amino acid sequence disclosed herein. For example, variants can be obtained that contain one or more amino acid substitutions of SEQ ID NO:38 or SEQ ID NO:48, in which an alkyl amino acid is substituted for an alkyl amino acid in a mouse Zcytor16 amino acid sequence, an aromatic amino acid is substituted for an aromatic amino acid in a mouse Zcytor16 amino acid sequence, a sulfur-containing amino acid is substituted for a sulfur-containing amino acid in a mouse Zcytor16 amino acid sequence, a hydroxy-containing amino acid is substituted for a hydroxy-containing amino acid in a mouse Zcytor16 amino acid sequence, an acidic amino acid is substituted for an acidic amino acid in a mouse Zcytor16 amino acid sequence, a basic amino acid is substituted for a basic amino acid in a mouse Zcytor16 amino acid sequence, or a dibasic monocarboxylic amino acid is substituted for a dibasic monocarboxylic amino acid in a mouse Zcytor16 amino acid sequence. Among the common amino acids, for example, a "conservative amino acid substitution" is illustrated by a substitution among amino acids within each of the following groups: (1) glycine, alanine, valine, leucine, and isoleucine, (2) phenylalanine, tyrosine, and tryptophan, (3) serine and threonine, (4) aspartate and glutamate, (5) glutamine and asparagine, and (6) lysine, arginine and histidine. The BLOSUM62 table is an amino acid substitution matrix derived from about 2,000 local multiple alignments of protein sequence segments, representing highly conserved regions of more than 500 groups of related proteins (Henikoff and Henikoff, Proc. Nat'l Acad. Sci. USA 89:10915 (1992)). Accordingly, the BLOSUM62 substitution frequencies can be used to define conservative amino acid substitutions that may be introduced into the amino acid sequences of the present invention. Although it is possible to design amino acid substitutions based solely upon chemical properties (as discussed above), the language "conservative amino acid substitution" preferably refers to a substitution represented by a BLOSUM62 value of greater than −1. For example, an amino acid substitution is conservative if the substitution is characterized by a BLOSUM62 value of 0, 1, 2, or 3. According to this system, preferred conservative amino acid substitutions are characterized by a BLOSUM62 value of at least 1 (e.g., 1, 2 or 3), while more preferred conservative amino acid substitutions are characterized by a BLOSUM62 value of at least 2 (e.g., 2 or 3).

Particular variants of mouse Zcytor16 are characterized by having at least 70%, at least 80%, at least 90%, at least 95% or greater than 95% sequence identity to the corresponding amino acid sequence (e.g., SEQ ID NO:38 or SEQ ID NO:48), wherein the variation in amino acid sequence is due to one or more conservative amino acid substitutions.

Conservative amino acid changes in a mouse Zcytor16 gene can be introduced, for example, by substituting nucleotides for the nucleotides recited in SEQ ID NO:37 or SEQ ID NO:47. Such "conservative amino acid" variants can be obtained by oligonucleotide-directed mutagenesis, linker-scanning mutagenesis, mutagenesis using the polymerase chain reaction, and the like (see Ausubel (1995) at pages 8-10 to 8-22; and McPherson (ed.), Directed Mutagenesis: A Practical Approach (IRL Press 1991)). A variant mouse Zcytor16 polypeptide can be identified by the ability to specifically bind anti-mouse Zcytor16 antibodies.

The proteins of the present invention can also comprise non-naturally occurring amino acid residues. Non-naturally occurring amino acids include, without limitation, trans-3-methylproline, 2,4-methanoproline, cis-4-hydroxyproline, trans-4-hydroxyproline, N-methylglycine, allo-threonine, methylthreonine, hydroxyethylcysteine, hydroxyethylhomocysteine, nitroglutamine, homoglutamine, pipecolic acid, thiazolidine carboxylic acid, dehydroproline, 3- and 4-methylproline, 3,3-dimethylproline, tert-leucine, norvaline, 2-azaphenylalanine, 3-azaphenylalanine, 4-azaphenylalanine, and 4-fluorophenylalanine. Several methods are known in the art for incorporating non-naturally occurring amino acid residues into proteins. For example, an in vitro system can be employed wherein nonsense mutations are suppressed using chemically aminoacylated suppressor tRNAs. Methods for synthesizing amino acids and aminoacylating tRNA are known in the art. Transcription and translation of plasmids containing nonsense mutations is typically carried out in a cell-free system comprising an E. coli S30 extract and commercially available enzymes and other reagents. Proteins are purified by chromatography. See, for example, Robertson et al., J. Am. Chem. Soc. 113:2722 (1991), Ellman et al., Methods Enzymol. 202:301 (1991), Chung et al., Science 259:806 (1993), and Chung et al., Proc. Nat'l Acad. Sci. USA 90:10145 (1993).

In a second method, translation is carried out in Xenopus oocytes by microinjection of mutated mRNA and chemically aminoacylated suppressor tRNAs (Turcatti et al., J. Biol. Chem. 271:19991 (1996)). Within a third method; E. coli cells are cultured in the absence of a natural amino acid that is to be replaced (e.g., phenylalanine) and in the presence of the desired non-naturally occurring amino acid(s) (e.g., 2-azaphenylalanine, 3-azaphenylalanine, 4-azaphenylalanine, or 4-fluorophenylalanine). The non-naturally occurring amino acid is incorporated into the protein in place of its natural counterpart. See, Koide et al., Biochem. 33:7470 (1994). Naturally occurring amino acid residues can be converted to non-naturally occurring species by in vitro chemical modification. Chemical modification can be combined with site-directed mutagenesis to further expand the range of substitutions (Wynn and Richards, Protein Sci. 2:395 (1993)).

A limited number of non-conservative amino acids, amino acids that are not encoded by the genetic code, non-naturally occurring amino acids, and unnatural amino acids may be substituted for mouse Zcytor16 amino acid residues.

Essential amino acids in the polypeptides of the present invention can be identified according to procedures known in the art, such as site-directed mutagenesis or alanine-scanning mutagenesis (Cunningham and Wells, Science 244:1081 (1989), Bass et al., Proc. Nat'l Acad. Sci. USA 88:4498 (1991), Coombs and Corey, "Site-Directed Mutagenesis and Protein Engineering," in Proteins: Analysis and Design, Angeletti (ed.), pages 259–311 (Academic Press, Inc. 1998)). In the latter technique, single alanine mutations are introduced at every residue in the molecule, and the resultant mutant molecules are tested for biological activity to identify amino acid residues that are critical to the activity of the molecule. See also, Hilton et al., J. Biol. Chem. 271:4699 (1996).

Although sequence analysis can be used to further define the Zcytor16 ligand binding region, amino acids that play a role in mouse Zcytor16 binding activity (such as binding of mouse Zcytor16 to ligand IL-TIF, or to an anti-mouse Zcytor16 antibody) can also be determined by physical analysis of structure, as determined by such techniques as nuclear magnetic resonance, crystallography, electron diffraction or photoaffinity labeling, in conjunction with mutation of putative contact site amino acids. See, for example, de Vos et al., Science 255:306 (1992), Smith et al., J. Mol. Biol. 224:899 (1992), and Wlodaver et al., FEBS Lett. 309:59 (1992).

Multiple amino acid substitutions can be made and tested using known methods of mutagenesis and screening, such as those disclosed by Reidhaar-Olson and Sauer (Science 241:53 (1988)) or Bowie and Sauer (Proc. Nat'l Acad. Sci. USA 86:2152 (1989)). Briefly, these authors disclose methods for simultaneously randomizing two or more positions in a polypeptide, selecting for functional polypeptide, and then sequencing the mutagenized polypeptides to determine the spectrum of allowable substitutions at each position. Other methods that can be used include phage display (e.g., Lowman et al., Biochem. 30:10832 (1991), Ladner et al., U.S. Pat. No. 5,223,409, Huse, international publication No. WO 92/06204, and region-directed mutagenesis (Derbyshire et al., *Gene* 46:145 (1986), and Ner et al., *DNA* 7:127, (1988)). Moreover, mouse Zcytor16 labeled with biotin or FITC can be used for expression cloning of Zcytor16 ligands.

Variants of the disclosed mouse Zcytor16 nucleotide and polypeptide sequences can also be generated through DNA shuffling as disclosed by Stemmer, *Nature* 370:389 (1994), Stemmer, *Proc. Nat'l Acad. Sci. USA* 91:10747 (1994), and international publication No. WO 97/20078. Briefly, variant DNA molecules are generated by in vitro homologous recombination by random fragmentation of a parent DNA followed by reassembly using PCR, resulting in randomly introduced point mutations. This technique can be modified by using a family of parent DNA molecules, such as allelic variants or DNA molecules from different species, to introduce additional variability into the process. Selection or screening for the desired activity, followed by additional iterations of mutagenesis and assay provides for rapid "evolution" of sequences by selecting for desirable mutations while simultaneously selecting against detrimental changes.

Mutagenesis methods as disclosed herein can be combined with high-throughput, automated screening methods to detect activity of cloned, mutagenized polypeptides in host cells. Mutagenized DNA molecules that encode biologically active polypeptides, or polypeptides that bind with anti-mouse Zcytor16 antibodies, can be recovered from the host cells and rapidly sequenced using modern equipment. These methods allow the rapid determination of the importance of individual amino acid residues in a polypeptide of interest, and can be applied to polypeptides of unknown structure.

The present invention also includes "functional fragments" of mouse Zcytor16 polypeptides and nucleic acid molecules encoding such functional fragments. Routine deletion analyses of nucleic acid molecules can be performed to obtain functional fragments of a nucleic acid molecule that encodes a mouse Zcytor16 polypeptide. As an illustration, DNA molecules having the nucleotide sequence of SEQ ID NO:37 or SEQ ID NO:47 can be digested with Bal31 nuclease to obtain a series of nested deletions. The fragments are then inserted into expression vectors in proper reading frame, and the expressed polypeptides are isolated and tested for the ability to bind anti-mouse Zcytor16 antibodies. One alternative to exonuclease digestion is to use oligonucleotide-directed mutagenesis to introduce deletions or stop codons to specify production of a desired fragment. Alternatively, particular fragments of a mouse Zcytor16 gene can be synthesized using the polymerase chain reaction.

This general approach is exemplified by studies on the truncation at either or both termini of interferons have been summarized by Horisberger and Di Marco, *Pharmac. Ther.* 66:507 (1995). Moreover, standard techniques for functional analysis of proteins are described by, for example, Treuter et al., *Molec. Gen. Genet.* 240:113 (1993), Content et al., "Expression and preliminary deletion analysis of the 42 kDa 2–5A synthetase induced by human interferon," in *Biological Interferon Systems, Proceedings of ISIR-TNO Meeting on Interferon Systems*, Cantell (ed.), pages 65–72 (Nijhoff 1987), Herschman, "The EGF Receptor," in *Control of Animal Cell Proliferation, Vol.* 1, Boynton et al., (eds.) pages 169–199 (Academic Press 1985), Coumailleau et al., *J. Biol. Chem.* 270:29270 (1995); Fukunaga et al., *J. Biol. Chem.* 270:25291 (1995); Yamaguchi et al., *Biochem. Pharmacol.* 50:1295 (1995), and Meisel et al., *Plant Molec. Biol.* 30:1 (1996).

Analysis of the particular sequences disclosed herein provide a set of illustrative functional fragments presented in Table 4, wherein "$F_{III}$ Domain" is used to denote fibronectin III domains. The nucleotides encoding additional mouse zcytor16 functional varaint domains described herein, not show in Table 4, can be determined with reference to SEQ ID NO:37 or SEQ ID NO:47. Such functional fragments include for example, the following nucleotide sequences of SEQ ID NO:37 or SEQ ID NO:47: nucleotides 77, 86, or 100 to 373;, nucleotides 77, 86, or 100 to 694 or 697; nucleotides 401 to 694 or 697; and nucleotides 8 to 694 or 697, and amino acid sequences encoded thereby, e..g. such as those shown in SEQ ID NO:38 or SEQ ID NO:48 respectively.

TABLE 4

| Mouse Zcytor16 Feature | Amino acid residues (SEQ ID NO: 38 or SEQ ID NO: 48) | Nucleotides (SEQ ID NO: 37 or SEQ ID NO: 47) |
| --- | --- | --- |
| First $F_{III}$ Domain | 31–122 | 100–373 |
| Second $F_{III}$ Domain | 131–229 | 401–694 |
| Both $F_{III}$ Domains | 31–229 | 100–694 |

The present invention also contemplates functional fragments of a mouse Zcytor16 gene that have amino acid changes, compared with an amino acid sequence disclosed herein. A variant mouse Zcytor16 gene can be identified on the basis of structure by determining the level of identity with disclosed nucleotide and amino acid sequences, as discussed above. An alternative approach to identifying a variant gene on the basis of structure is to determine whether a nucleic acid molecule encoding a potential variant mouse Zcytor16 gene can hybridize to a nucleic acid molecule comprising a nucleotide sequence, such as SEQ ID NO:37 or SEQ ID NO:47.

For any mouse Zcytor16 polypeptide, including variants and fusion proteins, one of ordinary skill in the art can readily generate a fully degenerate polynucleotide sequence encoding that variant using the information set forth in Tables 1 and 2 above. Moreover, those of skill in the art can use standard software to devise mouse Zcytor16 variants based upon the nucleotide and amino acid sequences described herein. Accordingly, the present invention includes a computer-readable medium encoded with a data structure that provides at least one of the following sequences: SEQ ID NO:37 or SEQ ID NO:47, SEQ ID NO:38 or SEQ ID NO:48, and SEQ ID NO:39 or SEQ ID NO:49. Suitable forms of computer-readable media include magnetic media and optically-readable media. Examples of magnetic media include a hard or fixed drive, a random access memory (RAM) chip, a floppy disk, digital linear tape (DLT), a disk cache, and a ZIP disk. Optically readable media are exemplified by compact discs (e.g., CD-read only memory (ROM), CD-rewritable (RW), and CD-recordable), and digital versatile/video discs (DVD) (e.g., DVD-ROM, DVD-RAM, and DVD+RW).

The present invention also provides polypeptide fragments or peptides comprising an epitope-bearing portion of a mouse Zcytor16 polypeptide described herein. Such fragments or peptides may comprise an "immunogenic epitope," which is a part of a protein that elicits an antibody response when the entire protein is used as an immunogen. Immunogenic epitope-bearing peptides can be identified using standard methods (see, for example, Geysen et al., *Proc. Nat'l Acad. Sci. USA* 81:3998 (1983)).

In contrast, polypeptide fragments or peptides may comprise an "antigenic epitope," which is a region of a protein molecule to which an antibody can specifically bind. Certain epitopes consist of a linear or contiguous stretch of amino acids, and the antigenicity of such an epitope is not disrupted by denaturing agents. It is known in the art that relatively short synthetic peptides that can mimic epitopes of a protein can be used to stimulate the production of antibodies against the protein (see, for example, Sutcliffe et al., *Science* 219:660 (1983)). Accordingly, antigenic epitope-bearing peptides and polypeptides of the present invention are useful to raise antibodies that bind with the polypeptides described herein.

Antigenic epitope-bearing peptides and polypeptides can contain at least four to ten amino acids, at least ten to fifteen amino acids, or about 15 to about 30 amino acids of an amino acid sequence disclosed herein. Such epitope-bearing peptides and polypeptides can be produced by fragmenting a mouse Zcytor16 polypeptide, or by chemical peptide synthesis, as described herein. Moreover, epitopes can be selected by phage display of random peptide libraries (see, for example, Lane and Stephen, *Curr. Opin. Immunol.* 5:268 (1993), and Cortese et al., *Curr. Opin. Biotechnol.* 7:616 (1996)). Standard methods for identifying epitopes and producing antibodies from small peptides that comprise an epitope are described, for example, by Mole, "Epitope Mapping," in *Methods in Molecular Biology, Vol.* 10, Manson (ed.), pages 105–116 (The Humana Press, Inc. 1992), Price, "Production and Characterization of Synthetic Peptide-Derived Antibodies," in *Monoclonal Antibodies: Production, Engineering, and Clinical Application*, Ritter and Ladyman (eds.), pages 60–84 (Cambridge University Press 1995), and Coligan et al. (eds.), *Current Protocols in Immunology*, pages 9.3.1–9.3.5 and pages 9.4.1–9.4.11 (John Wiley & Sons 1997).

6. Production of Mouse Zcytor16 Polypeptides

The polypeptides of the present invention, including full-length polypeptides; soluble monomeric, homodimeric, heterodimeric and multimeric receptors; full-length receptors; receptor fragments (e.g. ligand-binding fragments), functional fragments, and fusion proteins, can be produced in recombinant host cells following conventional techniques. To express a mouse Zcytor16 gene, a nucleic acid molecule encoding the polypeptide must be operably linked to regulatory sequences that control transcriptional expression in an expression vector and then, introduced into a host cell. In addition to transcriptional regulatory sequences, such as promoters and enhancers, expression vectors can include translational regulatory sequences and a marker gene which is suitable for selection of cells that carry the expression vector.

Expression vectors that are suitable for production of a foreign protein in eukaryotic cells typically contain (1) prokaryotic DNA elements coding for a bacterial replication origin and an antibiotic resistance marker to provide for the growth and selection of the expression vector in a bacterial host; (2) eukaryotic DNA elements that control initiation of transcription, such as a promoter; and (3) DNA elements that control the processing of transcripts, such as a transcription termination/polyadenylation sequence. As discussed above, expression vectors can also include nucleotide sequences encoding a secretory sequence that directs the heterologous polypeptide into the secretory pathway of a host cell. For example, a mouse Zcytor16 expression vector may comprise a mouse Zcytor16 gene and a secretory sequence derived from any secreted gene.

Mouse Zcytor16 proteins of the present invention may be expressed in mammalian cells. Examples of suitable mammalian host cells include African green monkey kidney cells (Vero; ATCC CRL 1587), human embryonic kidney cells (293-HEK; ATCC CRL 1573), baby hamster kidney cells (BHK-21, BHK-570; ATCC CRL 8544, ATCC CRL 10314), canine kidney cells (MDCK; ATCC CCL 34), Chinese hamster ovary cells (CHO-K1; ATCC CCL61; CHO DG44 (Chasin et al., *Som. Cell. Molec. Genet.* 12:555, 1986)), rat pituitary cells (GH1; ATCC CCL82), HeLa S3 cells (ATCC CCL2.2), rat hepatoma cells (H-4-II-E; ATCC CRL 1548) SV40-transformed monkey kidney cells (COS-1; ATCC CRL 1650) and murine embryonic cells (NIH-3T3; ATCC CRL 1658).

For a mammalian host, the transcriptional and translational regulatory signals may be derived from viral sources, such as adenovirus, bovine papilloma virus, simian virus, or the like, in which the regulatory signals are associated with a particular gene which has a high level of expression. Suitable transcriptional and translational regulatory sequences also can be obtained from mammalian genes, such as actin, collagen, myosin, and metallothionein genes.

Transcriptional regulatory sequences include a promoter region sufficient to direct the initiation of RNA synthesis. Suitable eukaryotic promoters include the promoter of the mouse metallothionein I gene (Hamer et al., *J. Molec. Appl. Genet.* 1:273 (1982)), the TK promoter of *Herpes* virus (McKnight, *Cell* 31:355 (1982)), the SV40 early promoter (Benoist et al., *Nature* 290:304 (1981)), the *Rous* sarcoma virus promoter (Gorman et al., *Proc. Nat'l Acad. Sci. USA* 79:6777 (1982)), the cytomegalovirus promoter (Foecking et al., *Gene* 45:101 (1980)), and the mouse mammary tumor virus promoter (see, generally, Etcheverry, "Expression of Engineered Proteins in Mammalian Cell Culture," in *Protein Engineering: Principles and Practice*, Cleland et al. (eds.), pages 163–181 (John Wiley & Sons, Inc. 1996)).

Alternatively, a prokaryotic promoter, such as the bacteriophage T3 RNA polymerase promoter, can be used to control mouse Zcytor16 gene expression in mammalian cells if the prokaryotic promoter is regulated by a eukaryotic promoter (Zhou et al., *Mol. Cell. Biol.* 10:4529 (1990), and Kaufman et al., *Nucl. Acids Res.* 19:4485 (1991)).

In certain embodiments, a DNA sequence encoding a mouse Zcytor16 monomeric or homodimeric soluble receptor polypeptide, or a DNA sequence encoding an additional subunit of a heterodimeric or multimeric mouse Zcytor16 soluble receptor, e.g., CRF2-4 or IL10R, polypeptide is operably linked to other genetic elements required for its expression, generally including a transcription promoter and terminator, within an expression vector. The vector will also commonly contain one or more selectable markers and one or more origins of replication, although those skilled in the art will recognize that within certain systems selectable markers may be provided on separate vectors, and replication of the exogenous DNA may be provided by integration into the host cell genome. Selection of promoters, terminators, selectable markers, vectors and other elements is a matter of routine design within the level of ordinary skill in the art. Many such elements are described in the literature and are available through commercial suppliers. Multiple components of a soluble receptor complex can be co-transfected on individual expression vectors or be contained in a single expression vector. Such techniques of expressing multiple components of protein complexes are well known in the art.

An expression vector can be introduced into host cells using a variety of standard techniques including calcium phosphate transfection, liposome-mediated transfection, microprojectile-mediated delivery, electroporation, and the like. The transfected cells can be selected and propagated to provide recombinant host cells that comprise the expression vector stably integrated in the host cell genome. Techniques for introducing vectors into eukaryotic cells and techniques for selecting such stable transformants using a dominant selectable marker are described, for example, by Ausubel (1995) and by Murray (ed.), *Gene Transfer and Expression Protocols* (Humana Press 1991).

For example, one suitable selectable marker is a gene that provides resistance to the antibiotic neomycin. In this case, selection is carried out in the presence of a neomycin-type drug, such as G-418 or the like. Selection systems can also be used to increase the expression level of the gene of interest, a process referred to as "amplification." Amplification is carried out by culturing transfectants in the presence of a low level of the selective agent and then increasing the amount of selective agent to select for cells that produce high levels of the products of the introduced genes. A suitable amplifiable selectable marker is dihydrofolate reductase, which confers resistance to methotrexate. Other drug resistance genes (e.g., hygromycin resistance, multi-drug resistance, puromycin acetyltransferase) can also be used. Alternatively, markers that introduce an altered phenotype, such as green fluorescent protein, or cell surface proteins such as CD4, CD8, Class I MHC, placental alkaline phosphatase may be used to sort transfected cells from untransfected cells by such means as FACS sorting or magnetic bead separation technology.

Mouse Zcytor16 polypeptides can also be produced by cultured mammalian cells using a viral delivery system. Exemplary viruses for this purpose include adenovirus, retroviruses, herpesvirus, vaccinia virus and adeno-associated virus (AAV). Adenovirus, a double-stranded DNA virus, is currently the best studied gene transfer vector for delivery of heterologous nucleic acid (for a review, see Becker et al., *Meth. Cell Biol.* 43:161 (1994), and Douglas and Curiel, *Science & Medicine* 4:44 (1997)). Advantages of the adenovirus system include the accommodation of relatively large DNA inserts, the ability to grow to high-titer, the ability to infect a broad range of mammalian cell types, and flexibility that allows use with a large number of available vectors containing different promoters.

By deleting portions of the adenovirus genome, larger inserts (up to 7 kb) of heterologous DNA can be accommodated. These inserts can be incorporated into the viral DNA by direct ligation or by homologous recombination with a co-transfected plasmid. An option is to delete the essential E1 gene from the viral vector, which results in the inability to replicate unless the E1 gene is provided by the host cell. Adenovirus vector-infected human 293 cells (ATCC Nos. CRL-1573, 45504, 45505), for example, can be grown as adherent cells or in suspension culture at relatively high cell density to produce significant amounts of protein (see Garnier et al., *Cytotechnol.* 15:145 (1994)).

Mouse Zcytor16 can also be expressed in other higher eukaryotic cells, such as avian, fungal, insect, yeast, or plant cells. The baculovirus system provides an efficient means to introduce cloned mouse Zcytor16 genes into insect cells. Suitable expression vectors are based upon the *Autographa californica* multiple nuclear polyhedrosis virus (AcMNPV), and contain well-known promoters such as *Drosophila* heat shock protein (hsp) 70 promoter, *Autographa californica* nuclear polyhedrosis virus immediate-early gene promoter (ie-1) and the delayed early 39K promoter, baculovirus p10 promoter, and the *Drosophila metallothionein* promoter. A second method of making recombinant baculovirus utilizes a transposon-based system described by Luckow (Luckow, et al., *J. Virol.* 67:4566 (1993)). This system, which utilizes transfer vectors, is sold in the BAC-to-BAC kit (Life Technologies, Rockville, Md.). This system utilizes a transfer vector, PFASTBAC (Life Technologies) containing a Tn7 transposon to move the DNA encoding the mouse Zcytor16 polypeptide into a baculovirus genome maintained in *E. coli* as a large plasmid called a "bacmid." See, Hill-Perkins and Possee, *J. Gen. Virol.* 71:971 (1990), Bonning, et al., *J. Gen. Virol.* 75:1551 (1994), and Chazenbalk, and Rapoport, *J. Biol. Chem.* 270:1543 (1995). In addition, transfer vectors can include an in-frame fusion with DNA encoding an epitope tag at the C- or N-terminus of the expressed mouse Zcytor16 polypeptide, for example, a Glu-Glu epitope tag (Grussenmeyer et al., *Proc. Nat'l Acad. Sci.* 82:7952 (1985)). Using a technique known in the art, a transfer vector containing a mouse Zcytor16 gene is transformed into *E. coli*, and screened for bacmids which contain an interrupted lacZ gene indicative of recombinant baculovirus. The bacmid DNA containing the recombinant baculovirus genome is then isolated using common techniques.

The illustrative PFASTBAC vector can be modified to a considerable degree. For example, the polyhedrin promoter can be removed and substituted with the baculovirus basic protein promoter (also known as Pcor, p6.9 or MP promoter) which is expressed earlier in the baculovirus infection, and has been shown to be advantageous for expressing secreted proteins (see, for example, Hill-Perkins and Possee, *J. Gen. Virol.* 71:971 (1990), Bonning, et al., *J. Gen. Virol.* 75:1551 (1994), and Chazenbalk and Rapoport, *J. Biol. Chem.* 270:1543 (1995). In such transfer vector constructs, a short or long version of the basic protein promoter can be used. Moreover, transfer vectors can be constructed which replace the native mouse Zcytor16 secretory signal sequences with secretory signal sequences derived from insect proteins. For example, a secretory signal sequence from Ecdysteroid Glucosyltransferase (EGT), honey bee Melittin (Invitrogen Corporation; Carlsbad, Calif.), or baculovirus gp67 (PharMingen: San Diego, Calif.) can be used in constructs to replace the native mouse Zcytor16 secretory signal sequence.

The recombinant virus or bacmid is used to transfect host cells. Suitable insect host cells include cell lines derived from IPLB-Sf-21, a *Spodoptera frugiperda* pupal ovarian cell line, such as Sf9 (ATCC CRL 1711), Sf21AE, and Sf21 (Invitrogen Corporation; San Diego, Calif.), as well as *Drosophila* Schneider-2 cells, and the HIGH FIVEO cell line (Invitrogen) derived from *Trichoplusia ni* (U.S. Pat. No. 5,300,435). Commercially available serum-free media can be used to grow and to maintain the cells. Suitable media are Sf900 II™ (Life Technologies) or ESF 921™ (Expression Systems) for the Sf9 cells; and Ex-cellO405™ (JRH Biosciences, Lenexa, Kans.) or Express FiveO™ (Life Technologies) for the *T. ni* cells. When recombinant virus is used, the cells are typically grown up from an inoculation density of approximately $2-5 \times 10^5$ cells to a density of $1-2 \times 10^6$ cells at which time a recombinant viral stock is added at a multiplicity of infection (MOI) of 0.1 to 10, more typically near 3.

Established techniques for producing recombinant proteins in baculovirus systems are provided by Bailey et al., "Manipulation of Baculovirus Vectors," in *Methods in Molecular Biology, Volume 7: Gene Transfer and Expression Protocols*, Murray (ed.), pages 147–168 (The Humana Press, Inc. 1991), by Patel et al., "The baculovirus expression system," in *DNA Cloning 2: Expression Systems, 2nd Edition*, Glover et al. (eds.), pages 205–244 (Oxford University Press 1995), by Ausubel (1995) at pages 16-37 to 16-57, by Richardson (ed.), *Baculovirus Expression Protocols* (The Humana Press, Inc. 1995), and by Lucknow, "Insect Cell Expression Technology," in *Protein Engineering: Principles and Practice*, Cleland et al. (eds.), pages 183–218 (John Wiley & Sons, Inc. 1996).

Fungal cells, including yeast cells, can also be used to express the genes described herein. Yeast species of particular interest in this regard include *Saccharomyces cerevisiae, Pichia pastoris,* and *Pichia methanolica*. Suitable promoters for expression in yeast include promoters from GAL1 (galactose), PGK (phosphoglycerate kinase), ADH (alcohol dehydrogenase), AOX1 (alcohol oxidase), HIS4 (histidinol dehydrogenase), and the like. Many yeast cloning vectors have been designed and are readily available. These vectors include YIp-based vectors, such as YIp5, YRp vectors, such as YRp17, YEp vectors such as YEp13 and YCp vectors, such as YCp19. Methods for transforming *S. cerevisiae* cells with exogenous DNA and producing recombinant polypeptides therefrom are disclosed by, for example, Kawasaki, U.S. Pat. No. 4,599,311, Kawasaki et al., U.S. Pat. No. 4,931,373, Brake, U.S. Pat. No. 4,870,008, Welch et al., U.S. Pat. No. 5,037,743, and Murray et al., U.S. Pat. No. 4,845,075. Transformed cells are selected by phenotype determined by the selectable marker, commonly drug resistance or the ability to grow in the absence of a particular nutrient (e.g., leucine). A suitable vector system for use in *Saccharomyces cerevisiae* is the POT1 vector system disclosed by Kawasaki et al. (U.S. Pat. No. 4,931,373), which allows transformed cells to be selected by growth in glucose-containing media. Additional suitable promoters and terminators for use in yeast include those from glycolytic enzyme genes (see, e.g., Kawasaki, U.S. Pat. No. 4,599,311, Kingsman et al., U.S. Pat. No. 4,615,974, and Bitter, U.S. Pat. No. 4,977,092) and alcohol dehydrogenase genes. See also U.S. Pat. Nos. 4,990,446, 5,063,154, 5,139,936, and 4,661,454.

Transformation systems for other yeasts, including *Hansenula polymorpha, Schizosaccharomyces pombe, Kluyveromyces lactis, Kluyveromyces fragilis, Ustilago maydis, Pichia pastoris, Pichia methanolica, Pichia guillermondii* and *Candida maltosa* are known in the art. See, for example, Gleeson et al., *J. Gen. Microbiol.* 132:3459 (1986), and Cregg, U.S. Pat. No. 4,882,279. *Aspergillus* cells may be utilized according to the methods of McKnight et al., U.S. Pat. No. 4,935,349. Methods for transforming *Acremonium chrysogenum* are disclosed by Sumino et al., U.S. Pat. No. 5,162,228. Methods for transforming *Neurospora* are disclosed by Lambowitz, U.S. Pat. No. 4,486,533.

For example, the use of *Pichia methanolica* as host for the production of recombinant proteins is disclosed by Raymond, U.S. Pat. No. 5,716,808, Raymond, U.S. Pat. No. 5,736,383, Raymond et al., *Yeast* 14:11–23 (1998), and in international publication Nos. WO 97/17450, WO 97/17451, WO 98/02536, and WO 98/02565. DNA molecules for use in transforming *P. methanolica* will commonly be prepared as double-stranded, circular plasmids, which are preferably linearized prior to transformation. For polypeptide production in *P. methanolica*, the promoter and terminator in the plasmid can be that of a *P. methanolica* gene, such as a *P. methanolica* alcohol utilization gene (AUG1 or AUG2). Other useful promoters include those of the dihydroxyacetone synthase (DHAS), formate dehydrogenase (FMD), and catalase (CAT) genes. To facilitate integration of the DNA into the host chromosome, it is preferred to have the entire expression segment of the plasmid flanked at both ends by host DNA sequences. A suitable selectable marker for use in *Pichia methanolica* is a *P. methanolica* ADE2 gene, which encodes phosphoribosyl-5-aminoimidazole carboxylase (AIRC; EC 4.1.1.21), and which allows ade2 host cells to grow in the absence of adenine. For large-scale, industrial processes where it is desirable to minimize the use of methanol, host cells can be used in which both methanol utilization genes (AUG1 and AUG2) are deleted. For production of secreted proteins, host cells can be deficient in vacuolar protease genes (PEP4 and PRB1). Electroporation is used to facilitate the introduction of a plasmid containing DNA encoding a polypeptide of interest into *P. methanolica* cells. *P. methanolica* cells can be transformed by electroporation using an exponentially decaying, pulsed electric field having a field strength of from 2.5 to 4.5 kV/cm, preferably about 3.75 kV/cm, and a time constant (t) of from 1 to 40 milliseconds, most preferably about 20 milliseconds.

Expression vectors can also be introduced into plant protoplasts, intact plant tissues, or isolated plant cells. Methods for introducing expression vectors into plant tissue include the direct infection or co-cultivation of plant tissue with *Agrobacterium tumefaciens*, microprojectile-mediated delivery, DNA injection, electroporation, and the like. See, for example, Horsch et al., *Science* 227:1229 (1985), Klein et al., *Biotechnology* 10:268 (1992), and Miki et al., "Procedures for Introducing Foreign DNA into Plants," in *Methods in Plant Molecular Biology and Biotechnology*, Glick et al. (eds.), pages 67–88 (CRC Press, 1993).

Alternatively, mouse Zcytor16 genes can be expressed in prokaryotic host cells. Suitable promoters that can be used to express mouse Zcytor16 polypeptides in a prokaryotic host are well-known to those of skill in the art and include promoters capable of recognizing the T4, T3, Sp6 and T7 polymerases, the $P_R$ and $P_L$ promoters of bacteriophage lambda, the trp, recA, heat shock, lacUV5, tac, lpp-lacSpr, phoA, and lacZ promoters of *E. coli*, promoters of *B. subtilis*, the promoters of the bacteriophages of *Bacillus, Streptomyces* promoters, the int promoter of bacteriophage lambda, the bla promoter of pBR322, and the CAT promoter of the chloramphenicol acetyl transferase gene. Prokaryotic promoters have been reviewed by Glick, *J. Ind. Microbiol.* 1:277 (1987), Watson et al., *Molecular Biology of the Gene, 4th Ed.* (Benjamin Cummins 1987), and by Ausubel et al. (1995).

Suitable prokaryotic hosts include *E. coli* and *Bacillus subtilis*. Suitable strains of *E. coli* include BL21(DE3), BL21(DE3)pLysS, BL21(DE3)pLysE, DH1, DH4I, DH5, DH5I, DH5IF', DH5IMCR, DH10B, DH10B/p3, DH11S, C600, HB101, JM101, JM105, JM109, JM110, K38, RR1, Y1088, Y1089, CSH18, ER1451, and ER1647 (see, for example, Brown (ed.), *Molecular Biology Labfax* (Academic Press 1991)). Suitable strains of *Bacillus subtilus* include BR151, YB886, MI119, MI120, and B170 (see, for example, Hardy, "*Bacillus* Cloning Methods," in *DNA Cloning: A Practical Approach*, Glover (ed.) (IRL Press 1985)).

When expressing a mouse Zcytor16 polypeptide in bacteria such as *E. coli*, the polypeptide may be retained in the cytoplasm, typically as insoluble granules, or may be directed to the periplasmic space by a bacterial secretion sequence. In the former case, the cells are lysed, and the granules are recovered and denatured using, for example, guanidine isothiocyanate or urea. The denatured polypeptide can then be refolded and dimerized by diluting the denaturant, such as by dialysis against a solution of urea and a combination of reduced and oxidized glutathione, followed by dialysis against a buffered saline solution. In the latter case, the polypeptide can be recovered from the periplasmic space in a soluble and functional form by disrupting the cells (by, for example, sonication or osmotic shock) to release the contents of the periplasmic space and recovering the protein, thereby obviating the need for denaturation and refolding.

Methods for expressing proteins in prokaryotic hosts are well-known to those of skill in the art (see, for example, Williams et al., "Expression of foreign proteins in *E. coli* using plasmid vectors and purification of specific polyclonal antibodies," in *DNA Cloning 2: Expression Systems, 2nd Edition*, Glover et al. (eds.), page 15 (Oxford University Press 1995), Ward et al., "Genetic Manipulation and Expression of Antibodies," in *Monoclonal Antibodies: Principles and Applications*, page 137 (Wiley-Liss, Inc. 1995), and Georgiou, "Expression of Proteins in Bacteria," in *Protein Engineering: Principles and Practice*, Cleland et al. (eds.), page 101 (John Wiley & Sons, Inc. 1996)).

Standard methods for introducing expression vectors into bacterial, yeast, insect, and plant cells are provided, for example, by Ausubel (1995).

General methods for expressing and recovering foreign protein produced by a mammalian cell system are provided by, for example, Etcheverry, "Expression of Engineered Proteins in Mammalian Cell Culture," in *Protein Engineering: Principles and Practice*, Cleland et al. (eds.), pages 163 (Wiley-Liss, Inc. 1996). Standard techniques for recovering protein produced by a bacterial system is provided by, for example, Grisshammer et al., "Purification of over-produced proteins from *E. coli* cells," in *DNA Cloning 2: Expression Systems, 2nd Edition*, Glover et al. (eds.), pages 59–92 (Oxford University Press 1995). Established methods for isolating recombinant proteins from a baculovirus system are described by Richardson (ed.), *Baculovirus Expression Protocols* (The Humana Press, Inc. 1995).

As an alternative, polypeptides of the present invention can be synthesized by exclusive solid phase synthesis, partial solid phase methods, fragment condensation or classical solution synthesis. These synthesis methods are well-known to those of skill in the art (see, for example, Merrifield, *J. Am. Chem. Soc.* 85:2149 (1963), Stewart et al., "Solid Phase Peptide Synthesis" (2nd Edition), (Pierce Chemical Co. 1984), Bayer and Rapp, *Chem. Pept. Prot.* 3:3 (1986), Atherton et al., *Solid Phase Peptide Synthesis: A Practical Approach* (IRL Press 1989), Fields and Colowick, "Solid-Phase Peptide Synthesis," *Methods in Enzymology Volume* 289 (Academic Press 1997), and Lloyd-Williams et al., *Chemical Approaches to the Synthesis of Peptides and Proteins* (CRC Press, Inc. 1997)). Variations in total chemical synthesis strategies, such as "native chemical ligation" and "expressed protein ligation" are also standard (see, for example, Dawson et al., *Science* 266:776 (1994), Hackeng et al., *Proc. Nat'l Acad. Sci. USA* 94:7845 (1997), Dawson, *Methods Enzymol.* 287: 34 (1997), Muir et al, *Proc. Nat'l Acad. Sci. USA* 95:6705 (1998), and Severinov and Muir, *J. Biol. Chem.* 273:16205 (1998)).

Peptides and polypeptides of the present invention comprise at least six, at least nine, or at least 15 contiguous amino acid residues of SEQ ID NO:38 or SEQ ID NO:48. As an illustration, polypeptides can comprise at least six, at least nine, or at least 15 contiguous amino acid residues of any of the following amino acid sequences of SEQ ID NO:38 or SEQ ID NO:48: amino acid residues amino acid residues 1 to 230, amino acid residues 24 to 230, or 27 to 230, and amino acid residues 27 to 126, amino acid residues 131 to 230, or other fragments disclosed herein. Within certain embodiments of the invention, the polypeptides comprise 20, 30, 40, 50, 100, or more contiguous residues of these amino acid sequences. Nucleic acid molecules encoding such peptides and polypeptides are useful as polymerase chain reaction primers and probes.

Moreover, mouse Zcytor16 polypeptides can be expressed as monomers, homodimers, heterodimers, or multimers within higher eukaryotic cells. Such cells can be used to produce mouse Zcytor16 monomeric, homodimeric, heterodimeric and multimeric receptor polypeptides that comprise at least one mouse Zcytor16 polypeptide ("mouse Zcytor16-comprising receptors" or "mouse Zcytor16-comprising receptor polypeptides"), or can be used as assay cells in screening systems. Within one aspect of the present invention, a polypeptide of the present invention comprising the mouse Zcytor16 extracellular domain is produced by a cultured cell, and the cell is used to screen for ligands for the receptor, including the natural ligand, IL-TIF, as well as agonists and antagonists of the natural ligand. To summarize this approach, a cDNA or gene encoding the receptor is combined with other genetic elements required for its expression (e.g., a transcription promoter), and the resulting expression vector is inserted into a host cell. Cells that express the DNA and produce functional receptor are selected and used within a variety of screening systems. Each component of the monomeric, homodimeric, heterodimeric and multimeric receptor complex can be expressed in the same cell. Moreover, the components of the monomeric, homodimeric, heterodimeric and multimeric receptor complex can also be fused to a transmembrane domain or other membrane fusion moiety to allow complex assembly and screening of transfectants as described above.

Mammalian cells suitable for use in expressing mouse Zcytor16 receptors and transducing a receptor-mediated signal include cells that express other receptor subunits that may form a functional complex with mouse Zcytor16. These subunits may include those of the interferon receptor family or of other class II or class I cytokine receptors, e.g., CRF2-4 (Genbank Accession No. Z17227), IL-10R (Genbank Accession No.s U00672 and NM_001558), zcytor11 (U.S. Pat. No. 5,965,704), zcytor7 (U.S. Pat. No. 5,945,511), and IL-9R. It is also preferred to use a cell from the same species as the receptor to be expressed. Within a preferred embodiment, the cell is dependent upon an exogenously supplied hematopoietic growth factor for its proliferation. Preferred cell lines of this type are the human TF-1 cell line (ATCC number CRL-2003) and the AML-193 cell line (ATCC number CRL-9589), which are GM-CSF-dependent human leukemic cell lines and BaF3 (Palacios and Steinmetz, *Cell* 41: 727–734, (1985)) which is an IL-3 dependent murine pre-B cell line. Other cell lines include BHK, COS-1 and CHO cells.

Suitable host cells can be engineered to produce the necessary receptor subunits or other cellular component needed for the desired cellular response. This approach is advantageous because cell lines can be engineered to express receptor subunits from any species, thereby overcoming potential limitations arising from species specificity. Species orthologs of the mouse receptor cDNA can be cloned and used within cell lines from the same species, such as a mouse cDNA in the BaF3 cell line. Cell lines that are dependent upon one hematopoietic growth factor, such as GM-CSF or IL-3, can thus be engineered to become dependent upon another cytokine that acts through the mouse Zcytor16 receptor, such as IL-TIF.

Cells expressing functional receptor are used within screening assays. A variety of suitable assays are known in the art. These assays are based on the detection of a biological response in a target cell. One such assay is a cell proliferation assay. Cells are cultured in the presence or absence of a test compound, and cell proliferation is detected by, for example, measuring incorporation of tritiated thymidine or by colorimetric assay based on the metabolic breakdown of 3-(4,5-dimethylthiazol-2-yl)-2,5-diphenyl tetrazolium bromide (MTT) (Mosman, *J. Immunol. Meth.* 65: 55–63, (1983)). An alternative assay format uses cells that are further engineered to express a reporter gene. The reporter gene is linked to a promoter element that is responsive to the receptor-linked pathway, and the assay detects activation of transcription of the reporter gene. A preferred promoter element in this regard is a serum response element, or SRE. See, e.g., Shaw et al., *Cell* 56:563–572, (1989). A preferred such reporter gene is a luciferase gene (de Wet et al., *Mol. Cell. Biol.* 7:725, (1987)). Expression of the luciferase gene is detected by luminescence using methods known in the art (e.g., Baumgartner et al., *J. Biol. Chem.* 269:29094–29101, (1994); Schenbom and Goiffin, Promega_*Notes* 41:11, 1993). Luciferase activity assay kits are commercially available from, for example, Promega Corp., Madison, Wis. Target cell lines of this type can be used to screen libraries of chemicals, cell-conditioned culture media, fungal broths, soil samples, water samples, and the like. For example, a bank of cell-conditioned media samples can be assayed on a target cell to identify cells that produce ligand. Positive cells are then used to produce a cDNA library in a mammalian expression vector, which is divided into pools, transfected into host cells, and expressed. Media samples from the transfected cells are then assayed, with subsequent division of pools, re-transfection, subculturing, and re-assay of positive cells to isolate a cloned cDNA encoding the ligand.

A natural ligand for the mouse Zcytor16 receptor can also be identified by mutagenizing a cell line expressing the full-length receptor or receptor fusion (e.g., comprising the mouse Zcytor16 extracellular domain fused to the transmembrane and signaling domain of another cytokine receptor) and culturing it under conditions that select for autocrine growth. See WIPO publication WO 95/21930. Within a typical procedure, IL-3 dependent BaF3 cells expressing mouse Zcytor16 and the necessary additional subunits are mutagenized, such as with 2-ethylmethanesulfonate (EMS). The cells are then allowed to recover in the presence of IL-3, then transferred to a culture medium lacking IL-3 and IL-4. Surviving cells are screened for the production of a Zcytor16 ligand (e.g., IL-TIF), such as by adding soluble receptor to the culture medium or by assaying conditioned media on wild-type BaF3 cells and BaF3 cells expressing the receptor. Using this method, cells and tissues expressing IL-TIF can be identified. Such methods can be employed to detect IL-TIF from different species, e.g., human, and as such cells, cancers, and tissues expressing human IL-TIF can be identified using the mouse Zcytor16 polypeptides of the present invention.

Moreover several IL-TIF responsive cell lines are known (Dumontier et al., *J. Immunol.* 164:1814–1819, 2000; Dumoutier, L. et al., *Proc. Nat'l. Acad. Sci.* 97:10144–10149, 2000; Xie MH et al., *J. Biol. Chem.* 275: 31335–31339, 2000; Kotenko S V et al., JBC in press), as well as those that express the IL-TIF receptor subunit zcytor11. For example, the following cells are responsive to IL-TIF: TK-10 (Xie MH et al., supra.) (human renal carcinoma); SW480 (ATCC No. CCL-228) (human colon adenocarcinoma); HepG2 (ATCC No. HB-8065) (human hepatoma); PC12 (ATCC No. CRL-1721) (murine neuronal cell model; rat pheochromocytoma); and MES13 (ATCC No. CRL-1927) (murine kidney mesangial cell line). In addition, some cell lines express zcytor11 (IL-TIF receptor) are also candidates for responsive cell lines to IL-TIF: A549 (ATCC No. CCL-185) (human lung carcinoma); G-361 (ATCC No. CRL-1424) (human melanoma); and Caki-1 (ATCC No. HTB-46) (human renal carcinoma). These cells can be used in assays to assess the functionality of mouse Zcytor16 as an IL-TIF antagonist or anti-inflammatory factor, even in heterologous systems, such as human.

An additional screening approach provided by the present invention includes the use of hybrid receptor polypeptides. These hybrid polypeptides fall into two general classes. Within the first class, the intracellular domain of mouse Zcytor16, is joined to the ligand-binding domain of a second receptor. It is preferred that the second receptor be a hematopoietic cytokine receptor, such as mpl receptor (Souyri et al., *Cell* 63: 1137–1147, (1990). The hybrid receptor will further comprise a transmembrane domain, which may be derived from either receptor. A DNA construct encoding the hybrid receptor is then inserted into a host cell. Cells expressing the hybrid receptor are cultured in the presence of a ligand for the binding domain (e.g., TPO in the case the mpl receptor extracellular domain is used) and assayed for a response. This system provides a means for analyzing signal transduction mediated by mouse Zcytor16 while using readily available ligands. This system can also be used to determine if particular cell lines are capable of responding to signals transduced by mouse Zcytor16 monomeric, homodimeric, heterodimeric and multimeric receptors of the present invention.

A second class of hybrid receptor polypeptides comprise the extracellular (ligand-binding) domain of mouse Zcytor16 (approximately residues 24 to 230, or 27 to 230 of SEQ ID NO:38 or SEQ ID NO:48) with an intracellular domain of a second receptor, preferably a hematopoietic cytokine receptor, and a transmembrane domain. Hybrid zacytor11 monomers, homodimers, heterodimers and multimers of the present invention receptors of this second class are expressed in cells known to be capable of responding to signals transduced by the second receptor. Together, these two classes of hybrid receptors enable the identification of a responsive cell type for the development of an assay for detecting IL-TIF. Moreover, such cells can be used in the presence of IL-TIF to assay the soluble receptor antagonists of the present invention in a competition-type assay. In such assay, a decrease in the proliferation or signal transduction activity of IL-TIF in the presence of a soluble receptor of the present invention demonstrates antagonistic activity. Moreover IL-TIF-soluble receptor binding assays can also be used to assess whether a soluble receptor antagonizes IL-TIF activity.

7. Production of Mouse Zcytor16 Fusion Proteins and Conjugates

One general class of mouse Zcytor16 analogs are variants having an amino acid sequence that is a mutation of the amino acid sequence disclosed herein. Another general class of mouse Zcytor16 analogs is provided by anti-idiotype antibodies, and fragments thereof, as described below. Moreover, recombinant antibodies comprising anti-idiotype variable domains can be used as analogs (see, for example, Monfardini et al., *Proc. Assoc. Am. Physicians* 108:420 (1996)). Since the variable domains of anti-idiotype mouse Zcytor16 antibodies mimic mouse Zcytor16, these domains can provide mouse or human Zcytor16 binding activity, e.g., to IL-TIF. Methods of producing anti-idiotypic catalytic antibodies are known to those of skill in the art (see, for example, Joron et al., *Ann. NY Acad. Sci.* 672:216 (1992), Friboulet et al., *Appl. Biochem. Biotechnol.* 47:229 (1994), and Avalle et al., *Ann. NY Acad. Sci.* 864:118 (1998)).

Another approach to identifying Zcytor16 analogs is provided by the use of combinatorial libraries. Methods for constructing and screening phage display and other combinatorial libraries are provided, for example, by Kay et al., *Phage Display of Peptides and Proteins* (Academic Press 1996), Verdine, U.S. Pat. No. 5,783,384, Kay, et. al., U.S. Pat. No. 5,747,334, and Kauffman et al., U.S. Pat. No. 5,723,323.

Mouse Zcytor16 polypeptides have both in vivo and in vitro uses. As an illustration, a soluble form of mouse Zcytor16 can be added to cell culture medium to inhibit the effects of the Zcytor16 ligand produced by the cultured cells.

Fusion proteins of mouse Zcytor16 can be used to express mouse Zcytor16 in a recombinant host, and to isolate the produced mouse Zcytor16. As described below, particular mouse Zcytor16 fusion proteins also have uses in diagnosis and therapy. One type of fusion protein comprises a peptide that guides a mouse Zcytor16 polypeptide from a recombinant host cell. To direct a mouse Zcytor16 polypeptide into the secretory pathway of a eukaryotic host cell, a secretory signal sequence (also known as a signal peptide, a leader sequence, prepro sequence or pre sequence) is provided in the mouse Zcytor16 expression vector. While the secretory signal sequence may be derived from mouse Zcytor16, a suitable signal sequence may also be derived from another secreted protein or synthesized de novo. The secretory signal sequence is operably linked to a mouse Zcytor16-encoding sequence such that the two sequences are joined in the correct reading frame and positioned to direct the newly synthesized polypeptide into the secretory pathway of the host cell. Secretory signal sequences are commonly positioned 5' to the nucleotide sequence encoding the polypeptide of interest, although certain secretory signal sequences may be positioned elsewhere in the nucleotide sequence of interest (see, e.g., Welch et al., U.S. Pat. No. 5,037,743; Holland et al., U.S. Pat. No. 5,143,830).

Although the secretory signal sequence of mouse Zcytor16 or another protein produced by mammalian cells (e.g., tissue-type plasminogen activator signal sequence, as described, for example, in U.S. Pat. No. 5,641,655) is useful for expression of mouse Zcytor16 in recombinant mammalian hosts, a yeast signal sequence is preferred for expression in yeast cells. Examples of suitable yeast signal sequences are those derived from yeast mating phermone α-factor (encoded by the MFα1 gene), invertase (encoded by the SUC2 gene), or acid phosphatase (encoded by the PHO5 gene). See, for example, Romanos et al., "Expression of Cloned Genes in Yeast," in *DNA Cloning 2: A Practical Approach*, $2^{nd}$ Edition, Glover and Hames (eds.), pages 123–167 (Oxford University Press 1995).

Mouse Zcytor16 monomeric, homodimeric, heterodimeric and multimeric receptor polypeptides can be prepared by expressing a truncated DNA encoding the extracellular domain, for example, a polypeptide which contains 24 to 230, or 27 to 230 of SEQ ID NO:38 or SEQ ID NO:48, or the corresponding region of a non-mouse receptor. It is preferred that the extracellular domain polypeptides be prepared in a form substantially free of transmembrane and intracellular polypeptide segments. To direct the export of the receptor domain from the host cell, the receptor DNA is linked to a second DNA segment encoding a secretory peptide, such as a t-PA secretory peptide. To facilitate purification of the secreted receptor domain, a C-terminal extension, such as a poly-histidine tag, substance P, Flag™ peptide (Hopp et al., *Biotechnology* 6:1204–1210, (1988); available from Eastman Kodak Co., New Haven, Conn.) or another polypeptide or protein for which an antibody or other specific binding agent is available, can be fused to the receptor polypeptide.

Moreover, heterodimeric and multimeric non-mouse Zcytor16 subunit extracellular cytokine binding domains are a also prepared as above.

In an alternative approach, a receptor extracellular domain of mouse Zcytor16 or other class I or II cytokine receptor component can be expressed as a fusion with immunoglobulin heavy chain constant regions, typically an $F_C$ fragment, which contains two constant region domains and a hinge region but lacks the variable region (See, Sledziewski, AZ et al., U.S. Pat. Nos. 6,018,026 and 5,750,375). The soluble mouse Zcytor16, soluble mouse Zcytor16/CRF2-4 heterodimers, and monomeric, homodimeric, heterodimeric and multimeric polypeptides of the present invention include such fusions. Such fusions are typically secreted as multimeric molecules wherein the Fc portions are disulfide bonded to each other and two receptor polypeptides are arrayed in closed proximity to each other. Fusions of this type can be used to affinity purify the cognate ligand from solution, as an in vitro assay tool, to block signals in vitro by specifically titrating out ligand, and as antagonists in vivo by administering them parenterally to bind circulating ligand and clear it from the circulation. To purify ligand, a mouse Zcytor16-Ig chimera is added to a sample containing the ligand (e.g., cell-conditioned culture media or tissue extracts) under conditions that facilitate receptor-ligand binding (typically near-physiological temperature, pH, and ionic strength). The chimera-ligand complex is then separated by the mixture using protein A, which is immobilized on a solid support (e.g., insoluble resin beads). The ligand is then eluted using conventional chemical techniques, such as with a salt or pH gradient. In the alternative, the chimera itself can be bound to a solid support, with binding and elution carried out as above. The chimeras may be used in vivo to regulate inflammatory responses including acute phase responses such as serum amyloid A (SAA), C-reactive protein (CRP), and the like. Chimeras with high binding affinity are administered parenterally (e.g., by intramuscular, subcutaneous or intravenous injection). Circulating molecules bind ligand and are cleared from circulation by normal physiological processes. For use in assays, the chimeras are bound to a support via the $F_C$ region and used in an ELISA format. Moreover, susch methods can be applied using the polypeptides of the present invention to isolate mouse IL-TIF, as well as an orthologous ligand, e.g., human IL-TIF.

The present invention further provides a variety of other polypeptide fusions and related multimeric proteins comprising one or more polypeptide fusions. For example, a soluble mouse Zcytor16 receptor or soluble mouse Zcytor16 heterodimeric polypeptide, such as soluble mouse Zcytor16/CRF2-4, can be prepared as a fusion to a dimerizing protein as disclosed in U.S. Pat. Nos. 5,155,027 and 5,567,584. Preferred dimerizing proteins in this regard include immunoglobulin constant region domains, e.g., IgGγ1, and the human κ light chain. Immunoglobulin-soluble mouse Zcytor16 receptor or immunoglobulin-soluble mouse Zcytor16 heterodimeric or multimeric polypeptide, such as immunoglobulin-soluble mouse Zcytor16/CRF2-4 fusions can be expressed in genetically engineered cells to produce a variety of multimeric mouse Zcytor16 receptor analogs. Auxiliary domains can be fused to soluble mouse Zcytor16 receptor or soluble mouse Zcytor16 heterodimeric or multimeric polypeptides, such as soluble mouse Zcytor16/CRF2-4 to target them to specific cells, tissues, or macromolecules (e.g., collagen, or cells expressing the Zcytor16 ligand, IL-TIF). A mouse Zcytor16 polypeptide can be fused to two or more moieties, such as an affinity tag for purification and a targeting domain. Polypeptide fusions can also comprise one or more cleavage sites, particularly between domains. See, Tuan et al., *Connective Tissue Research* 34:1–9, 1996.

In bacterial cells, it is often desirable to express a heterologous protein as a fusion protein to decrease toxicity, increase stability, and to enhance recovery of the expressed protein. For example, mouse Zcytor16 can be expressed as a fusion protein comprising a glutathione S-transferase polypeptide. Glutathione S-transferease fusion proteins are typically soluble, and easily purifiable from *E. coli* lysates on immobilized glutathione columns. In similar approaches, a mouse Zcytor16 fusion protein comprising a maltose binding protein polypeptide can be isolated with an amylose resin column, while a fusion protein comprising the C-terminal end of a truncated Protein A gene can be purified using IgG-Sepharose. Established techniques for expressing a heterologous polypeptide as a fusion protein in a bacterial cell are described, for example, by Williams et al., "Expression of Foreign Proteins in *E. coli* Using Plasmid Vectors and Purification of Specific Polyclonal Antibodies," in *DNA Cloning 2: A Practical Approach*, $2^{nd}$ Edition, Glover and Hames (Eds.), pages 15–58 (Oxford University Press 1995). In addition, commercially available expression systems are available. For example, the PINPOINT Xa protein purification system (Promega Corporation; Madison, Wis.) provides a method for isolating a fusion protein comprising a polypeptide that becomes biotinylated during expression with a resin that comprises avidin.

Peptide tags that are useful for isolating heterologous polypeptides expressed by either prokaryotic or eukaryotic cells include polyHistidine tags (which have an affinity for nickel-chelating resin), c-myc tags, calmodulin binding protein (isolated with calmodulin affinity chromatography), substance P, the RYIRS tag (which binds with anti-RYIRS antibodies), the Glu-Glu tag, and the FLAG tag (which binds with anti-FLAG antibodies). See, for example, Luo et al., *Arch. Biochem. Biophys.* 329:215 (1996), Morganti et al., *Biotechnol. Appl. Biochem.* 23:67 (1996), and Zheng et al., *Gene* 186:55 (1997). Nucleic acid molecules encoding such peptide tags are available, for example, from Sigma-Aldrich Corporation (St. Louis, Mo.).

The present invention also contemplates that the use of the secretory signal sequence contained in the mouse Zcytor16 polypeptides of the present invention to direct other polypeptides into the secretory pathway. A signal fusion polypeptide can be made wherein a secretory signal sequence derived from amino acid residues 1 to 23 of SEQ ID NO:38 or SEQ ID NO:48 is operably linked to another polypeptide using methods known in the art and disclosed herein. The secretory signal sequence contained in the fusion polypeptides of the present invention is preferably fused amino-terminally to an additional peptide to direct the additional peptide into the secretory pathway. Such constructs have numerous applications known in the art. For example, these novel secretory signal sequence fusion constructs can direct the secretion of an active component of a normally non-secreted protein, such as a receptor. Such fusions may be used in a transgenic animal or in a cultured recombinant host to direct peptides through the secretory pathway. With regard to the latter, exemplary polypeptides include pharmaceutically active molecules such as Factor VIIa, proinsulin, insulin, follicle stimulating hormone, tissue type plasminogen activator, tumor necrosis factor, interleukins (e.g., interleukin-1 (IL-1), IL-2, IL-3, IL-4, IL-5, IL-6, IL-7, IL-8, IL-9, IL-10, IL-11, IL-12, IL-13, IL-14, and IL-15), colony stimulating factors (e.g., granulocyte-colony stimulating factor (G-CSF) and granulocyte macrophage-colony stimulating factor (GM-CSF)), interferons (e.g., interferons-$\alpha$,-$\beta$,-$\gamma$,-$\omega$,-$\delta$, and -$\tau$), the stem cell growth factor designated "S1 factor," erythropoietin, and thrombopoietin. The mouse Zcytor16 secretory signal sequence contained in the fusion polypeptides of the present invention is preferably fused amino-terminally to an additional peptide to direct the additional peptide into the secretory pathway. Fusion proteins comprising a mouse Zcytor16 secretory signal sequence can be constructed using standard techniques.

Another form of fusion protein comprises a mouse Zcytor16 polypeptide and an immunoglobulin heavy chain constant region, typically an $F_C$ fragment, which contains two or three constant region domains and a hinge region but lacks the variable region. As an illustration, Chang et al., U.S. Pat. No. 5,723,125, describe a fusion protein comprising a human interferon and a human immunoglobulin Fc fragment. The C-terminal of the interferon is linked to the N-terminal of the Fc fragment by a peptide linker moiety. An example of a peptide linker is a peptide comprising primarily a T cell inert sequence, which is immunologically inert. An exemplary peptide linker has the amino acid sequence: GGSGG SGGGG SGGGG S (SEQ ID NO:4). In this fusion protein, an illustrative Fc moiety is a human $\gamma$4 chain, which is stable in solution and has little or no complement activating activity. Accordingly, the present invention contemplates a mouse Zcytor16 fusion protein that comprises a mouse Zcytor16 moiety and a human Fc fragment, wherein the C-terminus of the mouse Zcytor16 moiety is attached to the N-terminus of the Fc fragment via a peptide linker, such as a peptide consisting of the amino acid sequence of SEQ ID NO:4. The mouse Zcytor16 moiety can be a mouse Zcytor16 molecule or a fragment thereof. For example, a fusion protein can comprise amino acid residues 24 to 230, or 27 to 230 of SEQ ID NO:38 or SEQ ID NO:48 and an Fc fragment (e.g., a human Fc fragment).

In another variation, a mouse Zcytor16 fusion protein comprises an IgG sequence, a mouse Zcytor16 moiety covalently joined to the aminoterminal end of the IgG sequence, and a signal peptide that is covalently joined to the aminoterminal of the mouse Zcytor16 moiety, wherein the IgG sequence consists of the following elements in the following order: a hinge region, a $CH_2$ domain, and a $CH_3$ domain. Accordingly, the IgG sequence lacks a $CH_1$ domain. The mouse Zcytor16 moiety displays a mouse Zcytor16 activity, as described herein, such as the ability to bind with a Zcytor16 ligand, including mouse and human IL-TIF. This general approach to producing fusion proteins that comprise both antibody and nonantibody portions has been described by LaRochelle et al., EP 742830 (WO 95/21258).

Fusion proteins comprising a mouse Zcytor16 moiety and an Fc moiety can be used, for example, as an in vitro assay tool. For example, the presence of a Zcytor16 ligand, including mouse or human IL-TIF, in a biological sample can be detected using a mouse Zcytor16-immunoglobulin fusion protein, in which the mouse Zcytor16 moiety is used to bind the ligand, and a macromolecule, such as Protein A or anti-Fc antibody, is used to bind the fusion protein to a solid support. Such systems can be used to identify agonists and antagonists that interfere with the binding of a Zcytor16 ligand to its receptor.

Other examples of antibody fusion proteins include polypeptides that comprise an antigen-binding domain and a mouse Zcytor16 fragment that contains a mouse Zcytor16 extracellular domain. Such molecules can be used to target particular tissues for the benefit of Zcytor16 binding activity.

The present invention further provides a variety of other polypeptide fusions. For example, part or all of a domain(s)

conferring a biological function can be swapped between mouse Zcytor16 of the present invention with the functionally equivalent domain(s) from another member of the cytokine receptor family. Polypeptide fusions can be expressed in recombinant host cells to produce a variety of mouse Zcytor16 fusion analogs. A mouse Zcytor16 polypeptide can be fused to two or more moieties or domains, such as an affinity tag for purification and a targeting domain. Polypeptide fusions can also comprise one or more cleavage sites, particularly between domains. See, for example, Tuan et al., *Connective Tissue Research* 34:1 (1996).

Fusion proteins can be prepared by methods known to those skilled in the art by preparing each component of the fusion protein and chemically conjugating them. Alternatively, a polynucleotide encoding both components of the fusion protein in the proper reading frame can be generated using known techniques and expressed by the methods described herein. General methods for enzymatic and chemical cleavage of fusion proteins are described, for example, by Ausubel (1995) at pages 16-19 to 16-25.

Mouse Zcytor16 polypeptides can be used to identify and to isolate Zcytor16 ligands, including mouse and human IL-TIF. For example, proteins and peptides of the present invention can be immobilized on a column and used to bind ligands from a biological sample that is run over the column (Hermanson et al. (eds.), *Immobilized Affinity Ligand Techniques*, pages 195–202 (Academic Press 1992)). As such, mouse Zcytor16 polypeptides of the present invention can be used to identify and isolate IL-TIF for either diagnostic, or production purposes.

The activity of a mouse Zcytor16 polypeptide can also be observed by a silicon-based biosensor microphysiometer, which measures the extracellular acidification rate or proton excretion associated with receptor binding and subsequent physiologic cellular responses. An exemplary device is the CYTOSENSOR Microphysiometer manufactured by Molecular Devices, Sunnyvale, Calif. A variety of cellular responses, such as cell proliferation, ion transport, energy production, inflammatory response, regulatory and receptor activation, and the like, can be measured by this method (see, for example, McConnell et al., *Science* 257:1906 (1992), Pitchford et al., *Meth. Enzymol.* 228:84 (1997), Arimilli et al., *J. Immunol. Meth.* 212:49 (1998), Van Liefde et al., *Eur. J. Pharnacol.* 346:87 (1998)). The microphysiometer can be used for assaying eukaryotic, prokaryotic, adherent, or non-adherent cells. By measuring extracellular acidification changes in cell media over time, the microphysiometer directly measures cellular responses to various stimuli, including agonists, ligands, or antagonists of mouse Zcytor16.

For example, the microphysiometer is used to measure responses of an mouse Zcytor16-expressing eukaryotic cell, compared to a control eukaryotic cell that does not express mouse Zcytor16 polypeptide. Suitable cells responsive to mouse Zcytor16-modulating stimuli include recombinant host cells comprising a mouse Zcytor16 expression vector, and cells that naturally express mouse Zcytor16. Extracellular acidification provides one measure for a mouse Zcytor16-modulated cellular response. In addition, this approach can be used to identify ligands, agonists, and antagonists of Zcytor16 ligand, IL-TIF. For example, a molecule can be identified as an agonist of Zcytor16 ligand by providing cells that express a mouse Zcytor16 polypeptide, culturing a first portion of the cells in the absence of the test compound, culturing a second portion of the cells in the pre sence of the test compound, and determining whether the second portion exhibits a cellular response, in comparison with the first portion.

Alternatively, a solid phase system can be used to identify a Zcytor16 ligand, or an agonist or antagonist of a Zcytor16 ligand. For example, a mouse Zcytor16 polypeptide or mouse Zcytor16 fusion protein, or mouse Zcytor16 monomeric, homodimeric, heterodimeric or multimeric soluble receptor can be immobilized onto the surface of a receptor chip of a commercially available biosensor instrument (BIACORE, Biacore AB; Uppsala, Sweden). The use of this instrument is disclosed, for example, by Karlsson, *Immunol. Methods* 145:229 (1991), and Cunningham and Wells, *J. Mol Biol.* 234:554 (1993).

In brief, a mouse Zcytor16 polypeptide or fusion protein is covalently attached, using amine or sulfhydryl chemistry, to dextran fibers that are attached to gold film within a flow cell. A test sample is then passed through the cell. If a ligand is present in the sample, it will bind to the immobilized polypeptide or fusion protein, causing a change in the refractive index of the medium, which is detected as a change in surface plasmon resonance of the gold film. This system allows the determination of on- and off-rates, from which binding affinity can be calculated, and assessment of stoichiometry of binding. This system can also be used to examine antibody-antigen interactions, and the interactions of other complement/anti-complement pairs.

Mouse Zcytor16 binding domains can be further characterized by physical analysis of structure, as determined by such techniques as nuclear magnetic resonance, crystallography, electron diffraction or photoaffinity labeling, in conjunction with mutation of putative contact site amino acids of Zcytor16 ligand agonists. See, for example, de Vos et al., *Science* 255:306 (1992), Smith et al., *J. Mol. Biol.* 224:899 (1992), and Wlodaver et al., *FEBS Lett.* 309:59 (1992).

The present invention also contemplates chemically modified mouse Zcytor16 compositions, in which a mouse Zcytor16 polypeptide is linked with a polymer. Illustrative mouse Zcytor16 polypeptides are soluble polypeptides that lack a functional transmembrane domain, such as a polypeptide consisting of amino acid residues 24 to 230, or 27 to 230 of SEQ ID NO:38 or SEQ ID NO:48. Typically, the polymer is water soluble so that the mouse Zcytor16 conjugate does not precipitate in an aqueous environment, such as a physiological environment. An example of a suitable polymer is one that has been modified to have a single reactive group, such as an active ester for acylation, or an aldehyde for alkylation, In this way, the degree of polymerization can be controlled. An example of a reactive aldehyde is polyethylene glycol propionaldehyde, or mono-(C1–C10) alkoxy, or aryloxy derivatives thereof (see, for example, Harris, et al., U.S. Pat. No. 5,252,714). The polymer may be branched or unbranched. Moreover, a mixture of polymers can be used to produce mouse Zcytor16 conjugates.

Mouse Zcytor16 conjugates used for therapy can comprise pharmaceutically acceptable water-soluble polymer moieties. Suitable water-soluble polymers include polyethylene glycol (PEG), monomethoxy-PEG, mono-(C1–C10) alkoxy-PEG, aryloxy-PEG, poly-(N-vinyl pyrrolidone) PEG, tresyl monomethoxy PEG, PEG propionaldehyde, bis-succinimidyl carbonate PEG, propylene glycol homopolymers, a polypropylene oxide/ethylene oxide co-polymer, polyoxyethylated polyols (e.g., glycerol), polyvinyl alcohol, dextran, cellulose, or other carbohydrate-based polymers. Suitable PEG may have a molecular weight from about 600 to about 60,000, including, for example, 5,000, 12,000, 20,000 and 25,000. A mouse Zcytor16 conjugate can also comprise a mixture of such water-soluble polymers.

One example of a mouse Zcytor16 conjugate comprises a mouse Zcytor16 moiety and a polyalkyl oxide moiety attached to the N-terminus of the mouse Zcytor16 moiety. PEG is one suitable polyalkyl oxide. As an illustration, mouse Zcytor16 can be modified with PEG, a process known as "PEGylation." PEGylation of mouse Zcytor16 can be carried out by any of the PEGylation reactions known in the art (see, for example, EP 0 154 316, Delgado et al., *Critical Reviews in Therapeutic Drug Carrier Systems* 9:249 (1992), Duncan and Spreafico, *Clin. Pharmacokinet.* 27:290 (1994), and Francis et al., *Int J Hematol* 68:1 (1998)). For example, PEGylation can be performed by an acylation reaction or by an alkylation reaction with a reactive polyethylene glycol molecule. In an alternative approach, mouse Zcytor16 conjugates are formed by condensing activated PEG, in which a terminal hydroxy or amino group of PEG has been replaced by an activated linker (see, for example, Karasiewicz et al., U.S. Pat. No. 5,382,657).

PEGylation by acylation typically requires reacting an active ester derivative of PEG with a mouse Zcytor16 polypeptide. An example of an activated PEG ester is PEG esterified to N-hydroxysuccinimide. As used herein, the term "acylation" includes the following types of linkages between mouse Zcytor16 and a water soluble polymer: amide, carbamate, urethane, and the like. Methods for preparing PEGylated mouse Zcytor16 by acylation will typically comprise the steps of (a) reacting a mouse Zcytor16 polypeptide with PEG (such as a reactive ester of an aldehyde derivative of PEG) under conditions whereby one or more PEG groups attach to mouse Zcytor16, and (b) obtaining the reaction product(s). Generally, the optimal reaction conditions for acylation reactions will be determined based upon known parameters and desired results. For example, the larger the ratio of PEG:mouse Zcytor16, the greater the percentage of polyPEGylated mouse Zcytor16 product.

The product of PEGylation by acylation is typically a polyPEGylated mouse Zcytor16 product, wherein the lysine ε-amino groups are PEGylated via an acyl linking group. An example of a connecting linkage is an amide. Typically, the resulting mouse Zcytor16 will be at least 95% mono-, di-, or tri-pegylated, although some species with higher degrees of PEGylation may be formed depending upon the reaction conditions. PEGylated species can be separated from unconjugated mouse Zcytor16 polypeptides using standard purification methods, such as dialysis, ultrafiltration, ion exchange chromatography, affinity chromatography, and the like.

PEGylation by alkylation generally involves reacting a terminal aldehyde derivative of PEG with mouse Zcytor16 in the presence of a reducing agent. PEG groups can be attached to the polypeptide via a —$CH_2$—NH group.

Derivatization via reductive alkylation to produce a monoPEGylated product takes advantage of the differential reactivity of different types of primary amino groups available for derivatization. Typically, the reaction is performed at a pH that allows one to take advantage of the pKa differences between the ε-amino groups of the lysine residues and the α-amino group of the N-terminal residue of the protein. By such selective derivatization, attachment of a water-soluble polymer that contains a reactive group such as an aldehyde, to a protein is controlled. The conjugation with the polymer occurs predominantly at the N-terminus of the protein without significant modification of other reactive groups such as the lysine side chain amino groups. The present invention provides a substantially homogenous preparation of mouse Zcytor16 monopolymer conjugates.

Reductive alkylation to produce a substantially homogenous population of monopolymer mouse Zcytor16 conjugate molecule can comprise the steps of: (a) reacting a mouse Zcytor16 polypeptide with a reactive PEG under reductive alkylation conditions at a pH suitable to permit selective modification of the α-amino group at the amino terminus of the mouse Zcytor16, and (b) obtaining the reaction product(s). The reducing agent used for reductive alkylation should be stable in aqueous solution and able to reduce only the Schiff base formed in the initial process of reductive alkylation. illustrative reducing agents include sodium borohydride, sodium cyanoborohydride, dimethylamine borane, trimethylamine borane, and pyridine borane.

For a substantially homogenous population of monopolymer mouse Zcytor16 conjugates, the reductive alkylation reaction conditions are those that permit the selective attachment of the water-soluble polymer moiety to the N-terminus of mouse Zcytor16. Such reaction conditions generally provide for pKa differences between the lysine amino groups and the α-amino group at the N-terminus. The pH also affects the ratio of polymer to protein to be used. In general, if the pH is lower, a larger excess of polymer to protein will be desired because the less reactive the N-terminal α-group, the more polymer is needed to achieve optimal conditions. If the pH is higher, the polymer:mouse Zcytor16 need not be as large because more reactive groups are available. Typically, the pH will fall within the range of 3 to 9, or 3 to 6. This method can be employed for making mouse Zcytor16-comprising homodimeric, heterodimeric or multimeric soluble receptor conjugates.

Another factor to consider is the molecular weight of the water-soluble polymer. Generally, the higher the molecular weight of the polymer, the fewer number of polymer molecules which may be attached to the protein. For PEGylation reactions, the typical molecular weight is about 2 kDa to about 100 kDa, about 5 kDa to about 50 kDa, or about 12 kDa to about 25 kDa. The molar ratio of water-soluble polymer to mouse Zcytor16 will generally be in the range of 1:1 to 100:1. Typically, the molar ratio of water-soluble polymer to mouse Zcytor16 will be 1:1 to 20:1 for polyPEGylation, and 1:1 to 5:1 for monoPEGylation.

General methods for producing conjugates comprising a polypeptide and water-soluble polymer moieties are known in the art. See, for example, Karasiewicz et al., U.S. Pat. No. 5,382,657, Greenwald et al., U.S. Pat. No. 5,738, 846, Nieforth et al., *Clin. Pharmacol. Ther.* 59:636 (1996), Monkarsh et al., *Anal. Biochem.* 247:434 (1997)). This method can be employed for making mouse Zcytor16-comprising homodimeric, heterodimeric or multimeric soluble receptor conjugates.

The present invention contemplates compositions comprising a peptide or polypeptide described herein. Such compositions can further comprise a carrier. The carrier can be a conventional organic or inorganic carrier. Examples of carriers include water, buffer solution, alcohol, propylene glycol, macrogol, sesame oil, corn oil, and the like.

8. Isolation of Mouse Zcytor16 Polypeptides

The polypeptides of the present invention can be purified to at least about 80% purity, to at least about 90% purity, to at least about 95% purity, or greater than 95% purity with respect to contaminating macromolecules, particularly other proteins and nucleic acids, and free of infectious and pyrogenic agents. The polypeptides of the present invention may also be purified to a pharmaceutically pure state, which is greater than 99.9% pure. In certain preparations, purified polypeptide is substantially free of other polypeptides, particularly other polypeptides of animal origin.

Fractionation and/or conventional purification methods can be used to obtain preparations of mouse Zcytor16 purified from natural sources (e.g., tonsil tissue), synthetic mouse Zcytor16 polypeptides, and recombinant mouse Zcytor16 polypeptides and fusion mouse Zcytor16 polypeptides purified from recombinant host cells. In general, ammonium sulfate precipitation and acid or chaotrope extraction may be used for fractionation of samples. Exemplary purification steps may include hydroxyapatite, size exclusion, FPLC and reverse-phase high performance liquid chromatography. Suitable chromatographic media include derivatized dextrans, agarose, cellulose, polyacrylamide, specialty silicas, and the like. PEI, DEAE, QAE and Q derivatives are suitable. Exemplary chromatographic media include those media derivatized with phenyl, butyl, or octyl groups, such as Phenyl-Sepharose FF (Pharmacia), Toyopearl butyl 650 (Toso Haas, Montgomeryville, Pa.), Octyl-Sepharose (Pharmacia) and the like; or polyacrylic resins, such as Amberchrom CG 71 (Toso Haas) and the like. Suitable solid supports include glass beads, silica-based resins, cellulosic resins, agarose beads, cross-linked agarose beads, polystyrene beads, cross-linked polyacrylamide resins and the like that are insoluble under the conditions in which they are to be used. These supports may be modified with reactive groups that allow attachment of proteins by amino groups, carboxyl groups, sulfhydryl groups, hydroxyl groups and/or carbohydrate moieties.

Examples of coupling chemistries include cyanogen bromide activation, N-hydroxysuccinimide activation, epoxide activation, sulfhydryl activation, hydrazide activation, and carboxyl and amino derivatives for carbodiimide coupling chemistries. These and other solid media are well known and widely used in the art, and are available from commercial suppliers. Selection of a particular method for polypeptide isolation and purification is a matter of routine design and is determined in part by the properties of the chosen support. See, for example, *Affinity Chromatography: Principles & Methods* (Pharmacia LKB Biotechnology 1988), and Doonan, *Protein Purification Protocols* (The Humana Press 1996).

Additional variations in mouse Zcytor16 isolation and purification can be devised by those of skill in the art. For example, anti-mouse Zcytor16 antibodies, obtained as described below, can be used to isolate large quantities of protein by immunoaffinity purification.

The polypeptides of the present invention can also be isolated by exploitation of particular properties. For example, immobilized metal ion adsorption (IMAC) chromatography can be used to purify histidine-rich proteins, including those comprising polyhistidine tags. Briefly, a gel is first charged with divalent metal ions to form a chelate (Sulkowski, *Trends in Biochem.* 3:1 (1985)). Histidine-rich proteins will be adsorbed to this matrix with differing affinities, depending upon the metal ion used, and will be eluted by competitive elution, lowering the pH, or use of strong chelating agents. Other methods of purification include purification of glycosylated proteins by lectin affinity chromatography and ion exchange chromatography (M. Deutscher, (ed.), *Meth. Enzymol.* 182:529 (1990)). Within additional embodiments of the invention, a fusion of the polypeptide of interest and an affinity tag (e.g., maltose-binding protein, an immunoglobulin domain) may be constructed to facilitate purification. Moreover, the ligand-binding properties of mouse Zcytor16 extracellular domain can be exploited for purification, for example, of mouse Zcytor16-comprising soluble receptors; for example, by using affinity chromatography wherein IL-TIF ligand is bound to a column and the mouse Zcytor16-comprising receptor is bound and subsequently eluted using standard chromatography methods. mouse Zcytor16 polypeptides or fragments thereof may also be prepared through chemical synthesis, as described above. mouse Zcytor16 polypeptides may be monomers or multimers; glycosylated or non-glycosylated; PEGylated or non-PEGylated; and may or may not include an initial methionine amino acid residue.

9. Production of Antibodies to Mouse Zcytor16 Proteins

Antibodies to mouse Zcytor16 can be obtained, for example, using the product of a mouse Zcytor16 expression vector or mouse Zcytor16 isolated from a natural source as an antigen. Particularly useful anti-mouse Zcytor16 antibodies "bind specifically" with mouse Zcytor16. Antibodies are considered to be specifically binding if the antibodies exhibit at least one of the following two properties: (1) antibodies bind to mouse Zcytor16 with a threshold level of binding activity, and (2) antibodies do not significantly cross-react with polypeptides related to mouse Zcytor16.

With regard to the first characteristic, antibodies specifically bind if they bind to a mouse Zcytor16 polypeptide, peptide or epitope with a binding affinity ($K_a$) of $10^6 M^{-1}$ or greater, preferably $10^7 M^{-1}$ or greater, more preferably $10^8 M^{-1}$ or greater, and most preferably $10^9 M^{-1}$ or greater. The binding affinity of an antibody can be readily determined by one of ordinary skill in the art, for example, by Scatchard analysis (Scatchard, *Ann. NY Acad. Sci.* 51:660 (1949)). With regard to the second characteristic, antibodies do not significantly cross-react with related polypeptide molecules, for example, if they detect mouse Zcytor16, but not presently known polypeptides using a standard Western blot analysis. Examples of known related polypeptides include known cytokine receptors.

Anti-mouse Zcytor16 antibodies can be produced using antigenic mouse Zcytor16 epitope-bearing peptides and polypeptides. Antigenic epitope-bearing peptides and polypeptides of the present invention contain a sequence of at least nine, or between 15 to about 30 amino acids contained within SEQ ID NO:38 or SEQ ID NO:48 or another amino acid sequence disclosed herein. However, peptides or polypeptides comprising a larger portion of an amino acid sequence of the invention, containing from 30 to 50 amino acids, or any length up to and including the entire amino acid sequence of a polypeptide of the invention, also are useful for inducing antibodies that bind with mouse Zcytor16. It is desirable that the amino acid sequence of the epitope-bearing peptide is selected to provide substantial solubility in aqueous solvents (i.e., the sequence includes relatively hydrophilic residues, while hydrophobic residues are typically avoided). Moreover, amino acid sequences containing proline residues may be also be desirable for antibody production.

As an illustration, potential antigenic sites in mouse Zcytor16 were identified using the Jameson-Wolf method, Jameson and Wolf, *CABIOS* 4:181, (1988), as implemented by the PROTEAN program (version 3.14) of LASERGENE (DNASTAR; Madison, Wis.). Default parameters were used in this analysis.

The Jameson-Wolf method predicts potential antigenic determinants by combining six major subroutines for protein structural prediction. Briefly, the Hopp-Woods method, Hopp et al., *Proc. Nat'l Acad. Sci. USA* 78:3824 (1981), was first used to identify amino acid sequences representing areas of greatest local hydrophilicity (parameter: seven residues averaged). In the second step, Emini's method, Emini et al., *J. Virology* 55:836 (1985), was used to calculate surface probabilities (parameter: surface decision threshold (0.6)=1). Third, the Karplus-Schultz method, Karplus and Schultz, *Naturwissenschaften* 72:212 (1985), was used to predict backbone chain flexibility (parameter: flexibility threshold (0.2)=1). In the fourth and fifth steps of the analysis, secondary structure predictions were applied to the data using the methods of Chou-Fasman, Chou, "Prediction of Protein Structural Classes from Amino Acid Composition," in *Prediction of Protein Structure and the Principles of Protein Conformation*, Fasman (ed.), pages 549–586 (Plenum Press 1990), and Garnier-Robson, Garnier et al., *J. Mol. Biol.* 120:97 (1978) (Chou-Fasman parameters: conformation table=64 proteins; α region threshold=103; β region threshold=105; Garnier-Robson parameters: α and β decision constants=0). In the sixth subroutine, flexibility parameters and hydropathy/solvent accessibility factors were combined to determine a surface contour value, designated as the "antigenic index." Finally, a peak broadening function was applied to the antigenic index, which broadens major surface peaks by adding 20, 40, 60, or 80% of the respective peak value to account for additional free energy derived from the mobility of surface regions relative to interior regions. This calculation was not applied, however, to any major peak that resides in a helical region, since helical regions tend to be less flexible.

The results of this analysis indicated that the following amino acid sequences of SEQ ID NO:38 or SEQ ID NO:48 would provide suitable antigenic peptides: amino acids 35 to 40 ("antigenic peptide 1"), amino acids 67 to 77 ("antigenic peptide 2"), 88 to 94 ("antigenic peptide 3"), amino acids 108 to 119 ("antigenic peptide 4"), amino acids 108 to 130 ("antigenic peptide 5"), amino acids 125 to 130 ("antigenic peptide 6"), amino acids 147 to 161 ("antigenic peptide 7"), amino acids 177 to 190 ("antigenic peptide 8"), and amino acids 216 to 225 ("antigenic peptide 9"). The present invention contemplates the use of any one of antigenic peptides 1 to 9 to generate antibodies to mouse Zcytor16. The present invention also contemplates polypeptides comprising at least one of antigenic peptides 1 to 9. A Hopp/Woods hydrophilicity profile of the Zcytor16 protein sequence as shown in SEQ ID NO:38 or SEQ ID NO:48 can be generated (Hopp et al., *Proc. Natl. Acad. Sci.* 78:3824–3828, 1981; Hopp, *J. Immun. Meth.* 88:1–18, 1986 and Triquier et al., *Protein Engineering* 11:153–169, 1998). The profile is based on a sliding six-residue window. Buried G, S, and T residues and exposed H, Y, and W residues were ignored. For example, in Zcytor16, hydrophilic regions that serve as suitable antigens, include in reference to SEQ ID NO:38 or SEQ ID NO:48: (1) amino acid number 220 to 225; (2) amino acid number 216 to 221; (3) amino acid number 180 to 185; (4) amino acid number 179 to 184; and (5) amino acid number 71 to 76. Moreover other suitable antigens comprise residues, 24, 27 or 31 to 122 or 126; 131 to 229 or 230; 1 to 229 or 230; and 24 to to 229 or 230 of SEQ ID NO:38 or SEQ ID NO:48.

Moreover, suitable antigens also include the mouse Zcytor16 polypeptides comprising a mouse Zcytor16 cytokine binding, or extracellular domain disclosed above in combination with another class I or II cytokine extracellular domain, such as those that form soluble mouse Zcytor16 heterodimeric or multimeric polypeptides, such as soluble mouse Zcytor16/CRF2-4, mouse Zcytor16/zcytor11, mouse Zcytor16/zcytor7, and the like.

Polyclonal antibodies to recombinant mouse Zcytor16 protein or to mouse Zcytor16 isolated from natural sources can be prepared using methods well-known to those of skill in the art. See, for example, Green et al., "Production of Polyclonal Antisera," in *Immunochemical Protocols* (Manson, ed.), pages 1–5 (Humana Press 1992), and Williams et al., "Expression of foreign proteins in *E. coli* using plasmid vectors and purification of specific polyclonal antibodies," in *DNA Cloning 2: Expression Systems*, 2nd Edition, Glover et al. (eds.), page 15 (Oxford University Press 1995). The immunogenicity of a mouse Zcytor16 polypeptide can be increased through the use of an adjuvant, such as alum (aluminum hydroxide) or Freund's complete or incomplete adjuvant. Polypeptides useful for immunization also include fusion polypeptides, such as fusions of mouse Zcytor16 or a portion thereof with an immunoglobulin polypeptide or with maltose binding protein. The polypeptide immunogen may be a full-length molecule or a portion thereof. If the polypeptide portion is "hapten-like," such portion may be advantageously joined or linked to a macromolecular carrier (such as keyhole limpet hemocyanin (KLH), bovine serum albumin (BSA) or tetanus toxoid) for immunization.

Although polyclonal antibodies are typically raised in animals such as horses, cows, dogs, chicken, rats, mice, rabbits, guinea pigs, goats, or sheep, an anti-mouse Zcytor16 antibody of the present invention may also be derived from a subhuman primate antibody. General techniques for raising diagnostically and therapeutically useful antibodies in baboons may be found, for example, in Goldenberg et al., international patent publication No. WO 91/11465, and in Losman et al., *Int. J. Cancer* 46:310 (1990).

Alternatively, monoclonal anti-mouse Zcytor16 antibodies can be generated. Rodent monoclonal antibodies to specific antigens may be obtained by methods known to those skilled in the art (see, for example, Kohler et al., *Nature* 256:495 (1975), Coligan et al. (eds.), *Current Protocols in Immunology*, Vol. 1, pages 2.5.1–2.6.7 (John Wiley & Sons 1991) ["Coligan"], Picksley et al., "Production of monoclonal antibodies against proteins expressed in *E. coli*," in *DNA Cloning 2: Expression Systems*, 2nd Edition, Glover et al. (eds.), page 93 (Oxford University Press 1995)).

Briefly, monoclonal antibodies can be obtained by injecting mice with a composition comprising a mouse Zcytor16 gene product, verifying the presence of antibody production by removing a serum sample, removing the spleen to obtain B-lymphocytes, fusing the B-lymphocytes with myeloma cells to produce hybridomas, cloning the hybridomas, selecting positive clones which produce antibodies to the antigen, culturing the clones that produce antibodies to the antigen, and isolating the antibodies from the hybridoma cultures.

In addition, an anti-mouse Zcytor16 antibody of the present invention may be derived from a human monoclonal antibody. Human monoclonal antibodies are obtained from transgenic mice that have been engineered to produce specific human antibodies in response to antigenic challenge. In this technique, elements of the human heavy and light chain locus are introduced into strains of mice derived from embryonic stem cell lines that contain targeted disruptions of the endogenous heavy chain and light chain loci. The transgenic mice can synthesize human antibodies against specific antigens, e.g., Zcytor16, and the mice can be used to produce human antibody-secreting hybridomas. Methods for obtaining human antibodies from transgenic mice are described, for example, by Green et al., *Nature Genet.* 7:13 (1994), Lonberg et al., *Nature* 368:856 (1994), and Taylor et al., *Int. Immun.* 6:579 (1994).

Monoclonal antibodies can be isolated and purified from hybridoma cultures by a variety of well-established techniques. Such isolation techniques include affinity chromatography with Protein-A Sepharose, size-exclusion chromatography, and ion-exchange chromatography (see, for example, Coligan at pages 2.7.1–2.7.12 and pages 2.9.1–2.9.3; Baines et al., "Purification of Immunoglobulin G (IgG)," in *Methods in Molecular Biology, Vol.* 10, pages 79–104 (The Humana Press, Inc. 1992)).

For particular uses, it may be desirable to prepare fragments of anti-mouse Zcytor16 antibodies. Such antibody fragments can be obtained, for example, by proteolytic hydrolysis of the antibody. Antibody fragments can be obtained by pepsin or papain digestion of whole antibodies by conventional methods. As an illustration, antibody fragments can be produced by enzymatic cleavage of antibodies with pepsin to provide a 5S fragment denoted $F(ab')_2$. This fragment can be further cleaved using a thiol reducing agent to produce 3.5S Fab ' monovalent fragments. Optionally, the cleavage reaction can be performed using a blocking group for the sulfhydryl groups that result from cleavage of disulfide linkages. As an alternative, an enzymatic cleavage using pepsin produces two monovalent Fab fragments and an Fc fragment directly. These methods are described, for example, by Goldenberg, U.S. Pat. No. 4,331,647, Nisonoff et al., *Arch Biochem. Biophys.* 89:230 (1960), Porter, *Biochem. J.* 73:119 (1959), Edelman et al., in *Methods in Enzymology Vol.* 1, page 422 (Academic Press 1967), and by Coligan at pages 2.8.1–2.8.10 and 2.10.–2.10.4.

Other methods of cleaving antibodies, such as separation of heavy chains to form monovalent light-heavy chain fragments, further cleavage of fragments, or other enzymatic, chemical or genetic techniques may also be used, so long as the fragments bind to the antigen that is recognized by the intact antibody.

For example, Fv fragments comprise an association of $V_H$ and $V_L$ chains. This association can be noncovalent, as described by Inbar et al., *Proc. Nat'l Acad. Sci. USA* 69:2659 (1972). Alternatively, the variable chains can be linked by an intermolecular disulfide bond or cross-linked by chemicals such as glutaraldehyde (see, for example, Sandhu, *Crit. Rev. Biotech.* 12:437 (1992)).

The Fv fragments may comprise $V_H$ and $V_L$ chains which are connected by a peptide linker. These single-chain antigen binding proteins (scFv) are prepared by constructing a structural gene comprising DNA sequences encoding the $V_H$ and $V_L$ domains which are connected by an oligonucleotide. The structural gene is inserted into an expression vector which is subsequently introduced into a host cell, such as *E. coli*. The recombinant host cells synthesize a single polypeptide chain with a linker peptide bridging the two V domains. Methods for producing scFvs are described, for example, by Whitlow et al., *Methods: A Companion to Methods in Enzymology* 2:97 (1991) (also see, Bird et al., *Science* 242:423 (1988), Ladner et al., U.S. Pat. No. 4,946,778, Pack et al., *Bio/Technology* 11:1271 (1993), and Sandhu, supra).

As an illustration, a scFV can be obtained by exposing lymphocytes to mouse Zcytor16 polypeptide in vitro, and selecting antibody display libraries in phage or similar vectors (for instance, through use of immobilized or labeled mouse Zcytor16 protein or peptide). Genes encoding polypeptides having potential mouse Zcytor16 polypeptide binding domains can be obtained by screening random peptide libraries displayed on phage (phage display) or on bacteria, such as *E. coli*. Nucleotide sequences encoding the polypeptides can be obtained in a number of ways, such as through random mutagenesis and random polynucleotide synthesis. These random peptide display libraries can be used to screen for peptides which interact with a known target which can be a protein or polypeptide, such as a ligand or receptor, a biological or synthetic macromolecule, or organic or inorganic substances. Techniques for creating and screening such random peptide display libraries are known in the art (Ladner et al., U.S. Pat. No. 5,223,409, Ladner et al., U.S. Pat. No. 4,946,778, Ladner et al., U.S. Pat. No. 5,403,484, Ladner et al., U.S. Pat. No. 5,571,698, and Kay et al., *Phage Display of Peptides and Proteins* (Academic Press, Inc. 1996)) and random peptide display libraries and kits for screening such libraries are available commercially, for instance from CLONTECH Laboratories, Inc. (Palo Alto, Calif.), Invitrogen Inc. (San Diego, Calif.), New England Biolabs, Inc. (Beverly, Mass.), and Pharmacia LKB Biotechnology Inc. (Piscataway, N.J.). Random peptide display libraries can be screened using the mouse Zcytor16 sequences disclosed herein to identify proteins which bind to mouse Zcytor16.

Another form of an antibody fragment is a peptide coding for a single complementarity-determining region (CDR). CDR peptides ("minimal recognition units ") can be obtained by constructing genes encoding the CDR of an antibody of interest. Such genes are prepared, for example, by using the polymerase chain reaction to synthesize the variable region from RNA of antibody-producing cells (see, for example, Larrick et al., *Methods: A Companion to Methods in Enzymology* 2:106 (1991), Courtenay-Luck, "Genetic Manipulation of Monoclonal Antibodies," in *Monoclonal Antibodies: Production, Engineering and Clinical Application*, Ritter et al. (eds.), page 166 (Cambridge University Press 1995), and Ward et al., "Genetic Manipulation and Expression of Antibodies," in *Monoclonal Antibodies: Principles and Applications*, Birch et al., (eds.), page 137 (Wiley-Liss, Inc. 1995)).

Alternatively, an anti-mouse Zcytor16 antibody may be derived from a "humanized" monoclonal antibody. Humanized monoclonal antibodies are produced by transferring mouse complementary determining regions from heavy and light variable chains of the mouse immunoglobulin into a human variable domain. Typical residues of human antibodies are then substituted in the framework regions of the murine counterparts. The use of antibody components derived from humanized monoclonal antibodies obviates potential problems associated with the immunogenicity of murine constant regions. General techniques for cloning murine immunoglobulin variable domains are described, for example, by Orlandi et al., *Proc. Nat'l Acad. Sci. USA* 86:3833 (1989). Techniques for producing humanized monoclonal antibodies are described, for example, by Jones et al., *Nature* 321:522 (1986), Carter et al., *Proc. Nat'l Acad. Sci. USA* 89:4285 (1992), Sandhu, *Crit. Rev. Biotech.* 12:437 (1992), Singer et al., *J. Immun.* 150:2844 (1993), Sudhir (ed.), *Antibody Engineering Protocols* (Humana Press, Inc. 1995), Kelley, "Engineering Therapeutic Antibodies," in *Protein Engineering: Principles and Practice*, Cleland et al. (eds.), pages 399–434 (John Wiley & Sons, Inc. 1996), and by Queen et al., U.S. Pat. No. 5,693,762 (1997).

Polyclonal anti-idiotype antibodies can be prepared by immunizing animals with anti-mouse Zcytor16 antibodies or antibody fragments, using standard techniques. See, for example, Green et al., "Production of Polyclonal Antisera," in *Methods In Molecular Biology: Immunochemical Protocols*, Manson (ed.), pages 1–12 (Humana Press 1992). Also, see Coligan at pages 2.4.1–2.4.7. Alternatively, monoclonal anti-idiotype antibodies can be prepared using anti-mouse Zcytor16 antibodies or antibody fragments as immunogens with the techniques, described above. As another alternative, humanized anti-idiotype antibodies or subhuman primate anti-idiotype antibodies can be prepared using the above-described techniques. Methods for producing anti-idiotype antibodies are described, for example, by Irie, U.S. Pat. No. 5,208,146, Greene, et. al., U.S. Pat. No. 5,637,677, and Varthakavi and Minocha, *J. Gen. Virol.* 77:1875 (1996).

10. Use of Mouse Zcytor16 Nucleotide Sequences to Detect Gene Expression and Gene Structure Nucleic acid molecules can be used to detect the expression of a mouse Zcytor16 gene in a biological sample. Suitable probe molecules include double-stranded nucleic acid molecules comprising the nucleotide sequence of SEQ ID NO:37 or SEQ ID NO:47, or a portion thereof, as well as single-stranded nucleic acid molecules having the complement of the nucleotide sequence of SEQ ID NO:37 or SEQ ID NO:47, or a portion thereof. Probe molecules may be DNA, RNA, oligonucleotides, and the like. As used herein, the term "portion" refers to at least eight nucleotides to at least 20 or more nucleotides. Illustrative probes bind with regions of the mouse Zcytor16 gene that have a low sequence similarity to comparable regions in other cytokine receptor genes.

In a basic assay, a single-stranded probe molecule is incubated with RNA, isolated from a biological sample, under conditions of temperature and ionic strength that promote base pairing between the probe and target mouse Zcytor16 RNA species. After separating unbound probe from hybridized molecules, the amount of hybrids is detected.

In addition, as Zcytor16 expression in humans and mice is tissue-specific, polynucleotide probes, anti-mouse Zcytor16 antibodies, and detection the presence of Zcytor16 polypeptides in tissue can be used to assess whether a specific tissue is present, for example, after surgery involving the excision of a diseased or cancerous tissue. As such, the polynucleotides, polypeptides, and antibodies of the present invention can be used as an aid to determine whether all spleen tissue is excised after surgery, for example, after surgery for spleen cancer. In such instances, it is especially important to remove all potentially diseased tissue to maximize recovery from the cancer, and to minimize recurrence. Preferred embodiments include fluorescent, radiolabeled, or calorimetrically labeled antibodies, that can be used in situ.

Moreover, anti-mouse Zcytor16 antibodies and binding frangments can be used for tagging and sorting cells that specifically-express mouse Zcytor16, such as mononuclear cells, lymphoid cells, e.g, activated CD4+ T-cells and CD19+ B-cells, and other described herein. Such methods of cell tagging and sorting are well known in the art (see, e.g., "Molecular Biology of the Cell", $3^{rd}$ Ed., Albert, B. et al. (Garland Publishing, London & New York, 1994). One of skill in the art would recognize the importance of separating cell tissue types to study cells, and the use of antibodies to separate specific cell tissue types. Basically, antibodies that bind to the surface of a cell type are coupled to various matrices such as collagen, polysaccharide beads, or plastic to form an affinity surface to which only cells recognized by the antibodies will adhere. The bound cells are then recovered by conventional techniques. Other methods involve separating cells by a fluorescence-activated cell sorter (FACS). In this technique one labels cells with antibodies that are coupled to a fluorescent dye. The labeled cells are then separated from unlabeled cells in a FACS machine. In FACS sorting individual cells traveling in single file pass through a laser beam and the fluorescence of each cell is measured. Slightly further down-stream, tiny droplets, most containing either one or no cells, are formed by a vibrating nozzle. The droplets containing a single cell are automatically give a positive or negative charge at the moment of formation, depending on whether the cell they contain is fluorescent, and then deflected by a strong electric field into an appropriate container. Such machines can select 1 cell in 1000 and sort about 5000 cells each second. This produces a uniform population of cells for cell culture.

One of skill in the art would recognize that the antibodies to the mouse Zcytor16 polypeptides of the present invention are useful, because not all tissue types express the mouse Zcytor16 receptor and because it is important that biologists be able to separate specific cell types for further study and/or therapeutic re-implantation into the body. This is particularly relevant in cells such as immune cells, wherein mouse Zcytor16 is expressed.

Moreover, use of mouse Zcytor16 polynucleotide probes, anti-mouse Zcytor16 antibodies, and detection the presence of mouse Zcytor16 polypeptides in tissue can be used in the diagnosis and/or prevention of spontaneous abortions, or to monitor placental health and function. Since mouse Zcytor16 is expressed in the placenta, it could play a role in the critical functions of placenta, such as proliferation or survival of trophoblast cells, and the like. Thus, mouse Zcytor16 could be essential for the function of the placenta, thus maturation of embryos. Therefore, a supplement of mouse Zcytor16 polypeptide, or anti-mouse Zcytor16 antibodies may be beneficial in the prevention and treatment of certain types of spontaneous abortions, or premature birth of babies caused by abnormal expression of Zcytor16 in the placenta, or as a diagnostic to assess the function of the placenta. For exanple, as mouse Zcytor16 is normally expressed in placenta, the absence of mouse Zcytor16 expression may be indicative of abnormal placenta function. Similarly, use of mouse Zcytor16 polynucleotide probes, anti-mouse Zcytor16 antibodies, can be used in animal husbandry, for example in commercial mouse breeding colonies and transgenic mouse embryo recipients in the prevention and treatment of certain types of spontaneous abortions, or premature birth of pups caused by abnormal expression of mouse Zcytor16 in the placenta, or as a diagnostic to assess the function of the placenta.

Well-established hybridization methods of RNA detection include northern analysis and dot/slot blot hybridization (see, for example, Ausubel (1995) at pages 4-1 to 4-27, and Wu et al. (eds.), "Analysis of Gene Expression at the RNA Level," in *Methods in Gene Biotechnology*, pages 225–239 (CRC Press, Inc. 1997)). Nucleic acid probes can be detectably labeled with radioisotopes such as $^{32}P$ or $^{35}S$. Alternatively, mouse Zcytor16 RNA can be detected with a nonradioactive hybridization method (see, for example, Isaac (ed.), *Protocols for Nucleic Acid Analysis by Nonradioactive Probes* (Humana Press, Inc. 1993)). Typically, nonradioactive detection is achieved by enzymatic conversion of chromogenic or chemiluminescent substrates. Illustrative nonradioactive moieties include biotin, fluorescein, and digoxigenin.

Mouse Zcytor16 oligonucleotide probes are also useful for in vivo diagnosis. As an illustration, $^{18}F$-labeled oligonucleotides can be administered to a subject and visualized by positron emission tomography (Tavitian et al., *Nature Medicine* 4:467 (1998)).

Numerous diagnostic procedures take advantage of the polymerase chain reaction (PCR) to increase sensitivity of detection methods. Standard techniques for performing PCR are well-known (see, generally, Mathew (ed.), *Protocols in Human Molecular Genetics* (Humana Press, Inc. 1991), White (ed.), *PCR Protocols: Current Methods and Applications* (Humana Press, Inc. 1993), Cotter (ed.), *Molecular Diagnosis of Cancer* (Humana Press, Inc. 1996), Hanausek and Walaszek (eds.), *Tumor Marker Protocols* (Humana Press, Inc. 1998), Lo (ed.), *Clinical Applications of PCR (Humana Press, Inc.* 1998), and Meltzer (ed.), *PCR in Bioanalysis* (Humana Press, Inc. 1998)).

PCR primers can be designed to amplify a portion of the mouse Zcytor16 gene that has a low sequence similarity to a comparable region in other proteins, such as other cytokine receptor proteins.

One variation of PCR for diagnostic assays is reverse transcriptase-PCR (RT-PCR). In the RT-PCR technique, RNA is isolated from a biological sample, reverse transcribed to cDNA, and the cDNA is incubated with mouse Zcytor16 primers (see, for example, Wu et al. (eds.), "Rapid Isolation of Specific cDNAs or Genes by PCR," in *Methods in Gene Biotechnology*, pages 15–28 (CRC Press, Inc. 1997)). PCR is then performed and the products are analyzed using standard techniques.

As an illustration, RNA is isolated from biological sample using, for example, the gunadinium-thiocyanate cell lysis procedure described above. Alternatively, a solid-phase technique can be used to isolate mRNA from a cell lysate. A reverse transcription reaction can be primed with the isolated RNA using random oligonucleotides, short homopolymers of dT, or mouse Zcytor16 anti-sense oligomers. Oligo-dT primers offer the advantage that various mRNA nucleotide sequences are amplified that can provide control target sequences. mouse Zcytor16 sequences are amplified by the polymerase chain reaction using two flanking oligonucleotide primers that are typically 20 bases in length.

PCR amplification products can be detected using a variety of approaches. For example, PCR products can be fractionated by gel electrophoresis, and visualized by ethidium bromide staining. Alternatively, fractionated PCR products can be transferred to a membrane, hybridized with a detectably-labeled mouse Zcytor16 probe, and examined by autoradiography. Additional alternative approaches include the use of digoxigenin-labeled deoxyribonucleic acid triphosphates to provide chemiluminescence detection, and the C-TRAK calorimetric assay.

Another approach for detection of mouse Zcytor16 expression is cycling probe technology (CPT), in which a single-stranded DNA target binds with an excess of DNA-RNA-DNA chimeric probe to form a complex, the RNA portion is cleaved with RNAase H, and the presence of cleaved chimeric probe is detected (see, for example, Beggs et al., *J. Clin. Microbiol.* 34:2985 (1996), Bekkaoui et al., *Biotechniques* 20:240 (1996)). Alternative methods for detection of mouse Zcytor16 sequences can utilize approaches such as nucleic acid sequence-based amplification (NASBA), cooperative amplification of templates by cross-hybridization (CATCH), and the ligase chain reaction (LCR) (see, for example, Marshall et al., U.S. Pat. No. 5,686,272 (1997), Dyer et al., *J. Virol. Methods* 60:161 (1996), Ehricht et al., *Eur. J. Biochem.* 243:358 (1997), and Chadwick et al., *J. Virol. Methods* 70:59 (1998)). Other standard methods are known to those of skill in the art.

Mouse Zcytor16 probes and primers can also be used to detect and to localize Zcytor16 gene expression in tissue samples. Methods for such in situ hybridization are well-known to those of skill in the art (see, for example, Choo (ed.), *In Situ Hybridization Protocols* (Humana Press, Inc. 1994), Wu et al. (eds.), "Analysis of Cellular DNA or Abundance of mRNA by Radioactive In Situ Hybridization (RISH)," in *Methods in Gene Biotechnology*, pages 259–278 (CRC Press, Inc. 1997), and Wu et al. (eds.), "Localization of DNA or Abundance of mRNA by Fluorescence In Situ Hybridization (RISH)," in *Methods in Gene Biotechnology*, pages 279–289 (CRC Press, Inc. 1997)). Various additional diagnostic approaches are well-known to those of skill in the art (see, for example, Mathew (ed.), *Protocols in Human Molecular Genetics* (Humana Press, Inc. 1991), Coleman and Tsongalis, *Molecular Diagnostics* (Humana Press, Inc. 1996), and Elles, *Molecular Diagnosis of Genetic Diseases* (Humana Press, Inc., 1996)). Suitable test samples include blood, urine, saliva, tissue biopsy, and autopsy material.

11. Use of Anti-mouse Zcytor16 Antibodies to Detect Zcytor16 or Antagonize Zcytor16 Binding to IL-TIF The present invention contemplates the use of anti-mouse Zcytor16 antibodies to screen biological samples in vitro for the presence of Zcytor16. In one type of in vitro assay, anti-mouse Zcytor16 antibodies are used in liquid phase. For example, the presence of mouse Zcytor16 in a biological sample can be tested by mixing the biological sample with a trace amount of labeled mouse Zcytor16 and an anti-mouse Zcytor16 antibody under conditions that promote binding between mouse Zcytor16 and its antibody. Complexes of mouse Zcytor16 and anti-mouse Zcytor16 in the sample can be separated from the reaction mixture by contacting the complex with an immobilized protein which binds with the antibody, such as an Fc antibody or *Staphylococcus* protein A. The concentration of mouse Zcytor16 in the biological sample will be inversely proportional to the amount of labeled mouse Zcytor16 bound to the antibody and directly related to the amount of free labeled mouse Zcytor16. illustrative biological samples include blood, urine, saliva, tissue biopsy, and autopsy material.

Alternatively, in vitro assays can be performed in which anti-mouse Zcytor16 antibody is bound to a solid-phase carrier. For example, antibody can be attached to a polymer, such as aminodextran, in order to link the antibody to an insoluble support such as a polymer-coated bead, a plate or a tube. Other suitable in vitro assays will be readily apparent to those of skill in the art.

In another approach, anti-mouse Zcytor16 antibodies can be used to detect Zcytor16 in tissue sections prepared from a biopsy specimen. Such immunochemical detection can be used to determine the relative abundance of mouse Zcytor16 and to determine the distribution of Zcytor16 in the examined tissue. General immunochemistry techniques are well established (see, for example, Ponder, "Cell Marking Techniques and Their Application," in *Mammalian Development: A Practical Approach*, Monk (ed.), pages 115–38 (IRL Press 1987), Coligan at pages 5.8.1–5.8.8, Ausubel (1995) at pages 14.6.1 to 14.6.13 (Wiley Interscience 1990), and Manson (ed.), *Methods In Molecular Biology, Vol. 10: Immunochemical Protocols* (The Humana Press, Inc. 1992)).

Immunochemical detection can be performed by contacting a biological sample with an anti-mouse Zcytor16 antibody, and then contacting the biological sample with a detectably labeled molecule which binds to the antibody. For example, the detectably labeled molecule can comprise an antibody moiety that binds to anti-mouse Zcytor16 antibody. Alternatively, the anti-mouse Zcytor16 antibody can be conjugated with avidin/streptavidin (or biotin) and the detectably labeled molecule can comprise biotin (or avidin/streptavidin). Numerous variations of this basic technique are well-known to those of skill in the art.

Alternatively, an anti-mouse Zcytor16 antibody can be conjugated with a detectable label to form an anti-mouse Zcytor16 immunoconjugate. Suitable detectable labels include, for example, a radioisotope, a fluorescent label, a chemiluminescent label, an enzyme label, a bioluminescent label or colloidal gold. Methods of making and detecting such detectably-labeled immunoconjugates are well-known to those of ordinary skill in the art, and are described in more detail below.

The detectable label can be a radioisotope that is detected by autoradiography. Isotopes that are particularly useful for the purpose of the present invention are $^{3}$H, $^{125}$I, $^{131}$I, $^{35}$S and $^{14}$C.

Anti-mouse Zcytor16 immunoconjugates can also be labeled with a fluorescent compound. The presence of a fluorescently-labeled antibody is determined by exposing the immunoconjugate to light of the proper wavelength and detecting the resultant fluorescence. Fluorescent labeling compounds include fluorescein isothiocyanate, rhodamine, phycoerytherin, phycocyanin, allophycocyanin, o-phthaldehyde and fluorescamine.

Alternatively, anti-mouse Zcytor16 immunoconjugates can be detectably labeled by coupling an antibody component to a chemiluminescent compound. The presence of the chemiluminescent-tagged immunoconjugate is determined by detecting the presence of luminescence that arises during the course of a chemical reaction. Examples of chemiluminescent labeling compounds include luminol, isoluminol, an aromatic acridinium ester, an imidazole, an acridinium salt and an oxalate ester.

Similarly, a bioluminescent compound can be used to label anti-mouse Zcytor16 immunoconjugates of the present invention. Bioluminescence is a type of chemiluminescence found in biological systems in which a catalytic protein increases the efficiency of the chemiluminescent reaction. The presence of a bioluminescent protein is determined by detecting the presence of luminescence. Bioluminescent compounds that are useful for labeling include luciferin, luciferase and aequorin.

Alternatively, anti-mouse Zcytor16 immunoconjugates can be detectably labeled by linking an anti-mouse Zcytor16 antibody component to an enzyme. When the anti-mouse Zcytor16-enzyme conjugate is incubated in the presence of the appropriate substrate, the enzyme moiety reacts with the substrate to produce a chemical moiety which can be detected, for example, by spectrophotometric, fluorometric or visual means. Examples of enzymes that can be used to detectably label polyspecific immunoconjugates include β-galactosidase, glucose oxidase, peroxidase and alkaline phosphatase.

Those of skill in the art will know of other suitable labels which can be employed in accordance with the present invention. The binding of marker moieties to anti-mouse Zcytor16 antibodies can be accomplished using standard techniques known to the art. Typical methodology in this regard is described by Kennedy et al., *Clin. Chim. Acta* 70:1 (1976), Schurs et al., *Clin. Chim. Acta* 81:1 (1977), Shih et al., *Int'l J. Cancer* 46:1101 (1990), Stein et al., *Cancer Res.* 50:1330 (1990), and Coligan, supra.

Moreover, the convenience and versatility of immunochemical detection can be enhanced by using anti-mouse Zcytor16 antibodies that have been conjugated with avidin, streptavidin, and biotin (see, for example, Wilchek et al. (eds.), "Avidin-Biotin Technology," *Methods In Enzymology,* Vol. 184 (Academic Press 1990), and Bayer et al., "Immunochemical Applications of Avidin-Biotin Technology," in *Methods In Molecular Biology,* Vol. 10, Manson (ed.), pages 149–162 (The Humana Press, Inc. 1992).

Methods for performing immunoassays are well-established. See, for example, Cook and Self, "Monoclonal Antibodies in Diagnostic Immunoassays," in *Monoclonal Antibodies: Production, Engineering, and Clinical Application,* Ritter and Ladyman (eds.), pages 180–208, (Cambridge University Press, 1995), Perry, "The Role of Monoclonal Antibodies in the Advancement of Immunoassay Technology," in *Monoclonal Antibodies: Principles and Applications,* Birch and Lennox (eds.), pages 107–120 (Wiley-Liss, Inc. 1995), and Diamandis, *Immunoassay* (Academic Press, Inc. 1996).

The present invention also contemplates kits for performing an immunological diagnostic assay for Zcytor16 gene expression. Such kits comprise at least one container comprising an anti-mouse Zcytor16 antibody, or antibody fragment. A kit may also comprise a second container comprising one or more reagents capable of indicating the presence of mouse Zcytor16 antibody or antibody fragments. Examples of such indicator reagents include detectable labels such as a radioactive label, a fluorescent label, a chemiluminescent label, an enzyme label, a bioluminescent label, colloidal gold, and the like. A kit may also comprise a means for conveying to the user that mouse Zcytor16 antibodies or antibody fragments are used to detect Zcytor16 protein. For example, written instructions may state that the enclosed antibody or antibody fragment can be used to detect mouse Zcytor16. The written material can be applied directly to a container, or the written material can be provided in the form of a packaging insert.

Alternative techniques for generating or selecting antibodies useful herein include in vitro exposure of lymphocytes to soluble mouse Zcytor16 monomeric receptor or soluble mouse Zcytor16 homodimeric, heterodimeric or multimeric polypeptides, and selection of antibody display libraries in phage or similar vectors (for instance, through use of immobilized or labeled soluble mouse Zcytor16 monomeric receptor or soluble mouse Zcytor16 homodimeric, heterodimeric or multimeric polypeptides). Genes encoding polypeptides having potential binding domains such as soluble mouse Zcytor16 monomeric receptor or soluble mouse Zcytor16 homodimeric, heterodimeric or multimeric polypeptide can be obtained by screening random peptide libraries displayed on phage (phage display) or on bacteria, such as *E. coli.* Nucleotide sequences encoding the polypeptides can be obtained in a number of ways, such as through random mutagenesis and random polynucleotide synthesis. These random peptide display libraries can be used to screen for peptides which interact with a known target which can be a protein or polypeptide, such as a ligand or receptor, a biological or synthetic macromolecule, or organic or inorganic substances. Techniques for creating and screening such random peptide display libraries are known in the art (Ladner et al., U.S. Pat. No. 5,223,409; Ladner et al., U.S. Pat. No. 4,946,778; Ladner et al., U.S. Pat. No. 5,403,484 and Ladner et al., U.S. Pat. No. 5,571,698) and random peptide display libraries and kits for screening such libraries are available commercially, for instance from Clontech (Palo Alto, Calif.), Invitrogen Inc. (San Diego, Calif.), New England Biolabs, Inc. (Beverly, Mass.) and Pharmacia LKB Biotechnology Inc. (Piscataway, N.J.). Random peptide display libraries can be screened using the soluble mouse Zcytor16 monomeric receptor or soluble mouse Zcytor16 homodimeric, heterodimeric or multimeric polypeptide sequences disclosed herein to identify proteins which bind to mouse Zcytor16-comprising receptor polypeptides. These "binding polypeptides," which interact with soluble mouse Zcytor16-comprising receptor polypeptides, can be used for tagging cells, for example, those in which Zcytor16 is expressed; for isolating homolog polypeptides by affinity purification; they can be directly or indirectly conjugated to drugs, toxins, radionuclides and the like. These binding polypeptides can also be used in analytical methods such as for screening expression libraries and neutralizing activity, e.g., for blocking interaction between IL-TIF ligand and receptor, or viral binding to a receptor. The binding polypeptides can also be used for diagnostic assays for determining circulating levels of soluble mouse Zcytor16-comprising receptor polypeptides; for detecting or quantitating soluble or non-soluble Zcytor16-comprising receptors as marker of underlying pathology or disease. These binding polypeptides can also act as "antagonists" to block soluble or membrane-bound mouse Zcytor16 monomeric receptor or mouse Zcytor16 homodimeric, heterodimeric or multimeric polypeptide binding (e.g. to ligand) and signal transduction in vitro and in vivo. Again, these binding polypeptides serve as anti-mouse Zcytor16 monomeric receptor or anti-mouse Zcytor16 homodimeric, heterodimeric or multimeric polypeptides and are useful for inhibiting IL-TIF activity, as well as receptor activity or protein-binding. Antibodies raised to the natural receptor complexes of the present invention may be preferred embodiments, as they may act more specifically against the IL-TIEF, or more potently than antibodies raised to only one subunit. Moreover, the antagonistic and binding activity of the antibodies of the present invention can be assayed in the IL-TIF proliferation, signal trap, luciferase or binding assays in the presence of IL-TIF and Zcytor16-comprising soluble receptors, and other biological or biochemical assays described herein.

Antibodies to monomeric mouse Zcytor16 receptor or mouse Zcytor16 homodimeric, heterodimeric or multimeric mouse Zcytor16-containing receptors may be used for tagging cells that express Zcytor16 receptors; for isolating soluble Zcytor16-comprising receptor polypeptides by affinity purification; for diagnostic assays for determining circulating levels of soluble Zcytor16-comprising receptor polypeptides; for detecting or quantitating soluble Zcytor16-comprising receptors as marker of underlying pathology or disease; in analytical methods employing FACS; for screening expression libraries; for generating anti-idiotypic antibodies that can act as IL-TIF agonists; and as neutralizing antibodies or as antagonists to block Zcytor16 receptor function, or to block IL-TIF activity in vitro and in vivo. Suitable direct tags or labels include radionuclides, enzymes, substrates, cofactors, biotin, inhibitors, fluorescent markers, chemiluminescent markers, magnetic particles and the like; indirect tags or labels may feature use of biotin-avidin or other complement/anti-complement pairs as intermediates. Antibodies herein may also be directly or indirectly conjugated to drugs, toxins, radionuclides and the like, and these conjugates used for in vivo diagnostic or therapeutic applications. Moreover, antibodies to soluble mouse Zcytor16-comprising receptor polypeptides, or fragments thereof may be used in vitro to detect denatured or non-denatured mouse or orthologous Zcytor16-comprising receptor polypeptides or fragments thereof in assays, for example, Western Blots or other assays known in the art.

Antibodies to soluble mouse Zcytor16 receptor or soluble mouse Zcytor16 homodimeric, heterodimeric or multimeric receptor polypeptides are useful for tagging cells that express the corresponding receptors and assaying their expression levels, for affinity purification, within diagnostic assays for determining circulating levels of receptor polypeptides, analytical methods employing fluorescence-activated cell sorting. Moreover, divalent antibodies, and anti-idiotypic antibodies may be used as agonists to mimic the effect of the Zcytor16 ligand, IL-TIF.

Antibodies herein can also be directly or indirectly conjugated to drugs, toxins, radionuclides and the like, and these conjugates used for in vivo diagnostic or therapeutic applications. For instance, antibodies or binding polypeptides which recognize soluble mouse Zcytor16 receptor or soluble mouse Zcytor16 homodimeric, heterodimeric or multimeric receptor polypeptides of the present invention can be used to identify or treat tissues or organs that express a corresponding anti-complementary molecule (i.e., a mouse Zcytor16-comprising soluble or membrane-bound receptor). More specifically, antibodies to soluble mouse Zcytor16-comprising receptor polypeptides, or bioactive fragments or portions thereof, can be coupled to detectable or cytotoxic molecules and delivered to a mammal having cells, tissues or organs that express a Zcytor16-comprising receptor such as Zcytor16-expressing cancers, or certain disease states.

Suitable detectable molecules may be directly or indirectly attached to polypeptides that bind mouse Zcytor16-comprising receptor polypeptides, such as "binding polypeptides," (including binding peptides disclosed above), antibodies, or bioactive fragments or portions thereof. Suitable detectable molecules include radionuclides, enzymes, substrates, cofactors, inhibitors, fluorescent markers, chemiluminescent markers, magnetic particles and the like. Suitable cytotoxic molecules may be directly or indirectly attached to the polypeptide or antibody, and include bacterial or plant toxins (for instance, diphtheria toxin, *Pseudomonas* exotoxin, ricin, abrin and the like), as well as therapeutic radionuclides, such as iodine-131, rhenium-188 or yttrium-90 (either directly attached to the polypeptide or antibody, or indirectly attached through means of a chelating moiety, for instance). Binding polypeptides or antibodies may also be conjugated to cytotoxic drugs, such as adriamycin. For indirect attachment of a detectable or cytotoxic molecule, the detectable or cytotoxic molecule can be conjugated with a member of a complementary/anticomplementary pair, where the other member is bound to the binding polypeptide or antibody portion. For these purposes, biotin/streptavidin is an exemplary complementary/anticomplementary pair.

In another embodiment, binding polypeptide-toxin fusion proteins or antibody-toxin fusion proteins can be used for targeted cell or tissue inhibition or ablation (for instance, to treat cancer cells or tissues). Alternatively, if the binding polypeptide has multiple functional domains (i.e., an activation domain or a ligand binding domain, plus a targeting domain), a fusion protein including only the targeting domain may be suitable for directing a detectable molecule, a cytotoxic molecule or a complementary molecule to a cell or tissue type of interest. In instances where the fusion protein including only a single domain includes a complementary molecule, the anti-complementary molecule can be conjugated to a detectable or cytotoxic molecule. Such domain-complementary molecule fusion proteins thus represent a generic targeting vehicle for cell/tissue-specific delivery of generic anti-complementary-detectable/cytotoxic molecule conjugates.

In another embodiment, mouse Zcytor16 binding polypeptide-cytokine or antibody-cytokine fusion proteins can be used for enhancing in vivo killing of target tissues (for example, spleen, pancreatic, blood, lymphoid, colon, and bone marrow cancers), if the binding polypeptide-cytokine or anti- mouse Zcytor16 receptor antibody targets the hyperproliferative cell (See, generally, Hornick et al., *Blood* 89:4437–47, 1997). The described fusion proteins enable targeting of a cytokine to a desired site of action, thereby providing an elevated local concentration of cytokine. Suitable anti-mouse Zcytor16 monomer, homodimer, heterodimer or multimer antibodies target an undesirable cell or tissue (i.e., a tumor or a leukemia), and the fused cytokine mediates improved target cell lysis by effector cells. Suitable cytokines for this purpose include interleukin 2 and granulocyte-macrophage colony-stimulating factor (GM-CSF), for instance.

Alternatively, mouse Zcytor16 receptor binding polypeptides or antibody fusion proteins described herein can be used for enhancing in vivo killing of target tissues by directly stimulating a Zcytor16 receptor-modulated apoptotic pathway, resulting in cell death of hyperproliferative cells expressing Zcytor16-comprising receptors.

12. Production of Transgenic Mice

Mice engineered to overexpress the mouse Zcytor16 gene, referred to as "transgenic mice," and mice that exhibit a complete absence of mouse Zcytor16 gene function, referred to as "knockout mice," may also be generated (Snouwaert et al., *Science* 257:1083, 1992; Lowell et al., *Nature* 366:740–42, 1993; Capecchi, M. R., Science 244: 1288–1292, 1989; Palmiter, R. D. et al. *Annu Rev Genet.* 20: 465–499, 1986). For example, transgenic mice that overexpress mouse Zcytor16, either ubiquitously or under a tissue-specific or tissue-restricted promoter can be used to ask whether over-expression causes a phenotype. For example, over-expression of a wild-type Zcytor16 polypeptide, polypeptide fragment or a mutant thereof may alter normal cellular processes, or repress function of the Zcytor16 ligand IL-TIF, resulting in a phenotype that identifies a tissue in which Zcytor16 expression is functionally relevant and may indicate a therapeutic target for the Zcytor16, its agonists or antagonists. For example, a preferred transgenic mouse to engineer is one that overexpresses the full length human Zcytor16 polypeptide (SEQ ID NO:2); or more preferably the full length mouse Zcytor16 polypeptide (SEQ ID NO:38 or SEQ ID NO:48), or mature nouse polypeptide (Amino acids 24 to 230, or 27 to 230 of SEQ ID NO:38 or SEQ ID NO:48). Preferred tissue-specific or tissue-restricted promoters include monocyte and lymphoid-restricted, epithelial-specific, lung-specific, ovary-specific and skin-restricted promoters. Moreover, such over-expression may result in a phenotype that shows similarity with human diseases, or that counteracts the effects of increased or administered IL-TIF (IL-TIF adenovirus in mice suggests that IL-TIF over-expression increases the level of neutrophils and platelets in vivo).

Similarly, knockout mouse Zcytor16 mice can be used to determine where Zcytor16 is absolutely required in vivo. Such knockout animals serve as models to understand the requirements of Zcytor16 function in humans. A transgenic mouse that is a knockout mouse would not expresses residue 1 to 230 or 24 to 230, or 27 to 230 of SEQ ID NO:38 or SEQ ID NO:48, because they would exhibit a complete absence of endogenous Zcytor16 gene function. The phenotype of knockout mice is predictive of the in vivo effects of that a Zcytor16 antagonist, such as those described herein, may have. The murine Zcytor16 MRNA, and cDNA is isolated (SEQ ID NO:37 or SEQ ID NO:47) and can be used to isolate mouse Zcytor16 genomic DNA, which are subsequently used to generate knockout mice. These transgenic and knockout mice may be employed to study the Zcytor16 gene and the protein encoded thereby in an in vivo system, and can be used as in vivo models for corresponding human or animal diseases (such as those in commercially viable animal populations). The mouse models of the present invention are particularly relevant as tumor models for the study of immune function, inflammatory disease, cancer biology and progression. Such models are useful in the development and efficacy of therapeutic molecules used in human cancers, immune and inflammatory diseases. For example, because increases in human Zcytor16 expression are associated with specific human cancers, such as ovarian cancer, both transgenic mice and knockout mice would serve as useful animal models for cancer. Moreover, because increases in human Zcytor16 expression are associated with specific monocyte cells, such CD4+ T-cells and CD19+ B-cells, both mouse Zcytor16 transgenic mice and knockout mice would serve as useful animal models for immune function, inflammation, immune disorders, infection, anemia, hematopoietic and other cancers. Moreover, because Zcytor16 is a receptor for IL-TIF, use of mouse Zcytor16 transgenic and knockout micein a mouse model employing IL-TIF (e.g., with and without IL-TIF) cans serve as an additional animal model to study the development and efficacy of therapeutic molecules used in human cancers, immune and inflammatory diseases associated with IL-TIF, as well as assess the efficacy and usefulness of IL-TIF antagonists in vivo, such as the zcyr16 soluble receptors discussed herein. Moreover, in a preferred embodiment, Zcytor16 transgenic mouse can serve as an animal model for specific tumors, particularly ovarian cancer, stomach cancer, uterine cancer, rectal cancer, lung cancer and esophageal cancer; and as a model for IL-TIF-induced inflammation where Zcytor16 polypeptide is an antagonist. Such mouse zcytor16 transgenic and knowckout mouse models can also be used to assess the therapeutic aspects of IL-TIF, chemical therapeutics, anti-IL-TIF antibodies, anti-Zcytor16 antibodies, or Zcytor16 soluble receptors therein. Moreover, transgenic mice expression of mouse Zcytor16 antisense polynucleotides or ribozymes directed against mouse Zcytor16, described herein, can be used analogously to transgenic mice described above.

Transgenic mice can be engineered to over-express the mouse Zcytor16 gene in all tissues or under the control of a tissue-specific or tissue-preferred regulatory element. These over-producers of mouse Zcytor16 can be used to characterize the phenotype that results from over-expression, and the transgenic animals can serve as models for human disease caused by excess mouse Zcytor16. Transgenic mice that over-express mouse Zcytor16 also provide model bioreactors for production of mouse Zcytor16, such as soluble mouse Zcytor16, in the milk or blood of larger animals. Methods for producing transgenic mice are well-known to those of skill in the art (see, for example, Jacob, "Expression and Knockout of Interferons in Transgenic Mice," in *Overexpression and Knockout of Cytokines in Transgenic Mice,* Jacob (ed.), pages 111–124 (Academic Press, Ltd. 1994), Monastersky and Robl (eds.), *Strategies in Transgenic Animal Science* (ASM Press 1995), and Abbud and Nilson, "Recombinant Protein Expression in Transgenic Mice," in *Gene Expression Systems: Using Nature for the Art of Expression,* Fernandez and Hoeffler (eds.), pages 367–397 (Academic Press, Inc. 1999)).

For example, a method for producing a transgenic mouse that expresses a mouse Zcytor16 gene can begin with adult, fertile males (studs) (B6C3f1, 2–8 months of age (Taconic Farms, Germantown, N.Y.)), vasectomized males (duds) (B6D2f1, 2–8 months, (Taconic Farms)), prepubescent fertile females (donors) (B6C3f1, 4–5 weeks, (Taconic Farms)) and adult fertile females (recipients) (B6D2f1, 2–4 months, (Taconic Farms)). The donors are acclimated for one week and then injected with approximately 8 IU/mouse of Pregnant Mare's Serum gonadotrophin (Sigma Chemical Company; St. Louis, Mo.) I.P., and 46–47 hours later, 8 IU/mouse of human Chorionic Gonadotropin (hCG (Sigma)) I.P. to induce superovulation. Donors are mated with studs subsequent to hormone injections. Ovulation generally occurs within 13 hours of hCG injection. Copulation is confirmed by the presence of a vaginal plug the morning following mating.

Fertilized eggs are collected under a surgical scope. The oviducts are collected and eggs are released into urinanalysis slides containing hyaluronidase (Sigma). Eggs are washed once in hyaluronidase, and twice in Whitten's W640 medium (described, for example, by Menino and O'Claray, *Biol. Reprod.* 77:159 (1986), and Dienhart and Downs, *Zygote* 4:129 (1996)) that has been incubated with 5% $CO_2$, 5% $O_2$, and 90% $N_2$ at 37° C. The eggs are then stored in a 37° C./5% $CO_2$ incubator until microinjection.

Ten to twenty micrograms of plasmid DNA containing a mouse Zcytor16 encoding sequence is linearized, gel-purified, and resuspended in 10 mM Tris-HCl (pH 7.4), 0.25 mM EDTA (pH 8.0), at a final concentration of 5–10 nanograms per microliter for microinjection. For example, the mouse Zcytor16 encoding sequences can encode a polypeptide comprising the amino acid sequence of SEQ ID NO:38 or SEQ ID NO:48.

Plasmid DNA is microinjected into harvested eggs contained in a drop of W640 medium overlaid by warm, $CO_2$-equilibrated mineral oil. The DNA is drawn into an injection needle (pulled from a 0.75 mm ID, 1 mm OD borosilicate glass capillary), and injected into individual eggs. Each egg is penetrated with the injection needle, into one or both of the haploid pronuclei.

Picoliters of DNA are injected into the pronuclei, and the injection needle withdrawn without coming into contact with the nucleoli. The procedure is repeated until all the eggs are injected. Successfully microinjected eggs are transferred into an organ tissue-culture dish with pre-gassed W640 medium for storage overnight in a 37° C./5% $CO_2$ incubator.

The following day, two-cell embryos are transferred into pseudopregnant recipients. The recipients are identified by the presence of copulation plugs, after copulating with vasectomized duds. Recipients are anesthetized and shaved on the dorsal left side and transferred to a surgical microscope. A small incision is made in the skin and through the muscle wall in the middle of the abdominal area outlined by the ribcage, the saddle, and the hind leg, midway between knee and spleen. The reproductive organs are exteriorized onto a small surgical drape. The fat pad is stretched out over the surgical drape, and a baby serrefine (Roboz, Rockville, Md.) is attached to the fat pad and left hanging over the back of the mouse, preventing the organs from sliding back in.

With a fine transfer pipette containing mineral oil followed by alternating W640 and air bubbles, 12–17 healthy two-cell embryos from the previous day's injection are transferred into the recipient. The swollen ampulla is located and holding the oviduct between the ampulla and the bursa, a nick in the oviduct is made with a 28 g needle close to the bursa, making sure not to tear the ampulla or the bursa.

The pipette is transferred into the nick in the oviduct, and the embryos are blown in, allowing the first air bubble to escape the pipette. The fat pad is gently pushed into the peritoneum, and the reproductive organs allowed to slide in. The peritoneal wall is closed with one suture and the skin closed with a wound clip. The mice recuperate on a 37° C. slide warmer for a minimum of four hours.

The recipients are returned to cages in pairs, and allowed 19–21 days gestation. After birth, 19–21 days postpartum is allowed before weaning. The weanlings are sexed and placed into separate sex cages, and a 0.5 cm biopsy (used for genotyping) is snipped off the tail with clean scissors.

Genomic DNA is prepared from the tail snips using, for example, a QIAGEN DNEASY kit following the manufacturer's instructions. Genomic DNA is analyzed by PCR using primers designed to amplify a mouse Zcytor16 gene or a selectable marker gene that was introduced in the same plasmid. After animals are confirmed to be transgenic, they are back-crossed into an inbred strain by placing a transgenic female with a wild-type male, or a transgenic male with one or two wild-type female(s). As pups are born and weaned, the sexes are separated, and their tails snipped for genotyping.

To check for expression of a transgene in a live animal, a partial hepatectomy is performed. A surgical prep is made of the upper abdomen directly below the zyphoid process. Using sterile technique, a small 1.5–2 cm incision is made below the sternum and the left lateral lobe of the liver exteriorized. Using 4-0 silk, a tie is made around the lower lobe securing it outside the body cavity. An atraumatic clamp is used to hold the tie while a second loop of absorbable Dexon (American Cyanamid; Wayne, N.J.) is placed proximal to the first tie. A distal cut is made from the Dexon tie and approximately 100 mg of the excised liver tissue is placed in a sterile petri dish. The excised liver section is transferred to a 14 ml polypropylene round bottom tube and snap frozen in liquid nitrogen and then stored on dry ice. The surgical site is closed with suture and wound clips, and the animal's cage placed on a 37° C. heating pad for 24 hours post operatively. The animal is checked daily post operatively and the wound clips removed 7–10 days after surgery. The expression level of mouse Zcytor16 MRNA is examined for each transgenic mouse using an RNA solution hybridization assay or polymerase chain reaction.

In addition to producing transgenic mice that over-express mouse Zcytor16, it is useful to engineer transgenic mice with either abnormally low or no expression of the gene. Such transgenic mice provide useful models for diseases associated with a lack of mouse Zcytor16. As discussed above, mouse Zcytor16 gene expression can be inhibited using anti-sense genes, ribozyme genes, or external guide sequence genes. To produce transgenic mice that under-express the mouse Zcytor16 gene, such inhibitory sequences are targeted to mouse Zcytor16 mRNA. Methods for producing transgenic mice that have abnormally low expression of a particular gene are known to those in the art (see, for example, Wu et al., "Gene Underexpression in Cultured Cells and Animals by Antisense DNA and RNA Strategies," in *Methods in Gene Biotechnology*, pages 205–224 (CRC Press 1997)).

An alternative approach to producing transgenic mice that have little or no mouse Zcytor16 gene expression is to generate mice having at least one normal mouse Zcytor16 allele replaced by a nonfunctional mouse Zcytor16 gene. One method of designing a nonfunctional mouse Zcytor16 gene is to insert another gene, such as a selectable marker gene, within a nucleic acid molecule that encodes mouse Zcytor16. Standard methods for producing these so-called "knockout mice" are known to those skilled in the art (see, for example, Jacob, "Expression and Knockout of Interferons in Transgenic Mice," in *Overexpression and Knockout of Cytokines in Transgenic Mice,* Jacob (ed.), pages 111–124 (Academic Press, Ltd. 1994), and Wu et al., "New Strategies for Gene Knockout," in *Methods in Gene Biotechnology,* pages 339–365 (CRC Press 1997)).

13. Therapeutic Uses of Polypeptides having Zcytor16 Activity

Amino acid sequences having mouse Zcytor16 activity can be used to modulate the immune system by binding Zcytor16 ligand, and thus, preventing the binding of Zcytor16 ligand with endogenous Zcytor16 receptor. Zcytor16 antagonists, such as anti-mouse Zcytor16 antibodies, can also be used to modulate the immune system by inhibiting the binding of Zcytor16 ligand with the endogenous Zcytor16 receptor. Accordingly, the present invention includes the use of proteins, polypeptides, and peptides having mouse Zcytor16 activity (such as mouse Zcytor16 polypeptides, mouse Zcytor16 analogs (e.g., anti-mouse Zcytor16 anti-idiotype antibodies), and mouse Zcytor16 fusion proteins) to a subject which lacks an adequate amount of this polypeptide, or which produces an excess of Zcytor16 ligand. Mouse Zcytor16 antagonists (e.g., anti-mouse Zcytor16 antibodies) can be also used to treat a subject that produces an excess of either Zcytor16 ligand or Zcytor16 receptor. Suitable subjects include mammals, such as humans. In addition, human Zcytor16 and IL-TIF activity described herein emphasizes the usefulness of using mouse Zcytor16 in animal models, such as a mouse model described above for studying human inflammation, inflammatory diseases, immune function and diseases and cancer, or assessing therapeutic aspects of IL-TIF, chemical therapeutics, anti-L-TIF antibodies, anti-Zcytor16 antibodies, or Zcytor16 soluble receptors therein.

Moreover, we have shown that the human Zcytor16 receptor binds a ligand called T-cell inducible Factor (IL-TIF) (SEQ ID NO:15) ; Dumoutier, L. et al., *Proc. Nat'l. Acad. Sci.* 97:10144–10149, 2000; mouse IL-TIF sequence (SEQ ID NO:41) is shown in Dumontier et al., *J. Immunol.* 164:1814–1819, 2000). Moreover, commonly owned zcytor11 (U.S. Pat. No. 5,965,704) and CRF2-4 receptor also bind IL-TIF (See, WIPO publication WO 00/24758; Dumontier et al., *J. Immunol.* 164:1814–1819, 2000; Spencer, S D et al., *J. Exp. Med.* 187:571–578, 1998; Gibbs, V C and Pennica Gene 186:97–101, 1997 (CRF2-4 cDNA); Xie, M H et al., *J. Biol. Chem.* 275: 31335–31339, 2000; and Kotenko, S V et al., *J. Biol. Chem.* manuscript in press M007837200). Moreover, IL-10β receptor may be involved as a receptor for IL-TIF, and it is believed to be synonymous with CRF2-4 (Dumoutier, L. et al., *Proc. Nat'l. Acad. Sci.* 97:10144–10149, 2000; Liu Y et al, *J Immunol.* 152; 1821–1829, 1994 (IL-10R cDNA). Within preferred embodiments, the soluble receptor form of mouse Zcytor16, residues 24–230 of SEQ ID NO:38 or SEQ ID NO:48 is a monomer, homodimer, heterodimer, or multimer that antagonizes the effects of IL-TIF in vivo. Antibodies and binding polypeptides to such mouse Zcytor16 monomer, homodimer, heterodimer, or multimers also serve as antagonists of Zcytor16 activity.

IL-TIF has been shown to be induced in the presence of IL-9, and is suspected to be involved in promoting Th1-type immune responses, and inflammation. IL-9 stimulates proliferation, activation, differentiation and/or induction of immune function in a variety of ways and is implicated in asthma, lung mastocytosis, and other diseases, as well as activates STAT pathways. Antagonists of IL-TIF or IL-9 function can have beneficial use against such human diseases. The present invention provides such novel antagonists of IL-TIF.

IL-TIF has been show to be involved in up-regulate the production of acute phase reactants, such as serum amyloid A (SAA), α1-antichymotrypsin, and haptoglobin, and that IL-TIF expression is increased upon injection of lipopolysaccharide (LPS) in vivo suggesting that IL-TIF is involved in inflammatory response (Dumoutier, L. et al., *Proc. Nat'l. Acad. Sci.* 97:10144–10149, 2000). Production of acute phase proteins, such as SAA, is considered s short-term survival mechanism where inflammation is beneficial; however, maintenance of acute phase proteins for longer periods contributes to chronic inflammation and can be harmful to human health. For review, see Uhlar, C M and Whitehead, A S, *Eur. J. Biochem.* 265:501–523, 1999, and Baumann H. and Gauldie, *J. Immunology Today* 15:74–80, 1994. Moreover, the acute phase protein SAA is implicated in the pathogenesis of several chronic inflammatory diseases, is implicated in atherosclerosis and rheumatoid arthritis, and is the precursor to the amyloid A protein deposited in amyloidosis (Uhlar, CM and Whitehead, supra.). Thus, as IL-TIF acts as a pro-inflammatory molecule and induces production of SAA, antagonists would be useful in treating inflammatory disease and other diseases associated with acute phase response proteins induced by IL-TIF. Such antagonists are provided by the present invention. For example, method of reducing IL-TIF-induced or IL-9 induced inflammation comprises administering to a mammal with inflammation an amount of a composition of soluble mouse Zcytor16-comprising receptor sufficient to reduce inflammation. Moreover, a method of suppressing an inflammatory response in a mammal with inflammation can comprise: (1) determining a level of serum amyloid A protein; (2) administering a composition comprising a soluble mouse Zcytor16 cytokine receptor polypeptide as described herein in an acceptable pharmaceutical vehicle; (3) determining a post administration level of serum amyloid A protein; (4) comparing the level of serum amyloid A protein in step (1) to the level of serum amyloid A protein in step (3), wherein a lack of increase or a decrease in serum amyloid A protein level is indicative of suppressing an inflammatory response.

The receptors of the present invention include at least one mouse Zcytor16 receptor subunit. A second receptor polypeptide included in the heterodimeric soluble receptor belongs to the receptor subfamily that includes Interleukin-10 receptor, the interferons (e.g., interferon-gamma alpha and beta chains and the interferon-alpha/beta receptor alpha and beta chains), zcytor7, zcytor11, and CRF2-4. A second soluble receptor polypeptide included in a heterodimeric soluble receptor can also include a zcyto11 soluble receptor subunit, disclosed in the commonly owned U.S. Pat. No. 5,965,704; an IL-10R subunit, such as IL-10Rα; or a zcytor7 soluble receptor subunit, disclosed in the commonly owned U.S. Pat. No. 5,945,511. The zcytor11 receptor in conjunction with CRF2-4 and IL-10 Receptor was shown to signal JAK-STAT pathway in response to IL-TIF (Xie et al., supra.; Kotenko et al., supra.). According to the present invention, in addition to a monomeric or homodimeric mouse Zcytor16 receptor polypeptide, a heterodimeric soluble mouse Zcytor16 receptor, as exemplified by an embodiment comprising a soluble mouse Zcytor16 receptor+soluble CRF2-4 receptor heterodimer (mouse Zcytor16/CRF2-4), can act as an antagonist of the IL-TIF. Other embodiments include soluble heterodimers comprising mouse Zcytor16/IL-10R, mouse Zcytor16/IL-9R, mouse Zcytor16/zcytor11, mouse Zcytor16/zcytor7, and other class II receptor subunits, as well as multimeric receptors including but not limited to mouse Zcytor16/CRF2-4/zcytor11 or mouse Zcytor16/CRF2-4/IL-10R.

Analysis of the tissue distribution of the mRNA corresponding mouse Zcytor16 cDNA was similar to human Zcytor16 tissue dstribution (U.S. patent application Ser. No. 09/728,911), and showed that mRNA was espressed in placenta and spleen, and the ligand to which Zcytor16 binds (IL-TIF) is implicated in inducing inflammatory response including induction of the acute-phase response (Dumoutier, L. et al., *Proc. Nat'l. Acad. Sci.* 97:10144–10149, 2000). Thus, particular embodiments of the present invention are directed toward use of soluble mouse Zcytor16 heterodimers as antagonists in inflammatory and immune diseases or conditions such as pancreatitis, type I diabetes (IDDM), pancreatic cancer, pancreatitis, Graves Disease, inflammatory bowel disease (IBD), Crohn's Disease, colon and intestinal cancer, diverticulosis, autoimmune disease, sepsis, organ or bone marrow transplant; inflammation due to trauma, sugery or infection; amyloidosis; splenomegaly; graft versus host disease; and where inhibition of inflammation, immune suppression, reduction of proliferation of hematopoietic, immune, inflammatory or lymphoid cells, macrophages, T-cells (including Th1 and Th2 cells), suppression of immune response to a pathogen or antigen, or other instances where inhibition of IL-TIF or IL-9 cytokine production is desired.

Moreover, antibodies or binding polypeptides that bind mouse Zcytor16 polypeptides, monomers, homodimers, heterodimers and multimers described herein and/or mouse Zcytor16 polypeptides, monomers, homodimers, heterodimers and multimers themselves are useful to:

1) Antagonize or block signaling via the IL-TIF receptors in the treatment of acute inflammation, inflammation as a result of trauma, tissue injury, surgery, sepsis or infection, and chronic inflammatory diseases such as asthma, inflammatory bowel disease (IBD), chronic colitis, splenomegaly, rheumatoid arthritis, recurrent acute inflammatory episodes (e.g., tuberculosis), and treatment of amyloidosis, and atherosclerosis, Castleman's Disease, asthma, and other diseases associated with the induction of acute-phase response.

2) Antagonize or block signaling via the IL-TIF receptors in the treatment of autoimmune diseases such as IDDM, multiple sclerosis (MS), systemic Lupus erythematosus (SLE), myasthenia gravis, rheumatoid arthritis, and IBD to prevent or inhibit signaling in immune cells (e.g. lymphocytes, monocytes, leukocytes) via mouse Zcytor16 (Hughes C et al., *J. Immunol* 153: 3319–3325, 1994). Alternatively antibodies, such as monoclonal antibodies (MAb) to mouse Zcytor16-comprising receptors, can also be used as an antagonist to deplete unwanted immune cells to treat autoimmune disease. Asthma, allergy and other atopic disease may be treated with an MAb against, for example, soluble mouse Zcytor16 soluble receptors or mouse Zcytor16/CRF2-4 heterodimers, to inhibit the immune response or to deplete offending cells. Blocking or inhibiting signaling via Zcytor16, using the polypeptides and antibodies of the present invention, may also benefit diseases of the pancreas, kidney, pituitary and neuronal cells. IDDM, NIDDM, pancreatitis, and pancreatic carcinoma may benefit. Mouse Zcytor16 may serve as a target for MAb therapy of cancer where an antagonizing MAb inhibits cancer growth and targets immune-mediated killing. (Holliger P, and Hoogenboom, H: *Nature Biotech.* 16: 1015–1016, 1998). Mabs to soluble mouse Zcytor16 monomers, homodimers, heterodimers and multimers may also be useful to treat nephropathies such as glomerulosclerosis, membranous neuropathy, amyloidosis (which also affects the kidney among other tissues), renal arteriosclerosis, glomerulonephritis of various origins, fibroproliferative diseases of the kidney, as well as kidney dysfunction associated with SLE, IDDM, type II diabetes (NIDDM), renal tumors and other diseases.

3) Agonize or initiate signaling via the IL-TIF receptors in the treatment of autoimmune diseases such as IDDM, MS, SLE, myasthenia gravis, rheumatoid arthritis, and IBD. Anti-soluble mouse Zcytor16, anti-soluble mouse Zcytor16/CRF2-4 heterodimers and multimer monoclonal antibodies may signal lymphocytes or other immune cells to differentiate, alter proliferation, or change production of cytokines or cell surface proteins that ameliorate autoimmunity. Specifically, modulation of a T-helper cell response to an alternate pattern of cytokine secretion may deviate an autoimmune response to ameliorate disease (Smith J A et al., *J. Immunol.* 160:4841–4849, 1998). Similarly, agonistic Anti-soluble mouse Zcytor16, anti-solublemouse Zcytor16/CRF2-4 heterodimers and multimer monoclonal antibodies may be used to signal, deplete and deviate immune cells involved in asthma, allergy and atopoic disease. Signaling via mouse Zcytor16 may also benefit diseases of the pancreas, kidney, pituitary and neuronal cells. IDDM, NIDDM, pancreatitis, and pancreatic carcinoma may benefit. mouse Zcytor16 may serve as a target for MAb therapy of pancreatic cancer where a signaling MAb inhibits cancer growth and targets immunemediated killing (Tutt, A L et al., *J Immunol.* 161: 3175–3185, 1998). Similarly renal cell carcinoma may be treated with monoclonal antibodies to mouse Zcytor16-comprising soluble receptors of the present invention.

Soluble mouse Zcytor16 monomeric, homodimeric, heterodimeric and multimeric polypeptides described herein can be used to neutralize/block IL-TIF activity in the treatment of autoimmune disease, atopic disease, NIDDM, pancreatitis and kidney dysfunction as described above. A soluble form of mouse Zcytor16 may be used to promote an antibody response mediated by Th cells and/or to promote the production of IL-4 or other cytokines by lymphocytes or other immune cells.

The soluble mouse Zcytor16-comprising receptors of the present invention are useful as antagonists of the IL-TIF cytokine. Such antagonistic effects can be achieved by direct neutralization or binding of the IL-TIF. In addition to antagonistic uses, the soluble receptors of the present invention can bind IL-TIF and act as carrier proteins for the IL-TIF cytokine, in order to transport the Ligand to different tissues, organs, and cells within the body. As such, the soluble receptors of the present invention can be fused or coupled to molecules, polypeptides or chemical moieties that direct the soluble-receptor-Ligand complex to a specific site, such as a tissue, specific immune cell, or tumor. For example, in acute infection or some cancers, benefit may result from induction of inflammation and local acute phase response proteins by the action of IL-TIF. Thus, the soluble receptors of the present invention can be used to specifically direct the action of the IL-TIF. See, Cosman, D. *Cytokine* 5:95–106, 1993; and Fernandez-Botran, R. *Exp. Opin. Invest. Drugs* 9:497–513, 2000.

Moreover, the soluble receptors of the present invention can be used to stabilize the IL-TIF, to increase the bioavailability, therapeutic longevity, and/or efficacy of the Ligand by stabilizing the Ligand from degradation or clearance, or by targeting the ligand to a site of action within the body. For example the naturally occurring IL-6/soluble IL-6R complex stabilizes IL-6 and can signal through the gp103 receptor. See, Cosman, D. supra., and Fernandez-Botran, R. supra. Moreover, mouse Zcytor16 may be combined with a cognate ligand such as IL-TIF to comprise a ligand/soluble receptor complex. Such complexes may be used to stimulate responses from cells presenting a companion receptor subunit such as, for example, zcytor11 or CRF2-4. The cell specificity of mouse Zcytor16/ligand complexes may differ from that seen for the ligand administered alone. Furthermore the complexes may have distinct pharmacokinetic properties such as affecting half-life, dose/response and organ or tissue specificity. ZcytoR16/IL-TIF complexes thus may have agonist activity to enhance an immune response or stimulate mesangial cells or to stimulate hepatic cells. Alternatively only tissues expressing a signaling subunit the heterodimerizes with the complex may be affected analogous to the response to IL6/IL6R complexes (Hirota H. et al., *Proc. Nat'l. Acad. Sci.* 92:4862–4866, 1995; Hirano, T. in Thomason, A. (Ed.) "The Cytokine Handbook", $3^{rd}$ Ed., p. 208–209). Soluble receptor/cytokine complexes for IL12 and CNTF display similar activities.

Mouse Zcytor16 homodimeric, heterodimeric and multimeric receptor polypeptides may also be used within diagnostic systems for the detection of circulating levels of IL-TIF ligand, and in the detection of IL-TIF associated with acute phase inflammatory response. Within a related embodiment, antibodies or other agents that bind to mouse Zcytor16 soluble receptors of the present invention can be used to detect circulating receptor polypeptides; conversely, mouse Zcytor16 soluble receptors themselves can be used to detect circulating or locally-acting IL-TIF polypeptides. Elevated or depressed levels of ligand or receptor polypeptides may be indicative of pathological conditions, including inflammation or cancer. IL-TIF is known to induce associated acute phase inflammatory response. Moreover, detection of acute phase proteins or molecules such as IL-TIF can be indicative of a chronic inflammatory condition in certain disease states (e.g., rheumatoid arthritis). Detection of such conditions serves to aid in disease diagnosis as well as help a physician in choosing proper therapy.

Moreover, soluble mouse Zcytor16 receptor polypeptides of the present invention can be used as a "ligand sink," i.e., antagonist, to bind ligand in vivo or in vitro in therapeutic or other applications where the presence of the ligand is not desired. For example, in chronic inflammatory conditions or cancers that are expressing large amounts of bioactive IL-TIF, soluble mouse Zcytor16 receptor or soluble mouse Zcytor16 heterodimeric and multimeric receptor polypeptides, such as soluble mouse Zcytor16/CRF2-4 can be used as a direct antagonist of the ligand in vivo, and may aid in reducing progression and symptoms associated with the disease, and can be used in conjunction with other therapies (e.g., steroid or chemotherapy) to enhance the effect of the therapy in reducing progression and symptoms, and preventing relapse. Moreover, soluble mouse Zcytor16 receptor polypeptides can be used to slow the progression of cancers that over-express Zcytor16 receptors, by binding ligand in vivo that could otherwise enhance proliferation of those cancers.

Moreover, soluble mouse Zcytor16 receptor polypeptides of the present invention can be used in vivo or in diagnostic applications to detect IL-TIF-expressing inflammation or cancers in vivo or in tissue samples. For example, the soluble mouse Zcytor16 receptors of the present invention can be conjugated to a radio-label or fluorescent label as described herein, and used to detect the presence of the IL-TIF in a tissue sample using an in vitro ligand-receptor type binding assay, or fluorescent imaging assay. Moreover, radiolabeled soluble mouse Zcytor16 receptors of the present invention could be administered in vivo to detect Ligand-expressing solid tumors through a radio-imaging method known in the art.

Generally, the dosage of administered mouse Zcytor16 (or mouse Zcytor16 analog or fusion protein) will vary depending upon such factors as the patient's age, weight, height, sex, general medical condition and previous medical history. Typically, it is desirable to provide the recipient with a dosage of mouse Zcytor16 polypeptide which is in the range of from about 1 pg/kg to 10 mg/kg (amount of agent/body weight of patient), although a lower or higher dosage also may be administered as circumstances dictate.

Administration of a mouse Zcytor16 polypeptide to a subject can be intravenous, intraarterial, intraperitoneal, intramuscular, subcutaneous, intrapleural, intrathecal, by perfusion through a regional catheter, or by direct intralesional injection. When administering therapeutic proteins by injection, the administration may be by continuous infusion or by single or multiple boluses.

Additional routes of administration include oral, mucosal-membrane, pulmonary, and transcutaneous. Oral delivery is suitable for polyester microspheres, zein microspheres, proteinoid microspheres, polycyanoacrylate microspheres, and lipid-based systems (see, for example, DiBase and Morrel, "Oral Delivery of Microencapsulated Proteins," in *Protein Delivery: Physical Systems,* Sanders and Hendren (eds.), pages 255–288 (Plenum Press 1997)). The feasibility of an intranasal delivery is exemplified by such a mode of insulin administration (see, for example, Hinchcliffe and Illum, *Adv. Drug Deliv. Rev.* 35:199 (1999)). Dry or liquid particles comprising mouse Zcytor16 can be prepared and inhaled with the aid of dry-powder dispersers, liquid aerosol generators, or nebulizers (e.g., Pettit and Gombotz, *TIBTECH* 16:343 (1998); Patton et al., *Adv. Drug Deliv. Rev.* 35:235 (1999)). This approach is illustrated by the AERX diabetes management system, which is a hand-held electronic inhaler that delivers aerosolized insulin into the lungs. Studies have shown that proteins as large as 48,000 kDa have been delivered across skin at therapeutic concentrations with the aid of low-frequency ultrasound, which illustrates the feasibility of trascutaneous administration (Mitragotri et al., *Science* 269:850 (1995)). Transdermal delivery using electroporation provides another means to administer a molecule having mouse Zcytor16 binding activity (Potts et al., *Pharm. Biotechnol.* 10:213 (1997)).

A pharmaceutical composition comprising a protein, polypeptide, or peptide having mouse Zcytor16 binding activity can be formulated according to known methods to prepare pharmaceutically useful compositions, whereby the therapeutic proteins are combined in a mixture with a pharmaceutically acceptable carrier. A composition is said to be a "pharmaceutically acceptable carrier" if its administration can be tolerated by a recipient patient. Sterile phosphate-buffered saline is one example of a pharmaceutically acceptable carrier. Other suitable carriers are well-known to those in the art. See, for example, Gennaro (ed.), *Remington's Pharmaceutical Sciences,* 19th Edition (Mack Publishing Company 1995).

For purposes of therapy, molecules having mouse Zcytor16 binding activity and a pharmaceutically acceptable carrier are administered to a patient in a therapeutically effective amount. A combination of a protein, polypeptide, or peptide having mouse Zcytor16 binding activity and a pharmaceutically acceptable carrier is said to be administered in a "therapeutically effective amount" if the amount administered is physiologically significant. An agent is physiologically significant if its presence results in a detectable change in the physiology of a recipient patient. For example, an agent used to treat inflammation is physiologically significant if its presence alleviates the inflammatory response.

A pharmaceutical composition comprising mouse Zcytor16 (or mouse Zcytor16 analog or fusion protein) can be furnished in liquid form, in an aerosol, or in solid form.

Liquid forms, are illustrated by injectable solutions and oral suspensions. Exemplary solid forms include capsules, tablets, and controlled-release forms. The latter form is illustrated by miniosmotic pumps and implants (Bremer et al., *Pharm. Biotechnol.* 10:239 (1997); Ranade, "Implants in Drug Delivery," in *Drug Delivery Systems*, Ranade and Hollinger (eds.), pages 95–123 (CRC Press 1995); Bremer et al., "Protein Delivery with Infusion Pumps," in *Protein Delivery: Physical Systems*, Sanders and Hendren (eds.), pages 239–254 (Plenum Press 1997); Yewey et al., "Delivery of Proteins from a Controlled Release Injectable Implant," in *Protein Delivery: Physical Systems*, Sanders and Hendren (eds.), pages 93–117 (Plenum Press 1997)).

Liposomes provide one means to deliver therapeutic polypeptides to a subject intravenously, intraperitoneally, intrathecally, intramuscularly, subcutaneously, or via oral administration, inhalation, or intranasal administration. Liposomes are microscopic vesicles that consist of one or more lipid bilayers surrounding aqueous compartments (see, generally, Bakker-Woudenberg et al., *Eur. J. Clin. Microbiol. Infect. Dis.* 12 (*Suppl.* 1):S61 (1993), Kim, *Drugs* 46:618 (1993), and Ranade, "Site-Specific Drug Delivery Using Liposomes as Carriers," in *Drug Delivery Systems*, Ranade and Hollinger (eds.), pages 3–24 (CRC Press 1995)). Liposomes are similar in composition to cellular membranes and as a result, liposomes can be administered safely and are biodegradable. Depending on the method of preparation, liposomes may be unilamellar or multilamellar, and liposomes can vary in size with diameters ranging from 0.02 µm to greater than 10 µm. A variety of agents can be encapsulated in liposomes: hydrophobic agents partition in the bilayers and hydrophilic agents partition within the inner aqueous space(s) (see, for example, Machy et al., *Liposomes In Cell Biology And Pharmacology* (John Libbey 1987), and Ostro et al., *American J. Hosp. Pharm.* 46:1576 (1989)). Moreover, it is possible to control the therapeutic availability of the encapsulated agent by varying liposome size, the number of bilayers, lipid composition, as well as the charge and surface characteristics of the liposomes.

Liposomes can adsorb to virtually any type of cell and then slowly release the encapsulated agent. Alternatively, an absorbed liposome may be endocytosed by cells that are phagocytic. Endocytosis is followed by intralysosomal degradation of liposomal lipids and release of the encapsulated agents (Scherphof et al., *Ann. N.Y. Acad. Sci.* 446:368 (1985)). After intravenous administration, small liposomes (0.1 to 1.0 µm) are typically taken up by cells of the reticuloendothelial system, located principally in the liver and spleen, whereas liposomes larger than 3.0 µm are deposited in the lung. This preferential uptake of smaller liposomes by the cells of the reticuloendothelial system has been used to deliver chemotherapeutic agents to macrophages and to tumors of the liver.

The reticuloendothelial system can be circumvented by several methods including saturation with large doses of liposome particles, or selective macrophage inactivation by pharmacological means (Claassen et al., *Biochim. Biophys. Acta* 802:428 (1984)). In addition, incorporation of glycolipid- or polyethelene glycol-derivatized phospholipids into liposome membranes has been shown to result in a significantly reduced uptake by the reticuloendothelial system (Allen et al., *Biochim. Biophys. Acta* 1068:133 (1991); Allen et al., *Biochim. Biophys. Acta* 1150:9 (1993)).

Liposomes can also be prepared to target particular cells or organs by varying phospholipid composition or by inserting receptors or ligands into the liposomes. For example, liposomes, prepared with a high content of a nonionic surfactant, have been used to target the liver (Hayakawa et al., Japanese Patent 04-244,018; Kato et al., *Biol. Pharm. Bull.* 16:960 (1993)). These formulations were prepared by mixing soybean phospatidylcholine, α-tocopherol, and ethoxylated hydrogenated castor oil (HCO-60) in methanol, concentrating the mixture under vacuum, and then reconstituting the mixture with water. A liposomal formulation of dipalmitoylphosphatidylcholine (DPPC) with a soybean-derived sterylglucoside mixture (SG) and cholesterol (Ch) has also been shown to target the liver (Shimizu et al., *Biol. Pharm. Bull.* 20:881 (1997)).

Alternatively, various targeting ligands can be bound to the surface of the liposome, such as antibodies, antibody fragments, carbohydrates, vitamins, and transport proteins. For example, liposomes can be modified with branched type galactosyllipid derivatives to target asialoglycoprotein (galactose) receptors, which are exclusively expressed on the surface of liver cells (Kato and Sugiyama, *Crit. Rev. Ther. Drug Carrier Syst.* 14:287 (1997); Murahashi et al., *Biol. Pharm. Bull.* 20:259 (1997)). Similarly, Wu et al., *Hepatology* 27:772 (1998), have shown that labeling liposomes with asialofetuin led to a shortened liposome plasma half-life and greatly enhanced uptake of asialofetuin-labeled liposome by hepatocytes. On the other hand, hepatic accumulation of liposomes comprising branched type galactosyllipid derivatives can be inhibited by preinjection of asialofetuin (Murahashi et al., *Biol. Pharm. Bull.* 20:259 (1997)). Polyaconitylated human serum albumin liposomes provide another approach for targeting liposomes to liver cells (Kamps et al., *Proc. Nat'l Acad. Sci. USA* 94:11681 (1997)). Moreover, Geho, et al. U.S. Pat. No. 4,603,044, describe a hepatocyte-directed liposome vesicle delivery system, which has specificity for hepatobiliary receptors associated with the specialized metabolic cells of the liver.

In a more general approach to tissue targeting, target cells are prelabeled with biotinylated antibodies specific for a ligand expressed by the target cell (Harasym et al., *Adv. Drug Deliv. Rev.* 32:99 (1998)). After plasma elimination of free antibody, streptavidin-conjugated liposomes are administered. In another approach, targeting antibodies are directly attached to liposomes (Harasym et al., *Adv. Drug Deliv. Rev.* 32:99 (1998)).

Polypeptides having mouse Zcytor16 binding activity can be encapsulated within liposomes using standard techniques of protein microencapsulation (see, for example, Anderson et al., *Infect. Immun.* 31:1099 (1981), Anderson et al., *Cancer Res.* 50:1853 (1990), and Cohen et al., *Biochim. Biophys. Acta* 1063:95 (1991), Alving et al. "Preparation and Use of Liposomes in Immunological Studies," in *Liposome Technology,* 2nd Edition, Vol. III, Gregoriadis (ed.), page 317 (CRC Press 1993), Wassef et al., *Meth. Enzymol.* 149:124 (1987)). As noted above, therapeutically useful liposomes may contain a variety of components. For example, liposomes may comprise lipid derivatives of poly (ethylene glycol) (Allen et al., *Biochim. Biophys. Acta* 1150:9 (1993)).

Degradable polymer microspheres have been designed to maintain high systemic levels of therapeutic proteins. Microspheres are prepared from degradable polymers such as poly(lactide-co-glycolide) (PLG), polyanhydrides, poly (ortho esters), nonbiodegradable ethylvinyl acetate polymers, in which proteins are entrapped in the polymer (Gombotz and Pettit, *Bioconjugate Chem.* 6:332 (1995); Ranade, "Role of Polymers in Drug Delivery," in *Drug Delivery Systems,* Ranade and Hollinger (eds.), pages 51–93 (CRC Press 1995); Roskos and Maskiewicz, "Degradable Controlled Release Systems Useful for Protein Delivery," in

*Protein Delivery: Physical Systems,* Sanders and Hendren (eds.), pages 45–92 (Plenum Press 1997); Bartus et al., *Science* 281:1161 (1998); Putney and Burke, *Nature Biotechnology* 16:153 (1998); Putney, *Curr. Opin. Chem. Biol.* 2:548 (1998)). Polyethylene glycol (PEG)-coated nanospheres can also provide carriers for intravenous administration of therapeutic proteins (see, for example, Gref et al., *Pharm. Biotechnol.* 10:167 (1997)).

The present invention also contemplates chemically modified polypeptides having binding mouse Zcytor16 activity such as mouse Zcytor16 monomeric, homodimeric, heterodimeric or multimeric soluble receptors, and mouse Zcytor16 antagonists, for example anti-mouse Zcytor16 antibodies or binding polypeptides, which a polypeptide is linked with a polymer, as discussed above.

Other dosage forms can be devised by those skilled in the art, as shown, for example, by Ansel and Popovich, *Pharmaceutical Dosage Forms and Drug Delivery Systems,* 5th Edition (Lea & Febiger 1990), Gennaro (ed.), *Remington's Pharmaceutical Sciences,* 19th Edition (Mack Publishing Company 1995), and by Ranade and Hollinger, *Drug Delivery Systems* (CRC Press 1996).

As an illustration, pharmaceutical compositions may be supplied as a kit comprising a container that comprises a polypeptide with a mouse Zcytor16 extracellular domain, e.g., mouse Zcytor16 monomeric, homodimeric, heterodimeric or multimeric soluble receptors, or a mouse Zcytor16 antagonist (e.g., an antibody or antibody fragment that binds a mouse Zcytor16 polypeptide). Therapeutic polypeptides can be provided in the form of an injectable solution for single or multiple doses, or as a sterile powder that will be reconstituted before injection. Alternatively, such a kit can include a dry-powder disperser, liquid aerosol generator, or nebulizer for administration of a therapeutic polypeptide. Such a kit may further comprise written information on indications and usage of the pharmaceutical composition. Moreover, such information may include a statement that the mouse Zcytor16 composition is contraindicated in patients with known hypersensitivity to mouse Zcytor16.

Polynucleotides and polypeptides of the present invention will additionally find use as educational tools as a laboratory practicum kits for courses related to genetics and molecular biology, protein chemistry and antibody production and analysis. Due to its unique polynucleotide and polypeptide sequence molecules of mouse Zcytor16 can be used as standards or as "unknowns" for testing purposes. For example, mouse Zcytor16 polynucleotides can be used as an aid, such as, for example, to teach a student how to prepare expression constructs for bacterial, viral, and/or mammalian expression, including fusion constructs, wherein mouse Zcytor16 is the gene to be expressed; for determining the restriction endonuclease cleavage sites of the polynucleotides; determining mRNA and DNA localization of mouse Zcytor16 polynucleotides in tissues (i.e., by Northern and Southern blotting as well as polymerase chain reaction); and for identifying related polynucleotides and polypeptides by nucleic acid hybridization.

Mouse Zcytor16 polypeptides can be used educationally as an aid to teach preparation of antibodies; identifying proteins by Western blotting; protein purification; determining the weight of expressed mouse Zcytor16 polypeptides as a ratio to total protein expressed; identifying peptide cleavage sites; coupling amino and carboxyl terminal tags; amino acid sequence analysis, as well as, but not limited to monitoring biological activities of both the native and tagged protein (i.e., receptor binding, signal transduction, proliferation, and differentiation) in vitro and in vivo. mouse Zcytor16 polypeptides can also be used to teach analytical skills such as mass spectrometry, circular dichroism to determine conformation, especially of the four alpha helices, x-ray crystallography to determine the three-dimensional structure in atomic detail, nuclear magnetic resonance spectroscopy to reveal the structure of proteins in solution. For example, a kit containing the mouse Zcytor16 can be given to the student to analyze. Since the amino acid sequence would be known by the professor, the specific protein can be given to the student as a test to determine the skills or develop the skills of the student, the teacher would then know whether or not the student has correctly analyzed the polypeptide. Since every polypeptide is unique, the educational utility of mouse Zcytor16 would be unique unto itself.

Moreover, since mouse Zcytor16 has a tissue-specific expression and is a polypeptide with a class II cytokine receptor structure and a distinct expression pattern, activity can be measured using proliferation assays; luciferase and binding assays described herein. Moreover, expression of mouse Zcytor16 polynucleotides and polypeptides in lymphoid and other tissues can be analyzed in order to train students in the use of diagnostic and tissue-specific identification and methods. Moreover mouse Zcytor16 polynucleotides can be used to train students on the use of chromosomal detection and diagnostic methods. Such assays are well known in the art, and can be used in an educational setting to teach students about cytokine receptor proteins and examine different properties, such as cellular effects on cells, enzyme kinetics, varying antibody binding affinities, tissue specificity, and the like, between mouse Zcytor16 and other cytokine receptor polypeptides in the art.

The antibodies which bind specifically to mouse Zcytor16 can be used as a teaching aid to instruct students how to prepare affinity chromatography columns to purify mouse Zcytor16, cloning and sequencing the polynucleotide that encodes an antibody and thus as a practicum for teaching a student how to design humanized antibodies. Moreover, antibodies which bind specifically to mouse Zcytor16 can be used as a teaching aid for use in detection e.g., of activated CD91+ cells, cell sorting, or ovarian cancer tissue using histological, and in situ methods amongst others known in the art. The mouse Zcytor16 gene, polypeptide or antibody would then be packaged by reagent companies and sold to universities and other educational entities so that the students gain skill in art of molecular biology. Because each gene and protein is unique, each gene and protein creates unique challenges and learning experiences for students in a lab practicum. Such educational kits containing the mouse Zcytor16 gene, polypeptide or antibody are considered within the scope of the present invention.

Within one aspect, the present invention provides an isolated polypeptide, comprising at least 15 contiguous amino acid residues of an amino acid sequence of SEQ ID NO:38 or SEQ ID NO:48 selected from the group consisting of: an amino acid sequence of SEQ ID NO:38 or SEQ ID NO:48 selected from the group consisting of: (a) amino acid residues 24 to 230; (b) amino acid residues 27 to 230; (c) amino acid residues 27 to 126; and (d) amino acid residues 131 to 230. In one embodiment, the isolated polypeptide disclosed above comprises an amino acid sequence of SEQ ID NO:38 or SEQ ID NO:48 selected from the group consisting of: (a) amino acid residues 24 to 230; (b) amino acid residues 27 to 230; (c) amino acid residues 27 to 126; and (d) amino acid residues 131 to 230. In another embodiment, the isolated polypeptide disclosed above consists of an amino acid sequence of SEQ ID NO:38 or SEQ ID NO:48 selected from the group consisting of: (a) amino acid residues 24 to 230; (b) amino acid residues 27 to 230; (c) amino acid residues 27 to 126; and (d) amino acid residues 131 to 230. In another embodiment, the isolated polypeptide disclosed above comprises an amino acid sequence that is at least 90% identical to a reference amino acid sequence of SEQ ID NO:38 or SEQ ID NO:48 selected from the group consisting of: (a) amino acid residues 24 to 230; (b) amino acid residues 27 to 230; (c) amino acid residues 27 to 126; and (d) amino acid residues 131 to 230. In another embodiment, the isolated polypeptide disclosed above comprises an amino acid sequence of SEQ ID NO:38 or SEQ ID NO:48 selected from the group consisting of: (a) amino acid residues 24 to 230; (b) amino acid residues 27 to 230; (c) amino acid residues 27 to 126; and (d) amino acid residues 131 to 230.

Within a second aspect, the present invention provides an isolated nucleic acid molecule, wherein the nucleic acid molecule is either (a) a nucleic acid molecule comprising the nucleotide sequence of SEQ ID NO:39 or SEQ ID NO:49, or (b) a nucleic acid molecule that remains hybridized following stringent wash conditions to a nucleic acid molecule consisting of the nucleotide sequence of nucleotides 8 to 697 or 77 to 697 or 86 to 697 of SEQ ID NO:37 or SEQ ID NO:47, or the complement of the nucleotide sequence of nucleotides 8 to 697 or 77 to 697 or 86 to 697 of SEQ ID NO:37 or SEQ ID NO:47. In one embodiment, the isolated nucleic acid molecule is as disclosed above, wherein any difference between the amino acid sequence encoded by the nucleic acid molecule and the corresponding amino acid sequence of SEQ ID NO:38 or SEQ ID NO:48 is due to a conservative amino acid substitution. In another embodiment, the isolated nucleic acid molecule disclosed above comprises the nucleotide sequence of nucleotides 8 to 697 or 77 to 697 or 86 to 697 of SEQ ID NO:37 or SEQ ID NO:47.

Within a third aspect, the present invention provides a vector, comprising the isolated nucleic acid molecule as disclosed above.

Within another aspect, the present invention provides an expression vector, comprising the isolated nucleic acid molecule as disclosed above, a transcription promoter, and a transcription terminator, wherein the promoter is operably linked with the nucleic acid molecule, and wherein the nucleic acid molecule is operably linked with the transcription terminator.

Within another aspect, the present invention provides a recombinant host cell comprising the expression vector as disclosed above, wherein the host cell is selected from the group consisting of bacterium, yeast cell, fungal cell, insect cell, mammalian cell, and plant cell.

Within another aspect, the present invention provides a method of producing mouse Zcytor16 protein, the method comprising culturing recombinant host cells that comprise the expression vector as disclosed above, and that produce the mouse Zcytor16 protein. In one embodiment, the method disclosed above further comprises isolating the mouse Zcytor16 protein from the cultured recombinant host cells.

Within another aspect, the present invention provides an antibody or antibody fragment that binds with the polypeptide as disclosed above. In one embodiment, the antibody disclosed above is selected from the group consisting of: (a) polyclonal antibody, (b) murine monoclonal antibody, (c) humanized antibody derived from (b), and (d) human monoclonal antibody.

Within another aspect, the present invention provides an anti-idiotype antibody that specifically binds with the antibody as disclosed above.

Within another aspect, the present invention provides a fusion protein, comprising the polypeptide as disclosed above. In one embodiment, the fusion protein disclosed above further comprises an immunoglobulin moiety.

Within another aspect, the present invention provides an isolated polynucleotide that encodes a soluble cytokine receptor polypeptide comprising a sequence of amino acid residues that is at least 90% identical to the amino acid sequence as shown in SEQ ID NO:38 or SEQ ID NO:48 from amino acid 24 to 230, or 27 to 230; and wherein amino acid differences consist of conservative amino acid substitutions; and wherein the soluble cytokine receptor polypeptide encoded by the polynucleotide sequence binds IL-TIF or antagonizes IL-TIF activity. In one embodiment, the isolated polynucleotide is as disclosed above, wherein the soluble cytokine receptor polypeptide encoded by the polynucleotide forms a homodimeric, heterodimeric or multimeric receptor complex. In another embodiment, the isolated polynucleotide is as disclosed above, wherein the soluble cytokine receptor polypeptide encoded by the polynucleotide forms a heterodimeric or multimeric receptor complex further comprising a soluble Class I or Class II cytokine receptor. In another embodiment, the isolated polynucleotide is as disclosed above, wherein the soluble cytokine receptor polypeptide encoded by the polynucleotide forms a heterodimeric or multimeric receptor complex further comprising a soluble CRF2-4 receptor polypeptide (SEQ ID NO:35), a soluble IL-10 receptor polypeptide (SEQ ID NO:36), or soluble zcytor11 receptor polypeptide (SEQ ID NO:34).

Within another aspect, the present invention provides an isolated polynucleotide that encodes a soluble cytokine receptor polypeptide comprising a sequence of amino acid residues as shown in SEQ ID NO:38 or SEQ ID NO:48 from amino acid 24 to 230, or 27 to 230, wherein the soluble cytokine receptor polypeptide encoded by the polynucleotide forms a homodimeric, heterodimeric or multimeric receptor complex. In one embodiment, the isolated polynucleotide is as disclosed above, wherein the soluble cytokine receptor polypeptide encoded by the polynucleotide further comprises a soluble Class I or Class II cytokine receptor. In another embodiment, the isolated polynucleotide is as disclosed above, wherein the soluble cytokine receptor polypeptide encoded by the polynucleotide forms a heterodimeric or multimeric receptor complex further comprising a soluble CRF2-4 receptor polypeptide (SEQ ID NO:35), a soluble IL-10 receptor polypeptide (SEQ ID NO:36), or soluble zcytor11 receptor polypeptide (SEQ ID NO:34). In another embodiment, the isolated polynucleotide is as disclosed above, wherein the soluble cytokine receptor polypeptide further encodes an intracellular domain. In another embodiment, the isolated polynucleotide is as disclosed above, wherein the soluble cytokine receptor polypeptide further comprises an affinity tag.

Within another aspect, the present invention provides an expression vector comprising the following operably linked elements: (a) a transcription promoter; a first DNA segment encoding a soluble cytokine receptor polypeptide having an amino acid sequence as shown in SEQ ID NO:38 or SEQ ID NO:48 from amino acid 24 to 230, or 27 to 230; and a transcription terminator; and (b) a second transcription promoter; a second DNA segment encoding a soluble Class I or Class II cytokine receptor polypeptide; and a transcription terminator; and wherein the first and second DNA segments are contained within a single expression vector or are contained within independent expression vectors. In one embodiment, the expression vector disclosed above further comprises a secretory signal sequence operably linked to the first and second DNA segments. In another embodiment, the expression vector is as disclosed above, wherein the second DNA segment encodes a polypeptide comprising a soluble CRF2-4 receptor polypeptide (SEQ ID NO:35), a soluble IL-10 receptor polypeptide (SEQ ID NO:36), or soluble zcytor11 receptor polypeptide (SEQ ID NO:34).

Within another aspect, the present invention provides a cultured cell comprising an expression vector as disclosed above, wherein the cell expresses the polypeptides encoded by the DNA segments. In one embodiment, the cultured cell comprising an expression vector is as disclosed above, wherein the first and second DNA segments are located on independent expression vectors and are co-transfected into the cell, and cell expresses the polypeptides encoded by the DNA segments. In another embodiment, the cultured cell comprising an expression vector is as disclosed above, wherein the cell expresses a heterodimeric or multimeric soluble receptor polypeptide encoded by the DNA segments. In another embodiment, the cell disclosed above secretes a soluble cytokine receptor polypeptide heterodimer or multimeric complex. In another embodiment, the cell disclosed above secretes a soluble cytokine receptor polypeptide heterodimer or multimeric complex that binds IL-TIF or antagonizes IL-TIF activity.

Within another aspect, the present invention provides a DNA construct encoding a fusion protein comprising: a first DNA segment encoding a polypeptide having a sequence of amino acid residues as shown in SEQ ID NO:38 or SEQ ID NO:48 from amino acid 24 to 230, or 27 to 230; and at least one other DNA segment encoding a soluble Class I or Class II cytokine receptor polypeptide, wherein the first and other DNA segments are connected in-frame; and wherein the first and other DNA segments encode the fusion protein. In one embodiment, the DNA construct encoding a fusion protein is as disclosed above, wherein at least one other DNA segment encodes a polypeptide comprising a soluble CRF2-4 receptor polypeptide (SEQ ID NO:35), a soluble IL-10 receptor polypeptide (SEQ ID NO:36), or soluble zcytor11 receptor polypeptide (SEQ ID NO:34).

Within another aspect, the present invention provides an expression vector comprising the following operably linked elements: a transcription promoter; a DNA construct encoding a fusion protein as disclosed above; and a transcription terminator, wherein the promoter is operably linked to the DNA construct, and the DNA construct is operably linked to the transcription terminator.

Within another aspect, the present invention provides a cultured cell comprising an expression vector as disclosed above, wherein the cell expresses a polypeptide encoded by the DNA construct.

Within another aspect, the present invention provides a method of producing a fusion protein comprising: culturing a cell according as disclosed above; and isolating the polypeptide produced by the cell.

Within another aspect, the present invention provides an isolated soluble cytokine receptor polypeptide comprising a sequence of amino acid residues that is at least 90% identical to an amino acid sequence as shown in SEQ ID NO:38 or SEQ ID NO:48 from amino acid 24 to 230, or 27 to 230, and wherein the soluble cytokine receptor polypeptide binds IL-TIF or antagonizes IL-TIF activity. In one embodiment, the isolated polypeptide is as disclosed above, wherein the soluble cytokine receptor polypeptide forms a homodimeric, heterodimeric or multimeric receptor complex. In another embodiment, the isolated polypeptide is as disclosed above, wherein the soluble cytokine receptor polypeptide forms a heterodimeric or multimeric receptor complex further comprising a soluble Class I or Class II cytokine receptor. In another embodiment, the isolated polypeptide is as disclosed above, wherein the soluble cytokine receptor polypeptide forms a heterodimeric or multimeric receptor complex further comprising a soluble CRF2-4 receptor polypeptide (SEQ ID NO:35), a soluble IL-10 receptor polypeptide (SEQ ID NO:36), or soluble zcytor11 receptor polypeptide (SEQ ID NO:34).

Within another aspect, the present invention provides an isolated soluble cytokine receptor polypeptide comprising a sequence of amino acid residues as shown in SEQ ID NO:38 or SEQ ID NO:48 from amino acid 24 to 230, or 27 to 230, wherein the soluble cytokine receptor polypeptide forms a homodimeric, heterodimeric or multimeric receptor complex. In another embodiment, the isolated polypeptide is as disclosed above, wherein the soluble cytokine receptor polypeptide forms a heterodimeric or multimeric receptor complex further comprising a soluble Class I or Class II cytokine receptor. In another embodiment, the isolated polypeptide is as disclosed above, wherein the soluble cytokine receptor polypeptide forms a heterodimeric or multimeric receptor complex comprising a soluble CRF2-4 receptor polypeptide (SEQ ID NO:35), a soluble IL-10 receptor polypeptide (SEQ ID NO:36), or soluble zcytor11 receptor polypeptide (SEQ ID NO:34). In another embodiment, the isolated polypeptide is as disclosed above, wherein the soluble cytokine receptor polypeptide further comprises an affinity tag, chemical moiety, toxin, or label.

Within another aspect, the present invention provides an isolated heterodimeric or multimeric soluble receptor complex comprising soluble receptor subunits, wherein at least one of the soluble receptor subunits comprises a soluble cytokine receptor polypeptide comprising a sequence of amino acid residues as shown in SEQ ID NO:38 or SEQ ID NO:48 from amino acid 24 to 230, or 27 to 230. In one embodiment, the isolated heterodimeric or multimeric soluble receptor complex disclosed above further comprises a soluble Class I or Class II cytokine receptor polypeptide. In another embodiment, the isolated heterodimeric or multimeric soluble receptor complex disclosed above further comprises a soluble CRF2-4 receptor polypeptide (SEQ ID NO:35), a soluble IL-10 receptor polypeptide (SEQ ID NO:36), or soluble zcytor11 receptor polypeptide (SEQ ID NO:34).

Within another aspect, the present invention provides a method of producing a soluble cytokine receptor polypeptide that forms a heterodimeric or multimeric complex comprising: culturing a cell as disclosed above; and isolating the soluble receptor polypeptides produced by the cell.

Within another aspect, the present invention provides a method of producing an antibody to soluble cytokine receptor polypeptide comprising: inoculating an animal with a soluble cytokine receptor polypeptide selected from the group consisting of: (a) a polypeptide comprising a monomeric or homodimeric soluble cytokine receptor comprising a polypeptide as shown in SEQ ID NO:38 or SEQ ID NO:48 from amino acid 24 to 230, or 27 to 230; (b) a polypeptide of (a) further comprising a soluble cytokine receptor heterodimeric or multimeric receptor complex comprising a soluble Class I or Class II cytokine receptor polypeptide; (c) a polypeptide of (a) further comprising a soluble cytokine receptor heterodimeric or multimeric receptor complex comprising a soluble CRF2-4 receptor polypeptide (SEQ ID NO:35); (d) a polypeptide of (a) further comprising a soluble cytokine receptor heterodimeric or multimeric receptor complex comprising a soluble IL-10 receptor polypeptide (SEQ ID NO:36); and wherein the polypeptide elicits an immune response in the animal to produce the antibody; and isolating the antibody from the animal.

Within another aspect, the present invention provides an antibody produced by the method as disclosed above, which specifically binds to a homodimeric, heterodimeric or multimeric receptor complex comprising a polypeptide as shown in SEQ ID NO:38 or SEQ ID NO:48 from amino acid 24 to 230, or 27 to 230. In one embodiment, the antibody disclosed above is a monoclonal antibody.

Within another aspect, the present invention provides an antibody which specifically binds to a homodimeric, heterodimeric or multimeric receptor complex as disclosed above.

Within another aspect, the present invention provides a method for inhibiting IL-TIF-induced proliferation or differentiation of hematopoietic cells and hematopoietic cell progenitors comprising culturing bone marrow or peripheral blood cells with a composition comprising an amount of soluble cytokine receptor polypeptide as shown in SEQ ID NO:38 or SEQ ID NO:48 from amino acid 24 to 230, or 27 to 230, sufficient to reduce proliferation or differentiation of the hematopoietic cells in the bone marrow or peripheral blood cells as compared to bone marrow or peripheral blood cells cultured in the absence of soluble cytokine receptor. In one embodiment, the method is as disclosed above, wherein the hematopoietic cells and hematopoietic progenitor cells are lymphoid cells. In another embodiment, the method is as disclosed above, wherein the lymphoid cells are macrophages or T cells.

Within another aspect, the present invention provides a method of reducing IL-TIF-induced or IL-9 induced inflammation comprising administering to a mammal with inflammation an amount of a composition of a polypeptide as shown in SEQ ID NO:38 or SEQ ID NO:48 from amino acid 24 to 230, or 27 to 230 sufficient to reduce inflammation.

Within another aspect, the present invention provides a method of suppressing an inflammatory response in a mammal with inflammation comprising: (1) determining a level of serum amyloid A protein; (2) administering a composition comprising a soluble mouse Zcytor16 cytokine receptor polypeptide as disclosed above in an acceptable pharmaceutical vehicle; (3) determining a post administration level of serum amyloid A protein; (4) comparing the level of serum amyloid A protein in step (1) to the level of serum amyloid A protein in step (3), wherein a lack of increase or a decrease in serum amyloid A protein level is indicative of suppressing an inflammatory response.

Within another aspect, the present invention provides a method for detecting a cancer in a patient, comprising: obtaining a tissue or biological sample from a patient; incubating the tissue or biological sample with an antibody as disclosed above under conditions wherein the antibody binds to its complementary polypeptide in the tissue or biological sample; visualizing the antibody bound in the tissue or biological sample; and comparing levels of antibody bound in the tissue or biological sample from the patient to a normal control tissue or biological sample, wherein an increase in the level of antibody bound to the patient tissue or biological sample relative to the normal control tissue or biological sample is indicative of a cancer in the patient.

Within another aspect, the present invention provides a method for detecting a cancer in a patient, comprising: obtaining a tissue or biological sample from a patient; labeling a polynucleotide comprising at least 14 contiguous nucleotides of SEQ ID NO:37 or SEQ ID NO:47 or the complement of SEQ ID NO:37 or SEQ ID NO:47; incubating the tissue or biological sample with under conditions wherein the polynucleotide will hybridize to complementary polynucleotide sequence; visualizing the labeled polynucleotide in the tissue or biological sample; and comparing the level of labeled polynucleotide hybridization in the tissue or biological sample from the patient to a normal control tissue or biological sample, wherein an increase in the labeled polynucleotide hybridization to the patient tissue or biological sample relative to the normal control tissue or biological sample is indicative of a cancer in the patient.

Within another aspect, the present invention provides a transgenic mouse, wherein the mouse over-expresses residues 1 to 230 or 24 to 230, or 27 to 230 of SEQ ID NO:38 or SEQ ID NO:48. In one embodiment, the transgenic mouse is as disclosed above, wherein the expression of residues 1 to 230 or 24 to 230, or 27 to 230 of SEQ ID NO:38 or SEQ ID NO:48 is expressed using a tissue-specific or tissue-restricted promoter. In another embodiment, the transgenic mouse is as disclosed above, wherein the expression of residues 1 to 230 or 24 to 230, or 27 to 230 of SEQ ID NO:38 or SEQ ID NO:48 is expressed using an epithelial-specific, colon-specific, or ovary-specific promoter. In another embodiment, the transgenic mouse is as disclosed above,, wherein the mouse does not expresses residues 1 to 230 or 24 to 230, or 27 to 230 of SEQ ID NO:38 or SEQ ID NO:48, relative to a normal mouse.

The invention is further illustrated by the following non-limiting examples.

EXAMPLES

Example 1

Cloning of Mouse Zcytor16 and Construction of Mammalian Expression Vectors that Express Human and Mouse Zcytor16 Soluble Receptors: Zcytor16CEE, Zcytor16CFLG, Zcytor16CHIS and Zcytor16-Fc4

A. Cloning of Mouse Zcytor16 Extracellular Domain

A mouse ortholog of human Zcytor16 (U.S. patent application Ser. No. 09/728,911) was identified and designated "mouse Zcytor16." The polynucleotide sequence of the mouse Zcytor16 clone is shown in SEQ ID NO:37 and SEQ ID NO:47 and polypeptide sequence shown in SEQ ID NO:38 and SEQ ID NO:48 respectively.

B. Mammalian Expression Construction of Soluble Zcytor16 Receptor Zcytor16-Fc4 Construction of Mammalian Expression Vectors That Express Zcytor16 Soluble Receptor Zcytor16sR/Fc4

An expression vector was prepared to express the soluble human Zcytor16 polypeptide (Zcytor16sR, i.e., from residue 22 (Thr) to residue 231 (Pro) of SEQ ID NO:2; SEQ ID NO:13) fused to a C-terminal Fc4 tag (SEQ ID NO:5).

A PCR generated Zcytor16 DNA fragment of about 630 bp was created using oligo ZC29,181 (SEQ ID NO:6) and oligo ZC29,182 (SEQ ID NO:7) as PCR primers to add BamHI and Bgl2 restriction sites at 5' and 3'0 ends respectively, of the Zcytor16 DNA encoding the soluble receptor. A plasmid containing the Zcytor16 cDNA (SEQ ID NO:1) (Example 1A) was used as a template. PCR amplification of the Zcytor16 fragment was performed as follows: One cycle at 94° C. for 1 minute; 25 cycles at 94° C. for 30 seconds, 68° C. for 90 seconds, followed by an additional 68° C. incubation for 4 minutes, and hold at 10° C. The reaction was purified by chloroform/phenol extraction and isopropanol precipitation, and digested with BamHI and Bgl2 (Boehringer Mannheim, Indianapolis, Ind.). A band of approximately 630 bp, as visualized by 1% agarose gel electrophoresis, was excised and the DNA was purified using a QiaexII™ purification kit (Qiagen, Valencia, Calif.) according to the manufacturer's instruction.

The Fc4/pzmp20 plasmid is a mammalian expression vector containing an expression cassette having the CMV promoter, human tPA leader peptide, multiple restriction sites for insertion of coding sequences, a Fc4 tag, and a human growth hormone terminator. The plasmid also has an E. coli origin of replication, a mammalian selectable marker expression unit having an SV40 promoter, an enhancer and an origin of replication, as well as a DHFR gene, and SV40 terminator. The Zcytor16sR/Fc4/pzmp20 expression vector uses the human tPA leader peptide (SEQ ID NO:8 and SEQ ID NO:9) and attaches the Fc4 tag (SEQ ID NO:5) to the C-terminus of the extracellular portion of the Zcytor16 polypeptide sequence. Fc4 is the Fc region derived from human IgG, which contains a mutation so that it no longer binds the Fc receptor.

About 30 ng of the restriction digested Zcytor16sR insert and about 10 ng of the digested vector (which had been cut with Bgl2) were ligated at 11° C. overnight. One microliter of ligation reaction was electroporated into DH10B competent cells (Gibco BRL, Rockville, Md.) according to manufacturer's direction and plated onto LB plates containing 50 mg/ml ampicillin, and incubated overnight. Colonies were screened by restriction analysis of DNA, which was prepared from 2 ml liquid cultures of individual colonies. The insert sequence of positive clones was verified by sequence analysis. A large-scale plasmid preparation was done using a Qiagen® Mega prep kit (Qiagen) according to manufacturer's instruction.

Similar methods are used to prepare mouse Zcytor16-Fc4 fusions, and Fc4 fusions of non-Zcytor16 subunits of heterodimeric and multimeric receptors, such as CRF2-4 and IL-10R tagged with Fc4.

C. Construction of Zcytor16 Mammalian Expression Vector Containing Zcytor16CEE, Zcytor16CFLG and Zcytor16CHIS An expression vector is prepared for the expression of the soluble, extracellular domain of the Zcytor16 polypeptide (e.g., amino acids 22–231 of SEQ ID NO:2; SEQ ID NO:13; or amino acids 24–230 or SEQ ID NO:38 or SEQ ID NO:48), pC4Zcytor16CEE, wherein the construct is designed to express a Zcytor16 polypeptide comprised of the predicted initiating methionine and truncated adjacent to the predicted transmembrane domain, and with a C-terminal Glu-Glu tag (SEQ ID NO:10).

A Zcytor16 DNA fragment comprising the Zcytor16 extracellular cytokine binding domain is created using PCR, and purified. The excised DNA is subcloned into a plasmid expression vector that has a signal peptide, e.g., the native Zcytor16 signal peptide, tPA leader, and attaches a Glu-Glu tag (SEQ ID NO:10) to the C-terminus of the Zcytor16 polypeptide-encoding polynucleotide sequence. Such an expression vector mammalian expression vector contains an expression cassette having a mammalian promoter, multiple restriction sites for insertion of coding sequences, a stop codon and a mammalian terminator. The plasmid can also have an E. coli origin of replication, a mammalian selectable marker expression unit having an SV40 promoter, enhancer and origin of replication, a DHFR gene and the SV40 terminator.

Restriction digested Zcytor16 insert and previously digested vector are ligated using standard molecular biological techniques, and electroporated into competent cells such as DH10B competent cells (GIBCO BRL, Gaithersburg, Md.) according to manufacturer's direction and plated onto LB plates containing 50 mg/ml ampicillin, and incubated overnight. Colonies are screened by restriction analysis of DNA prepared from individual colonies. The insert sequence of positive clones is verified by sequence analysis. A large-scale plasmid preparation is done using a QIAGEN® Maxi prep kit (Qiagen) according to manufacturer's instructions.

The same process is used to prepare mouse Zcytor16 soluble homodimeric, heterodimeric or multimeric receptors (including non-Zcytor16 soluble receptor subunits, such as, soluble CRF2-4 or IL-10R), or soluble receptors with a C-terminal HIS tag, composed of 6 His residues in a row (SEQ ID NO:12); and a C-terminal FLAG (SEQ ID NO:11) tag, Zcytor16CFLAG. To construct these constructs, the aforementioned vector has either the HIS or the FLAG® tag in place of the glu-glu tag (SEQ ID NO:10).

Example 2

Transfection and Expression of Soluble Receptor Polypeptides

The day before the transfection, BHK 570 cells (ATCC No. CRL-10314; ATCC, Manasas, Va.) were plated in a 10-cm plate with 50% confluence in normal BHK DMEM (Gibco/BRL High Glucose) media. The day of the transfection, the cells were washed once with Serum Free (SF) DMEM, followed by transfection with the Zcytor16sR/Fc4/pzmp20 expression plasmids. Sixteen micrograms of human Zcytor16sR-Fc4 DNA construct (Example 1B) were diluted into a total final volume of 640 μl SF DMEM. A diluted LipofectAMINE™ (Gibco BRL, Gaithersburg, Md.) mixture (35 μl LipofectAMINE™ in 605 μl SF media) was added to the DNA mix, and incubated for 30 minutes at room temperature. Five milliliters of SF media was added to the DNA/LipofectAMINE™ mixture, which was then added to BHK cells. The cells were incubated at 37° C./5% $CO_2$ for 5 hours, after which 6.4 mil of BHK media with 10% FBS was added. The cells were incubated overnight at 37° C./5% $CO_2$.

Approximately 24 hours post-transfection, the BHK cells were split into selection media with 1 μM methotrexate (MTX). The cells were repeatedly split in this manner until stable Zcytor16sR-Fc4/BHK cell lines were identified. To detect the expression level of the Zcytor16 soluble receptor fusion proteins, the transfected BHK cells were washed with PBS and incubated in SF media for 72 hours. The SF condition media was collected and 20 μl of the sample was run on 10% SDS-PAGE gel under reduced conditions. The protein bands were transferred to nitrocellulose filter by Western blot, and the fusion proteins were detected using goat-anti-human IgG/HRP conjugate (Jackson ImmunoResearch Laboratories, Inc, West Grove, Pa.). An expression vector containing a different soluble receptor fused to the Fc4 was used as a control. The expression level of the stable Zcytor16sR-Fc4/BHK cells was approximately 2 mg/L.

For protein purification, the transfected BHK cells were transferred into T-162 flasks. Once the cells reached about 80% confluence, they were washed with PBS and incubated in 100 ml SF media for 72 hours, and then the condition media was collected for protein purification (Example 11).

Using the above methods, mouse Zcytor16 soluble receptor fusion proteins are similarly expressed.

Example 3

Expression of Zcytor16 Soluble Receptor in *E. coli*
A. Construction of Expression Vector pCZR225 that Expresses huZcytor16/MBP-6H Fusion Polypeptide An expression plasmid containing a polynucleotide encoding a Zcytor16 soluble receptor fused C-terminally to maltose binding protein (MBP) is constructed via homologous recombination. The fusion polypeptide contains an N-terminal approximately 388 amino acid MBP portion fused to the human Zcytor16 soluble receptor (e.g., SEQ ID NO:13; or for the mouse Zcytor16, amino acids 24 to 230 of SEQ ID NO:38 or SEQ ID NO:48). A fragment of Zcytor16 cDNA (SEQ ID NO:1; or SEQ ID NO:37 or SEQ ID NO:47) is isolated using PCR as described herein. Two primers are used in the production of the Zcytor16 fragment in a standard PCR reaction: (1) one containing about 40 bp of the vector flanking sequence and about 25 bp corresponding to the amino terminus of the Zcytor16, and (2) another containing about 40 bp of the 3' end corresponding to the flanking vector sequence and about 25 bp corresponding to the carboxyl terminus of the Zcytor16. Two µl of the 100 µl PCR reaction is run on a 1.0% agarose gel with 1×TBE buffer for analysis, and the expected approximately fragment is seen. The remaining PCR reaction is combined with the second PCR tube and precipitated with 400 µl of absolute ethanol. The precipitated DNA used for recombining into an appropriately restriction digested recipient vector pTAP98 to produce the construct encoding the MBP-Zcytor16 fusion, as described below.

Plasmid pTAP98 is derived from the plasmids pRS316 and pMAL-c2. The plasmid pRS316 is a *Saccharomyces cerevisiae* shuttle vector (Hieter P. and Sikorski, R., *Genetics* 122:19–27, 1989). pMAL-C2 (NEB) is an *E. coli* expression plasmid. It carries the tac promoter driving MalE (gene encoding MBP) followed by a His tag, a thrombin cleavage site, a cloning site, and the rrnB terminator. The vector pTAP98 is constructed using yeast homologous recombination. 100 ng of EcoR1 cut pMAL-c2 is recombined with 1 µg Pvu1 cut pRS316, 1 µg linker, and 1 µg Sca1/EcoR1 cut pRS316 are combined in a PCR reaction. PCR products are concentrated via 100% ethanol precipitation.

Competent yeast cells (*S. cerevisiae*) are combined with about 10 µl of a mixture containing approximately 1 µg of the Zcytor16 receptor PCR product above, and 100 ng of digested pTAP98 vector, and electroporated using standard methods and plated onto URA-D plates and incubated at 30° C.

After about 48 hours, the Ura+ yeast transformants from a single plate are picked, DNA isolated, and transformed into electrocompetent *E. coli* cells (e.g., MC1061, Casadaban et. al. *J. Mol. Biol.* 138, 179–207), and plated on MM/CA +AMP 100 mg/L plates (Pryor and Leiting, *Protein Expression and Pruification* 10:309–319, 1997).using standard procedures. Cells are grown in MM/CA with 100 µg/ml Ampicillin for two hours, shaking, at 37° C. 1 ml of the culture is induced with 1 mM IPTG. 2–4 hours later the 250 µl of each culture is mixed with 250 µl acid washed glass beads and 250 µl Thorner buffer with 5% βME and dye (8M urea, 100 mM Tris pH7.0, 10% glycerol, 2 mM EDTA, 5% SDS). Samples are vortexed for one minute and heated to 65° C. for 10 minutes. 20 µl are loaded per lane on a 4%–12% PAGE gel (NOVEX). Gels are run in 1×MES buffer. The positive clones are subjected to sequence analysis.

One microliter of sequencing DNA is used to transform strain BL21. The cells are electropulsed at 2.0 kV, 25 µF and 400 ohms. Following electroporation, 0.6 ml MM/CA with 100 mg/L Ampicillin. Cells are grown in MM/CA and induced with ITPG as described above. The positive clones are used to grow up for protein purification of the human or mouse Zcytor16/MBP-6H fusion protein using standard techniques.

Example 4

Mouse Zcytor16 Soluble Receptor Polyclonal Antibodies

Polyclonal antibodies are prepared by immunizing female New Zealand white rabbits with the purified mouse Zcytor16/MBP-6H polypeptide (Example 3), or the purified recombinant mouse Zcytor16CEE or mouse Zcytor16-Fc4 soluble receptor (Example 1; Example 11). The rabbits are each given an initial intraperitoneal (IP) injection of about 200 mg of purified protein in Complete Freund's Adjuvant (Pierce, Rockford, Ill.) followed by booster IP injections of 100 mg purified protein in Incomplete Freund's Adjuvant every three weeks. Seven to ten days after the administration of the third booster injection, the animals are bled and the serum is collected. The rabbits are then boosted and bled every three weeks.

The mouse Zcytor16-specific polyclonal antibodies are affinity purified from the rabbit serum using an CNBr-SEPHAROSE 4B protein column (Pharmacia LKB) that is prepared using about 10 mg of the appropriate purified mouse Zcytor16 polypeptide per gram CNBr-SEPHAROSE, followed by 20×dialysis in PBS overnight. Zcytor16-specific antibodies are characterized by an ELISA titer check using 1 mg/ml of the appropriate protein antigen as an antibody target. The lower limit of detection (LLD) of the rabbit anti-Zcytor16 affinity purified antibodies is determined using standard methods.

Example 5

Mouse Zcytor16 Receptor Monoclonal Antibodies

Mouse Zcytor16 receptor Monoclonal antibodies are prepared by immunizing male BalbC mice (Harlan Sprague Dawley, Indianapolis, Ind.) with the purified recombinant mouse Zcytor16 proteins described herein. The mice are each given an initial intraperitoneal (IP) injection of 20 mg of purified protein in Complete Freund's Adjuvant (Pierce, Rockford, Ill.) followed by booster IP injections of 10 mg purified protein in Incomplete Freund's Adjuvant every two weeks. Seven to ten days after the administration of the third booster injection, the animals are bled and the serum is collected, and antibody titer assessed.

Splenocytes are harvested from high-titer mice and fused to murine SP2/0 myeloma cells using PEG 1500 (Boerhinger Mannheim, UK) in two separate fusion procedures using a 4:1 fusion ratio of splenocytes to myeloma cells (*Antibodies: A Laboratory Manual,* E. Harlow and D. Lane, Cold Spring Harbor Press). Following 10 days growth post-fusion, specific antibody-producing hybridomas are identified by ELISA using purified recombinant mosue Zcytor16 soluble receptor protein (Example 6C) as an antibody target and by FACS using Baf3 cells expressing the Zcytor16 sequence (Example 8) as an antibody target. The resulting hybridomas positive by both methods are cloned three times by limiting dilution.

Example 6

Assessing Mouse Zcytor16 Receptor Heterodimerization Using ORIGEN Assay

Soluble mouse Zcytor16 receptor (Example 11), or gp130 (Hibi, M. et al., *Cell* 63:1149–1157, 1990) are biotinylated by reaction with a five-fold molar excess of sulfo-NHS-LC-Biotin (Pierce, Inc., Rockford, Ill.) according to the manufacturer's protocol. Soluble mouse Zcytor16 receptor and another soluble receptor subunit, for example, soluble IL-10R (sIL-10R) or CRF2-4 receptor (CRF2-4), soluble zcytor11 receptor (U.S. Pat. No. 5,965,704) or soluble zcytor7 receptor (U.S. Pat. No. 5,945,511) are labeled with a five fold molar excess of Ru-BPY-NHS (Igen, Inc., Gaithersburg, Md.) according to manufacturer's protocol. The biotinylated and Ru-BPY-NHS-labeled forms of the soluble mouse Zcytor16 receptor can be respectively designated Bio-Zcytor16 receptor and Ru-Zcytor16; the biotinylated and Ru-BPY-NHS-labeled forms of the other soluble receptor subunit can be similarly designated. Assays can be carried out using conditioned media from cells expressing a ligand, such as IL-TIF, that binds mouse Zcytor16 heterodimeric receptors, or using purified IL-TIF.

For initial receptor binding characterization a panel of cytokines or conditioned medium are tested to determine whether they can mediate homodimerization of mouse Zcytor16 receptor and if they can mediate the heterodimerization of mouse Zcytor16 receptor with the soluble receptor subunits described above. To do this, 50 µl of conditioned media or TBS-B containing purified cytokine, is combined with 50 µl of TBS-B (20 mM Tris, 150 mM NaCl, 1 mg/ml BSA, pH 7.2) containing e.g., 400 ng/ml of Ru-mZcytor16 receptor and Bio-mZcytor16, or 400 ng/ml of Ru-Zcytor16 receptor and e.g., Bio-gp130, or 400 ng/ml of e.g., Ru-CRF2-4 and Bio-mZcytor16. Following incubation for one hour at room temperature, 30 µg of streptavidin coated, 2.8 mm magnetic beads (Dynal, Inc., Oslo, Norway) are added and the reaction incubated an additional hour at room temperature. 200 µl ORIGEN assay buffer (Igen, Inc., Gaithersburg, Md.) is then added and the extent of receptor association measured using an M8 ORIGEN analyzer (Igen, Inc.).

Example 7

Construct for Generating a Mouse Zcytor16 Receptor Heterodimer

A vector expressing a secreted mouse Zcytor16 heterodimer is constructed. In this construct, the extracellular cytokine-binding domain of Zcytor16 (e.g., amino acids 24 to 230 of SEQ ID NO:38 or SEQ ID NO:48) is fused to the heavy chain of IgG gamma 1 (IgGγ1) while the extracellular portion of the heteromeric cytokine receptor subunit (e.g., an CRF2-4, IL-9, IL-10, zcytor7, zcytor11, IL-4 receptor component) is fused to a human kappa light chain (human κ light chain).

A. Construction of IgG Gamma 1 and Human κ Light Chain Fusion Vectors

The heavy chain of IgGγ1 can be cloned into the Zem229R mammalian expression vector (ATCC deposit No. 69447) such that any desired cytokine receptor extracellular domain having a 5' EcoRI and 3' NheI site can be cloned in resulting in an N-terminal extracellular domain-C-terninal IgGγ1 fusion. The IgGγ1 fragment used in this construct is made by using PCR to isolate the IgGγ1 sequence from a Clontech hfetal Liver cDNA library as a template. PCR products are purified using methods described herein and digested with MluI and EcoRI (Boerhinger-Mannheim), ethanol precipitated and ligated with oligos which comprise an desired restriction site linker, into Zem229R previously digested with and EcoRI using standard molecular biology techniques disclosed herein.

The human κ light chain can be cloned in the Zem228R mammalian expression vector (ATCC deposit No. 69446) such that any desired cytokine receptor extracellular domain having a 5' EcoRI site and a 3' KpnI site can be cloned in resulting in a N-terminal cytokine extracellular domain-C-terminal human κ light chain fusion. As a KpnI site is located within the human κ light chain sequence, a special primer is designed to clone the 3' end of the desired extracellular domain of a cytokine receptor into this KpnI site: The primer is designed so that the resulting PCR product contains the desired cytokine receptor extracellular domain with a segment of the human κ light chain up to the KpnI site. This primer preferably comprises a portion of at least 10 nucleotides of the 3' end of the desired cytokine receptor extracellular domain fused in frame 5' to fragment cleaved at the KpnI site. The human κ light chain fragment used in this construct is made by using PCR to isolate the human κ light chain sequence from the same Clontech human Fetal Liver cDNA library used above. PCR products are purified using methods described herein and digested with MluI and EcoRI (Boerhinger-Mannheim), ethanol precipitated and ligated with the MluI/EcoRI linker described above, into Zem228R previously digested with and EcoRI using standard molecular biology techniques disclosed herein.

B. Insertion of Zcyor16 Receptor or Heterodimeric Subunit Extracellular Domains into Fusion Vector Constructs Using the construction vectors above, a construct having mouse Zcytor16 fused to IgGγ1 is made. This construction is done by PCRing the extracellular cytokine-binding domain of the mouse Zcytor16 receptor (amino acids 24–230 of SEQ ID NO:38 or SEQ ID NO:48) from a placenta or other cDNA library (Clontech) or plasmid (Example 1A) using standard methods and oligos that provide EcoRI and NheI restriction sites. The resulting PCR product is digested with EcoRI and NheI, gel purified, as described herein, and ligated into a previously EcoRI and NheI digested and band-purified Zem229R/IgGγ1 described above. The resulting vector is sequenced to confirm that the Zcytor16/IgG gamma 1 fusion is correct.

A separate construct having a heterodimeric cytokine receptor subunit extracellular domain fused to κ light is also constructed as above. The CRF2-4/human κ light chain construction is performed as above by PCRing from, e.g., a lymphocyte cDNA library (Clontech) using standard methods, and oligos that provide EcoRI and KpnI restriction sites. The resulting PCR product is digested with EcoRI and KpnI and then ligating this product into a previously EcoRI and KpnI digested and band-purified Zem228R/human κ light chain vector described above. The resulting vector is sequenced to confirm that the cytokine receptor subunit/human κ light chain fusion is correct.

D. Co-expression of the Mouse Zcytor16 and Heterodimeric Cytokine Receptor Subunit Extracellular Domain Approximately 15 µg of each of vectors above, are co-transfected into mammalian cells, e.g., BHK-570 cells (ATCC No. CRL-10314) using LipofectaminePlus™ reagent (Gibco/BRL), as per manufacturer's instructions. The transfected cells are selected for 10 days in DMEM+5% FBS (Gibco/BRL) containing 1 µM of methotrexate (MTX) (Sigma, St. Louis, Mo.) and 0.5 mg/ml G418 (Gibco/BRL) for 10 days. The resulting pool of transfectants is selected again in 10 µm of MTX and 0.5 mg/ml G418 for about 10 days.

The resulting pool of doubly selected cells is used to generate protein. Three Factories (Nunc, Denmark) of this pool are used to generate 10 L of serum free conditioned medium. This conditioned media is passed over a 1 ml protein-A column and eluted in about 10, 750 microliter fractions. The fractions having the highest protein concentration are pooled and dialyzed (10 kD MW cutoff) against PBS. Finally the dialyzed material is submitted for amino acid analysis (AAA) using routine methods.

Example 8

Determination of Receptor Subunits that Heterodimerize or Multimerize With Mouse Zcytor16 Receptor Using a Proliferation Assay Using standard methods described herein, cells expressing a BaF3/mZcytor16-MPL chimera (wherein the extracellular domain of the mouse Zcytor16 (e.g., amino acids 24 to 230 of SEQ ID NO:38 or SEQ ID NO:48) is fused in frame to the intracellular signaling domain of the mpl receptor) are tested for proliferative response in the presence of IL-TIF. Such cells serve as a bioassay cell line to measure ligand binding of monomeric or homodimeric mouse Zcytor16 receptors. In addition, BaF3/mZcytor16-MPL chimera cells transfected with an additional heterodimeric cytokine receptor subunit can be assessed for proliferative response in the presence of IL-TIF. In the presence of IL-TIF, if the BaF3/mZcytor16-MPL cells signal, this would suggest that Zcytor16 receptor can homodimerize to signal. Transfection of the BaF3/MPL-mZcytor16 cell line with and additional MPL-class II cytokine receptor fusion that signals in the presence of the IL-TIF ligand, such as CRF2-4, determines which heterodimeric cytokine receptor subunits are required for mouse Zcytor16 receptor signaling. Use of MPL-receptor fusions for this purpose alleviates the requirement for the presence of an intracellular signaling domain for the mouse Zcytor16 receptor.

Each independent receptor complex cell line is then assayed in the presence of IL-TIF and proliferation measured using routine methods (e.g., Alamar Blue assay). The BaF3/MPL-mZcytor16 bioassay cell line serves as a control for the monomeric or homodimeric receptor activity, and is thus used as a baseline to compare signaling by the various receptor complex combinations. The untransfected bioassay cell line serves as a control for the background activity, and is thus used as a baseline to compare signaling by the various receptor complex combinations. A BaF3/MPL-mZcytor16 without ligand (IL-TIF) is also used as a control. The IL-TIF in the presence of the correct receptor complex, is expected to increase proliferation of the BaF3/mZcytor16-MPL receptor cell line approximately 5 fold over background or greater in the presence of IL-TIF. Cells expressing the components of Zcytor16 heterodimeric and multimeric receptors should proliferate in the presence of IL-TIF.

Example 9

Reconstitution of Mouse Zcytor16 Receptor in Vitro

To identify components involved in the Zcytor16-signaling complex, receptor reconstitution studies are performed as follows. BHK 570 cells (ATCC No. CRL-10314) transfected, using standard methods described herein, with a luciferase reporter mammalian expression vector plasmid serve as a bioassay cell line to measure signal transduction response from a transfected mouse Zcytor16 receptor complex to the luciferase reporter in the presence of IL-TIF. BHK cells do not endogenously express the mouse Zcytor16 receptor. An exemplary luciferase reporter mammalian expression vector is the KZ134 plasmid that was constructed with complementary oligonucleotides that contain STAT transcription factor binding elements from 4 genes. A modified c-fos Sis inducible element (m67SIE, or hSIE) (Sadowski, H. et al., Science 261:1739–1744, 1993), the p21 SIE1 from the p21 WAF1 gene (Chin, Y. et al., Science 272:719–722, 1996), the mammary gland response element of the β-casein gene (Schmitt-Ney, M. et al., Mol. Cell. Biol. 11:3745–3755, 1991), and a STAT inducible element of the Fcg RI gene, (Seidel, H. et al., Proc. Natl. Acad. Sci. 92:3041–3045, 1995). These oligonucleotides contain Asp718-XhoI compatible ends and are ligated, using standard methods, into a recipient firefly luciferase reporter vector with a c-fos promoter (Poulsen, L. K. et al., J. Biol. Chem. 273:6229–6232, 1998) digested with the same enzymes and containing a neomycin selectable marker. The KZ134 plasmid is used to stably transfect BHK, or BaF3 cells, using standard transfection and selection methods, to make a BHK/KZ134 or BaF3/KZ134 cell line respectively.

The bioassay cell line is transfected with mZcytor16-mp1 fusion receptor alone, or co-transfected along with one of a variety of other known receptor subunits. Receptor complexes include but are not limited to mZcytor16-mp1 receptor only, various combinations of mZcytor16-mp1 receptor with one or more of the CRF2-4, IL-9, IL-10, zcytor11, zcytor7 class II cytokine receptor subunits, or IL-4 receptor components, or the IL-2 receptor components (IL-2Rα, IL-2Rβ, IL-2Rγ); Zcytor16-mp1 receptor with one or more of the IL-4/IL-13 receptor family receptor components (IL-4αIL-13Rα, IL-13Rα'), as well as other Interleukin receptors (e.g., L-15 Rα, IL-7Rα, IL-9Rα, IL-21R (Zcytor16)). Each independent receptor complex cell line is then assayed in the presence of cytokine-conditioned media or purified cytokines and luciferase activity measured using routine methods. The untransfected bioassay cell line serves as a control for the background luciferase activity, and is thus used as a baseline to compare signaling by the various receptor complex combinations. The conditioned medium or cytokine that binds the mousezyctor16 receptor in the presence of the correct receptor complex, is expected to give a luciferase readout of approximately 5 fold over background or greater.

As an alternative, a similar assay can be performed wherein Baf3/mZcytor16-mp1 cell lines are co-transfected as described above and proliferation measured (Example 8).

Example 10

COS Cell Transfection and Secretion Trap

COS cell transfections were performed as follows: A mixture of 0.5 µg DNA and 5 µl lipofectamine (Gibco BRL) in 92 ul serum free DMEM media (55 mg sodium pyruvate, 146 mg L-glutamine, 5 mg transferrin, 2.5 mg insulin, 1 µg selenium and 5 mg fetuin in 500 ml DMEM) was incubated at room temperature for 30 minutes and then 400 µl serum free DMEM media added. A 500 µl mixture was added onto COS cells plated on 12-well tissue culture plate at 1.5×10⁵ COS cells/well and previously incubated for 5 hours at 37° C. An additional 500 µl 20% FBS DMEM media (100 ml FBS, 55 mg sodium pyruvate and 146 mg L-glutamine in 500 ml DMEM) was added and the plates were incubated overnight.

The secretion trap was performed as follows: Media was rinsed off cells with PBS and fixed for 15 minutes with 1.8% Formaldehyde in PBS. Cells were then washed with TNT (0.1M Tris-HCl, 0.15M NaCl, and 0.05% Tween-20 in H₂O). Cells were permeated with 0.1% Triton-X in PBS for 15 minutes and washed again with TNT. Cells were blocked for 1 hour with TNB (0.1M Tris-HCl, 0.15M NaCl and 0.5% Blocking Reagent (NEN Renaissance TSA-Direct Kit; NEN) in $H_2O$. Cells were again washed with TNT. Cells were then incubated for 1 hour with 1–3 µg/ml human Zcytor16 soluble receptor Fc4 fusion protein (Zcytor16sR-Fc4) (Example 11) in TNB. Cells were washed with TNT, and then incubated for another hour with 1:200 diluted goat-anti-human Ig-HRP (Fc specific; Jackson ImmunoResearch Laboratories, Inc.) in TNB. Cells were again washed with TNT. Antibodies positively binding to the human Zcytor16sR-Fc4 were detected with fluorescein tyramide reagent diluted 1:50 in dilution buffer (NEN kit) and incubated for 4–6 minutes. Cells were again washed with TNT. Cells were preserved with Vectashield Mounting Media (Vector Labs) diluted 1:5 in TNT. Cells were visualized using FITC filter on fluorescent microscope.

Since Zcytor16 is a Class II cytokine receptor, the binding of human Zcytor16sR/Fc4 fusion protein with known or orphan Class II cytokines was tested. The pZP7 expression vectors containing cDNAs of cytokines (including IL-TIF, interferon alpha, interferon beta, interferon gamma, IL-10, amongst others were transfected into COS cells, and the binding of Zcytor16sR/Fc4 to transfected COS cells were carried out using the secretion trap assay described above. Human IL-TIF showed positive binding. Based on these data, human IL-TIF and human Zcytor16 is a potential ligand-receptor pair. Similar methods are used to show that mouse Zcytor16 is an orthologous class II receptor that binds IL-TIF.

Example 11

Purification of Zcytor16-Fc4 Polypeptide From Transfected BHK 570 Cells

Unless otherwise noted, all operations were carried out at 4° C. The following procedure was used for purifying human Zcytor16 polypeptide containing C-terminal fusion to human Fc4 (Zcytor16-Fc4; Example 1). About 16,500 ml of conditioned media from BHK 570 cells transfected with human Zcytor16-Fc4 (Example 2) was filtered through a 0.2 um sterilizing filter and then supplemented with a solution of protease inhibitors, to final concentrations of, 0.001 mM leupeptin (Boerhinger-Mannheim, Indianapolis, Ind.), 0.001 mM pepstatin (Boerhinger-Mannheim) and 0.4 mM Pefabloc (Boerhinger-Mannheim). A Poros protein A50 column (20 ml bed volume, Applied Biosystems) was packed and washed with 400 ml PBS (Gibco/BRL) The supplemented conditioned media was passed over the column with a flow rate of 15 ml/minute, followed by washing with 800 ml PBS (BRL/Gibco). Zcytor16-Fc4 was eluted from the column with 0.1 M Glycine pH 3.0 and 5 ml fractions were collected directly into 0.5 ml 2M Tris pH 7.8, to adjust the final pH to 7.4 in the fractions.

Column performance was characterized through western blotting of reducing SDS-PAGE gels of the starting media and column pass through. Western blotting used anti-human IgG HRP (Amersham) antibody, which showed an immunoreactive protein at 60,000 Da in the starting media, with nothing in the pass through, suggesting complete capture. The protein A50 eluted fractions were characterized by reducing SDS PAGE gel. This gel showed an intensely Coomassie stained band at 60,000 Da in fractions 3 to 11. Fractions 3 to 11 were pooled.

Protein A 50 elution pool was concentrated from 44 ml to 4 ml using a 30,000 Da Ultrafree Biomax centrifugal concentrator (15 ml volume, Millipore). A Sephacryl S-300 gel filtration column (175 ml bed volume; Pharmacia) was washed with 350 ml PBS (BRL/Gibco). The concentrated pool was injected over the column with a flow rate of 1.5 ml/min, followed by washing with 225 ml PBS (BRL/Gibco). Eluted peaks were collected into 2 ml fractions.

Eluted fractions were characterized by reducing and non-reducing silver stained (Geno Technology) SDS PAGE gels. Reducing silver stained SDS PAGE gels showed an intensely stained band at 60,000 Da in fractions 14–31, while non-reducing silver stained SDS PAGE gels showed an intensely stained band at 160,000 Da in fractions 14–31. Fractions 1–13 showed many bands of various sizes. Fractions 14–31 were pooled, concentrated to 22 ml using 30,000 Da Ultrafree Biomax centrifugal concentrator (15 ml volume, Millipore). This concentrate was filtered through a 0.2 µm Acrodisc sterilizing filter (Pall Corporation).

The protein concentration of the concentrated pooled fractions was performed by BCA analysis (Pierce, Rockford, Ill.) and the material was aliquoted, and stored at −80° C. according to our standard procedures. The concentration of the pooled fractions was 1.50 mg/ml.

This method is also used to purify the mouse Zcytor16-Fc4 and heterologous class II receptor Fc4 fusions.

Example 12

Human and Mouse Zcytor16 Tissue Distribution in Tissue Panels Using Northern Blot and PCR A. Human Zcytor16 Tissue Distribution using Northern Blot and Dot Blot Northern blot analysis was performed using Human Multiple Tissue Northern Blots I, II, I (Clontech) and an in house generated U-937 northern blot. U-937 is a human monoblastic promonocytic cell line. The cDNA probe was generated using oligos ZC25,963 (SEQ ID NO:16) and ZC28,354 (SEQ ID NO:17). The PCR conditions were as follows: 94° for 1 minute; 30 cycles of 94°, 15 seconds; 60°, 30 seconds; 72°, 30 seconds and a final extension for 5 minutes at 72°. The 364 bp product was gel purified by gel electrophoresis on a 1% TBE gel and the band was excised with a razor blade. The cDNA was extracted from the agarose using the QIAquick Gel Extraction Kit (Qiagen). 94 ng of this fragment was radioactively labeled with $^{32}$P-dCTP using Rediprime II (Amersham), a random prime labeling system, according to the manufacturer's specifications. Unincorporated radioactivity was removed using a Nuc-Trap column (Stratagene) according to manufacturer's instructions. Blots were prehybridized at 65° for 3 hours in ExpressHyb (Clontech) solution. Blots were hybridized overnight at 65° in Expresshyb solution containing $1.0 \times 10^6$ cpm/ml of labeled probe, 0.1 mg/ml of salmon sperm DNA and 0.5 µg/ml of human cot-1 DNA. Blots were washed in 2×SSC, 0.1% SDS at room temperature with several solution changes then washed in 0.1×SSC. 0.1% SDS at 55° for 30 minutes twice. Transcripts of approximately 1.6 kb and 3.0 kb size were detected in spleen and placenta, but not other tissues examined. The same sized transcripts plus an additional approximate 1.2 kb transcript was detected in U-937 cell line.

B. Tissue Distribution of Human Zcytor16 in Tissue cDNA Panels Using PCR

A panel of cDNAs from human tissues was screened for Zcytor16 expression using PCR. The panel was made in-house and contained 77 marathon cDNA and cDNA samples from various normal and cancerous human tissues and cell lines are shown in Table 5, below. The cDNAs came from in-house libraries or marathon cDNAs from in-house RNA preps, Clontech RNA, or Invitrogen RNA. The marathon cDNAs were made using the marathon-Ready™ kit (Clontech, Palo Alto, Calif.) and QC tested with clathrin primers ZC21195 (SEQ ID NO:18) and ZC21196 (SEQ ID NO:19) and then diluted based on the intensity of the clathrin band. To assure quality of the panel samples, three tests for quality control (QC) were run: (1) To assess the RNA quality used for the libraries, the in-house cDNAs were tested for average insert size by PCR with vector oligos that were specific for the vector sequences for an individual cDNA library; (2) Standardization of the concentration of the cDNA in panel samples was achieved using standard PCR methods to amplify full length alpha tubulin or G3PDH cDNA using a 5' vector oligo ZC14,063 (SEQ ID NO:20) and 3' alpha tubulin specific oligo primer ZC17,574 (SEQ ID NO:21) or 3' G3PDH specific oligo primer ZC17,600 (SEQ ID NO:22); and (3) a sample was sent to sequencing to check for possible ribosomal or mitochondrial DNA contamination. The panel was set up in a 96-well format that included a human genomic DNA (Clontech, Palo Alto, Calif.) positive control sample. Each well contained approximately 0.2–100 pg/$\mu$l of cDNA.

The PCR reactions were set up using oligos ZC25,963 (SEQ ID NO:30) and ZC25,964 (SEQ ID NO:31), Advantage 2 DNA Polymerase Mix (Clontech) and Rediload dye (Research Genetics, Inc., Huntsville, Ala.). The amplification was carried out as follow: 1 cycle at 94° C. for 1 minute, 38 cycles of 94° C. for 10 seconds, 60° C. for 30 seconds and 72° C. for 30 seconds, followed by 1 cycle at 72° C. for 5 minutes. The correct predicted DNA fragment size was observed in bone marrow, fetal heart, fetal kidney, fetal muscle, fetal skin, heart, mammary gland, placenta, salivary gland, skeletal muscle, small intestine, spinal cord, spleen, kidney, fetal brain, esophageal tumor, uterine tumor, stomach tumor, ovarian tumor, rectal tumor, lung tumor and RPMI-1788 (a B-lymphocyte cell line). Zcytor16 expression was not observed in the other tissues and cell lines tested in this panel. The expression pattern of Zcytor16 shows expression in certain tissue-specific tumors especially, e.g., ovarian cancer, stomach cancer, uterine cancer, rectal cancer, lung cancer and esophageal cancer, where zcytor 16 is not expressed in normal tissue, but is expressed in the tumor tissue. One of skill in the art would recognize that the polynucleotides, polypeptides, antibodies, and binding partners of the present invention can be used as a diagnostic to detect cancer, or cancer tissue in a biopsy, tissue, or histologic sample, particularly e.g., ovarian cancer, stomach cancer, uterine cancer, rectal cancer, lung cancer and esophageal cancer tissue. Such diagnostic uses for the molecules of the present invention are known in the art and described herein.

In addition, because the expression pattern of human Zcytor16, one of IL-TIF's receptors, shows expression in certain specific tissues as well as tissue-specific tumors, binding partners including the natural liganed, IL-TIF, can also be used as a diagnostic to detect specific tissues (normal or abnormal), cancer, or cancer tissue in a biopsy, tissue, or histologic sample, where IL-TIF receptors are expressed, and particularly e.g., ovarian cancer, stomach cancer, uterine cancer, rectal cancer, lung cancer and esophageal cancer tissue. IL-TIF can also be used to target other tissues wherein its receptors, e.g., Zcytor16 and zcytor11 are expressed. Moreover, such binding partners could be conjugated to chemotherapeutic agents, toxic moieties and the like to target therapy to the site of a tumor or diseased tissue. Such diagnostic and targeted therapy uses are known in the art and described herein.

A commercial 1st strand cDNA panel (Human Blood Fractions MTC Panel, Clontech, Palo Alto, Calif.) was also assayed as above. The panel contained the following samples: mononuclear cells, activated mononuclear cells, resting CD4+ cells, activated CD4+ cells, resting CD8+ cells, activated CD8+ cells, resting CD14+ cells, resting CD19+ cells and activated CD19+ cells. Activated CD4+ cells and activated CD19+ cells showed Zcytor16 expression, whereas the other cells tested, including resting CD4+ cells and resting CD19+ cells, did not.

TABLE 5

| Tissue | #samples | Tissue | #samples |
|---|---|---|---|
| adrenal gland | 1 | bladder | 1 |
| bone marrow | 3 | brain | 2 |
| cervix | 1 | colon | 1 |
| fetal brain | 3 | fetal heart | 2 |
| fetal kidney | 1 | fetal liver | 2 |
| fetal lung | 1 | fetal skin | 1 |
| heart | 2 | fetal muscle | 1 |
| kidney | 2 | liver | 1 |
| lung | 1 | lymph node | 1 |
| mammary gland | 1 | melanoma | 1 |
| ovary | 1 | pancreas | 1 |
| pituitary | 2 | placenta | 3 |
| prostate | 3 | rectum | 1 |
| salivary gland | 2 | skeletal muscle | 1 |
| small intestine | 1 | spinal cord | 2 |
| spleen | 1 | uterus | 1 |
| stomach | 1 | adipocyte library | 1 |
| testis | 5 | islet | 1 |
| thymus | 1 | prostate SMC | 1 |
| thyroid | 2 | RPMI 1788 | 1 |
| trachea | 1 | WI38 | 1 |
| esophageal tumor | 1 | lung tumor | 1 |
| liver tumor | 1 | ovarian tumor | 1 |
| rectal tumor | 1 | stomach tumor | 1 |
| uterine tumor | 2 | CD3+ library | 1 |
| HaCAT library | 1 | HPV library | 1 |
| HPVS library | 1 | MG63 library | 1 |
| K562 | 1 | | |

C. Tissue Distribution of Human Zcytor16 in Human Tissue and Cell Line RNA Panels Using RT-PCR A panel of RNAs from human cell lines was screened for human Zcytor16 expression using RT-PCR. The panels were made in house and contained 84 RNAs from various normal and cancerous human tissues and cell lines as shown in Tables 6–9 below. The RNAs were made from in house or purchased tissues and cell lines using the RNAeasy Midi or Mini Kit (Qiagen, Valencia, Calif.). The panel was set up in a 96-well format with 100 ngs of RNA per sample. The RT-PCR reactions were set up using oligos ZC25,963 (SEQ ID NO:30) and ZC25,964 (SEQ ID NO:31), Rediload dye and SUPERSCRIPT One Step RT-PCR System (Life Technologies, Gaithersburg, Md.). The amplification was carried out as follows: one cycle at 55° for 30 minutes followed by 40 cycles of 94°, 15 seconds; 59°, 30 seconds; 72°, 30 seconds; then ended with a final extension at 72° for 5 minutes. 8 to 10 $\mu$ls of the PCR reaction product was subjected to standard Agarose gel electrophoresis using a 4% agarose gel. The correct predicted cDNA fragment size of 184 bps was observed in cell lines U-937, HL-60, ARPE-19, HaCat#1, HaCat#2, HaCat#3, and HaCat#4; bladder, cancerous breast, normal breast adjacent to a cancer, bronchus, colon, ulcerative colitis colon, duodenum, endometrium, esophagus, gastro-esophageal, heart left ventricle, heart ventricle, ileum, kidney, lung, lymph node, lymphoma, mammary adenoma, mammary gland, cancerous ovary, pancreas, parotid and skin, spleen lymphoma and small bowel. Zcytor16 expression was not observed in the other tissues and cell lines tested in this panel.

Zcytor16 is detectably expressed by PCR in normal tissues: such as, the digestive system, e.g., esophagus, gastro-esophageal, pancreas, duodenum, Ileum, colon, small bowel; the female reproductive system, e.g., mammary gland, endometrium, breast (adjacent to cancerous tissues); and others systems, e.g., lymph nodes, skin, parotid, bladder, bronchus, heart ventricles, and kidney. Moreover, Zcytor16 is detectably expressed by PCR in several human tumors: such as tumors associated with female reproductive tissues e.g., mammary adenoma, ovary cancer, uterine cancer, other breast cancers; and other tissues such as lymphoma, stomach tumor, and lung tumor. The expression of Zcytor16 is found in normal tissues of female reproductive organs, and in some tumors associated with these organs. As such, Zcytor16 can serve as a marker for these tumors wherein the Zcytor16 may be over-expressed. Several cancers positive for Zcytor16 are associated with ectodermal/epithelial origin (mammary adenoma, and other breast cancers). Hence, Zcytor16 can serve as a marker for epithelial tissue, such as epithelial tissues in the digestive system and female reproductive organs (e.g., endometrial tissue, columnar epithelium), as well as cancers involving epithelial tissues. Moreover, in a preferred embodiment, Zcytor16 can serve as a marker for certain tissue-specific tumors especially, e.g., ovarian cancer, stomach cancer, uterine cancer, rectal cancer, lung cancer and esophageal cancer, where zcytor16 is not expressed in normal tissue, but is expressed in the tumor tissue. Use of polynucleotides, polypeptides, and antibodies of the present invention for diagnostic purposes are known in the art, and disclosed herein.

TABLE 6

| Tissue | #samples | Tissue | #samples |
|---|---|---|---|
| adrenal gland | 6 | duodenum | 1 |
| bladder | 3 | endometrium | 5 |
| brain | 2 | cancerous endometrium | 1 |
| brain meningioma | 1 | gastric cancer | 1 |
| breast | 1 | esophagus | 7 |
| cancerous breast | 4 | gastro-esophageal | 1 |
| normal breast adjacent to cancer | 5 | heart aorta | 1 |
| bronchus | 3 | heart left ventricle | 4 |
| colon | 15 | heart right ventricle | 2 |
| cancerous colon | 1 | heart ventricle | 1 |
| normal colon adjacent to cancer | 1 | ileum | 3 |
| ulcerative colitis colon | 1 | kidney | 15 |
|  |  | cancerous kidney | 1 |

TABLE 7

| Tissue/Cell Line | #samples | Tissue/Cell Line | #samples |
|---|---|---|---|
| 293 | 1 | HBL-100 | 1 |
| C32 | 1 | Hs-294T | 1 |
| HaCat#1 | 1 | Molt4 | 1 |
| HaCat#2 | 1 | RPMI | 1 |
| HaCat#3 | 1 | U-937 | 1 |
| HaCat#4 | 1 | A-375 | 1 |
| WI-38 | 1 | HCT-15 | 1 |
| WI-38 + 2 um ionomycin #1 | 1 | HT-29 | 1 |
| WI-38 + 2 um ionomycin #2 | 1 | MRC-5 | 1 |
| WI-38 + 5 um ionomycin#1 | 1 | RPT-1 | 1 |
| WI-38 + 5 um ionomycin#2 | 1 | RPT-2 | 1 |
| Caco-2, | 1 | WM-115 | 1 |
| Caco-2, differentiated | 1 | A-431 | 1 |
| DLD-1 | 1 | WERI-Rb-1 | 1 |

TABLE 7-continued

| Tissue/Cell Line | #samples | Tissue/Cell Line | #samples |
|---|---|---|---|
| HRE | 1 | HEL-92.1.7 | 1 |
| HRCE | 1 | HuH-7 | 1 |
| MCF7 | 1 | MV-4-11 | 1 |
| PC-3 | 1 | U-138 | 1 |
| TF-1 | 1 | CCRF-CEM | 1 |
| 5637 | 1 | Y-79 | 1 |
| 143B | 1 | A-549 | 1 |
| ME-180 | 1 | EL-4 | 1 |
| prostate epithelia | 1 | HeLa 229 | 1 |
| U-2 OS | 1 | HUT 78 | 1 |
| T-47D | 1 | NCI-H69 | 1 |
| Mg-63 | 1 | SaOS2 | 1 |
| Raji | 1 | USMC | 1 |
| U-373 MG | 1 | UASMC | 2 |
| A-172 | 1 | AoSMC | 1 |
| CRL-1964 | 1 | UtSMC | 1 |
| CRL-1964 + butryic acid | 1 | HepG2 | 1 |
| HUVEC | 1 | HepG2-IL6 | 1 |
| SK-Hep-1 | 1 | NHEK#1 | 1 |
| SK-Lu-1 | 1 | NHEK#2 | 1 |
| Sk-MEL-2 | 1 | NHEK#3 | 1 |
| K562 | 1 | NHEK#4 | 1 |
| BeWo | 1 | ARPE-19 | 1 |
| FHS74.Int | 1 | G-361 | 1 |
| HL-60 | 1 | HISM | 1 |
| Malme 3M | 1 | 3AsubE | 1 |
| FHC | 1 | 1NT407 | 1 |
| HREC | 1 |  |  |

TABLE 8

| Tissue | #samples | Tissue | #samples |
|---|---|---|---|
| liver | 10 | lung | 13 |
| lymph node | 1 | cancerous lung | 2 |
| lymphoma | 4 | normal lung adjacent to cancer | 1 |
| mammary adenoma | 1 | muscle | 3 |
| mammary gland | 3 | neuroblastoma | 1 |
| melinorioma | 1 | omentum | 2 |
| osteogenic sarcoma | 2 | ovary | 6 |
| pancreas | 4 | cancerous ovary | 2 |
| skin | 5 | parotid | 7 |
| sarcoma | 2 | salivary gland | 4 |

TABLE 9

| Tissue | #samples | Tissue | #samples |
|---|---|---|---|
| small bowel | 10 | uterus | 11 |
| spleen | 3 | uterine cancer | 1 |
| spleen lymphoma | 1 | thyroid | 9 |
| stomach | 13 |  |  |
| stomach cancer | 1 |  |  |

D. Tissue Distribution of Mouse Zcytor16 in Tissue Panels Using PCR

A panel of cDNAs from murine tissues was screened for mouse Zcytor16 expression using PCR. The panel was made in-house and contained 49 marathon cDNA and cDNA samples from various normal and cancerous murine tissues and cell lines are shown in Table 10, below. The cDNAs are either in-house cDNA libraries marathon cDNAs. The RNA used to create these cDNA's came from either in-house RNA preps, Clontech RNA, or Invitrogen RNA. The mouse marathon cDNAs were made using the marathon-Ready™ kit (Clontech, Palo Alto, Calif.) and QC tested with mouse transferrin receptor primers ZC10,651 (SEQ ID NO:42) and ZC10,565 (SEQ ID NO:43) and then diluted based on the intensity of the transferrin band. The in-house libraries were diluted to provide 25 ng per well of cDNA. To assure quality of the amplified library samples in the panel, three tests for quality control (QC) were run: (1) To assess the RNA quality used for the libraries, the in-house cDNAs were tested for average insert size by PCR with vector oligos that were specific for the vector sequences for an individual cDNA library; (2) Standardization of the concentration of the cDNA in panel samples was achieved using standard PCR methods to amplify full length alpha tubulin or G3PDH cDNA using a 5' vector oligo: ZC14,063 (SEQ ID NO:20) and 3' alpha tubulin specific oligo primer ZC17,574 (SEQ ID NO:21) or 3' G3PDH specific oligo primer ZC17,600 (SEQ ID NO:22); and (3) a sample was sent to sequencing to check for possible ribosomal or ritochondrial DNA contamination. The panel was set up in a 96-well format that included a mouse genomic DNA (Clontech, Palo Alto, Calif.) positive control sample. Each well contained approximately 0.2–100 pg/µl of cDNA. The PCR was set up using oligos ZC38,001 (SEQ ID NO:44) and ZC38,022 (SEQ ID NO:45), Advantage 2 Taq Polymerase (Clontech, Palo Alto, Calif.), and Rediload dye (Research Genetics, Inc., Huntsville, Ala.). The amplification was carried out as follows: 1 cycle at 94° C. for 2 minutes; 35 cycles of 94° C. for 10 seconds, 60° C. for 20 seconds and 68° C. for 30 seconds, followed by 1 cycle at 68° C. for 7 minutes. About 12.5 µl of the PCR reaction product was subjected to standard Agarose gel electrophoresis using a ~4% agarose gel.

The correct predicted DNA fragment size of 114 base pairs was observed in Lung, Pancreas, Placenta, Salivary Gland, Skeletal Muscle, Skin, Small Intestine, Smooth Muscle, Spleen, Stomach, and Testis cDNAs. These initial expression results for the mouse Zcytor16 corroborated the expression data seen for human Zcytor16 discussed herein, suggesting that the use of mouse Zcytor16 in an animal model, such as mouse, would reasonably reflect the in vivo expression and function of Zcytor16 seen in humans, and discussed herein.

TABLE 10

| Tissue/Cell line | #samples | Tissue/Cell line | #samples |
|---|---|---|---|
| 229 | 1 | Pancreas | 1 |
| 7F2 | 1 | Placenta | 2 |
| Adipocytes-Amplified | 1 | Jakotay-Prostate Cell Line | 1 |
| aTC1.9 | 1 | Nelix-Prostate Cell Line | 1 |
| Brain | 4 | Paris-Prostate Cell Line | 1 |
| CCC4 | 1 | Torres-Prostate Cell Line | 1 |
| CD90 + Amplified | 1 | Tuvak-Prostate Cell Line | 1 |
| OC10B | 1 | Salivary Gland | 2 |
| Dentritic | 1 | Skeletal Muscle | 1 |
| Embyro | 1 | Skin | 2 |
| Heart | 2 | Small Intestine | 1 |
| Kidney | 3 | Smooth Muscle | 2 |
| Liver | 2 | Spleen | 2 |
| Lung | 2 | Stomach | 1 |
| MEWt#2 | 1 | Testis | 3 |
| P388D1 | 1 | Thymus | 1 |

Example 13

Construction of Expression Vector Expressing Full-length Zzcytor11

The entire zcytor11 receptor (commonly owned U.S. Pat. No. 5,965,704) was isolated by digestion with EcoRI and XhoI from plasmid pZP7P, containing full-length zcytor11 receptor cDNA (SEQ ID NO:24; amino acid sequence in SEQ ID NO:25) and a puromycin resistance gene. The digest was run on a 1% low melting point agarose (Boerhinger Mannheim) gel and the approximately 1.5 kb zcytor11 cDNA was isolated using Qiaquick™ gel extraction kit (Qiagen) as per manufacturer's instructions. The purified zcytor11 cDNA was inserted into an expression vector as described below.

Recipient expression vector pZP7Z was digested with EcoRI (BRL) and XhoI (Boehringer Mannheim) as per manufacturer's instructions, and gel purified as described above. This vector fragment was combined with the EcoRI and XhoI cleaved zcytor11 fragment isolated above in a ligation reaction. The ligation was run using T4 Ligase (BRL) at 12° C. overnight. A sample of the ligation was electroporated in to DH10B electroMAX™ electrocompetent E. coli cells (25 µF, 200Ω, 1.8V). Transformants were plated on LB+Ampicillin plates, and single colonies were picked into 2 ml LB+Ampicillin and grown overnight. Plasmid DNA was isolated using Wizard Minipreps (Promega), and each was digested with EcoRI and XhoI to confirm the presence of insert. The insert was approximately 1.5 kb, and was full-length. Digestion with SpeI and PstI was used to confirm the identity of the vector.

Example 14

Construction of BaF3 Cells Expressing the CRF2-4 Receptor (BaF3/CRF2-4 cells) and BaF3 Cells Expressing the CRF2-4 Receptor with the Zcytor11 Receptor (BaF3/CRF2-4/Zcytor11 cells)

BaF3 cells expressing the full-length CFR2–4 receptor were constructed, using 30 µg of a CFR2–4 expression vector, described below. The BaF3 cells expressing the CFR2–4 receptor were designated as BaF3/CFR2–4. These cells were used as a control, and were further transfected with full-length zcytor11 receptor (U.S. Pat. No. 5,965,704) and used to construct a screen for IL-TIF activity as described below.

A. Construction of BaF3 Cells Expressing the CRF2-4 Receptor

The full-length cDNA sequence of CRF2-4 (Genbank Accession No. Z17227) was isolated from a Daudi cell line cDNA library, and then cloned into an expression vector pZP7P.

BaF3, an interleukin-3 (IL-3) dependent pre-lymphoid cell line derived from murine bone marrow (Palacios and Steinmetz, Cell 41: 727–734, 1985; Mathey-Prevot et al., Mol. Cell. Biol. 6: 4133–4135, 1986), was maintained in complete media (RPMI medium (JRH Bioscience Inc., Lenexa, Kans.) supplemented with 10% heat-inactivated fetal calf serum, 2 ng/ml murine IL-3 (mIL-3) (R & D, Minneapolis, Minn.), 2 mM L-glutaMax-1™ (Gibco BRL), 1 mM Sodium Pyruvate (Gibco BRL), and PSN antibiotics (GIBCO BRL)). Prior to electroporation, CRF2-4/pZP7P was prepared and purified using a Qiagen Maxi Prep kit (Qiagen) as per manufacturer's instructions. For electroporation, BaF3 cells were washed once in serum-free RPMI media and then resuspended in serum-free RPMI media at a cell density of $10^7$ cells/ml. One ml of resuspended BaF3 cells was mixed with 30 µg of the CRF2-4/pZP7P plasmid DNA and transferred to separate disposable electroporation chambers (GIBCO BRL). Following a 15-minute incubation at room temperature the cells were given two serial shocks (800 1Fad/300 V.; 1180 1Fad/300 V.) delivered by an electroporation apparatus (CELL-PORATOR™; GIBCO BRL). After a 5-minute recovery time, the electroporated cells were transferred to 50 ml of complete media and placed in an incubator for 15–24 hours (37° C., 5% $CO_2$). The cells were then spun down and resuspended in 50 ml of complete media containing 2 μg/ml puromycin in a T-162 flask to isolate the puromycin-resistant pool. Pools of the transfected BaF3 cells, hereinafter called BaF3/CRF2-4 cells, were assayed for signaling capability as described below. Moreover these cells were further transfected with zcytor11 receptor as described below.

B. Construction of BaF3 Cells Expressing CRF2-4 and Zcytor11 Receptors

BaF3/CRF2-4 cells expressing the full-length zcytor11 receptor were constructed as per Example 5A above, using 30 μg of the zcytor11 expression vector, described in Example 6 above. Following recovery, transfectants were selected using 200 μg/ml zeocin and 2 μg/ml puromycin. The BaF3/CRF2-4 cells expressing the zcytor11 receptor were designated as BaF3/CRF2-4/zcytor11 cells. These cells were used to screen for IL-TIF activity as well as Zcytor16 antagonist activity described in Example 15.

Example 15

Screening for IL-TIF Antagonist Activity Using BaF3/CRF2-4/Zcytor11 Cells Using an Alamar Blue Proliferation Assay A. Screening for IL-TIF Activity Using BaF3/CRF2-4/Zcytor11 Cells Using an Alamar Blue Proliferation Assay Purified human IL-TIF-CEE (Example 19) was used to test for the presence of proliferation activity as described below. Purified humsn Zcytor16-Fc4 (Example 11) was used to antagonize the proliferative response of the IL-TIF in this assay as described below.

BaF3/CRF2-4/zcytor11 cells were spun down and washed in the complete media, described in Example 7A above, but without mIL-3 (hereinafter referred to as "mIL-3 free media"). The cells were spun and washed 3 times to ensure the removal of the mIL-3. Cells were then counted in a hemacytometer. Cells were plated in a 96-well format at 5000 cells per well in a volume of 100 μl per well using the mIL-3 free media.

Proliferation of the BaF3/CRF2-4/zcytor11 cells was assessed using IL-TIF-CEE protein diluted with mIL-3 free media to 50, 10, 2, 1, 0.5, 0.25, 0.13, 0.06 ng/ml concentrations. 100 μl of the diluted protein was added to the BaF3/CRF2-4/zcytor11 cells. The total assay volume is 200 μl. The assay plates were incubated at 37° C., 5% $CO_2$ for 3 days at which time Alamar Blue (Accumed, Chicago, Ill.) was added at 20 μl/well. Plates were again incubated at 37° C., 5% $CO_2$ for 24 hours. Alamar Blue gives a fluourometric readout based on number of live cells, and is thus a direct measurement of cell proliferation in comparison to a negative control. Plates were again incubated at 37° C., 5% $CO_2$ for 24 hours. Plates were read on the Fmax™ plate reader (Molecular Devices Sunnyvale, Calif.) using the SoftMax™ Pro program, at wavelengths 544 (Excitation) and 590 (Emmission). Results confirmed the dose-dependent proliferative response of the BaF3/CRF2-4/zcytor11 cells to IL-TIF-CEE. The response, as measured, was approximately 15-fold over background at the high end of 50 ng/ml down to a 2-fold induction at the low end of 0.06 ng/ml. The BaF3 wild type cells, and BaF3/CRF2-4 cells did not proliferate in response to IL-TIF-CEE, showing that IL-TIF is specific for the CRF2-4/zcytor11 heterodimeric receptor.

In order to determine if Zcytor16 is capable of antagonizing IL-TIF activity, the assay described above was repeated using purified soluble human Zcytor16/Fc4. When IL-TIF was combined with Zcytor16 at 10 μg/ml, the response to IL-TIF at all concentrations was brought down to background. That the presence of soluble human Zcytor16 ablated the proliferative effects of IL-TIF demonstrates that it is a potent antagonist of the IL-TIF ligand. This assay is also used to assess mouse Zcytor16 activity in antagonizing L-TIF. Similar results are expected.

Example 16

IL-TIF Activation of a Reporter Mini-gene in MES 13 Cells and Inhibition of Activity by Human Zcytor16-Fc4

MES 13 cells (ATCC No. CRL-1927) were plated at 10,000 cells/well in 96-well tissue culture clusters (Costar) in DMEM growth medium (Life Technologies) supplemented with pyruvate and 10% serum (HyClone). Next day, the medium was switched to serum free DMEM medium by substituting 0.1% BSA (Fraction V; Sigma) for serum. This medium also contained the adenoviral construct KZ136 (below) that encodes a luciferase reporter mini-gene driven by SRE and STAT elements, at a 1000:1 multiplicity of infection (m.o.i.), i.e. 1000 adenoviral particles per cell. After allowing 24 h for the incorporation of the adenoviral construct in the cells, the media were changed and replaced with serum-free media. Human recombinant IL-TIF with or without a recombinant Zcytor16-Fc4 fusion was added at the indicated final concentration in the well (as described in Table 11, below). Dilutions of both the IL-TIF and Zcytor16-Fc4 were performed in serum-free medium. 0.1% BSA was added for a basal assay control. 4 h later, cells were lysed and luciferase activity, denoting activation of the reporter gene, was determined in the lysate using an Luciferase Assay System assay kit (Promega) and a Labsystems Luminoskan luminometer (Labsystems, Helsinki, Finland). Activity was expressed as luciferase units (LU) in the lysate. Results are shown in Table 11, below.

TABLE 11

| Level of IL-TIF (ng/ml) | LU w/o zcytoR16 | LU w/10 μg/ml zcytoR16 |
|---|---|---|
| 0 (basalBSAcontrol) | 103 ± 2 | 104 ± 2 |
| 0.03 | 105 ± 3 | 104 ± 4 |
| 0.3 | 108 ± 4 | 99 ± 6 |
| 3 | 134 ± 8 | 98 ± 15 |
| 30 | 188 ± 16 | 110 ± 3 |
| 300 | 258 ± 21 | 112 ± 30 |

These results demonstrate two things: First, that MES 13 cells respond to human recombinant IL-TIF and therefore possess endogenous functional receptors for the cytokine. Second, that the human zcytoR16-Fc4 receptor fusion acts as an antagonist that effectively blocks the response to IL-TIF, even at the highest dose that this cytokine was used. Therefore, zcyto16 is an effective antagonist of IL-TIF on cells (MES 13) that are intrinsically capable of responding to IL-TIF, i.e. cells that do not require exogenous expression of additional receptor components to respond to the cytokine. This assay is also used to assess mouse Zcytor16 activity in antagonizing IL-TIF. Similar results are expected.

The construction of the adenoviral KZ136 vector was as follows. The original KZ136 vector is disclosed in Poulsen, L K et al. *J. Biol. Chem.* 273:6228–6232, 1998. The CMV promoter/enhancer and SV40 pA sequences were removed from pACCMV.pLpA (T. C. Becker et al., *Meth. Immunology* 43:161–189, 1994.) and replaced with a linker containing Asp718/KpnI and HindIII sites (oligos ZC13252 (SEQ ID NO:26) and ZC13453 (SEQ ID NO:27)). The STAT/SRE driven luciferase reporter cassette was exised from vector KZ136 (Poulsen, L K et al., supra.).) as a Asp718/KpnI- HindIII fragment and inserted into the adapted pAC vector. Recombinant KZ136 Adenovirus was produced by transfection with JM17 Adenovirus into 293 cells as described in T. C. Becker et al. supra.). Plaque purified virus was amplified and used to infect cultured cells at 5–50 pfu/cell 12–48 hours before assay. Luciferase reporter assays were performed as described in 96 well microplates as per Poulsen, L K et al., supra.).

Example 17

Construct for Generating CEE-tagged IL-TIF

Oligonucleotides were designed to generate a PCR fragment containing the Kozak sequence and the coding region for human IL-TIF, without its stop codon. These oligonucleotides were designed with a KpnI site at the 5' end and a BamHI site at the 3' end to facilitate cloning into pHZ200-CEE, our standard vector for mammalian expression of C-terminal Glu-Glu tagged (SEQ ID NO:10) proteins. The pHZ200 vector contains an MT-1 promoter.

PCR reactions were carried out using Turbo Pfu polymerase (Stratagene) to amplify a IL-TIF cDNA fragment. About 20 ng human IL-TIF polynucleotide template (SEQ ID NO:14), and oligonucleotides ZC28590 (SEQ ID NO:28) and ZC28580 (SEQ ID NO:29) were used in the PCR reaction. PCR reaction conditions were as follows: 95° C. for 5 minutes,; 30 cycles of 95° C. for 60 seconds, 55° C. for 60 seconds, and 72° C. for 60 seconds; and 72° C. for 10 minutes; followed by a 4° C. hold. PCR products were separated by agarose gel electrophoresis and purified using a QiaQuick™ (Qiagen) gel extraction kit. The isolated, approximately 600 bp, DNA fragment was digested with KpnI and BamHI (Boerhinger-Mannheim), gel purified as above and ligated into pHZ200-CEE that was previously digested with KpnI and BamHI.

About one microliter of the ligation reaction was electroporated into DH10B ElectroMax™ competent cells (GIBCO BRL, Gaithersburg, Md.) according to manufacturer's direction and plated onto LB plates containing 100 $\mu$g/ml ampicillin, and incubated overnight. Colonies were picked and screened by PCR using oligonucleotides ZC28,590 (SEQ ID NO:28) and ZC28,580 (SEQ ID NO:29), with PCR conditions as described above. Clones containing inserts were then sequenced to confirm error-free IL-TIF inserts. Maxipreps of the correct pHZ200-IL-TIF-CEE construct, as verified by sequence analysis, were performed.

Example 18

Transfection And Expression Of IL-TIF Soluble Receptor Polypeptides

BHK 570 cells (ATCC No. CRL-10314), were plated at about $1.2 \times 10^6$ cells/well (6-well plate) in 800 $\mu$l of serum free (SF) DMEM media (DMEM, Gibco/BRL High Glucose) (Gibco BRL, Gaithersburg, Md.). The cells were transfected with an expression plasmid containing IL-TIF-CEE described above (Example 17), using Lipofectin™ (Gibco BRL), in serum free (SF) DMEM according to manufacturer's instructions.

The cells were incubated at 37° C. for approximately five hours, then transferred to separate 150 mm MAXI plates in a final volume of 30 ml DMEM/5% fetal bovine serum (FBS) (Hyclone, Logan, Utah). The plates were incubated at 37° C., 5% $CO_2$, overnight and the DNA: Lipofectin™ mixture was replaced with selection media (5% FBS/DMEM with 1 $\mu$M methotrexate (MTX)) the next day.

Approximately 10–12 days post-transfection, colonies were mechanically picked to 12-well plates in one ml of 5%FCS/DMEM with 5 $\mu$M MTX, then grown to confluence. Positive expressing clonal colonies Conditioned media samples were then tested for expression levels via SDS-PAGE and Western analysis. A high-expressing clone was picked and expanded for ample generation of conditioned media for purification of the IL-TIF-CEE expressed by the cells (Example 19).

Example 19

Purification of IL-TIF Soluble Receptors from BHK 570 Cells

Unless otherwise noted, all operations were carried out at 4° C. The following procedure was used for purifying IL-TIF polypeptide containing C-terminal GluGlu (EE) tags (SEQ ID NO:10). Conditioned media from BHK cells expressing IL-TIF-CEE (Example 18) was concentrated with an Amicon S10Y3 spiral cartridge on a ProFlux A30. A Protease inhibitor solution was added to the concentrated conditioned media to final concentrations of 2.5 mM ethylenediaminetetraacetic acid (EDTA, Sigma Chemical Co. St. Louis, Mo.), 0.003 mM leupeptin (Boehringer-Mannheim, Indianapolis, Ind.), 0.001 mM pepstatin (Boehringer-Mannheim) and 0.4 mM Pefabloc (Boehringer-Mannheim). Samples were removed for analysis and the bulk volume was frozen at −80° C. until the purification was started. Total target protein concentrations of the concentrated conditioned media were determined via SDS-PAGE and Western blot analysis with the anti-EE HRP conjugated antibody.

About 100 ml column of anti-EE G-Sepharose (prepared as described below) was poured in a Waters AP-5, 5 cm×10 cm glass column. The column was flow packed and equilibrated on a BioCad Sprint (PerSeptive BioSystems, Framingham, Mass.) with phosphate buffered saline (PBS) pH 7.4. The concentrated conditioned media was thawed, 0.2 micron sterile filtered, pH adjusted to 7.4, then loaded on the column overnight with about 1 ml/minute flow rate. The column was washed with 10 column volumes (CVs) of phosphate buffered saline (PBS, pH 7.4), then plug eluted with 200 ml of PBS (pH 6.0) containing 0.5 mg/ml EE peptide (Anaspec, San Jose, Calif.) at 5 ml/minute. The EE peptide used has the sequence EYMPME (SEQ ID NO:10). The column was washed for 10 CVs with PBS, then eluted with 5 CVs of 0.2M glycine, pH 3.0. The pH of the glycine-eluted column was adjusted to 7.0 with 2 CVs of 5×PBS, then equilibrated in PBS (pH 7.4). Five ml fractions were collected over the entire elution chromatography and absorbance at 280 and 215 nM were monitored; the pass through and wash pools were also saved and analyzed. The EE-polypeptide elution peak fractions were analyzed for the target protein via SDS-PAGE Silver staining and Western Blotting with the anti-EE HRP conjugated antibody. The polypeptide elution fractions of interest were pooled and concentrated from 60 ml to 5.0 ml using a 10,000 Dalton molecular weight cutoff membrane spin concentrator (Millipore, Bedford, Mass.) according to the manufacturer's instructions.

To separate IL-TIF-CEE from other co-purifying proteins, the concentrated polypeptide elution pooled fractions were subjected to a POROS HQ-50 (strong anion exchange resin from PerSeptive BioSystems, Framingham, Mass.) at pH 8.0. A 1.0×6.0 cm column was poured and flow packed on a BioCad Sprint. The column was counter ion charged then equibrated in 20 mM TRIS pH 8.0 (Tris (Hydroxymethyl Aminomethane)). The sample was diluted 1:13 (to reduce the ionic strength of PBS) then loaded on the Poros HQ column at 5 ml/minute. The column was washed for 10 CVs with 20 mM Tris pH 8.0 then eluted with a 40 CV gradient of 20 mM Tris/ 1 M sodium chloride (NaCl) at 10 ml/minute. 1.5 ml fractions were collected over the entire chromatography and absorbance at 280 and 215 nM were monitored. The elution peak fractions were analyzed via SDS-PAGE Silver staining. Fractions of interest were pooled and concentrated to 1.5–2 ml using a 10,000 Dalton molecular weight cutoff membrane spin concentrator (Millipore, Bedford, Mass.) according to the manufacturer's instructions.

To separate IL-TIF-CEE polypeptide from free EE peptide and any contaminating co-purifying proteins, the pooled concentrated fractions were subjected to size exclusion chromatography on a 1.5×90 cm Sephadex S200 (Pharmacia, Piscataway, N.J.) column equilibrated and loaded in PBS at a flow rate of 1.0 ml/min using a BioCad Sprint. 1.5 ml fractions were collected across the entire chromatography and the absorbance at 280 and 215 nM were monitored. The peak fractions were characterized via SDS-PAGE Silver staining, and only the most pure fractions were pooled. This material represented purified IL-TIF-CEE polypeptide.

This purified material was finally subjected to a 4 ml ActiClean Etox (Sterogene) column to remove any remaining endotoxins. The sample was passed over the PBS equilibrated gravity column four times then the column was washed with a single 3 ml volume of PBS, which was pooled with the "cleaned" sample. The material was then 0.2 micron sterile filtered and stored at −80° C. until it was aliquoted.

On Western blotted, Coomassie Blue and Silver stained SDS-PAGE gels, the IL-TIF-CEE polypeptide was one major band. The protein concentration of the purified material was performed by BCA analysis (Pierce, Rockford, Ill.) and the protein was aliquoted, and stored at −80° C. according to standard procedures.

To prepare anti-EE Sepharose, a 100 ml bed volume of protein G-Sepharose (Pharmacia, Piscataway, N.J.) was washed 3 times with 100 ml of PBS containing 0.02% sodium azide using a 500 ml Nalgene 0.45 micron filter unit. The gel was washed with 6.0 volumes of 200 mM triethanolamine, pH 8.2 (TEA, Sigma, St. Louis, Mo.), and an equal volume of EE antibody solution containing 900 mg of antibody was added. After an overnight incubation at 4° C., unbound antibody was removed by washing the resin with 5 volumes of 200 mM TEA as described above. The resin was resuspended in 2 volumes of TEA, transferred to a suitable container, and dimethylpimilimidate-2HCl (Pierce, Rockford, Ill.) dissolved in TEA, was added to a final concentration of 36 mg/ml of protein G-Sepharose gel. The gel was rocked at room temperature for 45 min and the liquid was removed using the filter unit as described above. Nonspecific sites on the gel were then blocked by incubating for 10 min. at room temperature with 5 volumes of 20 mM ethanolamine in 200 mM TEA. The gel was then washed with 5 volumes of PBS containing 0.02% sodium azide and stored in this solution at 4° C.

Example 20

Human Zcytor11 Tissue Distribution in Tissue Panels Using Northern Blot and PCR

A. Human Zcytor11 Tissue Distribution in Tissue Panels Using PCR

A panel of cDNAs from human tissues was screened for zcytor11 expression using PCR. The panel was made in-house and contained 94 marathon cDNA and cDNA samples from various normal and cancerous human tissues and cell lines are shown in Table 6 above. Aside from the PCR reaction, the method used was as shown in Example 12. The PCR reactions were set up using oligos ZC14,666 (SEQ ID NO: 32) and ZC14,742 (SEQ ID NO:33), Advantage 2 cDNA polymerase mix (Clontech, Palo Alto, Calif.), and Rediload dye (Research Genetics, Inc., Huntsville, Ala.). The amplification was carried out as follows: 1 cycle at 94° C. for 2 minutes, 40 cycles of 94° C. for 15 seconds, 51° C. for 30 seconds and 72° C. for 30 seconds, followed by 1 at 72° C. for 7 minutes. The correct predicted DNA fragment size was observed in bladder, brain, cervix, colon, fetal brain, fetal heart, fetal kidney, fetal liver, fetal lung, fetal skin, heart, kidney, liver, lung, melanoma, ovary, pancreas, placenta, prostate, rectum, salivary gland, small intestine, testis, thymus, trachea, spinal cord, thyroid, lung tumor, ovarian tumor, rectal tumor, and stomach tumor. Zcytor11 expression was not observed in the other tissues and cell lines tested in this panel.

A commercial 1st strand cDNA panel (Human Blood Fractions MTC Panel, Clontech, Palo Alto, Calif.) was also assayed as above. The panel contained the following samples: mononuclear cells, activated mononuclear cells, resting CD4+ cells, activated CD4+ cells, resting CD8+ cells, activated CD8+ cells, resting CD14+ cells, resting CD19+ cells and activated CD19+ cells. All samples except activated CD8+ and Activated CD 19+ showed expression of zcytor11.

B. Tissue Distribution of Zcytor11 in Human Cell Line and Tissue Panels Using RT-PCR A panel of RNAs from human cell lines was screened for zcytor11 expression using RT-PCR. The panels were made in house and contained 84 RNAs from various normal and cancerous human tissues and cell lines as shown in Tables 7–10 above. The RNAs were made from in house or purchased tissues and cell lines using the RNAeasy Midi or Mini Kit (Qiagen, Valencia, Calif.). The panel was set up in a 96-well format with 100 ngs of RNA per sample. The RT-PCR reactions were set up using oligos ZC14,666 (SEQ ID NO:32) and ZC14,742 (SEQ ID NO:33), Rediload dye and SUPERSCRIPT One Step RT-PCR System(Life Technologies, Gaithersburg, Md.). The amplification was carried out as follows: one cycle at 50° for 30 minutes followed by 45 cycles of 94°, 15 seconds; 52°, 30 seconds; 72°, 30 seconds; then ended with a final extension at 72° for 7 minutes. 8 to 10 uls of the PCR reaction product was subjected to standard Agarose gel electrophoresis using a 4% agarose gel. The correct predicted cDNA fragment size was observed in adrenal gland, bladder, breast, bronchus, normal colon, colon cancer, duodenum, endometrium, esophagus, gastic cancer, gastro-esophageal cancer, heart ventricle, ileum, normal kidney, kidney cancer, liver, lung, lymph node, pancreas, parotid, skin, small bowel, stomach, thyroid, and uterus. Cell lines showing expression of zcytor11 were A-431, differentiated CaCO2, DLD-1, HBL-100, HCT-15, HepG2, HepG2+IL6, HuH7, and NHEK #1-4. Zcytor11 expression was not observed in the other tissues and cell lines tested in this panel.

In addition, because the expression pattern of zcytor11, one of IL-TIF's receptors, shows expression in certain specific tissues, binding partners including the natural ligand, IL-TIF, can also be used as a diagnostic to detect specific tissues (normal or abnormal), cancer, or cancer tissue in a biopsy, tissue, or histologic sample, particularly in tissues where IL-TIF receptors are expressed. IL-TIF can also be used to target other tissues wherein its receptors, e.g., Zcytor16 and zcytor11 are expressed. Moreover, such binding partners could be conjugated to chemotherapeutic agents, toxic moieties and the like to target therapy to the site of a tumor or diseased tissue. Such diagnostic and targeted therapy uses are known in the art and described herein.

The expression patterns of zcytor11 (above) and Zcytor16 (Example 12, and Example 21) indicated target tissues and cell types for the action of IL-TIF, and hence IL-TIF antagonsists, such as Zcytor16. The zcytor11 expression generally overlapped with Zcytor16 expression in three physiologic systems: digestive system, female reproductive system, and immune system. Moreover, the expression pattern of the receptor (zcytor11) indicated that an IL-TIF antagonist such as Zcytor16 would have therapeutic application for human disease in two areas: inflammation (e.g., IBD, Chron's disease, pancreatitis) and cancer (e.g., ovary, colon). That is, the polynucleotides, polypeptides and antibodies of the present invention can be used to antagonize the inflammatory, and other cytokine-induced effects of IL-TIF interaction with the cells expressing the zcytor11 receptor.

Moreover, the expression of zcytor11 appeared to be downregulated or absent in an ulcerative colitis tissue, HepG2 liver cell line induced by IL-6, activated CD8+ T-cells and CD19+ B-cells. However, Zcytor16 appeared to be upregulated in activated CD19+ B-cells (Example 12), while zcytor11 is downregulated in activated CD19+ cells, as compared to the resting CD19+ cells (above). The expression of zcytor11 and Zcytor16 has a reciprocal correlation in this case. These RT-PCR experiments demonstrate that CD19+ peripheral blood cells, B lymphocytes, express receptors for IL-TIF, namely zcytoR11 and zcytoR16. Furthermore B cells display regulated expression of zcytoR11 and zcytoR16. B-lymphocytes activated with mitogens decrease expression of zcytoR11 and increase expression of zcytoR16. This represents a classical feedback inhibition that would serve to dampen the activity of IL-TIF on B cells and other cells as well. Soluble zcytoR16 would act as an antagonist to neutralize the effects of IL-TIF on B cells. This would be beneficial in diseases where B cells are the key players: Autoimmune diseases including systemic lupus erythmatosus (SLE), myasthenia gravis, immune complex disease, and B-cell cancers that are exacerbated by IL-TIF. Also autoimmune diseases where B cells contribute to the disease pathology would be targets for zcytoR16 therapy: Multiple sclerosis, inflammatory bowel disease (IBD) and rheumatoid arthritis are examples. ZcytoR16 therapy would be beneficial to dampen or inhibit B cells producing IgE in atopic diseases including asthma, allergy and atopic dermatitis where the production of IgE contributes to the pathogenesis of disease.

B cell malignancies may exhibit a loss of the "feedback inhibition" described above. Administration of zcytoR16 would restore control of IL-TIF signaling and inhibit B cell tumor growth. The administration of zcytoR16 following surgical resection or chemotherapy may be useful to treat minimal residual disease in patients with B cell malignancies. The loss of regulation may lead to sustain or increased expression of zcytoR11. Thus creating a target for therapeutic monoclonal antibodies targeting zcytoR11.

Example 21

Identification of Cells Expressing Zcytor16 Using in situ Hybridization

Specific human tissues were isolated and screened for human Zcytor16 expression by in situ hybridization. Various human tissues prepared, sectioned and subjected to in situ hybridization included cartilage, colon, appendix, intestine, fetal liver, lung, lymph node, lymphoma, ovary, pancreas, placenta, prostate, skin, spleen, and thymus. The tissues were fixed in 10% buffered formalin and blocked in paraffin using standard techniques. Tissues were sectioned at 4 to 8 microns. Tissues were prepared using a standard protocol ("Development of non-isotopic in situ hybridization" at The Laboratory of Experimental Pathology (LEP), NIEHS, Research Triangle Park, N.C.; web address http://dir.niehs.nih.gov/dirlep/ish.html). Briefly, tissue sections were deparaffinized with HistoClear (National Diagnostics, Atlanta, Ga.) and then dehydrated with ethanol. Next they were digested with Proteinase K (50 $\mu$g/ml) (Boehringer Diagnostics, Indianapolis, Ind.) at 37° C. for 2 to 7 minutes. This step was followed by acetylation and re-hydration of the tissues.

One in situ probe was designed against the human Zcytor16 sequence (nucleotide 1–693 of SEQ ID NO:1), and isolated from a plasmid containing SEQ ID NO:1 using standard methods. T3 RNA polymerase was used to generate an antisense probe. The probe was labeled with digoxigenin (Boehringer) using an In Vitro transcription System (Promega, Madison, Wis.) as per manufacturer's instruction.

In situ hybridization was performed with a digoxigenin-labeled Zcytor16 probe (above). The probe was added to the slides at a concentration of 1 to 5 pmol/ml for 12 to 16 hours at 62.5° C. Slides were subsequently washed in 2×SSC and 0.1×SSC at 55° C. The signals were amplified using tyramide signal amplification (TSA) (TSA, in situ indirect kit; NEN) and visualized with Vector Red substrate kit (Vector Lab) as per manufacturer's instructions. The slides were then counter-stained with hematoxylin (Vector Laboratories, Burlingame, Calif.).

Signals were observed in several tissues tested: The lymph node, plasma cells and other mononuclear cells in peripheral tissues were strongly positive. Most cells in the lymphatic nodule were negative. In lymphoma samples, positive signals were seen in the mitotic and multinuclear cells. In spleen, positive signals were seen in scattered mononuclear cells at the periphery of follicles were positive. In thymus, positive signals were seen in scattered mononuclear cells in both cortex and medulla were positive. In fetal liver, a strong signal was observed in a mixed population of mononuclear cells in sinusoid spaces. A subset of hepatocytes might also have been positive. In the inflamed appendix, mononuclear cells in peyer's patch and infiltration sites were positive. In intestine, some plasma cells and ganglia nerve cells were positive. In normal lung, Zcytor16 was expressed in alveolar epithelium and mononuclear cells in interstitial tissue and circulation. In the lung carcinoma tissue, a strong signal was observed in mostly plasma cells and some other mononuclear cells in peripheral of lymphatic aggregates. In ovary carcinoma, epithelium cells were strongly positive. Some interstitial cells, most likely the mononuclear cells, were also positive. There was no signal observed in the normal ovary. In both normal and pancreatitis pancreas samples, acinar cells and some mononuclear cells in the mesentery were positive. In the early term (8 weeks) placenta, signal was observed in trophoblasts. In skin, some mononuclear cells in the inflamed infiltrates in the superficial dermis were positive. Keratinocytes were also weakly positive. In prostate carcinoma, scatted mononuclear cells in interstitial tissues were positive. In articular cartilage, chondrocytes were positive. Other tissues tested including normal ovary and a colon adenocarcinoma were negative.

In summary, the in situ data was consistent with expression data described above for the Zcytor16. Zcytor16 expression was observed predominately in mononuclear cells, and a subset of epithelium was also positive. These results confirmed the presence of Zcytor16 expression in immune cells and point toward a role in inflammation, autoimmune disease, or other immune function, for example, in binding pro-inflammatory cytokines, including but not limited to IL-TIF. Moreover, detection of Zcytor16 expression can be used for example as an marker for mononuclear cells in histologic samples.

Zcytor16 is expressed in mononuclear cells, including normal tissues (lymph nodes, spleen, thymus, pancreas and fetal liver, lung), and abnormal tissues (inflamed appendix, lung carcinoma, ovary carcinoma, pancreatitis, inflamed skin, and prostate carcinoma). It is notable that plasma cells in the lymph node, intestine, and lung carcinoma are positive for Zcytor16. Plasma cells are immunologically activated lymphocytes responsible for antibody synthesis. In addition, IL-TIF, is expressed in activated T cells. In addition, the expression of Zcytor16 is detected only in activated (but not in resting) CD4+ and CD19+ cells (Example 12). Thus, Zcytor16 can be used as a marker for or as a target in isolating certain lymphocytes, such as mononuclear leucocytes and limited type of activated leucocytes, such as activated CD4+ and CD19+.

Furthermore, the presence of Zcytor16 expression in activated immune cells such as activated CD4+ and CD19+ cells showed that Zcytor16 may be involved in the body's immune defensive reactions against foreign invaders: such as microorganisms and cell debris, and could play a role in immune responses during inflammation and cancer formation.

Moreover, as discussed herein, epithelium form several tissues was positive for Zcytor16 expression, such as hepatocytes (endoderm-derived epithelia), lung alveolar epithelium (endoderm-derived epithelia), and ovary carcinoma epithelium (mesoderm-derived epithelium). The epithelium expression of Zcytor16 could be altered in inflammatory responses and/or cancerous states in liver and lung. Thus, Zcyto16 could be used as marker to monitor changes in these tissues as a result of inflammation or cancer. Moreover, analysis of Zcytor16 in situ expression showed that normal ovary epithelium is negative for Zcytor16 expression, while it is strongly positive in ovary carcinoma epithelium providing further evidence that Zcytor16 polynucleotides, polypeptides and antibodies can be used as a diagnostic marker and/or therapeutic target for the diagnosis and treatment of ovarian cancers, and ovary carcinoma, as described herein.

Zcytor16 was also detected in other tissues, such as acinar cells in pancreas (normal and pancreatitis tissues), trophoblasts in placenta (ectoderm-derived), chondrocytes in cartilage (mesoderm-derived), and ganglia cells in intestine (ectoderm-derived). As such, Zcytor16 may be involved in differentiation and/or normal functions of corresponding cells in these organs. As such, potential utilities of Zcytor16 include maintenance of normal metabolism and pregnancy, bone formation/homeostasis, and physiological function of intestine, and the like.

Example 22

In vivo Affects of IL-TIF Polypeptide

Mice (female, C57B1, 8 weeks old; Charles River Labs, Kingston, N.Y.) were divided into three groups. An adenovirus expressing an IL-TIF polypeptide (SEQ ID NO:15) was previously made using standard methods. On day 0, parental or IL-TIF adenovirus was administered to the first (n=8) and second (n=8) groups, respectively, via the tail vein, with each mouse receiving a dose of ~1×10$^{11}$ particles in ~0.1 ml volume. The third group (n=8) received no treatment. On days 12, mice were weighed and blood was drawn from the mice. Samples were analyzed for complete blood count (CBC) and serum chemistry. Statistically significant elevations in neutrophil and platelet counts were detected in the blood samples from the IL-TIF adenovirus administered group relative to the parental adenovirus treated group. Also, lymphocyte and red blood cell counts were significantly reduced from the IL-TIF adenovirus administered group relative to the parental adenovirus treated group. In addition, the IL-TIF adenovirus treated mice decreased in body weight, while parental adenovirus treated mice gained weight.

The results suggested that IL-TIF affects hematopoiesis, i.e., blood cell formation in vivo. As such, IL-TIF could have biological activities effecting different blood stem cells, thus resulting increase or decrease of certain differentiated blood cells in a specific lineage. For instance, IL-TIF appears to reduce lymphocytes, which is likely due to inhibition of the committed progenitor cells that give rise to lymphoid cells. IL-TIF also decreases red blood cells. This finding agrees with the inhibitory effects of IL-TIF on the proliferation and/or growth of myeloid stem cells (Example 23), supporting the notion that IL-TIF could play a role in anemia, infection, inflammation, and/or immune diseases by influencing blood cells involved in these processes. Antagonists against IL-TIF, such as antibodies or its soluble receptor Zcytor16, could be used as therapeutic reagents in these diseases.

Moreover, these experiments using IL-TIF adenovirus in mice suggest that IL-TIF over-expression increases the level of neutrophils and platelets in vivo. Although this may appear contradictory to the finding seen in K562 cells (Example 23), it is not uncommon to observe diverse activities of a particular protein in vitro versus in vivo. It is conceivable that there are other factors (such as cytokines and modifier genes) involved in the responses to IL-TIF in the whole animal system. Nevertheless, these data strongly support the involvement of IL-TIF in hematopoiesis. Thus, IL-TIF and its receptors are suitable reagents/targets for the diagnosis and treatment in variety of disorders, such as inflammation, immune disorders, infection, anemia, hematopoietic and other cancers, and the like.

Example 23

The IL-TIF Polypeptide Lyses K-562 Cells in Cytotoxicity Assay

The K-562 cell line (CRL-243, ATCC) has attained widespread use as a highly sensitive in vitro target for cytotoxicity assays. K-562 blasts are multipotential, hematopoietic malignant cells that spontaneously differentiate into recognizable progenitors of the erythrocytic, granulocytic and monocytic series (Lozzio, B B et al., *Proc. Soc. Exp. Biol. Med.* 166: 546–550, 1981).

K562 cells were plated at 5,000 cells/well in 96-well tissue culture clusters (Costar) in DMEM phenol-free growth medium (Life Technologies) supplemented with pyruvate and 10% serum (HyClone). Next day, human recombinant IL-TIF (Example 19), BSA control or retinoic acid (known to be cytotoxic to K562 cells) were added. Seventy-two hours later, the vital stain MTT (Sigma, St Louis, Mo.), a widely used indicator of mitochondrial activity and cell growth, was added to the cells at a final concentration of 0.5 mg/ml. MMP is converted to a purple formazan derivative by mitochondrial dehydrogenases. Four hours later, converted MMP was solubilized by adding an equal volume of acidic isopropanol (0.04N HCl in absolute isopropanol) to the wells. Absorbance was measured at 570 nm, with background subtraction at 650 nm. In this experimental setting, absorbance reflects cell viability. Results shown in Table 12 are expressed as % cytotoxicity.

TABLE 12

| Agent | Concentration | % Cytotoxicity |
|---|---|---|
| BSA Control | 1 ug/ml | 1.3 |
| Retinoic acid | 100 uM | 62 |
| IL-TIF | 100 ng/ml | 16.2 |
| IL-TIF | 300 ng/ml | 32 |

The results indicate that IL-TIF may affect myeloid stem cells. Myeloid stem cells are daughter cells of the universal blood stem cells. They are progenitors of erythrocytes, platelets megakaryocytes, monocytes (or migrated macrophages), neutrophil and basophil, etc. Since K-562 blasts spontaneously differentiate into progenitors of the erythrocytic, granulocytic and monocytic series, it can be considered as myeloid stem cells. Thus, the results demonstrate that IL-TIF has an inhibitory activity on the proliferation and/or growth of myeloid stem cells. Thus IL-TIF could play a role in anemia, infection, inflammation, and/or immune diseases. In addition, an antaganist against IL-TIF, such as antibodies or its soluble receptor Zcytor16, could be used to block IL-TIF's activity on myeloid stem cells, or as therapeutic reagents in diseases such as anemia, infection, inflammation, and/or immune diseases.

Example 24

IL-TIF-Expressing Transgenic Mice
A. Generation of Transgenic Mice Expressing Mouse IL-TIF DNA fragments from a transgenic vector containing 5' and 3' flanking sequences of the lymphoid specific EμLCK promoter, mouse IL-TIF (SEQ ID NO:40), the rat insulin II intron, IL-TIF cDNA and the human growth hormone poly A sequence were prepared using standard methods, and used for microinjection into fertilized B6C3f1 (Taconic, Germantown, N.Y.) murine oocytes, using a standard microinjection protocol. See, Hogan, B. et al., *Manipulating the Mouse Embryo. A Laboratory Manual*, Cold Spring Harbor Laboratory Press, 1994.

Twenty-five mice transgenic for mouse IL-TIF with the lymphoid-specific EμLCK promoter were identified among 154 pups. Eleven of the transgenic pups died within hours of birth, 9 transgenic pups with a shiny appearance were necropsied the day of birth, and 2 grew to adulthood. Expression levels were low in one adult animal. Tissues from the necropsied pups were prepared and histologically examined as described below.

The shiny appearance of the neonate pups appeared to be associated with a stiffening of the skin, as if they were drying out, resulting in a reduction of proper nursing. Their movements became stiffened in general.

B. Genotypic and Expression Analysis from Transgenic Mice

From the mouse IL-TIF transgenic line driven by the EμLck promoter, described above, newborn pups were observed for abnormalities on day one (day of birth) and sacrificed for tissue collection. All pups were given a unique ear tag number, and those designated as having a shiny skin phenotype at the time of sacrifice were noted. Of the twelve pups, six were observed to have the shiny skin phenotype, with two designated as "severe" phenotypes. Severe phenotypes were defined as small pups with little mobility whose skin was especially shiny and very dry. Skin was collected from the left lateral side of each pup, and frozen in Tissue-Tek embedding medium.

Genotyping confirmed that shiny skin was a good indicator of transgenic status, although no expression data was collected. Frozen skin blocks were sectioned to 7 microns on a cryostat and stained to look for the presence of CD3, CD4, CD8, mouse macrophages, B-cells, CD80, and MHC class II. The staining protocol involved binding of commercially available antibodies to the tissue, detection with a peroxidase labeled secondary antibody, and DAB chromogen reaction to visualize staining.

Transgenic animals were found to be higher in MHC class II and CD80, which stain for antigen-presenting cells and dendritic cells respectively. The macrophage marker also detected more cells in the severe and non-severe transgenics than in the wild type animals, although the distribution of these cells was very localized in the high dermis. Animals classified as severe phenotypes had the most robust staining with all three of these markers, showing a dramatic increase in cell intensity and number when compared to the wild type. This variability may be due to a difference in expression level of IL-TIF in these transgenic founder pups. The MHC class II positive cells were located in the lower dermis arranged in loose open clusters, while the CD80 positive cells were predominantly below the dermis either in or just above the muscle/fat layer. These two cell populations do not appear to overlap. All other markers were of equivalent staining in all animals. Toluidine blue staining for mast cells revealed slight to no difference between wild type and transgenic animals.

C. Microscopic Evaluation of Tissues from Transgenic Mice: IL-TIF TG with EuLck Promoter has a Neonatal Lethal-histology On the day of birth, pups from litters containing IL-TIF transgenics were humanely euthanized and the whole body immersion fixed in 10% buffered formalin. Six transgenic and two non-transgenic pups were submitted for further workup. Four of the six transgenics were noted to have shiny skin at the time of euthanasia. The fixed tissues were trimmed into 5 sections (longitudinal section of the head and cross sections of the upper and lower thorax and upper and lower abdomen). The tissues were embedded in paraffin, routinely processed, sectioned at 5 um (Jung 2065 Supercut microtome, Leica Microsystems, Wetzlar, Germany) and stained with H&E. The stained tissues were evaluated under a light microscope (Nikon Eclipse E600, Nikon Inc., Melville, N.Y.) by a board (ACVP) certified veterinary pathologist.

On microscopic examination, the epidermis of two of the transgenic pups was observed to be thicker than the epidermis of the other six mice including the controls. No other abnormalities were noted in the skin and other tissues of any of the mice. Representative areas of skin from corresponding regions of the thorax and abdomen were imaged with the 40× objective lens and with a CoolSnap digital camera (Roper Scientific, Inc., San Diego, Calif.) that was attached to the microscope. The thickness of the epidermis was then determined using histomorphometry software (Scion Image for Windows (NIH Image), Scion Corp., Frederick, Md., v. B4.0.2). The results were as follows:

| Genotype/phenotype | Average thoracic skin thickness (μm) | Average abdominal skin thickness (μm) |
|---|---|---|
| Non-transgenic/normal | 5.2 | 5.4 |
| Transgenic/non-shiny | 5.0 | 6.7 |
| Transgenic/shiny | 8.2 | 7.4 |
| Transgenic/all | 7.1 | 7.1 |

There were insufficient numbers of mice to determine statistical significance; however, the transgenics, especially those with shiny skin, tended to have a thicker epidermis than the non-shiny transgenics and non-transgenic controls. The shiny transgenics may have a higher expression level of IL-TIF than the non-shiny transgenics.; however, expression levels were not determined for these mice.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

We claim:

1. An isolated polypeptide, comprising at least 15 contiguous amino acid residues of an amino acid sequence of SEQ ID NO:48 selected from the group consisting of:

(a) amino acid residues 24 to 230 of SEQ ID NO:48;

(b) amino acid residues 27 to 230 of SEQ ID NO:48;

(c) amino acid residues 27 to 126 of SEQ ID NO:48;

(d) amino acid residues 131 to 230 of SEQ ID NO:48; and (e) amino acid residues 1 to 230 of SEQ ID NO:48.

2. An isolated polypeptide comprising an amino acid sequence of SEQ ID NO:48 selected from the group consisting of:

(a) amino acid residues 24 to 230 of SEQ ID NO:48;

(b) amino acid residues 27 to 230 of SEQ ID NO:48;

(c) amino acid residues 27 to 126 of SEQ ID NO:48;

(d) amino acid residues 131 to 230 of SEQ ID NO:48; and (e) amino acid residues 1 to 230 of SEQ ID NO:48.

3. The isolated polypeptide of claim 2, wherein the polypeptide consists of an amino acid sequence of SEQ ID NO:48 selected from the group consisting of:

(a) amino acid residues 24 to 230 of SEQ ID NO:48;

(b) amino acid residues 27 to 230 of SEQ ID NO:48;

(c) amino acid residues 27 to 126 of SEQ ID NO:48;

(d) amino acid residues 131 to 230 of SEQ ID NO:48; and (e) amino acid residues 1 to 230 of SEQ ID NO:48.

4. A fusion protein, comprising the polypeptide of claim 2.

5. The fusion protein of claim 4, wherein the fusion protein further comprises an immunoglobulin moiety.

6. An isolated soluble cytokine receptor polypeptide comprising a sequence of amino acid residues as shown in SEQ ID NO:48 from amino acid 24 to 230, or 27 to 230, wherein the soluble cytokine receptor polypeptide further comprises a homodimeric, heterodimeric or multimeric receptor complex of cytokine receptors.

7. The isolated polypeptide according to claim 6, wherein the soluble cytokine receptor polypeptide further comprises a heterodimeric or multimeric receptor complex further comprising a soluble Class I or Class II cytokine receptor.

8. The isolated polypeptide according to claim 6, wherein the soluble cytokine receptor polypeptide further comprises a heterodimeric or multimeric receptor complex comprising a soluble Cytokine Receptor Family 2–4 (CRF2–4) receptor polypeptide (SEQ ID NO:35), a soluble IL-10 receptor polypeptide (SEQ ID NO:36), or soluble zcytor11 receptor polypeptide (SEQ ID NO:34).

9. The isolated polypeptide according to claim 6, wherein the soluble cytokine receptor polypeptide further comprises an affinity tag, chemical moiety, toxin, label, biotin/avidin label, radionuclide, enzyme, substrate, cofactor, inhibitor, fluorescent marker, chemiluminescent marker, cytotoxic molecule or an immunoglobulin Fc domain.

10. An isolated heterodimeric or multimeric soluble receptor complex comprising soluble cytokine receptor subunits, wherein at least one of the soluble cytokine receptor subunits comprises a soluble cytokine receptor polypeptide comprising a sequence of amino acid residues as shown in SEQ ID NO:48 from amino acid 24 to 230, or 27 to 230.

11. The isolated heterodimeric or multimeric soluble receptor complex according to claim 10, further comprising a soluble Class I or Class II cytokine receptor polypeptide.

12. The isolated heterodimeric or multimeric soluble receptor complex according to claim 10, further comprising a soluble Cytokine Receptor Family 2–4 (CRF2–4) receptor polypeptide (SEQ ID NO:35), a soluble IL-10 receptor polypeptide (SEQ ID NO:36), or soluble zcytor11 receptor polypeptide (SEQ ID NO:34).

13. The fusion protein of claim 4, wherein the fusion protein further comprises an affinity tag, chemical moiety, toxin, label, biotin/avidin label, radionuclide, enzyme, substrate, cofactor, inhibitor, fluorescent marker, chemiluminescent marker, cytotoxic molecule or an immunoglobulin Fc domain.

14. The fusion protein of claim 4, wherein the fusion protein binds IL-10-Related T Cell-Derived Inducible Factor (IL-TIF) or antagonizes IL-TIF activity.

15. The isolated heterodimeric or multimeric soluble receptor complex according to claim 10, wherein the soluble receptor complex further comprises an affinity tag, chemical moiety, toxin, label, biotin/avidin label, radionuclide, enzyme, substrate, cofactor, inhibitor, fluorescent marker, chemiluminescent marker, cytotoxic molecule or an immunoglobulin Fc domain.

16. An isolated soluble cytokine receptor polypeptide receptor complex comprising soluble cytokine receptor subunits, wherein at least one of soluble receptor subunits comprises a sequence of amino acid residues as shown in SEQ ID NO:48 from amino acid 24 to 230, or 27 to 230.

17. The isolated soluble cytokine receptor polypeptide receptor complex of claim 16, wherein the receptor complex further comprises an affinity tag, label, chemical moiety, toxin, biotin/avidin label, radionuclide, enzyme, substrate, cofactor, inhibitor, fluorescent marker, chemiluminescent marker, cytotoxic molecule or an immunoglobulin Fc domain.

18. The isolated soluble cytokine receptor polypeptide receptor complex of claim 16, wherein the receptor complex binds IL-10-Related T Cell-Derived Inducible Factor (IL-TIF) or antagonizes IL-TIF activity.

19. The isolated soluble cytokine receptor polypeptide receptor complex of claim 10, wherein the receptor complex binds IL-10-Related T Cell-Derived Inducible Factor (IL-TIF) or antagonizes IL-TIF activity.

* * * * *

SEQUENCE LISTING

```
<160> NUMBER OF SEQ ID NOS: 49

<210> SEQ ID NO 1
<211> LENGTH: 2149
<212> TYPE: DNA
<213> ORGANISM: Homo sapiens
<220> FEATURE:
<221> NAME/KEY: CDS
<222> LOCATION: (1)...(693)

<400> SEQUENCE: 1 atg atg cct aaa cat tgc ttt cta ggc ttc ctc atc agt ttc ttc ctt       48
Met Met Pro Lys His Cys Phe Leu Gly Phe Leu Ile Ser Phe Phe Leu
  1               5                  10                  15 act ggt gta gca gga act cag tca acg cat gag tct ctg aag cct cag       96
Thr Gly Val Ala Gly Thr Gln Ser Thr His Glu Ser Leu Lys Pro Gln
             20                  25                  30 agg gta caa ttt cag tcc cga aat ttt cac aac att ttg caa tgg cag      144
Arg Val Gln Phe Gln Ser Arg Asn Phe His Asn Ile Leu Gln Trp Gln
         35                  40                  45 cct ggg agg gca ctt act ggc aac agc agt gtc tat ttt gtg cag tac      192
Pro Gly Arg Ala Leu Thr Gly Asn Ser Ser Val Tyr Phe Val Gln Tyr
     50                  55                  60 aaa ata tat gga cag aga caa tgg aaa aat aaa gaa gac tgt tgg ggt      240
Lys Ile Tyr Gly Gln Arg Gln Trp Lys Asn Lys Glu Asp Cys Trp Gly
 65                  70                  75                  80 act caa gaa ctc tct tgt gac ctt acc agt gaa acc tca gac ata cag      288
Thr Gln Glu Leu Ser Cys Asp Leu Thr Ser Glu Thr Ser Asp Ile Gln
                 85                  90                  95 gaa cct tat tac ggg agg gtg agg gcg gcc tcg gct ggg agc tac tca      336
Glu Pro Tyr Tyr Gly Arg Val Arg Ala Ala Ser Ala Gly Ser Tyr Ser
            100                 105                 110 gaa tgg agc atg acg ccg cgg ttc act ccc tgg tgg gaa aca aaa ata      384
Glu Trp Ser Met Thr Pro Arg Phe Thr Pro Trp Trp Glu Thr Lys Ile
        115                 120                 125 gat cct cca gtc atg aat ata acc caa gtc aat ggc tct ttg ttg gta      432
Asp Pro Pro Val Met Asn Ile Thr Gln Val Asn Gly Ser Leu Leu Val
    130                 135                 140 att ctc cat gct cca aat tta cca tat aga tac caa aag gaa aaa aat      480
Ile Leu His Ala Pro Asn Leu Pro Tyr Arg Tyr Gln Lys Glu Lys Asn
145                 150                 155                 160 gta tct ata gaa gat tac tat gaa cta cta tac cga gtt ttt ata att      528
Val Ser Ile Glu Asp Tyr Tyr Glu Leu Leu Tyr Arg Val Phe Ile Ile
                165                 170                 175 aac aat tca cta gaa aag gag caa aag gtt tat gaa ggg gct cac aga      576
Asn Asn Ser Leu Glu Lys Glu Gln Lys Val Tyr Glu Gly Ala His Arg
            180                 185                 190
```

-continued

```
gcg gtt gaa att gaa gct cta aca cca cac tcc agc tac tgt gta gtg      624
Ala Val Glu Ile Glu Ala Leu Thr Pro His Ser Ser Tyr Cys Val Val
        195                 200                 205 gct gaa ata tat cag ccc atg tta gac aga aga agt cag aga agt gaa      672
Ala Glu Ile Tyr Gln Pro Met Leu Asp Arg Arg Ser Gln Arg Ser Glu
    210                 215                 220 gag aga tgt gtg gaa att cca tgacttgtgg aatttggcat tcagcaatgt         723
Glu Arg Cys Val Glu Ile Pro
225             230 ggaaattcta aagctccctg agaacaggat gactcgtgtt tgaaggatct tatttaaaat   783
tgttttttgta ttttcttaaa gcaatattca ctgttacacc ttggggactt ctttgtttat  843
ccattctttt atcctttata tttcatttta aactatattt gaacgacatt ccccccgaaa   903
aattgaaatg taaagatgag gcagagaata aagtgttcta tgaaattcag aactttattt   963
ctgaatgtaa catccctaat aacaaccttc attcttctaa tacagcaaaa taaaaattta   1023
acaaccaagg aatagtattt aagaaaatgt tgaataatt ttttttaaaaat agcattacag  1083
actgaggcgg tcctgaagca atggtttttc actctcttat tgagccaatt aaattgacat  1143
tgctttgaca atttaaaact tctataaagg tgaatatttt tcatacattt ctattttata  1203
tgaatatact ttttatatat ttattattat taaatatttc tacttaatga atcaaaattt  1263
tgttttaaag tctactttat gtaaataaga acaggttttg gggaaaaaaa tcttatgatt  1323
tctggattga tatctgaatt aaaactatca acaacaagga agtctactct gtacaattgt  1383
ccctcattta aaagatatat taagcttttc ttttctgttt gtttttgttt tgtttagttt  1443
ttaatcctgt cttagaagaa cttatcttta ttctcaaaat taaatgtaat ttttttagtg  1503
acaaagaaga aaggaaacct cattactcaa tccttctggc caagagtgtc ttgcttgtgg  1563
cgccttcctc atctctatat aggaggatcc catgaatgat ggtttattgg gaactgctgg  1623
ggtcgacccc atacagagaa ctcagcttga agctggaagc acacagtggg tagcaggaga  1683
aggaccggtg ttggtaggtg cctacagaga ctatagagct agacaaagcc ctccaaactg  1743
gcccctcctg ctcactgcct ctcctgagta gaaatctggt gacctaaggc tcagtgcggt  1803
caacagaaag ctgccttctt cacttgaggc taagtcttca tatatgttta aggttgtctt  1863
tctagtgagg agatacatat cagagaacat ttgtacaatt ccccatgaaa attgctccaa  1923
agttgataac aatatagtcg gtgcttctag ttatatgcaa gtactcagtg ataaatggat  1983
taaaaaatat tcagaaatgt attgggggt ggaggagaat aagaggcaga gcaagagcta  2043
gagaattggt ttccttgctt ccctgtatgc tcagaaaaca ttgatttgag catagacgca  2103
gagactgaaa aaaaaaaaat gctcgagcgg ccgccatatc cttggt                  2149
```

<210> SEQ ID NO 2
<211> LENGTH: 231
<212> TYPE: PRT
<213> ORGANISM: Homo sapiens

<400> SEQUENCE: 2

```
Met Met Pro Lys His Cys Phe Leu Gly Phe Leu Ile Ser Phe Phe Leu
  1               5                  10                  15

Thr Gly Val Ala Gly Thr Gln Ser Thr His Glu Ser Leu Lys Pro Gln
             20                  25                  30

Arg Val Gln Phe Gln Ser Arg Asn Phe His Asn Ile Leu Gln Trp Gln
         35                  40                  45

Pro Gly Arg Ala Leu Thr Gly Asn Ser Ser Val Tyr Phe Val Gln Tyr
```

```
                50                  55                  60
Lys Ile Tyr Gly Gln Arg Gln Trp Lys Asn Lys Glu Asp Cys Trp Gly
 65                  70                  75                  80

Thr Gln Glu Leu Ser Cys Asp Leu Thr Ser Glu Thr Ser Asp Ile Gln
                 85                  90                  95

Glu Pro Tyr Tyr Gly Arg Val Arg Ala Ala Ser Ala Gly Ser Tyr Ser
                100                 105                 110

Glu Trp Ser Met Thr Pro Arg Phe Thr Pro Trp Glu Thr Lys Ile
                115                 120                 125

Asp Pro Pro Val Met Asn Ile Thr Gln Val Asn Gly Ser Leu Leu Val
130                 135                 140

Ile Leu His Ala Pro Asn Leu Pro Tyr Arg Tyr Gln Lys Glu Lys Asn
145                 150                 155                 160

Val Ser Ile Glu Asp Tyr Tyr Glu Leu Leu Tyr Arg Val Phe Ile Ile
                165                 170                 175

Asn Asn Ser Leu Glu Lys Glu Gln Lys Val Tyr Glu Gly Ala His Arg
                180                 185                 190

Ala Val Glu Ile Glu Ala Leu Thr Pro His Ser Ser Tyr Cys Val Val
                195                 200                 205

Ala Glu Ile Tyr Gln Pro Met Leu Asp Arg Arg Ser Gln Arg Ser Glu
210                 215                 220

Glu Arg Cys Val Glu Ile Pro
225                 230

<210> SEQ ID NO 3
<211> LENGTH: 693
<212> TYPE: DNA
<213> ORGANISM: Artificial Sequence
<220> FEATURE:
<223> OTHER INFORMATION: This degenerate nucleotide sequence encodes the
      amino acid sequence of SEQ ID NO:2
<220> FEATURE:
<221> NAME/KEY: misc_feature
<222> LOCATION: (1)...(693)
<223> OTHER INFORMATION: n = A,T,C or G

<400> SEQUENCE: 3
atgatgccna arcaytgytt yytnggntty ytnathwsnt tyttyytnac nggngtngcn      60
ggnacncarw snacncayga rwsnytnaar ccncarmgng tncarttyca rwsnmgnaay    120
ttycayaaya thytncartg gcarccnggn mgngcnytna cnggnaayws nwsngtntay    180
ttygtncart ayaarathta yggncarmgn cartggaara ayaargarga ytgytgggn     240 acncargary tnwsntgyga yytnacnwsn garacnwsng ayathcarga rccntaytay    300
ggnmgngtnm gngcngcnws ncnggnwsn taywsngart ggwsnatgac ncnmgntty      360 acncntggt gggaracnaa rathgayccn ccngtnatga ayathacnca rgtnaayggn     420
wsnytnytng tnathytnca ygcnccnaay ytnccntaym gntaycaraa rgaraaraay    480
gtnwsnathg argaytayta ygarytnytn taymgngtnt tyathathaa yaaywsnytn    540
garaargarc araargtnta ygarggngcn caymgngcng tngarathga rgcnytnacn    600
ccncaywsnw sntaytgygt ngtngcngar athtaycarc cnatgytnga ymgnmgnwsn    660
carmgnwsng argarmgntg ygtngarath ccn                                693

<210> SEQ ID NO 4
<211> LENGTH: 16
<212> TYPE: PRT
<213> ORGANISM: Artificial Sequence
```

-continued

```
<220> FEATURE:
<223> OTHER INFORMATION: Peptide linker.

<400> SEQUENCE: 4

Gly Gly Ser Gly Gly Ser Gly Gly Gly Ser Gly Gly Gly Ser
 1               5                  10                  15

<210> SEQ ID NO 5
<211> LENGTH: 699
<212> TYPE: DNA
<213> ORGANISM: Homo sapiens

<400> SEQUENCE: 5
gagcccagat cttcagacaa aactcacaca tgcccaccgt gcccagcacc tgaagccgag     60
ggggcaccgt cagtcttcct cttccccca aacccaagg acaccctcat gatctcccgg    120 accctgagg tcacatgcgt ggtggtggac gtgagccacg aagaccctga ggtcaagttc    180
aactggtacg tggacggcgt ggaggtgcat aatgccaaga caaagccgcg ggaggagcag    240
tacaacagca cgtaccgtgt ggtcagcgtc ctcaccgtcc tgcaccagga ctggctgaat    300
ggcaaggagt acaagtgcaa ggtctccaac aaagccctcc catcctccat cgagaaaacc    360
atctccaaag ccaaagggca gccccgagaa ccacaggtgt acaccctgcc cccatcccgg    420
gatgagctga ccaagaacca ggtcagcctg acctgcctgg tcaaaggctt ctatcccagc    480
gacatcgccg tggagtggga gagcaatggg cagccggaga caactacaa gaccacgcct    540 cccgtgctgg actccgacgg ctccttcttc ctctacagca agctcaccgt ggacaagagc    600
aggtggcagc aggggaacgt cttctcatgc tccgtgatgc atgaggctct gcacaaccac    660
tacacgcaga agagcctctc cctgtctccg ggtaaataa                          699

<210> SEQ ID NO 6
<211> LENGTH: 32
<212> TYPE: DNA
<213> ORGANISM: Artificial Sequence
<220> FEATURE:
<223> OTHER INFORMATION: Oligonucleotide primer ZC29181

<400> SEQUENCE: 6
gcggatccac tcagtcaacg catgagtctc tg                                  32

<210> SEQ ID NO 7
<211> LENGTH: 33
<212> TYPE: DNA
<213> ORGANISM: Artificial Sequence
<220> FEATURE:
<223> OTHER INFORMATION: Oligonucleotide primer ZC29182

<400> SEQUENCE: 7
gcagatcttg gaatttccac acatctctct tca                                 33

<210> SEQ ID NO 8
<211> LENGTH: 108
<212> TYPE: DNA
<213> ORGANISM: Homo sapiens
<220> FEATURE:
<221> NAME/KEY: CDS
<222> LOCATION: (1)...(108)

<400> SEQUENCE: 8 atg gat gca atg aag aga ggg ctc tgc tgt gtg ctg ctg ctg tgt ggc     48
Met Asp Ala Met Lys Arg Gly Leu Cys Cys Val Leu Leu Leu Cys Gly
 1               5                  10                  15
```

```
gcc gtc ttc gtt tcg ctc agc cag gaa atc cat gcc gag ttg aga cgc    96
Ala Val Phe Val Ser Leu Ser Gln Glu Ile His Ala Glu Leu Arg Arg
             20                  25                  30 ttc cgt aga tcc                                                   108
Phe Arg Arg Ser
        35
```

<210> SEQ ID NO 9
<211> LENGTH: 36
<212> TYPE: PRT
<213> ORGANISM: Homo sapiens

<400> SEQUENCE: 9

```
Met Asp Ala Met Lys Arg Gly Leu Cys Cys Val Leu Leu Leu Cys Gly
 1               5                  10                  15

Ala Val Phe Val Ser Leu Ser Gln Glu Ile His Ala Glu Leu Arg Arg
             20                  25                  30

Phe Arg Arg Ser
        35
```

<210> SEQ ID NO 10
<211> LENGTH: 6
<212> TYPE: PRT
<213> ORGANISM: Artificial Sequence
<220> FEATURE:
<223> OTHER INFORMATION: Glu-Glu (CEE) Tag amino acid sequence

<400> SEQUENCE: 10

```
Glu Tyr Met Pro Met Glu
 1               5
```

<210> SEQ ID NO 11
<211> LENGTH: 8
<212> TYPE: PRT
<213> ORGANISM: Artificial Sequence
<220> FEATURE:
<223> OTHER INFORMATION: FLAG Tag amino acid sequence

<400> SEQUENCE: 11

```
Asp Tyr Lys Asp Asp Asp Asp Lys
 1               5
```

<210> SEQ ID NO 12
<211> LENGTH: 6
<212> TYPE: PRT
<213> ORGANISM: Artificial Sequence
<220> FEATURE:
<223> OTHER INFORMATION: His Tag amino acid sequence

<400> SEQUENCE: 12

```
His His His His His His
 1               5
```

<210> SEQ ID NO 13
<211> LENGTH: 210
<212> TYPE: PRT
<213> ORGANISM: Homo sapiens

<400> SEQUENCE: 13

```
Thr Gln Ser Thr His Glu Ser Leu Lys Pro Gln Arg Val Gln Phe Gln
 1               5                  10                  15

Ser Arg Asn Phe His Asn Ile Leu Gln Trp Gln Pro Gly Arg Ala Leu
             20                  25                  30

Thr Gly Asn Ser Ser Val Tyr Phe Val Gln Tyr Lys Ile Tyr Gly Gln
```

```
                    35                  40                  45
Arg Gln Trp Lys Asn Lys Glu Asp Cys Trp Gly Thr Gln Glu Leu Ser
    50                  55                  60

Cys Asp Leu Thr Ser Glu Thr Ser Asp Ile Gln Glu Pro Tyr Tyr Gly
65                  70                  75                  80

Arg Val Arg Ala Ala Ser Ala Gly Ser Tyr Ser Glu Trp Ser Met Thr
                85                  90                  95

Pro Arg Phe Thr Pro Trp Trp Glu Thr Lys Ile Asp Pro Pro Val Met
            100                 105                 110

Asn Ile Thr Gln Val Asn Gly Ser Leu Leu Val Ile Leu His Ala Pro
        115                 120                 125

Asn Leu Pro Tyr Arg Tyr Gln Lys Glu Lys Asn Val Ser Ile Glu Asp
    130                 135                 140

Tyr Tyr Glu Leu Leu Tyr Arg Val Phe Ile Ile Asn Asn Ser Leu Glu
145                 150                 155                 160

Lys Glu Gln Lys Val Tyr Glu Gly Ala His Arg Ala Val Glu Ile Glu
                165                 170                 175

Ala Leu Thr Pro His Ser Ser Tyr Cys Val Val Ala Glu Ile Tyr Gln
            180                 185                 190

Pro Met Leu Asp Arg Arg Ser Gln Arg Ser Glu Glu Arg Cys Val Glu
        195                 200                 205

Ile Pro
    210

<210> SEQ ID NO 14
<211> LENGTH: 1116
<212> TYPE: DNA
<213> ORGANISM: Homo sapiens
<220> FEATURE:
<221> NAME/KEY: CDS
<222> LOCATION: (21)...(557)

<400> SEQUENCE: 14
tcgagttaga attgtctgca atg gcc gcc ctg cag aaa tct gtg agc tct ttc    53
                     Met Ala Ala Leu Gln Lys Ser Val Ser Ser Phe
                      1               5                  10 ctt atg ggg acc ctg gcc acc agc tgc ctc ctt ctc ttg gcc ctc ttg    101
Leu Met Gly Thr Leu Ala Thr Ser Cys Leu Leu Leu Leu Ala Leu Leu
            15                  20                  25 gta cag gga gga gca gct gcg ccc atc agc tcc cac tgc agg ctt gac    149
Val Gln Gly Gly Ala Ala Ala Pro Ile Ser Ser His Cys Arg Leu Asp
        30                  35                  40 aag tcc aac ttc cag cag ccc tat atc acc aac cgc acc ttc atg ctg    197
Lys Ser Asn Phe Gln Gln Pro Tyr Ile Thr Asn Arg Thr Phe Met Leu
    45                  50                  55 gct aag gag gct agc ttg gct gat aac aac aca gac gtt cgt ctc att    245
Ala Lys Glu Ala Ser Leu Ala Asp Asn Asn Thr Asp Val Arg Leu Ile
60                  65                  70                  75 ggg gag aaa ctg ttc cac gga gtc agt atg agt gag cgc tgc tat ctg    293
Gly Glu Lys Leu Phe His Gly Val Ser Met Ser Glu Arg Cys Tyr Leu
                80                  85                  90 atg aag cag gtg ctg aac ttc acc ctt gaa gaa gtg ctg ttc cct caa    341
Met Lys Gln Val Leu Asn Phe Thr Leu Glu Glu Val Leu Phe Pro Gln
            95                 100                 105 tct gat agg ttc cag cct tat atg cag gag gtg gtg ccc ttc ctg gcc    389
Ser Asp Arg Phe Gln Pro Tyr Met Gln Glu Val Val Pro Phe Leu Ala
        110                 115                 120 agg ctc agc aac agg cta agc aca tgt cat att gaa ggt gat gac ctg    437
```

```
                Arg Leu Ser Asn Arg Leu Ser Thr Cys His Ile Glu Gly Asp Asp Leu
                    125                 130                 135 cat atc cag agg aat gtg caa aag ctg aag gac aca gtg aaa aag ctt              485
His Ile Gln Arg Asn Val Gln Lys Leu Lys Asp Thr Val Lys Lys Leu
140                 145                 150                 155 gga gag agt gga gag atc aaa gca att gga gaa ctg gat ttg ctg ttt              533
Gly Glu Ser Gly Glu Ile Lys Ala Ile Gly Glu Leu Asp Leu Leu Phe
                160                 165                 170 atg tct ctg aga aat gcc tgc att tgaccagagc aaagctgaaa atgaataac              587
Met Ser Leu Arg Asn Ala Cys Ile
            175 taaccccctt tccctgctag aaataacaat tagatgcccc aaagcgattt tttttaacca            647 aaaggaagat gggaagccaa actccatcat gatgggtgga ttccaaatga accctgcgt             707 tagttacaaa ggaaaccaat gccactttg tttataagac cagaaggtag actttctaag             767 catagatatt tattgataac atttcattgt aactggtgtt ctatacacag aaaacaattt            827 atttttaaa taattgtctt tttccataaa aaagattact ttccattcct ttaggggaaa             887 aaaccctaa atagcttcat gtttccataa tcagtacttt atatttataa atgtattat             947 tattattata agactgcatt ttatttatat cattttatta atatggattt atttatagaa            1007 acatcattcg atattgctac ttgagtgtaa ggctaatatt gatatttatg acaataatta            1067 tagagctata acatgtttat ttgacctcaa taaacacttg gatatccta                       1116
```

<210> SEQ ID NO 15
<211> LENGTH: 179
<212> TYPE: PRT
<213> ORGANISM: Homo sapiens

<400> SEQUENCE: 15

```
Met Ala Ala Leu Gln Lys Ser Val Ser Ser Phe Leu Met Gly Thr Leu
1               5                   10                  15

Ala Thr Ser Cys Leu Leu Leu Ala Leu Leu Val Gln Gly Gly Ala
                20                  25                  30

Ala Ala Pro Ile Ser Ser His Cys Arg Leu Asp Lys Ser Asn Phe Gln
                35                  40                  45

Gln Pro Tyr Ile Thr Asn Arg Thr Phe Met Leu Ala Lys Glu Ala Ser
        50                  55                  60

Leu Ala Asp Asn Asn Thr Asp Val Arg Leu Ile Gly Glu Lys Leu Phe
65                  70                  75                  80

His Gly Val Ser Met Ser Glu Arg Cys Tyr Leu Met Lys Gln Val Leu
                85                  90                  95

Asn Phe Thr Leu Glu Glu Val Leu Phe Pro Gln Ser Asp Arg Phe Gln
                100                 105                 110

Pro Tyr Met Gln Glu Val Val Pro Phe Leu Ala Arg Leu Ser Asn Arg
            115                 120                 125

Leu Ser Thr Cys His Ile Glu Gly Asp Asp Leu His Ile Gln Arg Asn
        130                 135                 140

Val Gln Lys Leu Lys Asp Thr Val Lys Lys Leu Gly Glu Ser Gly Glu
145                 150                 155                 160

Ile Lys Ala Ile Gly Glu Leu Asp Leu Leu Phe Met Ser Leu Arg Asn
                165                 170                 175

Ala Cys Ile
```

<210> SEQ ID NO 16
<211> LENGTH: 23

```
<212> TYPE: DNA
<213> ORGANISM: Artificial Sequence
<220> FEATURE:
<223> OTHER INFORMATION: Oligonucleotide primer ZC25963

<400> SEQUENCE: 16
agtcaacgca tgagtctctg aag                                       23

<210> SEQ ID NO 17
<211> LENGTH: 23
<212> TYPE: DNA
<213> ORGANISM: Artificial Sequence
<220> FEATURE:
<223> OTHER INFORMATION: Oligonucleotide primer ZC28354

<400> SEQUENCE: 17
accaacaaag agccattgac ttg                                       23

<210> SEQ ID NO 18
<211> LENGTH: 23
<212> TYPE: DNA
<213> ORGANISM: Artificial Sequence
<220> FEATURE:
<223> OTHER INFORMATION: Oligonucleotide primer ZC21195

<400> SEQUENCE: 18
gaggagacca taaccccga cag                                        23

<210> SEQ ID NO 19
<211> LENGTH: 23
<212> TYPE: DNA
<213> ORGANISM: Artificial Sequence
<220> FEATURE:
<223> OTHER INFORMATION: Oligonucleotide primer ZC21196

<400> SEQUENCE: 19
catagctccc accacacgat ttt                                       23

<210> SEQ ID NO 20
<211> LENGTH: 25
<212> TYPE: DNA
<213> ORGANISM: Artificial Sequence
<220> FEATURE:
<223> OTHER INFORMATION: Oligonucleotide primer ZC14063

<400> SEQUENCE: 20
caccagacat aatagctgac agact                                     25

<210> SEQ ID NO 21
<211> LENGTH: 21
<212> TYPE: DNA
<213> ORGANISM: Artificial Sequence
<220> FEATURE:
<223> OTHER INFORMATION: Oligonucleotide primer ZC17574

<400> SEQUENCE: 21
ggtrttgctc agcatgcaca c                                         21

<210> SEQ ID NO 22
<211> LENGTH: 24
<212> TYPE: DNA
<213> ORGANISM: Artificial Sequence
<220> FEATURE:
<223> OTHER INFORMATION: Oligonucleotide primer ZC17600

<400> SEQUENCE: 22
```

```
catgtaggcc atgaggtcca ccac                                              24
```

<210> SEQ ID NO 23
<211> LENGTH: 22
<212> TYPE: DNA
<213> ORGANISM: Artificial Sequence
<220> FEATURE:
<223> OTHER INFORMATION: Oligonucleotide primer ZC27659

<400> SEQUENCE: 23

```
tcaagctgag ttctctgtat gg                                                22
```

<210> SEQ ID NO 24
<211> LENGTH: 2831
<212> TYPE: DNA
<213> ORGANISM: Homo sapiens
<220> FEATURE:
<221> NAME/KEY: CDS
<222> LOCATION: (34)...(1755)

<400> SEQUENCE: 24

```
tagaggccaa gggagggctc tgtgccagcc ccg atg agg acg ctg ctg acc atc          54
                                   Met Arg Thr Leu Leu Thr Ile
                                     1               5 ttg act gtg gga tcc ctg gct gct cac gcc cct gag gac ccc tcg gat         102
Leu Thr Val Gly Ser Leu Ala Ala His Ala Pro Glu Asp Pro Ser Asp
         10                  15                  20 ctg ctc cag cac gtg aaa ttc cag tcc agc aac ttt gaa aac atc ctg         150
Leu Leu Gln His Val Lys Phe Gln Ser Ser Asn Phe Glu Asn Ile Leu
     25                  30                  35 acg tgg gac agc ggg cca gag ggc acc cca gac acg gtc tac agc atc         198
Thr Trp Asp Ser Gly Pro Glu Gly Thr Pro Asp Thr Val Tyr Ser Ile
 40                  45                  50                  55 gag tat aag acg tac gga gag agg gac tgg gtg gca aag aag ggc tgt         246
Glu Tyr Lys Thr Tyr Gly Glu Arg Asp Trp Val Ala Lys Lys Gly Cys
                 60                  65                  70 cag cgg atc acc cgg aag tcc tgc aac ctg acg gtg gag acg ggc aac         294
Gln Arg Ile Thr Arg Lys Ser Cys Asn Leu Thr Val Glu Thr Gly Asn
             75                  80                  85 ctc acg gag ctc tac tat gcc agg gtc acc gct gtc agt gcg gga ggc         342
Leu Thr Glu Leu Tyr Tyr Ala Arg Val Thr Ala Val Ser Ala Gly Gly
         90                  95                 100 cgg tca gcc acc aag atg act gac agg ttc agc tct ctg cag cac act         390
Arg Ser Ala Thr Lys Met Thr Asp Arg Phe Ser Ser Leu Gln His Thr
    105                 110                 115 acc ctc aag cca cct gat gtg acc tgt atc tcc aaa gtg aga tcg att         438
Thr Leu Lys Pro Pro Asp Val Thr Cys Ile Ser Lys Val Arg Ser Ile
120                 125                 130                 135 cag atg att gtt cat cct acc ccc acg cca atc cgt gca ggc gat ggc         486
Gln Met Ile Val His Pro Thr Pro Thr Pro Ile Arg Ala Gly Asp Gly
                140                 145                 150 cac cgg cta acc ctg gaa gac atc ttc cat gac ctg ttc tac cac tta         534
His Arg Leu Thr Leu Glu Asp Ile Phe His Asp Leu Phe Tyr His Leu
            155                 160                 165 gag ctc cag gtc aac cgc acc tac caa atg cac ctt gga ggg aag cag         582
Glu Leu Gln Val Asn Arg Thr Tyr Gln Met His Leu Gly Gly Lys Gln
        170                 175                 180 aga gaa tat gag ttc ttc ggc ctg acc cct gac aca gag ttc ctt ggc         630
Arg Glu Tyr Glu Phe Phe Gly Leu Thr Pro Asp Thr Glu Phe Leu Gly
    185                 190                 195 acc atc atg att tgc gtt ccc acc tgg gcc aag gag agt gcc ccc tac         678
Thr Ile Met Ile Cys Val Pro Thr Trp Ala Lys Glu Ser Ala Pro Tyr
```

```
                200                 205                 210                 215
atg tgc cga gtg aag aca ctg cca gac cgg aca tgg acc tac tcc ttc          726
Met Cys Arg Val Lys Thr Leu Pro Asp Arg Thr Trp Thr Tyr Ser Phe
                    220                 225                 230 tcc gga gcc ttc ctg ttc tcc atg ggc ttc ctc gtc gca gta ctc tgc          774
Ser Gly Ala Phe Leu Phe Ser Met Gly Phe Leu Val Ala Val Leu Cys
            235                 240                 245 tac ctg agc tac aga tat gtc acc aag ccg cct gca cct ccc aac tcc          822
Tyr Leu Ser Tyr Arg Tyr Val Thr Lys Pro Pro Ala Pro Pro Asn Ser
        250                 255                 260 ctg aac gtc cag cga gtc ctg act ttc cag ccg ctg cgc ttc atc cag          870
Leu Asn Val Gln Arg Val Leu Thr Phe Gln Pro Leu Arg Phe Ile Gln
    265                 270                 275 gag cac gtc ctg atc cct gtc ttt gac ctc agc ggc ccc agc agt ctg          918
Glu His Val Leu Ile Pro Val Phe Asp Leu Ser Gly Pro Ser Ser Leu
280                 285                 290                 295 gcc cag cct gtc cag tac tcc cag atc agg gtg tct gga ccc agg gag          966
Ala Gln Pro Val Gln Tyr Ser Gln Ile Arg Val Ser Gly Pro Arg Glu
                300                 305                 310 ccc gca gga gct cca cag cgg cat agc ctg tcc gag atc acc tac tta         1014
Pro Ala Gly Ala Pro Gln Arg His Ser Leu Ser Glu Ile Thr Tyr Leu
            315                 320                 325 ggg cag cca gac atc tcc atc ctc cag ccc tcc aac gtg cca cct ccc         1062
Gly Gln Pro Asp Ile Ser Ile Leu Gln Pro Ser Asn Val Pro Pro Pro
        330                 335                 340 cag atc ctc tcc cca ctg tcc tat gcc cca aac gct gcc cct gag gtc         1110
Gln Ile Leu Ser Pro Leu Ser Tyr Ala Pro Asn Ala Ala Pro Glu Val
    345                 350                 355 ggg ccc cca tcc tat gca cct cag gtg acc ccc gaa gct caa ttc cca         1158
Gly Pro Pro Ser Tyr Ala Pro Gln Val Thr Pro Glu Ala Gln Phe Pro
360                 365                 370                 375 ttc tac gcc cca cag gcc atc tct aag gtc cag cct tcc tcc tat gcc         1206
Phe Tyr Ala Pro Gln Ala Ile Ser Lys Val Gln Pro Ser Ser Tyr Ala
                380                 385                 390 cct caa gcc act ccg gac agc tgg cct ccc tcc tat ggg gta tgc atg         1254
Pro Gln Ala Thr Pro Asp Ser Trp Pro Pro Ser Tyr Gly Val Cys Met
            395                 400                 405 gaa ggt tct ggc aaa gac tcc ccc act ggg aca ctt tct agt cct aaa         1302
Glu Gly Ser Gly Lys Asp Ser Pro Thr Gly Thr Leu Ser Ser Pro Lys
        410                 415                 420 cac ctt agg cct aaa ggt cag ctt cag aaa gag cca cca gct gga agc         1350
His Leu Arg Pro Lys Gly Gln Leu Gln Lys Glu Pro Pro Ala Gly Ser
    425                 430                 435 tgc atg tta ggt ggc ctt tct ctg cag gag gtg acc tcc ttg gct atg         1398
Cys Met Leu Gly Gly Leu Ser Leu Gln Glu Val Thr Ser Leu Ala Met
440                 445                 450                 455 gag gaa tcc caa gaa gca aaa tca ttg cac cag ccc ctg ggg att tgc         1446
Glu Glu Ser Gln Glu Ala Lys Ser Leu His Gln Pro Leu Gly Ile Cys
                460                 465                 470 aca gac aga aca tct gac cca aat gtg cta cac agt ggg gag gaa ggg         1494
Thr Asp Arg Thr Ser Asp Pro Asn Val Leu His Ser Gly Glu Glu Gly
            475                 480                 485 aca cca cag tac cta aag ggc cag ctc ccc ctc ctc tca tca gtc cag         1542
Thr Pro Gln Tyr Leu Lys Gly Gln Leu Pro Leu Leu Ser Ser Val Gln
        490                 495                 500 atc gag ggc cac ccc atg tcc ctc cct ttg caa cct cct tcc ggt cca         1590
Ile Glu Gly His Pro Met Ser Leu Pro Leu Gln Pro Pro Ser Gly Pro
    505                 510                 515 tgt tcc ccc tcg gac caa ggt cca agt ccc tgg ggc ctg ctg gag tcc         1638
```

-continued

```
Cys Ser Pro Ser Asp Gln Gly Pro Ser Pro Trp Gly Leu Leu Glu Ser
520                 525                 530                 535 ctt gtg tgt ccc aag gat gaa gcc aag agc cca gcc cct gag acc tca    1686
Leu Val Cys Pro Lys Asp Glu Ala Lys Ser Pro Ala Pro Glu Thr Ser
                540                 545                 550 gac ctg gag cag ccc aca gaa ctg gat tct ctt ttc aga ggc ctg gcc    1734
Asp Leu Glu Gln Pro Thr Glu Leu Asp Ser Leu Phe Arg Gly Leu Ala
            555                 560                 565 ctg act gtg cag tgg gag tcc tgaggggaat gggaaaggct tggtgcttcc       1785
Leu Thr Val Gln Trp Glu Ser
        570 tccctgtccc tacccagtgt cacatccttg gctgtcaatc ccatgcctgc ccatgccaca  1845
cactctgcga tctggcctca gacgggtgcc cttgagagaa gcagagggag tggcatgcag  1905
ggcccctgcc atgggtgcgc tcctcaccgg aacaaagcag catgataagg actgcagcgg  1965
gggagctctg gggagcagct tgtgtagaca agcgcgtgct cgctgagccc tgcaaggcag  2025
aaatgacagt gcaaggagga aatgcaggga actcccgag gtccagagcc ccacctccta   2085
acaccatgga ttcaaagtgc tcagggaatt tgcctctcct tgccccattc ctggccagtt  2145
tcacaatcta gctcgacaga gcatgaggcc cctgcctctt ctgtcattgt tcaaaggtgg  2205
gaagagagcc tggaaaagaa ccaggcctgg aaaagaacca gaaggaggct gggcagaacc  2265
agaacaacct gcacttctgc caaggccagg gccagcagga cggcaggact ctagggaggg  2325
gtgtggcctg cagctcattc ccagccaggg caactgcctg acgttgcacg atttcagctt  2385
cattcctctg atagaacaaa gcgaaatgca ggtccaccag ggagggagac acacaagcct  2445
tttctgcagg caggagtttc agaccctatc ctgagaatgg ggtttgaaag gaaggtgagg  2505
gctgtggccc ctggacgggt acaataacac actgtactga tgtcacaact ttgcaagctc  2565
tgccttgggt tcagcccatc tgggctcaaa ttccagcctc accactcaca agctgtgtga  2625
cttcaaacaa atgaaatcag tgcccagaac ctcggtttcc tcatctgtaa tgtggggatc  2685
ataacaccta cctcatggag ttgtggtgaa gatgaaatga agtcatgtct ttaaagtgct  2745
taatagtgcc tggtacatgg gcagtgccca ataaacggta gctatttaaa aaaaaaaaa  2805
aaaaaaaaaa atagcggccg cctcga                                       2831
```

<210> SEQ ID NO 25
<211> LENGTH: 574
<212> TYPE: PRT
<213> ORGANISM: Homo sapiens

<400> SEQUENCE: 25

```
Met Arg Thr Leu Leu Thr Ile Leu Thr Val Gly Ser Leu Ala Ala His
1               5                   10                  15

Ala Pro Glu Asp Pro Ser Asp Leu Leu Gln His Val Lys Phe Gln Ser
                20                  25                  30

Ser Asn Phe Glu Asn Ile Leu Thr Trp Asp Ser Gly Pro Glu Gly Thr
            35                  40                  45

Pro Asp Thr Val Tyr Ser Ile Glu Tyr Lys Thr Tyr Gly Glu Arg Asp
        50                  55                  60

Trp Val Ala Lys Lys Gly Cys Gln Arg Ile Thr Arg Lys Ser Cys Asn
65                  70                  75                  80

Leu Thr Val Glu Thr Gly Asn Leu Thr Glu Leu Tyr Tyr Ala Arg Val
                85                  90                  95

Thr Ala Val Ser Ala Gly Gly Arg Ser Ala Thr Lys Met Thr Asp Arg
            100                 105                 110
```

-continued

```
Phe Ser Ser Leu Gln His Thr Thr Leu Lys Pro Pro Asp Val Thr Cys
        115                 120                 125

Ile Ser Lys Val Arg Ser Ile Gln Met Ile Val His Pro Thr Pro Thr
130                 135                 140

Pro Ile Arg Ala Gly Asp Gly His Arg Leu Thr Leu Glu Asp Ile Phe
145                 150                 155                 160

His Asp Leu Phe Tyr His Leu Glu Leu Gln Val Asn Arg Thr Tyr Gln
                165                 170                 175

Met His Leu Gly Gly Lys Gln Arg Glu Tyr Glu Phe Phe Gly Leu Thr
            180                 185                 190

Pro Asp Thr Glu Phe Leu Gly Thr Ile Met Ile Cys Val Pro Thr Trp
        195                 200                 205

Ala Lys Glu Ser Ala Pro Tyr Met Cys Arg Val Lys Thr Leu Pro Asp
210                 215                 220

Arg Thr Trp Thr Tyr Ser Phe Ser Gly Ala Phe Leu Phe Ser Met Gly
225                 230                 235                 240

Phe Leu Val Ala Val Leu Cys Tyr Leu Ser Tyr Arg Tyr Val Thr Lys
                245                 250                 255

Pro Pro Ala Pro Pro Asn Ser Leu Asn Val Gln Arg Val Leu Thr Phe
            260                 265                 270

Gln Pro Leu Arg Phe Ile Gln Glu His Val Leu Ile Pro Val Phe Asp
        275                 280                 285

Leu Ser Gly Pro Ser Ser Leu Ala Gln Pro Val Gln Tyr Ser Gln Ile
290                 295                 300

Arg Val Ser Gly Pro Arg Glu Pro Ala Gly Ala Pro Gln Arg His Ser
305                 310                 315                 320

Leu Ser Glu Ile Thr Tyr Leu Gly Gln Pro Asp Ile Ser Ile Leu Gln
                325                 330                 335

Pro Ser Asn Val Pro Pro Pro Gln Ile Leu Ser Pro Leu Ser Tyr Ala
            340                 345                 350

Pro Asn Ala Ala Pro Glu Val Gly Pro Pro Ser Tyr Ala Pro Gln Val
        355                 360                 365

Thr Pro Glu Ala Gln Phe Pro Phe Tyr Ala Pro Gln Ala Ile Ser Lys
370                 375                 380

Val Gln Pro Ser Ser Tyr Ala Pro Gln Ala Thr Pro Asp Ser Trp Pro
385                 390                 395                 400

Pro Ser Tyr Gly Val Cys Met Glu Gly Ser Gly Lys Asp Ser Pro Thr
                405                 410                 415

Gly Thr Leu Ser Ser Pro Lys His Leu Arg Pro Lys Gly Gln Leu Gln
            420                 425                 430

Lys Glu Pro Pro Ala Gly Ser Cys Met Leu Gly Gly Leu Ser Leu Gln
        435                 440                 445

Glu Val Thr Ser Leu Ala Met Glu Glu Ser Gln Glu Ala Lys Ser Leu
450                 455                 460

His Gln Pro Leu Gly Ile Cys Thr Asp Arg Thr Ser Asp Pro Asn Val
465                 470                 475                 480

Leu His Ser Gly Glu Glu Gly Thr Pro Gln Tyr Leu Lys Gly Gln Leu
                485                 490                 495

Pro Leu Leu Ser Ser Val Gln Ile Glu Gly His Pro Met Ser Leu Pro
            500                 505                 510

Leu Gln Pro Pro Ser Gly Pro Cys Ser Pro Ser Asp Gln Gly Pro Ser
        515                 520                 525
```

-continued

```
Pro Trp Gly Leu Leu Glu Ser Leu Val Cys Pro Lys Asp Glu Ala Lys
    530                 535                 540

Ser Pro Ala Pro Glu Thr Ser Asp Leu Glu Gln Pro Thr Glu Leu Asp
545                 550                 555                 560

Ser Leu Phe Arg Gly Leu Ala Leu Thr Val Gln Trp Glu Ser
                565                 570

<210> SEQ ID NO 26
<211> LENGTH: 39
<212> TYPE: DNA
<213> ORGANISM: Artificial Sequence
<220> FEATURE:
<223> OTHER INFORMATION: Oligonucleotide linker ZC13252

<400> SEQUENCE: 26
ggcctgaaag cttcggataa tgaaggtacc tgttagaaa                            39

<210> SEQ ID NO 27
<211> LENGTH: 27
<212> TYPE: DNA
<213> ORGANISM: Artificial Sequence
<220> FEATURE:
<223> OTHER INFORMATION: Oligonucleotide linker ZC13453

<400> SEQUENCE: 27
ttaggatccg gcccttcccc agatact                                         27

<210> SEQ ID NO 28
<211> LENGTH: 36
<212> TYPE: DNA
<213> ORGANISM: Artificial Sequence
<220> FEATURE:
<223> OTHER INFORMATION: Oligonucleotide primer ZC28590

<400> SEQUENCE: 28
ttgggtacct ctgcaatggc cgccctgcag aaatct                               36

<210> SEQ ID NO 29
<211> LENGTH: 33
<212> TYPE: DNA
<213> ORGANISM: Artificial Sequence
<220> FEATURE:
<223> OTHER INFORMATION: Ooligonucleotide primer ZC28580

<400> SEQUENCE: 29
ttgggatcca atgcaggcat ttctcagaga cat                                  33

<210> SEQ ID NO 30
<211> LENGTH: 23
<212> TYPE: DNA
<213> ORGANISM: Artificial Sequence
<220> FEATURE:
<223> OTHER INFORMATION: Oligonucleotide primer ZC25963

<400> SEQUENCE: 30
agtcaacgca tgagtctctg aag                                             23

<210> SEQ ID NO 31
<211> LENGTH: 23
<212> TYPE: DNA
<213> ORGANISM: Artificial Sequence
<220> FEATURE:
<223> OTHER INFORMATION: Oligonucleotide primer ZC25964

<400> SEQUENCE: 31
```

-continued gttcttgagt accccaacag tct     23

<210> SEQ ID NO 32
<211> LENGTH: 18
<212> TYPE: DNA
<213> ORGANISM: Artificial Sequence
<220> FEATURE:
<223> OTHER INFORMATION: Oligonucleotide primer ZC14666

<400> SEQUENCE: 32
agccaccaag atgactga     18

<210> SEQ ID NO 33
<211> LENGTH: 22
<212> TYPE: DNA
<213> ORGANISM: Artificial Sequence
<220> FEATURE:
<223> OTHER INFORMATION: Oligonucleotide primer ZC14742

<400> SEQUENCE: 33
tgcatttggt aggtgcggtt ga     22

<210> SEQ ID NO 34
<211> LENGTH: 211
<212> TYPE: PRT
<213> ORGANISM: Homo sapiens

<400> SEQUENCE: 34

Pro Glu Asp Pro Ser Asp Leu Leu Gln His Val Lys Phe Gln Ser Ser
 1               5                  10                  15
Asn Phe Glu Asn Ile Leu Thr Trp Asp Ser Gly Pro Glu Gly Thr Pro
            20                  25                  30
Asp Thr Val Tyr Ser Ile Glu Tyr Lys Thr Tyr Gly Glu Arg Asp Trp
        35                  40                  45
Val Ala Lys Lys Gly Cys Gln Arg Ile Thr Arg Lys Ser Cys Asn Leu
    50                  55                  60
Thr Val Glu Thr Gly Asn Leu Thr Glu Leu Tyr Tyr Ala Arg Val Thr
65                  70                  75                  80
Ala Val Ser Ala Gly Gly Arg Ser Ala Thr Lys Met Thr Asp Arg Phe
                85                  90                  95
Ser Ser Leu Gln His Thr Thr Leu Lys Pro Pro Asp Val Thr Cys Ile
            100                 105                 110
Ser Lys Val Arg Ser Ile Gln Met Ile Val His Pro Thr Pro Thr Pro
        115                 120                 125
Ile Arg Ala Gly Asp Gly His Arg Leu Thr Leu Glu Asp Ile Phe His
    130                 135                 140
Asp Leu Phe Tyr His Leu Glu Leu Gln Val Asn Arg Thr Tyr Gln Met
145                 150                 155                 160
His Leu Gly Gly Lys Gln Arg Glu Tyr Glu Phe Phe Gly Leu Thr Pro
                165                 170                 175
Asp Thr Glu Phe Leu Gly Thr Ile Met Ile Cys Val Pro Thr Trp Ala
            180                 185                 190
Lys Glu Ser Ala Pro Tyr Met Cys Arg Val Lys Thr Leu Pro Asp Arg
        195                 200                 205
Thr Trp Thr
    210

<210> SEQ ID NO 35
<211> LENGTH: 199

```
<212> TYPE: PRT
<213> ORGANISM: Homo sapiens

<400> SEQUENCE: 35

Met Val Pro Pro Glu Asn Val Arg Met Asn Ser Val Asn Phe Lys
 1               5                  10                  15

Asn Ile Leu Gln Trp Glu Ser Pro Ala Phe Ala Lys Gly Asn Leu Thr
            20                  25                  30

Phe Thr Ala Gln Tyr Leu Ser Tyr Arg Ile Phe Gln Asp Lys Cys Met
        35                  40                  45

Asn Thr Thr Leu Thr Glu Cys Asp Phe Ser Ser Leu Ser Lys Tyr Gly
50                  55                  60

Asp His Thr Leu Arg Val Arg Ala Glu Phe Ala Asp Glu His Ser Asp
65                  70                  75                  80

Trp Val Asn Ile Thr Phe Cys Pro Val Asp Asp Thr Ile Ile Gly Pro
                    85                  90                  95

Pro Gly Met Gln Val Glu Val Leu Ala Asp Ser Leu His Met Arg Phe
                100                 105                 110

Leu Ala Pro Lys Ile Glu Asn Glu Tyr Glu Thr Trp Thr Met Lys Asn
            115                 120                 125

Val Tyr Asn Ser Trp Thr Tyr Asn Val Gln Tyr Trp Lys Asn Gly Thr
130                 135                 140

Asp Glu Lys Phe Gln Ile Thr Pro Gln Tyr Asp Phe Glu Val Leu Arg
145                 150                 155                 160

Asn Leu Glu Pro Trp Thr Thr Tyr Cys Val Gln Val Arg Gly Phe Leu
                    165                 170                 175

Pro Asp Arg Asn Lys Ala Gly Glu Trp Ser Glu Pro Val Cys Glu Gln
                180                 185                 190

Thr Thr His Asp Glu Thr Val
            195

<210> SEQ ID NO 36
<211> LENGTH: 211
<212> TYPE: PRT
<213> ORGANISM: Homo sapiens

<400> SEQUENCE: 36

Ser Asp Ala His Gly Thr Glu Leu Pro Ser Pro Ser Val Trp Phe
 1               5                  10                  15

Glu Ala Glu Phe Phe His His Ile Leu His Trp Thr Pro Ile Pro Asn
            20                  25                  30

Gln Ser Glu Ser Thr Cys Tyr Glu Val Ala Leu Leu Arg Tyr Gly Ile
        35                  40                  45

Glu Ser Trp Asn Ser Ile Ser Asn Cys Ser Gln Thr Leu Ser Tyr Asp
    50                  55                  60

Leu Thr Ala Val Thr Leu Asp Leu Tyr His Ser Asn Gly Tyr Arg Ala
65                  70                  75                  80

Arg Val Arg Ala Val Asp Gly Ser Arg His Ser Asn Trp Thr Val Thr
                    85                  90                  95

Asn Thr Arg Phe Ser Val Asp Glu Val Thr Leu Thr Val Gly Ser Val
                100                 105                 110

Asn Leu Glu Ile His Asn Gly Phe Ile Leu Gly Lys Ile Gln Leu Pro
            115                 120                 125

Arg Pro Lys Met Ala Pro Ala Asn Asp Thr Tyr Glu Ser Ile Phe Ser
130                 135                 140
```

```
His Phe Arg Glu Tyr Glu Ile Ala Ile Arg Lys Val Pro Gly Asn Phe
145                 150                 155                 160

Thr Phe Thr His Lys Lys Val Lys His Glu Asn Phe Ser Leu Leu Thr
            165                 170                 175

Ser Gly Glu Val Gly Phe Cys Val Gln Val Lys Pro Ser Val Ala
        180                 185                 190

Ser Arg Ser Asn Lys Gly Met Trp Ser Lys Glu Glu Cys Ile Ser Leu
        195                 200                 205

Thr Arg Gln
    210

<210> SEQ ID NO 37
<211> LENGTH: 2464
<212> TYPE: DNA
<213> ORGANISM: Mus musculus
<220> FEATURE:
<221> NAME/KEY: CDS
<222> LOCATION: (8)...(697)

<400> SEQUENCE: 37 ggcaacc atg atg cct aag cat tgc ctt cta ggt ctc ctc atc ata ctc        49
        Met Met Pro Lys His Cys Leu Leu Gly Leu Leu Ile Ile Leu
        1               5                   10 ttg agc agt gca aca gaa ata caa cca gct cgt gta tct ctg acg ctc        97
Leu Ser Ser Ala Thr Glu Ile Gln Pro Ala Arg Val Ser Leu Thr Leu
15              20                  25                  30 cag aag gtc cga ttt cag tcc aga aat ttc cac aat att ttg cac tgg       145
Gln Lys Val Arg Phe Gln Ser Arg Asn Phe His Asn Ile Leu His Trp
                35                  40                  45 caa gca ggg agc tct ctc ccc agc aac aac agc atc tac ttt gtg cag       193
Gln Ala Gly Ser Ser Leu Pro Ser Asn Asn Ser Ile Tyr Phe Val Gln
            50                  55                  60 tac aag atg tat gga cag agc caa tgg gaa gat aaa gtt gac tgc tgg       241
Tyr Lys Met Tyr Gly Gln Ser Gln Trp Glu Asp Lys Val Asp Cys Trp
        65                  70                  75 ggg acc acg gcg ctc ttc tgt gac ctg acc aat gaa acc tta gac cca       289
Gly Thr Thr Ala Leu Phe Cys Asp Leu Thr Asn Glu Thr Leu Asp Pro
    80                  85                  90 tac gag ctg tat tac ggg agg gtg atg acg gcc tgt gct gga cgc cac       337
Tyr Glu Leu Tyr Tyr Gly Arg Val Met Thr Ala Cys Ala Gly Arg His
95                  100                 105                 110 tct gcc tgg acc agg aca ccc cgc ttc act cca tgg tgg gaa aca aaa       385
Ser Ala Trp Thr Arg Thr Pro Arg Phe Thr Pro Trp Trp Glu Thr Lys
                115                 120                 125 cta gat cct ccg gtc gtg act ata acc cga gtt aac gca tct ttg cgg       433
Leu Asp Pro Pro Val Val Thr Ile Thr Arg Val Asn Ala Ser Leu Arg
            130                 135                 140 gtg ctt ctc cgt cct cca gag ttg cca aat aga aac caa agt gga aaa       481
Val Leu Leu Arg Pro Pro Glu Leu Pro Asn Arg Asn Gln Ser Gly Lys
        145                 150                 155 aat gca tcc atg gaa act tac tac ggc tta gta tac aga gtt ttc aca       529
Asn Ala Ser Met Glu Thr Tyr Tyr Gly Leu Val Tyr Arg Val Phe Thr
    160                 165                 170 atc aac aat tca cta gag aag gag caa aaa gcc tat gaa gga act cag       577
Ile Asn Asn Ser Leu Glu Lys Glu Gln Lys Ala Tyr Glu Gly Thr Gln
175                 180                 185                 190 aga gct gtt gaa att gaa ggt ctg ata cct cat tcc agc tac tgc gta       625
Arg Ala Val Glu Ile Glu Gly Leu Ile Pro His Ser Ser Tyr Cys Val
                195                 200                 205 gtg gct gaa atg tac cag ccc atg ttt gac aga aga agc cca aga agc       673
```

| | | | | | | | | | | | | | | |
|---|---|---|---|---|---|---|---|---|---|---|---|---|---|---|
|Val|Ala|Glu|Met|Tyr|Gln|Pro|Met|Phe|Asp|Arg|Arg|Ser|Pro|Arg|Ser|
| | | |210| | | | |215| | | |220| | |

```
aag gag aga tgt gtg cag att cca tgaactggtc tgaggcgcta aaaccggaag      727
Lys Glu Arg Cys Val Gln Ile Pro
        225             230 catattgaga acaggatgtc ttctgcctag aacagcttac taaacttctg ttttgatttt      787
cttagagcaa tgtctaccca cacttttcaa ggatttcttt gtcagtactt tcttttctgt      847
ttatttcagt tataaagtaa atttgaacag attcaaaaat agaatttaaa gagaaggtaa      907
agaataaaga tcttgtggta aggcacatct ttaatcccag cattgaaagg cagaatcagt      967
cagatctctg acttttgggc caacctggtc tgcatagaga gttccaggct agccagggcc     1027
acacaatgag accatgcatc aacatgataa gatgttaaga tagaaatgtt ctataaaaaa     1087
tggaagctta tctgaatata tcaaccctaa caataatctt ttttctggtt taaccctcaa     1147
ataagaatca attaatagta ggcatttaat aaatgttgta ataagtttta aggtattata     1207
tatagaaaat cctgcaacaa taattttata ttctattaag cctttattt tgccagagat      1267
atactgattt aatattttgt gtgaatgagt atacttctgt gcattttat tttatatta      1327
tgtcttttt atttcttata aggtatttct acttagtgaa ctatctctct aaaaataaac      1387
ttgtggctct gaattgatct ctagaataag attttcaata atagcatgta aatatcgaag     1447
aaaatcttca taatgcaatt tcccatcact taacacataa tcttagtaag aatacccttt     1507
ctggttttgc ttttaatagt gccttagaat ttaacctatg ttgtctaaat gcagcatata     1567
tttttcagca gcaaagacag aagaaacata taagccacag tgataactca gccattcagg     1627
caaagtggcc tctctgtcca cagaatgaga gttgggctgg agacactgga gtccatacag     1687
gaaccttgac ttgaagccaa aggcacacag tggatgctta aattatttct gagattataa     1747
ggaaattcac agccctgtgg actacactgc atctcctgag caatgatcag gtggcctaag     1807
gctcaaaaag tgaccagctt ttctaagcct ttctctagct cttgagctta gactatcagc     1867
tactgaaaat acatgtagga gagaacattt gtgatcttta tgaaagatgc tccaaaatat     1927
aactctgaaa agtatagtcg gtacgtctgt cttcttacgt tttttaatgg taaatggtca     1987
cagaccatta agaacataag agacatgtga aaagcaagag cattgtcctg gctgtcctgt     2047
gtgttcagaa acactggcc ttcattctta tttttgaatt attcaatttt tatttctttt      2107
gtggcttagt acctgcttgg gaattctttg ggttttttgt tcgttgtttg tttattttct     2167
attttgtact ttgggaaggg tgagatttga gaaggataac tcctctttgg gaatcaggac     2227
catgtgtggt cccagcattt aggttgtaag actcagtagt ctaattcctc ataatacaaa     2287
aggcaattgt tggtttatga gtgttgtcag caatcagagt tttgctttga ctttgtttgc     2347
ttgggttttc cctcacacaa gtataagatg ctttgaaata tattacgatt ttcacattct     2407
ggatcatgtt aagaatatat tgtctaagta cttcaataaa tcttactttg tacttta       2464
```

<210> SEQ ID NO 38
<211> LENGTH: 230
<212> TYPE: PRT
<213> ORGANISM: Mus musculus

<400> SEQUENCE: 38

| | | | | | | | | | | | | | | |
|---|---|---|---|---|---|---|---|---|---|---|---|---|---|---|---|
|Met|Met|Pro|Lys|His|Cys|Leu|Leu|Gly|Leu|Leu|Ile|Ile|Leu|Leu|Ser|
|1| | | |5| | | | |10| | | | |15| |
|Ser|Ala|Thr|Glu|Ile|Gln|Pro|Ala|Arg|Val|Ser|Leu|Thr|Leu|Gln|Lys|
| | | |20| | | | |25| | | | |30| | |

```
Val Arg Phe Gln Ser Arg Asn Phe His Asn Ile Leu His Trp Gln Ala
        35                  40                  45

Gly Ser Ser Leu Pro Ser Asn Asn Ser Ile Tyr Phe Val Gln Tyr Lys
    50                  55                  60

Met Tyr Gly Gln Ser Gln Trp Glu Asp Lys Val Asp Cys Trp Gly Thr
65                  70                  75                  80

Thr Ala Leu Phe Cys Asp Leu Thr Asn Glu Thr Leu Asp Pro Tyr Glu
                85                  90                  95

Leu Tyr Tyr Gly Arg Val Met Thr Ala Cys Ala Gly Arg His Ser Ala
            100                 105                 110

Trp Thr Arg Thr Pro Arg Phe Thr Pro Trp Trp Glu Thr Lys Leu Asp
        115                 120                 125

Pro Pro Val Val Thr Ile Thr Arg Val Asn Ala Ser Leu Arg Val Leu
    130                 135                 140

Leu Arg Pro Pro Glu Leu Pro Asn Arg Asn Gln Ser Gly Lys Asn Ala
145                 150                 155                 160

Ser Met Glu Thr Tyr Tyr Gly Leu Val Tyr Arg Val Phe Thr Ile Asn
                165                 170                 175

Asn Ser Leu Glu Lys Glu Gln Lys Ala Tyr Gly Thr Gln Arg Ala
            180                 185                 190

Val Glu Ile Glu Gly Leu Ile Pro His Ser Ser Tyr Cys Val Val Ala
        195                 200                 205

Glu Met Tyr Gln Pro Met Phe Asp Arg Arg Ser Pro Arg Ser Lys Glu
    210                 215                 220

Arg Cys Val Gln Ile Pro
225                 230

<210> SEQ ID NO 39
<211> LENGTH: 690
<212> TYPE: DNA
<213> ORGANISM: Artificial Sequence
<220> FEATURE:
<223> OTHER INFORMATION: Degenerate polynucleotide sequence of SEQ ID
      NO:38
<220> FEATURE:
<221> NAME/KEY: misc_feature
<222> LOCATION: (1)...(690)
<223> OTHER INFORMATION: n = A,T,C or G

<400> SEQUENCE: 39
atgatgccna arcaytgyyt nytnggnytn ytnathathy tnytnwsnws ngcnacngar      60
athcarccng cnmgngtnws nytnacnytn caraargtnm gnttycarws nmgnaaytty     120
cayaayathy tncaytggca rgcnggnwsn wsnytnccnw snaayaayws nathtaytty    180
gtncartaya aratgtaygg ncarwsncar tgggargaya argtngaytg ytggggnacn    240
acngcnytnt tytgygayyt nacnaaygar acnytngayc cntaygaryt ntaytayggn    300 mgntnatga cngcntgygc nggnmgncay wsngcntgga cnmgnacncc nmgnttyacn    360
ccntggtggg aracnaaryt ngayccnccn gtngtnacna thacnmgngt naaygcnwsn    420
ytnmgngtny tnytnmgncc nccngaaryt ccnaaymgna aycarwsngg naaraaygcn    480
wsnatggara cntaytaygg nytngtntay mgngtnttya cnathaayaa ywsnytngar    540
aargarcara argcntayga rggnacncar mgngcngtng arathgargg nytnathccn    600
caywsnwsnt aytgygtngt ngcngaaratg taycarccna tgttygaymg nmgnwsnccn    660
mgnwsnaarg armgntgygt ncarathccn                                     690
```

-continued

```
<210> SEQ ID NO 40
<211> LENGTH: 1050
<212> TYPE: DNA
<213> ORGANISM: Mus musculus
<220> FEATURE:
<221> NAME/KEY: CDS
<222> LOCATION: (50)...(589)

<400> SEQUENCE: 40
aacaggctct cctctcactt atcaactttt gacacttgtg cgatcggtg atg gct gtc      58
                                                      Met Ala Val
                                                        1 ctg cag aaa tct atg agt ttt tcc ctt atg ggg act ttg gcc gcc agc     106
Leu Gln Lys Ser Met Ser Phe Ser Leu Met Gly Thr Leu Ala Ala Ser
        5                  10                  15 tgc ctg ctt ctc att gcc ctg tgg gcc cag gag gca aat gcg ctg ccc     154
Cys Leu Leu Leu Ile Ala Leu Trp Ala Gln Glu Ala Asn Ala Leu Pro
 20                  25                  30                  35 atc aac acc cgg tgc aag ctt gag gtg tcc aac ttc cag cag ccg tac     202
Ile Asn Thr Arg Cys Lys Leu Glu Val Ser Asn Phe Gln Gln Pro Tyr
                 40                  45                  50 atc gtc aac cgc acc ttt atg ctg gcc aag gag gcc agc ctt gca gat     250
Ile Val Asn Arg Thr Phe Met Leu Ala Lys Glu Ala Ser Leu Ala Asp
             55                  60                  65 aac aac aca gac gtc cgg ctc atc ggg gag aaa ctg ttc cga gga gtc     298
Asn Asn Thr Asp Val Arg Leu Ile Gly Glu Lys Leu Phe Arg Gly Val
         70                  75                  80 agt gct aag gat cag tgc tac ctg atg aag cag gtg ctc aac ttc acc     346
Ser Ala Lys Asp Gln Cys Tyr Leu Met Lys Gln Val Leu Asn Phe Thr
 85                  90                  95 ctg gaa gac att ctg ctc ccc cag tca gac agg ttc cgg ccc tac atg     394
Leu Glu Asp Ile Leu Leu Pro Gln Ser Asp Arg Phe Arg Pro Tyr Met
100                 105                 110                 115 cag gag gtg gtg cct ttc ctg acc aaa ctc agc aat cag ctc agc tcc     442
Gln Glu Val Val Pro Phe Leu Thr Lys Leu Ser Asn Gln Leu Ser Ser
                120                 125                 130 tgt cac atc agt ggt gac gac cag aac atc cag aag aat gtc aga agg     490
Cys His Ile Ser Gly Asp Asp Gln Asn Ile Gln Lys Asn Val Arg Arg
            135                 140                 145 ctg aag gag aca gtg aaa aag ctt gga gag agc gga gag atc aaa gcg     538
Leu Lys Glu Thr Val Lys Lys Leu Gly Glu Ser Gly Glu Ile Lys Ala
        150                 155                 160 atc ggg gaa ctg gac ctg ctg ttt atg tct ctg aga aat gct tgc gtc     586
Ile Gly Glu Leu Asp Leu Leu Phe Met Ser Leu Arg Asn Ala Cys Val
165                 170                 175 tga gcgagaagaa gctagaaaac gaagaactgc tccttcctgc cttctaaaaa          639
 * gaacaataag atccctgaat ggactttttt actaaaggaa agtgagaagc taacgtccac    699
catcattaga agatttcaca tgaaacctgg ctcagttgaa agagaaaata gtgtcaagtt    759
gtccatgaga ccagaggtag acttgataac cacaaagatt cattgacaat atttattgt    819 cattgataat gcaacagaaa aagtatgtac tttaaaaaat tgtttgaaag gaggttacct    879
ctcattcctc tagaagaaaa gcctatgtaa cttcatttcc ataaccaata ctttatatat    939
gtaagtttat ttattataag tatacatttt atttatgtca gtttattaat atggatttat    999
ttatagaaaa attatctgat gttgatattt gagtataaag caaataatat t           1050

<210> SEQ ID NO 41
<211> LENGTH: 179
<212> TYPE: PRT
```

<213> ORGANISM: Mus musculus

<400> SEQUENCE: 41

```
Met Ala Val Leu Gln Lys Ser Met Ser Phe Ser Leu Met Gly Thr Leu
 1               5                  10                  15

Ala Ala Ser Cys Leu Leu Ile Ala Leu Trp Ala Gln Glu Ala Asn
             20                  25                  30

Ala Leu Pro Ile Asn Thr Arg Cys Lys Leu Glu Val Ser Asn Phe Gln
         35                  40                  45

Gln Pro Tyr Ile Val Asn Arg Thr Phe Met Leu Ala Lys Glu Ala Ser
     50                  55                  60

Leu Ala Asp Asn Asn Thr Asp Val Arg Leu Ile Gly Glu Lys Leu Phe
65                  70                  75                  80

Arg Gly Val Ser Ala Lys Asp Gln Cys Tyr Leu Met Lys Gln Val Leu
                85                  90                  95

Asn Phe Thr Leu Glu Asp Ile Leu Leu Pro Gln Ser Asp Arg Phe Arg
            100                 105                 110

Pro Tyr Met Gln Glu Val Val Pro Phe Leu Thr Lys Leu Ser Asn Gln
        115                 120                 125

Leu Ser Ser Cys His Ile Ser Gly Asp Asp Gln Asn Ile Gln Lys Asn
    130                 135                 140

Val Arg Arg Leu Lys Glu Thr Val Lys Lys Leu Gly Glu Ser Gly Glu
145                 150                 155                 160

Ile Lys Ala Ile Gly Glu Leu Asp Leu Leu Phe Met Ser Leu Arg Asn
                165                 170                 175

Ala Cys Val
```

<210> SEQ ID NO 42
<211> LENGTH: 20
<212> TYPE: DNA
<213> ORGANISM: Artificial Sequence
<220> FEATURE:
<223> OTHER INFORMATION: Oligonucleotide primer ZC10651

<400> SEQUENCE: 42
agcttttctg cagcagctct                                           20

<210> SEQ ID NO 43
<211> LENGTH: 23
<212> TYPE: DNA
<213> ORGANISM: Artificial Sequence
<220> FEATURE:
<223> OTHER INFORMATION: Oligonucleotide primer ZC10565

<400> SEQUENCE: 43
tttgcagaaa aggttgcaaa tgc                                       23

<210> SEQ ID NO 44
<211> LENGTH: 20
<212> TYPE: DNA
<213> ORGANISM: Artificial Sequence
<220> FEATURE:
<223> OTHER INFORMATION: Oligonucleotide primer ZC38001

<400> SEQUENCE: 44
ccgttcgtga ctataacccg                                           20

<210> SEQ ID NO 45
<211> LENGTH: 19
<212> TYPE: DNA

<210> SEQ ID NO 45
<211> LENGTH: 19
<212> TYPE: DNA
<213> ORGANISM: Artificial Sequence
<220> FEATURE:
<223> OTHER INFORMATION: Oligonucleotide primer ZC38022

<400> SEQUENCE: 45
agccgtagta agtttccat                                            19

<210> SEQ ID NO 46
<211> LENGTH: 4
<212> TYPE: PRT
<213> ORGANISM: Artificial Sequence
<220> FEATURE:
<223> OTHER INFORMATION: SXWS polypeptide motif
<220> FEATURE:
<221> NAME/KEY: VARIANT
<222> LOCATION: (1)...(4)
<223> OTHER INFORMATION: Xaa = Any Amino Acid

<400> SEQUENCE: 46

Ser Xaa Trp Ser
 1

<210> SEQ ID NO 47
<211> LENGTH: 707
<212> TYPE: DNA
<213> ORGANISM: Mus musculus
<220> FEATURE:
<221> NAME/KEY: CDS
<222> LOCATION: (2)...(691)

<400> SEQUENCE: 47

```
c atg atg cct aag cat tgc ctt cta ggt ctc ctc atc ata ctc ttg agc      49
  Met Met Pro Lys His Cys Leu Leu Gly Leu Leu Ile Ile Leu Leu Ser
   1               5                  10                  15 agt gca aca gaa ata caa cca gct cgt gta tct ctg acg ccc cag aag         97
Ser Ala Thr Glu Ile Gln Pro Ala Arg Val Ser Leu Thr Pro Gln Lys
             20                  25                  30 gtc cga ttt cag tcc aga aat ttc cac aat att ttg cac tgg caa gca        145
Val Arg Phe Gln Ser Arg Asn Phe His Asn Ile Leu His Trp Gln Ala
         35                  40                  45 ggg agc tct ctc ccc agc aac aac agc atc tac ttt gtg cag tac aag        193
Gly Ser Ser Leu Pro Ser Asn Asn Ser Ile Tyr Phe Val Gln Tyr Lys
     50                  55                  60 atg tat gga cag agc caa tgg gaa gat aaa gtt gac tgc tgg ggg acc        241
Met Tyr Gly Gln Ser Gln Trp Glu Asp Lys Val Asp Cys Trp Gly Thr
 65                  70                  75                  80 acg gcg ctc ttc tgt gac ctg acc aat gaa acc tta gac cca tac gag        289
Thr Ala Leu Phe Cys Asp Leu Thr Asn Glu Thr Leu Asp Pro Tyr Glu
                 85                  90                  95 ctg tat tac ggg agg gtg atg acg gcc tgt gct gga cgc cac tct gcc        337
Leu Tyr Tyr Gly Arg Val Met Thr Ala Cys Ala Gly Arg His Ser Ala
            100                 105                 110 tgg acc agg aca ccc cgc ttc act cca tgg tgg gaa aca aaa cta gat        385
Trp Thr Arg Thr Pro Arg Phe Thr Pro Trp Trp Glu Thr Lys Leu Asp
        115                 120                 125 cct ccg gtc gtg act ata acc cga gtt aac gca tct ttg cgg gtg ctt        433
Pro Pro Val Val Thr Ile Thr Arg Val Asn Ala Ser Leu Arg Val Leu
    130                 135                 140 ctc cgt cct cca gag ttg cca aat aga aac caa agt gga aaa aat gca        481
Leu Arg Pro Pro Glu Leu Pro Asn Arg Asn Gln Ser Gly Lys Asn Ala
145                 150                 155                 160 tcc atg gaa act tac tac ggc tta gta tac aga gtt ttc aca atc aac        529
Ser Met Glu Thr Tyr Tyr Gly Leu Val Tyr Arg Val Phe Thr Ile Asn
                165                 170                 175
```

```
aat tca cta gag aag gag caa aaa gcc tat gaa gga act cag aga gct      577
Asn Ser Leu Glu Lys Glu Gln Lys Ala Tyr Glu Gly Thr Gln Arg Ala
        180                 185                 190 gtt gaa att gaa ggt ctg ata cct cat tcc agc tac tgc gta gtg gct      625
Val Glu Ile Glu Gly Leu Ile Pro His Ser Ser Tyr Cys Val Val Ala
            195                 200                 205 gaa atg tac cag ccc atg ttt gac aga aga agc cca aga agc aag gag      673
Glu Met Tyr Gln Pro Met Phe Asp Arg Arg Ser Pro Arg Ser Lys Glu
        210                 215                 220 aga tgt gtg cac att cca tgaactggtc tgaggc                            707
Arg Cys Val His Ile Pro
225                 230

<210> SEQ ID NO 48
<211> LENGTH: 230
<212> TYPE: PRT
<213> ORGANISM: Mus musculus

<400> SEQUENCE: 48

Met Met Pro Lys His Cys Leu Leu Gly Leu Leu Ile Ile Leu Leu Ser
 1               5                  10                  15

Ser Ala Thr Glu Ile Gln Pro Ala Arg Val Ser Leu Thr Pro Gln Lys
            20                  25                  30

Val Arg Phe Gln Ser Arg Asn Phe His Asn Ile Leu His Trp Gln Ala
        35                  40                  45

Gly Ser Ser Leu Pro Ser Asn Asn Ser Ile Tyr Phe Val Gln Tyr Lys
    50                  55                  60

Met Tyr Gly Gln Ser Gln Trp Glu Asp Lys Val Asp Cys Trp Gly Thr
65                  70                  75                  80

Thr Ala Leu Phe Cys Asp Leu Thr Asn Glu Thr Leu Asp Pro Tyr Glu
                85                  90                  95

Leu Tyr Tyr Gly Arg Val Met Thr Ala Cys Ala Gly Arg His Ser Ala
            100                 105                 110

Trp Thr Arg Thr Pro Arg Phe Thr Pro Trp Trp Glu Thr Lys Leu Asp
        115                 120                 125

Pro Pro Val Val Thr Ile Thr Arg Val Asn Ala Ser Leu Arg Val Leu
    130                 135                 140

Leu Arg Pro Pro Glu Leu Pro Asn Arg Asn Gln Ser Gly Lys Asn Ala
145                 150                 155                 160

Ser Met Glu Thr Tyr Tyr Gly Leu Val Tyr Arg Val Phe Thr Ile Asn
                165                 170                 175

Asn Ser Leu Glu Lys Glu Gln Lys Ala Tyr Glu Gly Thr Gln Arg Ala
            180                 185                 190

Val Glu Ile Glu Gly Leu Ile Pro His Ser Ser Tyr Cys Val Val Ala
        195                 200                 205

Glu Met Tyr Gln Pro Met Phe Asp Arg Arg Ser Pro Arg Ser Lys Glu
    210                 215                 220

Arg Cys Val His Ile Pro
225                 230

<210> SEQ ID NO 49
<211> LENGTH: 690
<212> TYPE: DNA
<213> ORGANISM: Artificial Sequence
<220> FEATURE:
<223> OTHER INFORMATION: Degenerate polynucleotide sequence of SEQ ID
      NO:48
<220> FEATURE:
```

-continued

```
<221> NAME/KEY: misc_feature
<222> LOCATION: (1)...(690)
<223> OTHER INFORMATION: n = A,T,C or G

<400> SEQUENCE: 49
atgatgccna arcaytgyyt nytnggnytn ytnathathy tnytnwsnws ngcnacngar     60
athcarccng cnmgngtnws nytnacnccn caraargtnm gnttycarws nmgnaaytty    120
cayaayathy tncaytggca rgcnggnwsn wsnytnccnw snaayaayws nathtaytty    180
gtncartaya aratgtaygg ncarwsncar tgggargaya argtngaytg ytggggnacn    240
acngcnytnt tytgygayyt nacnaaygar acnytngayc cntaygaryt ntaytayggn    300
mgngtnatga cngcntgygc nggnmgncay wsngcntgga cnmgnacncc nmgnttyacn    360
ccntggtggg aracnaaryt ngayccnccn gtngtnacna thacnmgngt naaygcnwsn    420
ytnmgngtny tnytnmgncc nccngarytn ccnaaymgna aycarwsngg naaraaygcn    480
wsnatggara cntaytaygg nytngtntay mgngtnttya cnathaayaa ywsnytngar    540
aargarcara argcntayga rggnacncar mgngcngtng arathgargg nytnathccn    600
caywsnwsnt aytgygtngt ngcngaratg taycarccna tgttygaymg nmgnwsnccn    660
mgnwsnaarg armgntgygt ncayathccn                                      690
```